(12) United States Patent
Muse et al.

(10) Patent No.: US 12,186,496 B2
(45) Date of Patent: Jan. 7, 2025

(54) CATHETER DELIVERY DEVICES, SYSTEMS, AND METHODS

(71) Applicant: Avia Vascular, LLC, Salt Lake City, UT (US)

(72) Inventors: Jay Muse, Salt Lake City, UT (US); Kevin Jerry Cook, Kaysville, UT (US)

(73) Assignee: Avia Vascular, LLC, Salt Lake City, UT (US)

( * ) Notice: Subject to any disclaimer, the term of this patent is extended or adjusted under 35 U.S.C. 154(b) by 0 days.

(21) Appl. No.: 17/339,199

(22) Filed: Jun. 4, 2021

(65) Prior Publication Data

US 2021/0290900 A1   Sep. 23, 2021

Related U.S. Application Data

(63) Continuation of application No. 15/992,144, filed on May 29, 2018, now Pat. No. 11,065,419, which is a
(Continued)

(51) Int. Cl.
*A61M 25/00* (2006.01)
*A61M 25/01* (2006.01)
*A61M 25/06* (2006.01)

(52) U.S. Cl.
CPC .... *A61M 25/0026* (2013.01); *A61M 25/0014* (2013.01); *A61M 25/0068* (2013.01);
(Continued)

(58) Field of Classification Search
CPC .......... A61M 25/0102; A61M 25/0631; A61M 25/008; A61M 25/0097; A61M 25/09016;
(Continued)

(56) References Cited

U.S. PATENT DOCUMENTS 3,094,122 A   6/1963   Gauthier et al.
3,459,188 A   8/1969   Roberts
(Continued)

FOREIGN PATENT DOCUMENTS

CN   203971141 U   12/2014
DE   102006013096 B4   2/2008
(Continued)

OTHER PUBLICATIONS

Japan Patent Office, Notice of Reasons for Rejection in Japanese Patent Application No. 2019-565450, dated Mar. 24, 2022, 10 pages.
(Continued)

*Primary Examiner* — Kami A Bosworth
*Assistant Examiner* — Avery Smale
(74) *Attorney, Agent, or Firm* — Laurence & Phillips IP Law; Daniel C. Higgs

(57) ABSTRACT

A system can include a needle that includes a distal tip configured to be inserted into a vessel of a patient, the needle defining an outer surface. The system can further include a catheter that includes a distal end and an inner surface that defines a lumen within which a portion of the needle is positioned, the distal tip of the needle being at a position that is distal to the distal end of the catheter, the catheter further comprising a catching region of reduced diameter that extends inwardly at the distal end of the catheter. The system can include a longitudinally extending stiffener positioned between the outer surface of the needle and the inner surface of the catheter, the stiffener including a distal end that engages the catching region of the catheter when the catheter and the stiffener are inserted distally into the vessel of the patient over the needle, the stiffener being configured to disengage from the catheter and translate proximally relative thereto to leave the catheter positioned within the vessel of
(Continued)

the patient as the stiffener is withdrawn from the catheter in a proximal direction.

33 Claims, 72 Drawing Sheets

Related U.S. Application Data continuation of application No. PCT/US2018/034788, filed on May 26, 2018.

(60) Provisional application No. 62/641,475, filed on Mar. 12, 2018, provisional application No. 62/619,535, filed on Jan. 19, 2018, provisional application No. 62/511,900, filed on May 26, 2017.

(52) U.S. Cl.
CPC ...... *A61M 25/008* (2013.01); *A61M 25/0102* (2013.01); *A61M 25/0606* (2013.01); *A61M 25/0631* (2013.01); *A61M 25/001* (2013.01); *A61M 25/0045* (2013.01); *A61M 25/0082* (2013.01); *A61M 25/0097* (2013.01); *A61M 25/0693* (2013.01)

(58) Field of Classification Search
CPC .... A61M 25/09025; A61M 2025/0063; A61M 2025/0915; A61M 25/0053; A61M 25/0026; A61M 25/0014; A61M 25/0068; A61M 25/001; A61M 25/0045; A61M 25/0082; A61M 25/0606; A61M 25/0693; A61M 25/065; A61M 2025/0018; A61M 25/0021; A61M 25/0023; A61M 25/003; A61M 25/0032; A61M 2025/0039; A61M 25/005; A61M 2025/0059; A61M 25/0067; A61M 2025/0098; A61M 25/01; A61M 2025/0175

See application file for complete search history.

(56) References Cited

U.S. PATENT DOCUMENTS

| | | | |
|---|---|---|---|
| 3,539,034 A | 11/1970 | Tafeen |
| 3,565,074 A | 2/1971 | Foti |
| 3,612,050 A | 10/1971 | Sheridan |
| 3,721,231 A | 3/1973 | Hubert |
| 3,727,613 A | 4/1973 | Sorenson et al. |
| 3,766,916 A | 10/1973 | Moorehead et al. |
| 3,792,703 A | 2/1974 | Moorehead |
| 3,811,440 A | 5/1974 | Moorehead et al. |
| 4,323,071 A | 4/1982 | Simpson et al. |
| 4,342,313 A | 8/1982 | Chittenden |
| 4,404,159 A | 9/1983 | McFarlane |
| 4,411,655 A | 10/1983 | Schreck |
| 4,512,766 A | 4/1985 | Vailancourt |
| 4,559,046 A | 12/1985 | Groshong et al. |
| 4,583,968 A | 4/1986 | Mahurkar |
| 4,588,398 A | 5/1986 | Daugherty et al. |
| 4,661,300 A | 4/1987 | Daugherty |
| 4,666,438 A | 5/1987 | Raulerson |
| 4,713,057 A | 12/1987 | Huttner et al. |
| 4,753,765 A | 6/1988 | Pande |
| 4,790,817 A | 12/1988 | Luther |
| 4,824,433 A | 4/1989 | Marz et al. |
| 4,944,728 A | 7/1990 | Carrell et al. |
| 4,963,306 A | 10/1990 | Weldon |
| 4,964,854 A | 10/1990 | Luther |
| 4,986,814 A | 1/1991 | Burney et al. |
| 4,995,866 A | 2/1991 | Amplatz et al. |
| 5,017,259 A | 5/1991 | Kohsai |
| 5,047,018 A | 9/1991 | Gay et al. |
| 5,053,004 A | 10/1991 | Markel et al. |
| 5,059,170 A | 10/1991 | Cameron |
| 5,064,416 A | 11/1991 | Newgard et al. |
| 5,120,317 A | 6/1992 | Luther |
| 5,135,599 A | 8/1992 | Martin et al. |
| 5,163,912 A | 12/1992 | Gay et al. |
| 5,180,376 A | 1/1993 | Fischell |
| 5,188,593 A | 2/1993 | Martin |
| 5,224,939 A | 7/1993 | Holman et al. |
| 5,242,410 A | 9/1993 | Melker |
| 5,248,301 A | 9/1993 | Koenig, Jr. et al. |
| 5,336,176 A | 8/1994 | Yoon |
| 5,350,358 A | 9/1994 | Martin |
| 5,380,276 A | 1/1995 | Miller et al. |
| 5,401,257 A | 3/1995 | Chevalier, Jr. et al. |
| 5,405,341 A | 4/1995 | Martin |
| 5,409,644 A | 4/1995 | Martin et al. |
| 5,472,435 A | 12/1995 | Sutton |
| 5,480,380 A | 1/1996 | Martin |
| 5,522,832 A | 6/1996 | Kugo et al. |
| 5,531,701 A | 7/1996 | Luther |
| 5,531,720 A | 7/1996 | Atkins |
| 5,533,988 A | 7/1996 | Dickerson et al. |
| 5,545,149 A | 8/1996 | Brin et al. |
| 5,589,120 A | 12/1996 | Khan et al. |
| 5,593,718 A | 1/1997 | Conway et al. |
| 5,624,413 A | 4/1997 | Markel et al. |
| 5,630,802 A | 5/1997 | Moellmann et al. |
| 5,649,911 A | 7/1997 | Trerotola |
| 5,683,370 A | 11/1997 | Luther et al. |
| 5,683,640 A | 11/1997 | Miller et al. |
| 5,695,479 A | 12/1997 | Jagpal |
| 5,700,250 A | 12/1997 | Erskine |
| 5,700,251 A | 12/1997 | Miyauchi et al. |
| 5,718,692 A | 2/1998 | Schon et al. |
| 5,736,085 A | 4/1998 | Brown et al. |
| 5,762,630 A | 6/1998 | Bley et al. |
| 5,792,401 A | 8/1998 | Burnham |
| 5,797,882 A | 8/1998 | Purdy et al. |
| 5,810,785 A | 9/1998 | Bogert et al. |
| 5,839,715 A | 11/1998 | Leinsing |
| 5,843,356 A | 12/1998 | Patel et al. |
| 5,913,848 A | 6/1999 | Luther et al. |
| 5,916,208 A | 6/1999 | Luther et al. |
| 5,919,164 A | 6/1999 | Andersen |
| 5,947,953 A | 9/1999 | Ash et al. |
| 5,954,698 A | 9/1999 | Pike |
| 5,957,893 A | 9/1999 | Luther et al. |
| 5,971,954 A | 10/1999 | Conway et al. |
| 5,976,103 A | 11/1999 | Martin |
| 5,985,195 A | 11/1999 | Muskatello |
| 6,001,079 A | 12/1999 | Pourchez |
| 6,001,080 A | 12/1999 | Kuracina et al. |
| 6,004,294 A | 12/1999 | Brimhall et al. |
| 6,012,213 A | 1/2000 | Change et al. |
| 6,013,190 A | 1/2000 | Berg et al. |
| 6,030,371 A | 2/2000 | Pursley |
| 6,045,734 A | 4/2000 | Luther et al. |
| 6,048,485 A | 4/2000 | Field et al. |
| 6,131,433 A | 10/2000 | Nakada et al. |
| 6,187,130 B1 | 2/2001 | Berard et al. |
| 6,280,788 B1 | 8/2001 | Rackhorst et al. |
| 6,350,253 B1 | 2/2002 | Deniega et al. |
| 6,443,927 B1 | 9/2002 | Cook |
| 6,533,751 B2 | 3/2003 | Cragg et al. |
| 6,613,014 B1 | 9/2003 | Chi |
| 6,673,060 B1 | 1/2004 | Fleming, III |
| 6,702,972 B1 | 3/2004 | Markle |
| 6,740,277 B2 | 5/2004 | Howell et al. |
| 6,890,321 B2 | 5/2005 | Luther et al. |
| 6,921,386 B2 | 7/2005 | Shue et al. |
| 7,008,404 B2 | 3/2006 | Nakajima |
| 7,291,128 B2 | 11/2007 | Rossi |
| 7,435,240 B2 | 10/2008 | Barkhahn et al. |
| 7,513,891 B2 | 4/2009 | Hunn et al. |
| 7,625,355 B2 | 12/2009 | Yu |
| 7,727,198 B2 | 6/2010 | Nakajima |
| 7,749,196 B2 | 7/2010 | Osborne et al. |
| 7,763,008 B2 | 7/2010 | Yu |
| 7,771,369 B2 | 8/2010 | Griffin et al. |

(56) References Cited

U.S. PATENT DOCUMENTS

| | | |
|---|---|---|
| 8,034,047 B2 | 10/2011 | Racz et al. |
| 8,075,529 B2 | 12/2011 | Nakajima et al. |
| 8,105,286 B2 | 1/2012 | Anderson et al. |
| 8,172,803 B2 | 5/2012 | Morrissey et al. |
| 8,192,402 B2 | 6/2012 | Anderson et al. |
| 8,277,438 B2 | 10/2012 | Griffin et al. |
| 8,308,674 B1 | 11/2012 | Motroni |
| 8,308,691 B2 | 11/2012 | Woehr et al. |
| 8,382,718 B2 | 2/2013 | Woehr |
| 8,403,911 B2 | 3/2013 | Adams et al. |
| 8,419,688 B2 | 4/2013 | Woehr et al. |
| 8,460,247 B2 | 6/2013 | Woehr et al. |
| 8,480,628 B2 | 7/2013 | Hawkins et al. |
| 8,579,805 B2 | 11/2013 | Accisano, III |
| 8,591,468 B2 | 11/2013 | Woehr et al. |
| 8,597,249 B2 | 12/2013 | Woehr et al. |
| 8,652,104 B2 | 2/2014 | Goral et al. |
| 8,657,790 B2 | 2/2014 | Tal et al. |
| 8,690,833 B2 | 4/2014 | Belson |
| 8,721,546 B2 | 5/2014 | Belson |
| 8,728,035 B2 | 5/2014 | Warring et al. |
| 8,814,833 B2 | 8/2014 | Farrell et al. |
| 8,834,422 B2 | 9/2014 | Walker et al. |
| 8,900,192 B2 | 12/2014 | Anderson et al. |
| 8,915,891 B2 | 12/2014 | Bornhoft |
| 8,932,258 B2 | 1/2015 | Blanchard et al. |
| 8,986,227 B2 | 3/2015 | Belson |
| 8,998,852 B2 | 4/2015 | Blanchard et al. |
| 9,095,683 B2 | 8/2015 | Hall et al. |
| 9,138,252 B2 | 9/2015 | Bierman et al. |
| 9,162,037 B2 | 10/2015 | Belson et al. |
| 9,242,071 B2 | 1/2016 | Morgan et al. |
| 9,259,553 B2 | 2/2016 | Delano et al. |
| 9,272,088 B2 | 3/2016 | Bornhoft |
| 9,308,354 B2 | 4/2016 | Farrell et al. |
| 9,358,335 B2 | 6/2016 | Wada et al. |
| 9,370,641 B2 | 6/2016 | Woehr et al. |
| 9,375,551 B2 | 6/2016 | Harding |
| 9,381,324 B2 | 7/2016 | Fuchs et al. |
| 9,393,382 B2 | 7/2016 | Heck |
| 9,399,116 B2 | 7/2016 | Goral et al. |
| 9,446,218 B2 | 9/2016 | Accisano, III |
| 9,468,462 B2 | 10/2016 | Rosenbaum et al. |
| 9,522,016 B2 | 12/2016 | Kellerman et al. |
| 9,522,229 B2 | 12/2016 | Sonderegger et al. |
| 9,533,120 B1 | 1/2017 | Kimmel et al. |
| 9,545,495 B2 | 1/2017 | Goral et al. |
| 9,675,784 B2 | 6/2017 | Belson |
| 9,744,334 B2 | 8/2017 | Lahme et al. |
| 9,750,928 B2 | 9/2017 | Burkholz et al. |
| 9,764,117 B2 | 9/2017 | Bierman et al. |
| 9,775,972 B2 | 10/2017 | Christensen et al. |
| 9,802,025 B2 | 10/2017 | Khalaj |
| 9,861,792 B2 | 1/2018 | Hall et al. |
| 9,867,966 B2 | 1/2018 | Tanabe et al. |
| 9,950,139 B2 | 4/2018 | Blanchard et al. |
| 10,010,343 B2 | 7/2018 | Bierman et al. |
| 10,080,867 B2 | 9/2018 | Goral et al. |
| 10,159,817 B2 | 12/2018 | Khalaj |
| 10,159,818 B2 | 12/2018 | Farrell et al. |
| 10,252,026 B2 | 4/2019 | Khalaj |
| 10,335,578 B2 | 7/2019 | Ishida |
| 10,335,579 B2 | 7/2019 | Baid |
| 10,384,039 B2 | 8/2019 | Ribelin et al. |
| 10,426,931 B2 | 10/2019 | Blanchard et al. |
| 10,441,752 B2 | 10/2019 | Bierman et al. |
| 10,682,157 B2 | 6/2020 | Bierman et al. |
| 10,682,500 B2 | 6/2020 | Woehr et al. |
| 10,729,882 B2 | 8/2020 | Morgan et al. |
| 10,786,653 B2 | 9/2020 | Galgano et al. |
| 10,799,681 B2 | 10/2020 | Khalaj |
| 10,828,465 B2 | 11/2020 | Keyser et al. |
| 10,828,466 B2 | 11/2020 | Yokota |
| 10,898,679 B2 | 1/2021 | Khalaj |
| 11,040,176 B2 | 6/2021 | Blanchard et al. |
| 11,110,253 B2 | 9/2021 | Asai |
| 11,110,254 B2 | 9/2021 | Ishida |
| 11,123,524 B2 | 9/2021 | Hall et al. |
| 11,357,962 B2 | 6/2022 | Burkholz et al. |
| 11,478,610 B2 | 10/2022 | Burkholz et al. |
| 2001/0053895 A1 | 12/2001 | Vaillancourt |
| 2002/0107506 A1* | 8/2002 | McGuckin, Jr. .. A61M 25/0068 604/523 |
| 2003/0153873 A1 | 8/2003 | Luther et al. |
| 2003/0204169 A1 | 10/2003 | Howell et al. |
| 2004/0215143 A1 | 10/2004 | Brady et al. |
| 2006/0015068 A1 | 1/2006 | Amisar et al. |
| 2006/0047246 A1 | 3/2006 | Anders |
| 2006/0258987 A1 | 11/2006 | Lentz et al. |
| 2007/0112302 A1 | 5/2007 | Yu |
| 2008/0039796 A1 | 2/2008 | Nakajima |
| 2008/0140022 A1 | 6/2008 | Pond et al. |
| 2008/0147010 A1 | 6/2008 | Nakajima et al. |
| 2009/0131872 A1 | 5/2009 | Popov |
| 2009/0221961 A1* | 9/2009 | Tal .................. A61M 25/0618 604/103.06 |
| 2010/0030141 A1 | 2/2010 | Chermoni |
| 2011/0125097 A1 | 5/2011 | Shaw et al. |
| 2011/0137266 A1 | 6/2011 | Schlitt |
| 2011/0282285 A1 | 11/2011 | Blanchard |
| 2011/0319825 A1 | 12/2011 | Goral et al. |
| 2012/0065590 A1 | 3/2012 | Bierman et al. |
| 2012/0116324 A1 | 5/2012 | Schlitt |
| 2013/0096604 A1 | 4/2013 | Hanson et al. |
| 2013/0237958 A1 | 9/2013 | Arrigo |
| 2014/0025036 A1* | 1/2014 | Bierman ........... A61M 25/0606 604/506 |
| 2014/0081210 A1 | 3/2014 | Bierman et al. |
| 2014/0336581 A1 | 11/2014 | Collin |
| 2015/0119806 A1 | 4/2015 | Blanchard et al. |
| 2015/0151078 A1 | 6/2015 | Bhitiyakul |
| 2015/0231364 A1 | 8/2015 | Blanchard et al. |
| 2015/0359995 A1* | 12/2015 | Khalaj ................ A61M 25/005 604/170.01 |
| 2015/0367103 A1 | 12/2015 | Pajunk et al. |
| 2016/0045715 A1* | 2/2016 | Galgano ........... A61M 25/0662 604/510 |
| 2016/0106954 A1 | 4/2016 | Hebbard |
| 2016/0114137 A1 | 4/2016 | Woehr et al. |
| 2016/0206852 A1 | 7/2016 | Morgan et al. |
| 2016/0256667 A1 | 9/2016 | Ribelin et al. |
| 2016/0296724 A1 | 10/2016 | Goral et al. |
| 2017/0197062 A1 | 7/2017 | Baid |
| 2017/0224961 A1 | 8/2017 | Amisar et al. |
| 2017/0333642 A1 | 11/2017 | Shevgoor et al. |
| 2018/0008803 A1 | 1/2018 | Muramatsu et al. |
| 2018/0126125 A1 | 5/2018 | Hall et al. |
| 2018/0133438 A1 | 5/2018 | Hulvershorn et al. |
| 2018/0369540 A1 | 12/2018 | Asai |
| 2019/0275301 A1 | 9/2019 | Ishida |
| 2019/0321598 A1 | 10/2019 | Harding et al. |
| 2019/0351191 A1 | 11/2019 | Bierman et al. |
| 2019/0351192 A1 | 11/2019 | Bierman et al. |
| 2020/0023167 A1 | 1/2020 | Ishida et al. |
| 2020/0060710 A1 | 2/2020 | Urbanski et al. |
| 2020/0108230 A1 | 4/2020 | Isaacson et al. |
| 2020/0147350 A1 | 5/2020 | Tal et al. |
| 2020/0197682 A1 | 6/2020 | Franklin et al. |
| 2020/0315656 A1 | 10/2020 | Bierman et al. |
| 2021/0008347 A1 | 1/2021 | Galgano et al. |
| 2021/0052858 A1 | 2/2021 | Isaacson et al. |
| 2021/0290900 A1 | 9/2021 | Muse et al. |
| 2024/0075254 A1 | 3/2024 | Muse et al. |
| 2024/0091518 A1 | 3/2024 | Muse et al. |

FOREIGN PATENT DOCUMENTS

| | | |
|---|---|---|
| DE | 102007028367 B4 | 11/2010 |
| EP | 0150281 A1 | 8/1985 |
| EP | 0341830 A1 | 11/1989 |
| EP | 0386408 A1 | 9/1990 |
| EP | 0608854 A2 | 8/1994 |
| EP | 1457229 A1 | 9/2004 |

(56) References Cited

FOREIGN PATENT DOCUMENTS

| | | | |
|---|---|---|---|
| EP | 2732847 | A1 | 5/2014 |
| GB | 2120947 | B | 7/1985 |
| JP | 06217988 | A | 8/1994 |
| JP | 2001149483 | A | 6/2001 |
| JP | 2008-173463 | A | 7/2008 |
| JP | 7237858 | B2 | 3/2023 |
| JP | 7505065 | B2 | 6/2024 |
| KR | 10-2615489 | B1 | 12/2023 |
| SE | 432527 | B | 4/1984 |
| WO | 1994023785 | A1 | 10/1994 |
| WO | 2009030788 | A1 | 3/2009 |
| WO | 2009049823 | A1 | 4/2009 |
| WO | 2012060328 | A1 | 5/2012 |
| WO | 2016052517 | A1 | 4/2016 |
| WO | 2016152377 | A1 | 8/2016 |
| WO | 2016178974 | A1 | 11/2016 |
| WO | 2017074673 | A1 | 5/2017 |
| WO | 2018218236 | A1 | 11/2018 |
| WO | 2019203998 | A1 | 10/2019 |
| WO | 2020191228 | A1 | 9/2020 |
| WO | 2021034862 | A1 | 2/2021 |
| WO | 2021113962 | A1 | 6/2021 |
| WO | 2024035814 | A1 | 2/2024 |
| WO | 2024/064308 | A2 | 3/2024 |

OTHER PUBLICATIONS

Japan Patent Office, Notice of Allowance in Japanese Patent Application No. 2019-565450, dated Jan. 30, 2023, 6 pages.
Korean Patent Office, Office Action in Korean Patent Application No. 10-2019-7038287, dated Feb. 20, 2023, 12 pages.
U.S. Appl. No. 15/992,144, filed May 29, 2018, Catheter Delivery Devices, Systems, and Methods.
U.S. Appl. No. 18/472,208, filed Sep. 21, 2023, Blood Control Valves, Systems, and Methods.
U.S. Appl. No. 18/232,333, filed Aug. 9, 2023, Catheter Delivery Devices, Systems, and Methods.
International Application No. PCT/US2023/033416, titled Blood Control Valves, Systems, and Methods, filed Sep. 21, 2023, 94 pages.
International Application No. PCT/US2023/029899, titled Catheter Delivery Devices, Systems, and Methods, filed Aug. 9, 2023, 77 pages.
International Searching Authority, International Search Report and Written Opinion of the International Searching Authority in International Application No. PCT/US2023/029899, dated Nov. 28, 2023, 15 pages.
Japan Patent Office, Notice of Reasons for Rejection in Japanese Patent Application No. 2023-030245, dated Jan. 15, 2024 (6 pages).
European Patent Office, Communication pursuant to Article 94(3) EPC in European Patent Application No. 18805782.2, dated Oct. 16, 2023, 4 pages.
Korean Patent Office, Notice of Allowance in Korean Patent Application No. 10-2019-7038287, dated Sep. 19, 2023, 3 pages.
U.S. Appl. No. 18/232,333, titled Catheter Delivery Devices, Systems, and Methods, filed Aug. 9, 2023, 82 pages.
U.S. Appl. No. 18/472,208, titled Blood Control Valves, Systems, and Methods, filed Sep. 21, 2023, 89 pages.
International Bureau of WIPO, International Search Report and Written Opinion of the International Searching Authority for International Application No. PCT/US2018/034788, dated Oct. 15, 2018, 18 pages.
International Bureau of WIPO, International Preliminary Report on Patentability for International Application No. PCT/US2018/034788, dated Nov. 26, 2019, 9 pages.
European Patent Office, Supplementary European Search Report for European Patent Application No. 18805782.2, dated Feb. 17, 2021, 9 pages.
International Searching Authority, International Search Report for International Application No. PCT/US2023/033416, dated Apr. 8, 2024, 4 pages.
International Searching Authority, Written Opinion of the International Searching Authority for International Application No. PCT/US2023/033416, dated Apr. 8, 2024, 11 pages.
European Patent Office, Communication pursuant to Article 94(3) EPC in European Patent Application No. 18805782.2, dated Aug. 16, 2024, 4 pages.
China National Intellectual Property Administration, Notice of Frist Examination Opinion for Chinese Patent Application No. 201880042285.1, dated Sep. 12, 2024, 5 pages.

* cited by examiner

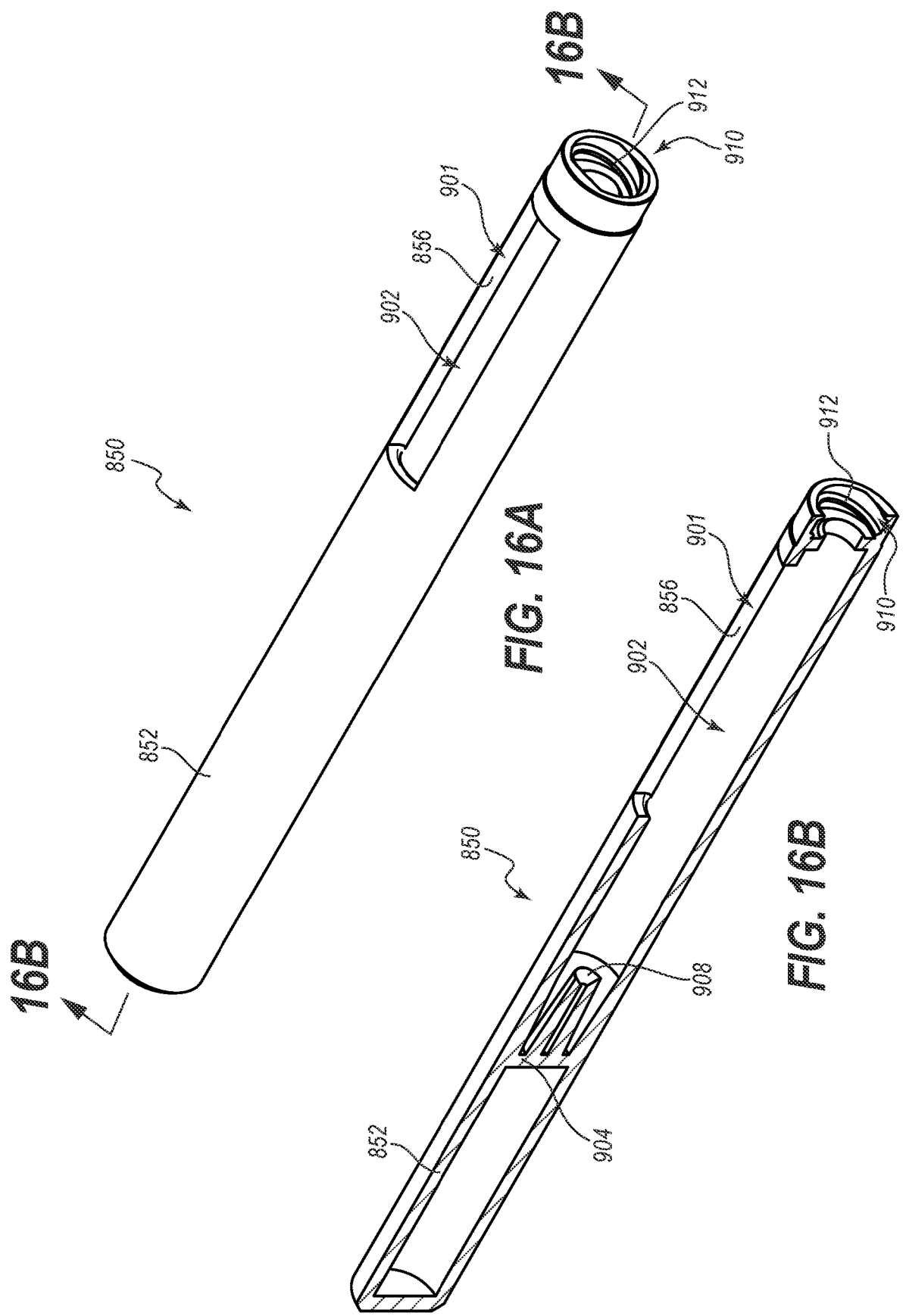

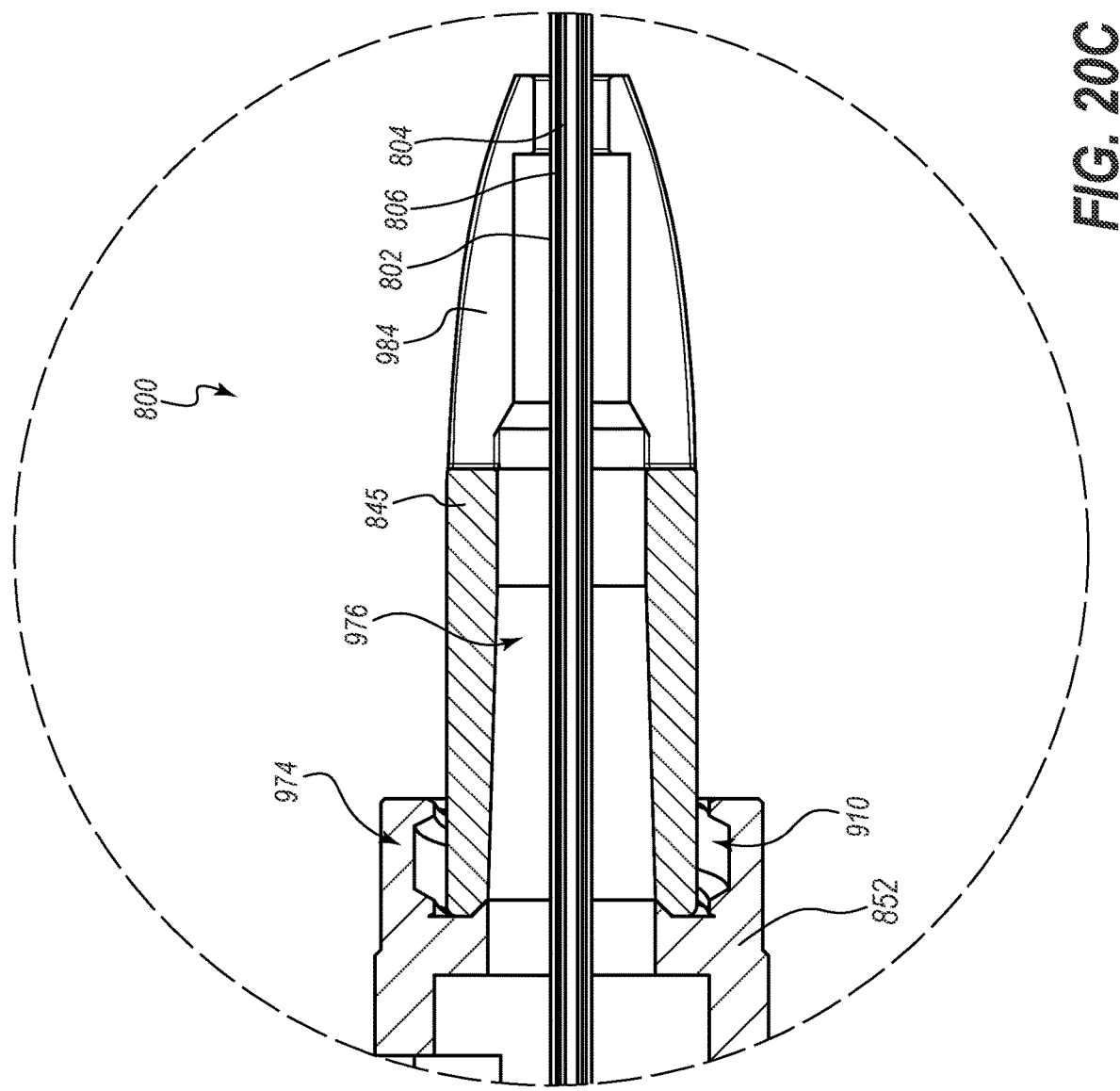

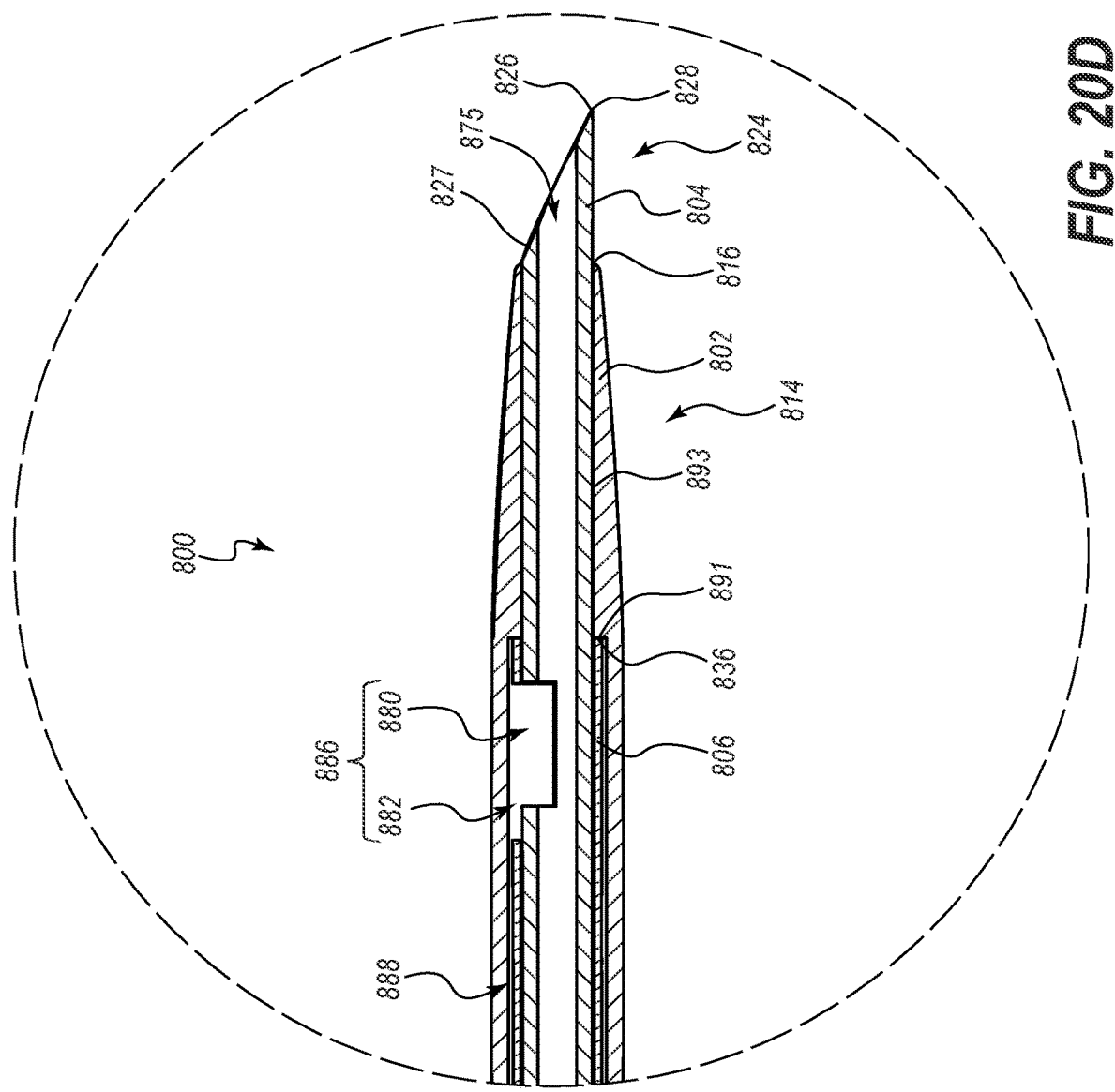

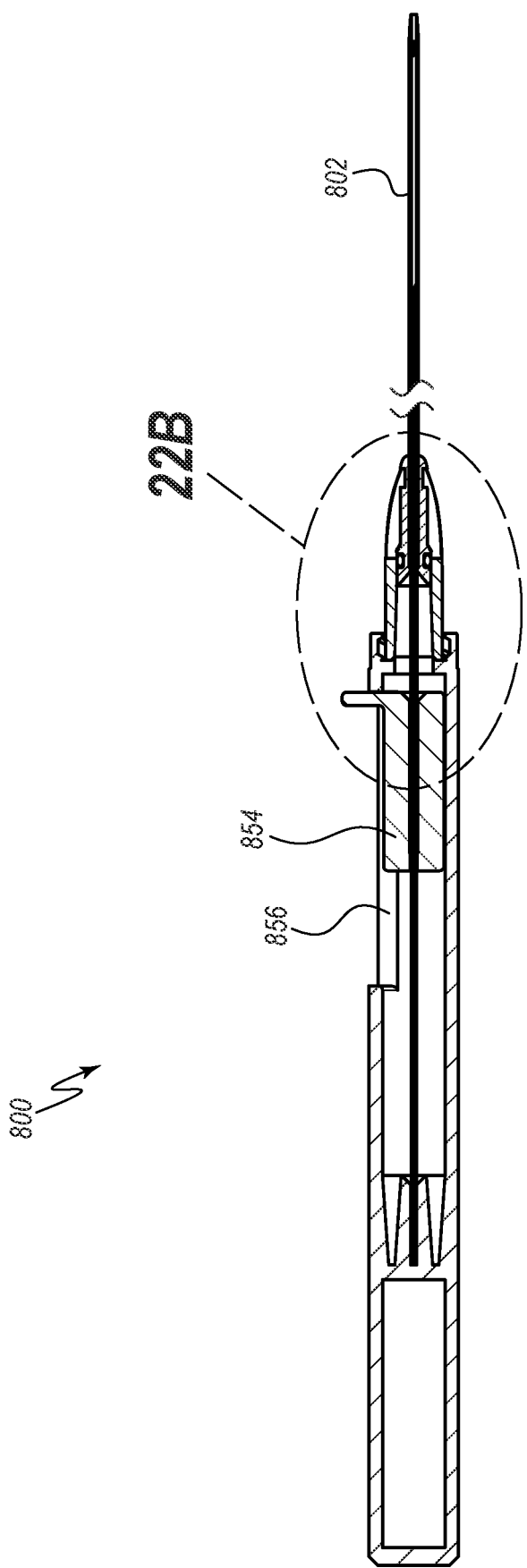

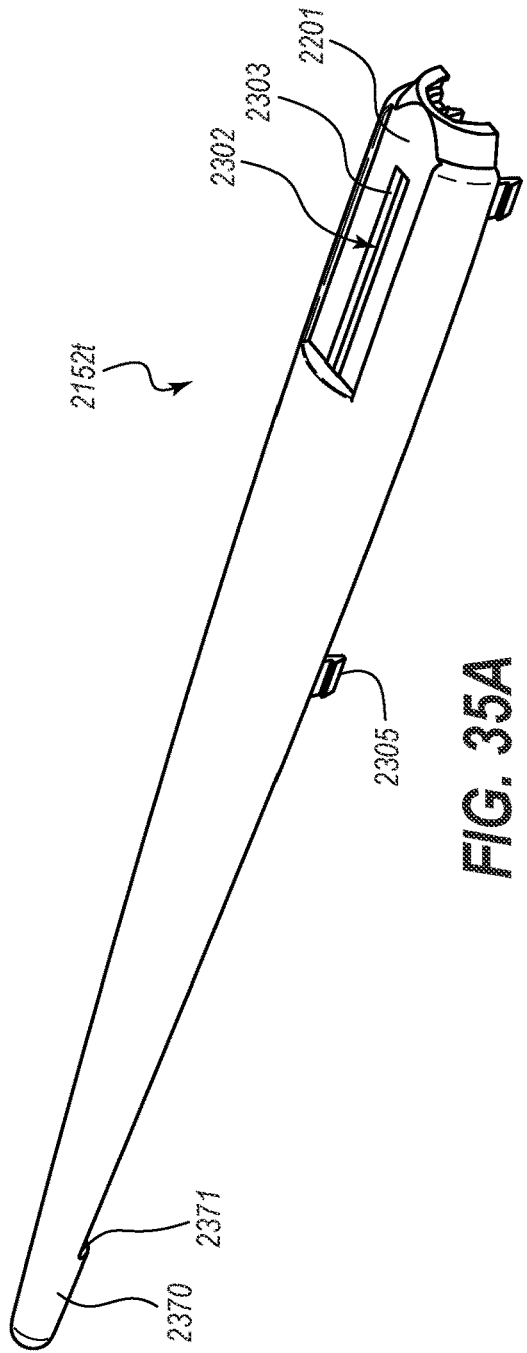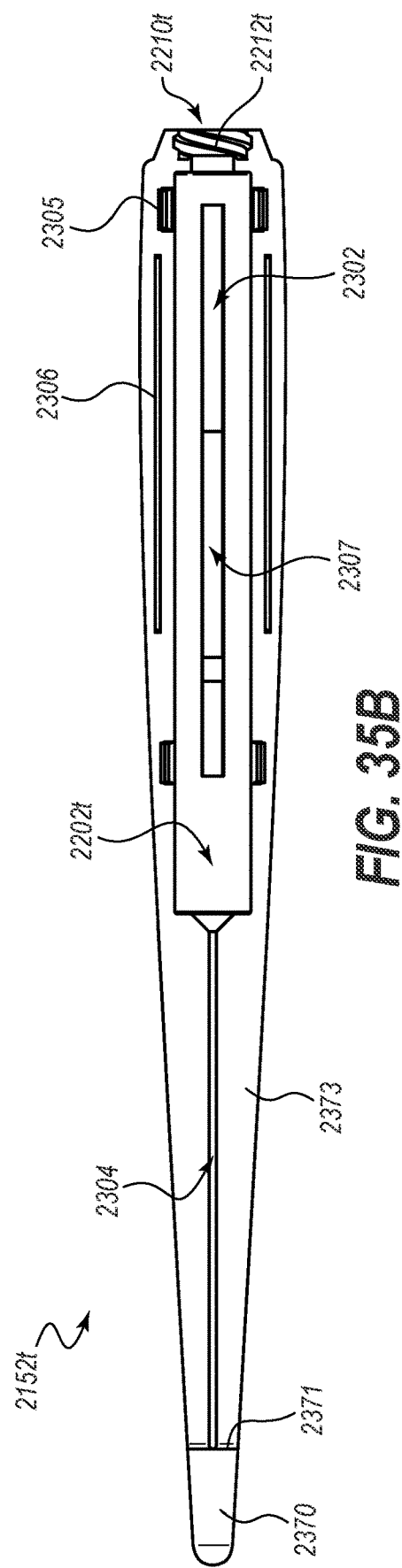
FIG. 35A
FIG. 35B

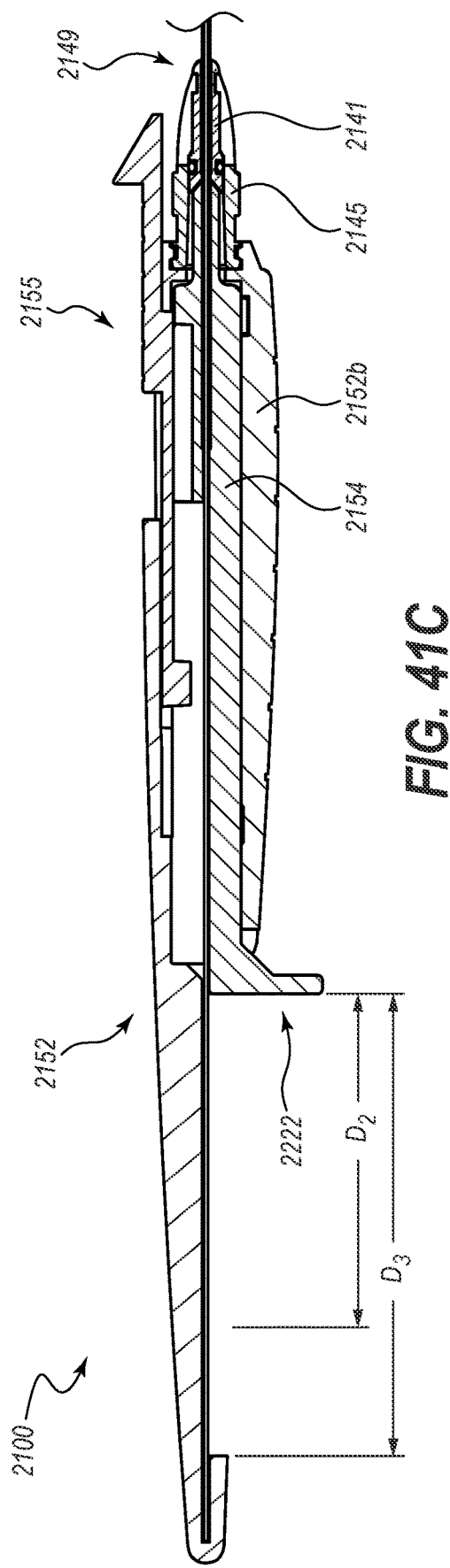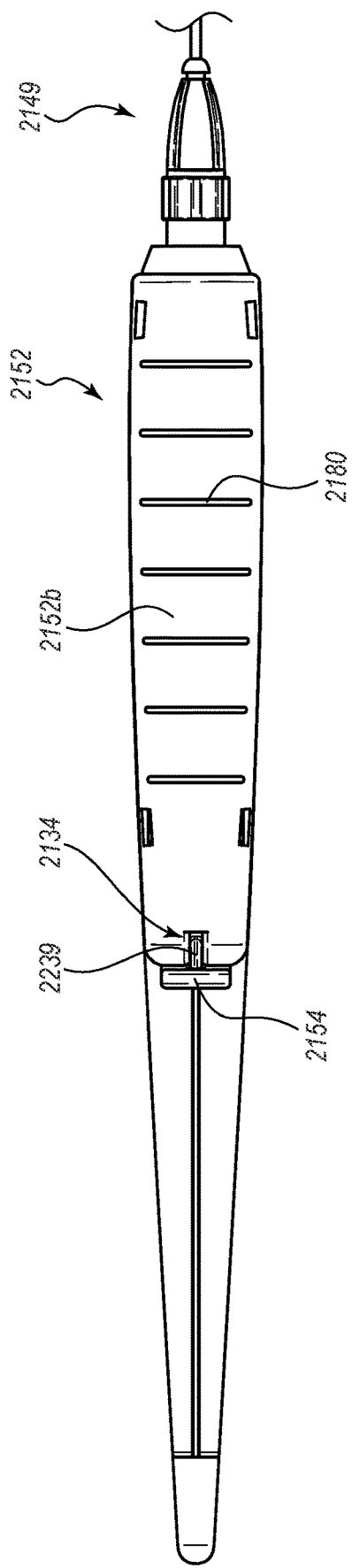

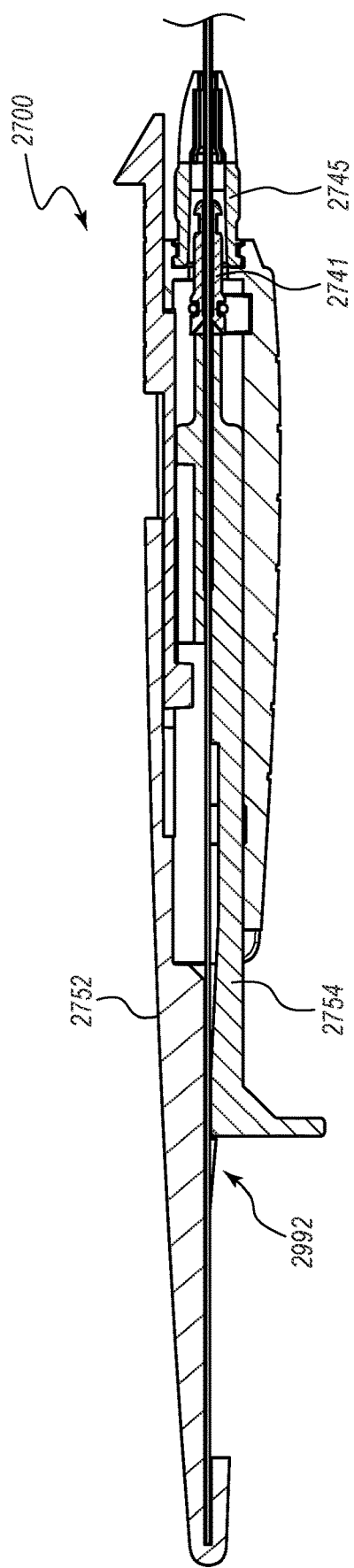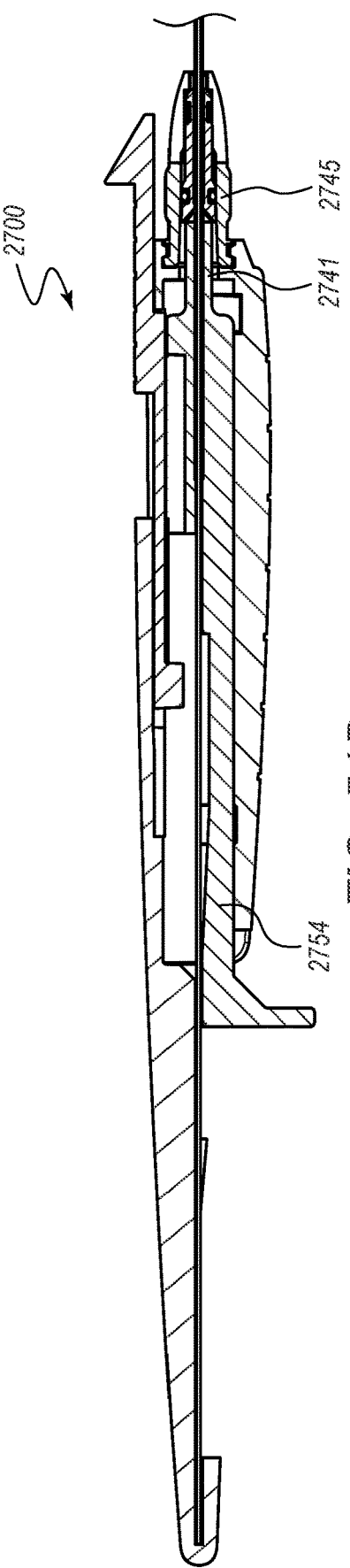

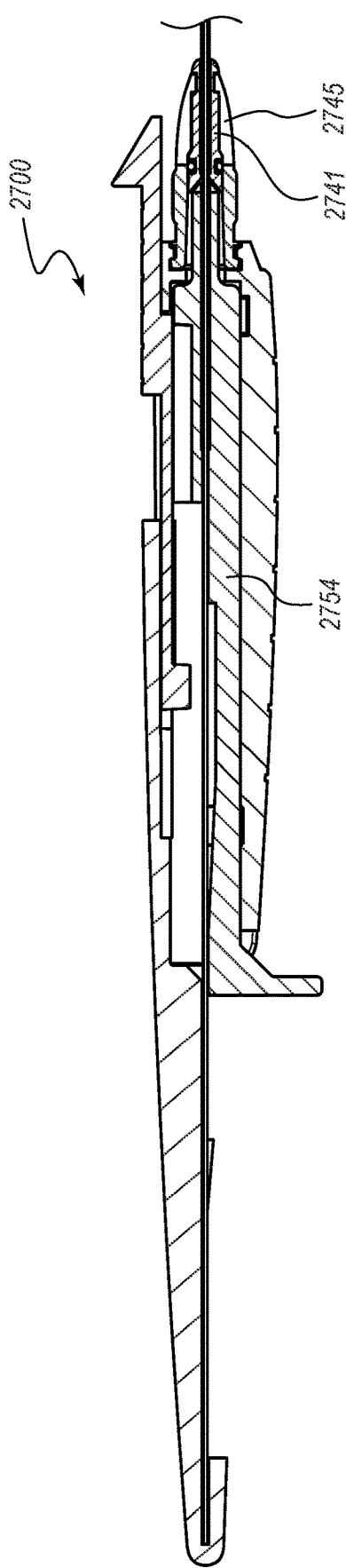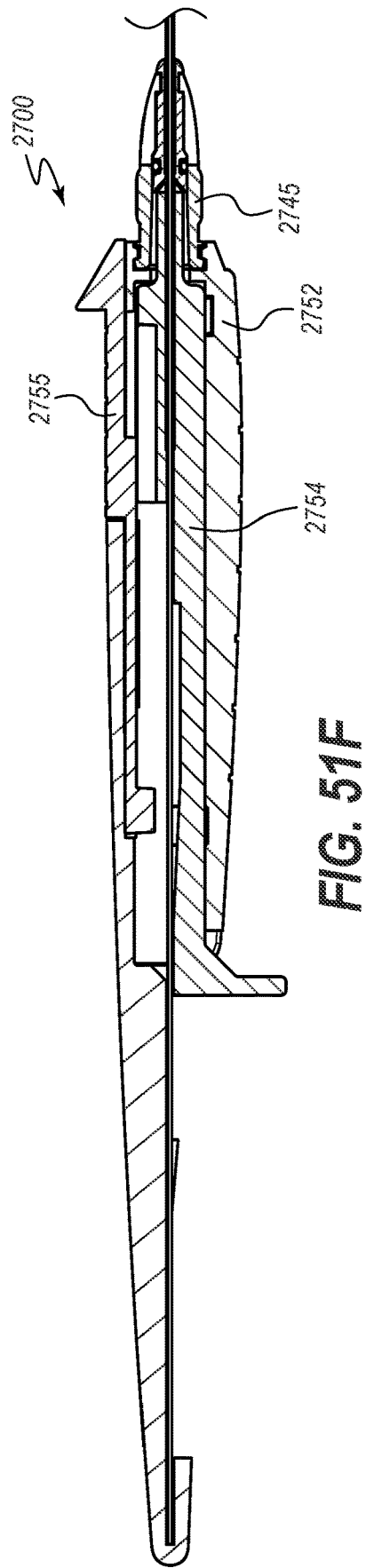

CATHETER DELIVERY DEVICES, SYSTEMS, AND METHODS

CROSS-REFERENCE TO RELATED APPLICATIONS

This application is a continuation of U.S. patent application Ser. No. 15/992,144, filed on May 29, 2018, titled CATHETER DELIVERY DEVICES, SYSTEMS, AND METHODS, now U.S. Pat. No. 11,065,419, issued on Jul. 20, 2021, which claims the benefit under 35 U.S.C. § 119(e) of U.S. Provisional Patent Application No. 62/511,900, filed on May 26, 2017, titled CATHETER DELIVERY DEVICES, SYSTEMS, AND METHODS; U.S. Provisional Patent Application No. 62/619,535, filed on Jan. 19, 2018, titled CATHETER DELIVERY DEVICES, SYSTEMS, AND METHODS; and U.S. Provisional Patent Application No. 62/641,475, filed on Mar. 12, 2018, titled CATHETER DELIVERY DEVICES, SYSTEMS, AND METHODS; and which, pursuant to 35 U.S.C. §§ 120 and 365(c), is a continuation of prior International Application No. PCT/US2018/034788, which has an international filing date of May 26, 2018, and is titled CATHETER DELIVERY DEVICES, SYSTEMS, AND METHODS, which International Application claims the benefit of U.S. Provisional Patent Application No. 62/511,900, filed on May 26, 2017, titled CATHETER DELIVERY DEVICES, SYSTEMS, AND METHODS; U.S. Provisional Patent Application No. 62/619,535, filed on Jan. 19, 2018, titled CATHETER DELIVERY DEVICES, SYSTEMS, AND METHODS; and U.S. Provisional Patent Application No. 62/641,475, filed on Mar. 12, 2018, titled CATHETER DELIVERY DEVICES, SYSTEMS, AND METHODS; the entire contents of each of the foregoing applications are hereby incorporated by reference herein.

TECHNICAL FIELD

Certain embodiments described herein relate generally to catheters, and further embodiments relate more particularly to catheter delivery devices, systems, and methods.

BACKGROUND

Many catheters are introduced into a patient via insertion needles. Some catheter systems include a catheter that is positioned over an insertion needle prior to introduction of the catheter into the patient. At least a distal tip of the needle can extend past a distal end of the catheter, and the distal end of the catheter may be tipped so as to have a smaller diameter than does a remainder of the catheter. The distal tip of the needle can be inserted into a vessel of the patient, and the catheter can follow through the opening thus created by the needle. Some systems exist for advancing the catheter over the needle and into the vessel. Known devices, systems, and methods, however, suffer from one or more drawbacks that can be resolved, remedied, ameliorated, or avoided by certain embodiments described herein.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 16A is a perspective view of an embodiment of a handle that is compatible with the catheter delivery system of FIG. 15A;

FIG. 16B is a cross-sectional view of the handle of FIG. 16A taken along the view line 16B-16B in FIG. 16A;

FIG. 20C is another enlarged cross-sectional view of the catheter delivery system taken along the view region 20C identified in FIG. 20A;

FIG. 20D is another enlarged cross-sectional view of the catheter delivery system taken along the view region 20D identified in FIG. 20A;

FIG. 22A is another cross-sectional view of the catheter delivery system of FIG. 15A in a fully deployed state;

FIG. 35A is a perspective view of an embodiment of an upper housing element compatible with the catheter delivery system;

FIG. 35B is a bottom plan view thereof;

FIG. 41C is another cross-sectional view of the catheter delivery system in a fully deployed or fully actuated state;

FIG. 42 is a bottom plan view of the catheter delivery system in the fully deployed or fully actuated state;

FIGS. 51B through 51F are further cross-sectional views of the catheter delivery system of FIG. 46 in further operational states or phases of use;

DETAILED DESCRIPTION

Figure 1:
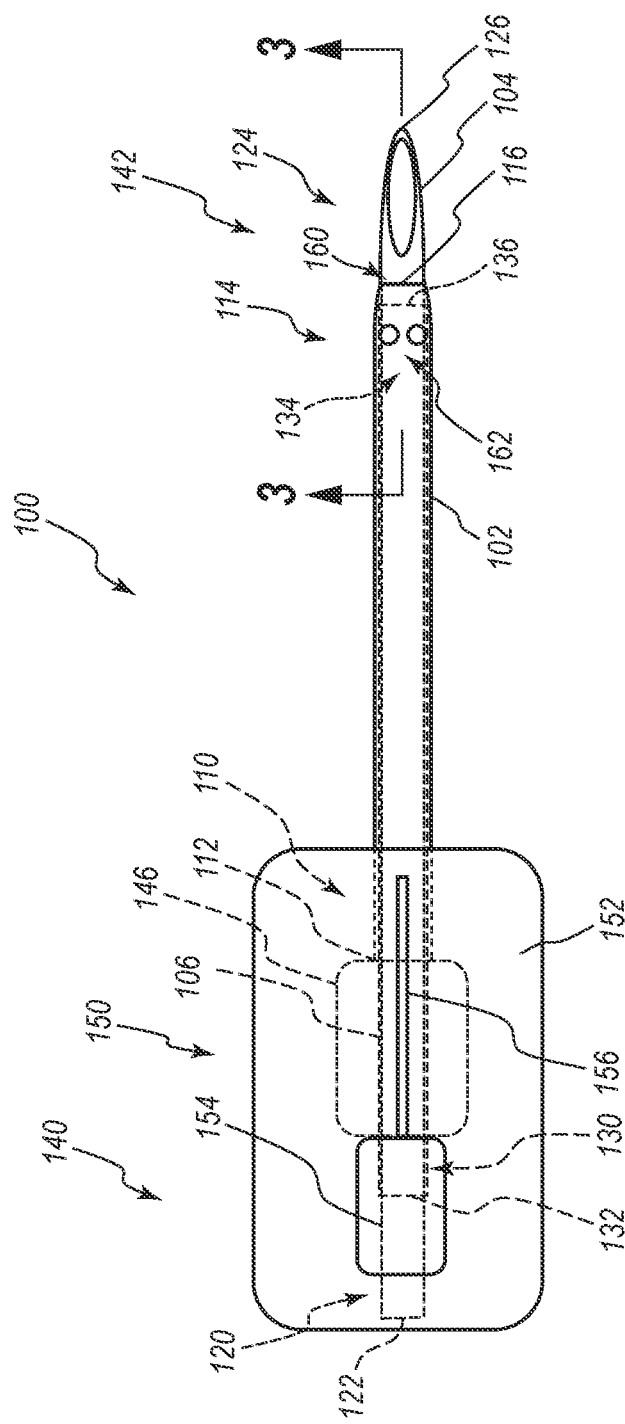
FIG. 1 is a top plan view of an embodiment of a catheter delivery system that includes a catheter, a needle, and a stiffener positioned within the catheter and external to the needle.

The present disclosure relates generally to devices, systems, and methods for delivering catheters into the vasculature of patients. While specific examples of catheters are discussed with respect to the drawings, this discussion applies equally to additional types of catheters that may not specifically be shown or mentioned. For example, while some of the catheters depicted in the drawings and described in detail herein may be relatively short, some or all of the features described with respect to these shorter catheters may be just as advantageous, if not more so, in certain embodiments that have longer catheters, or stated otherwise, that are capable of deploying a catheter to a relatively greater depth within a vessel of a patient.

Certain known catheter delivery devices, systems, and methods involve over-the-needle catheters. Such systems can include a catheter and a needle that extends through a distal end of the catheter. In many cases, the catheter is attached to at least a distal end of the needle. For example, the catheter may be extruded, and then a distal end of the catheter may be "tipped" to provide a rounded and/or narrowed distal end that may more readily be inserted into the vessel. The tipping process may be performed by heating the distal end of the catheter and/or by compressing the distal end against a mandrel, which may be sized slightly smaller than a distal end of the needle. After the catheter is tipped, the needle may be inserted through a distal opening in the tipped catheter, and the catheter may then adhere to the distal end of the needle.

The strength of the adhesion between the distal ends of the catheter and the needle may be difficult to manage, however. In many instances, the adhesion is achieved by using a mandrel having an outer diameter that is slightly smaller than an outer diameter of the needle, and thus the distal end of the catheter may grip the distal end of the needle. The strength of adhesion may naturally increase over time due to interactions between the material of which the catheter is formed and the surface of the needle.

It may be desirable to have sufficient adhesion to permit the distal ends of the catheter and the needle to remain attached to each other as the distal end of the catheter is inserted into the vessel through an insertion site that is formed by the distal tip of the needle. The vessel can provide significant resistance to introduction of the distal tip of the catheter. In some instances, if the adhesion strength is insufficient, the distal tip of the catheter may be pushed backward (i.e., proximally) by some distance as the needle is advanced further into the vessel (generally at an angle relative to a longitudinal axis of the vessel). If an outer surface of the vessel wall, as it resists entry of the catheter into the vessel, pushes the catheter tip proximally relative to the needle by too great an amount as the needle is advanced, the distal tip of the needle may ultimately puncture the backwall of the vessel before the distal tip of the catheter has even entered the vessel. In other or further instances, the skin and tissue can tend to push the distal tip of the catheter body backward and resist advancement of the catheter therethrough, which may cause the catheter body to wrinkle in an accordion or bellows-like manner proximally relative to the needle as the needle is advanced distally. Accordingly, there can be danger in having insufficient adhesion strength.

However, it may also be desirable for the adhesion not to be too strong, as an overly strong bond can prevent the catheter from separating from the needle at a desired stage—e.g., after the needle tip and the catheter tip have been advanced into the vessel lumen—so that the catheter may be advanced further into the vessel past a distal end of the needle. For example, if the adhesion is too strong such that the catheter tip remains engaged with the needle as the catheter is advanced distally relative to the needle, more proximal portions of the catheter can bunch up or compress in an accordion-like fashion, which can prevent the catheter from being advanced deeper into the vessel and/or can damage the vessel. Moreover, it can be desirable for the adhesion to not be so strong that during separation from the catheter from the needle, tension builds until the distal tip of the catheter ultimately breaks free from its bond with the needle with excessive energy and thrusts forward to strike the vessel wall, which could damage the vessel wall. In other or further instances, an overly strong adhesion can damage, deform, or otherwise undesirably alter the distal tip of the catheter and/or can damage the vessel wall as the catheter is advanced further into the vessel.

Accordingly, known catheter delivery systems must contend with a narrow window of acceptable adhesion conditions that are neither too weak nor too strong. Failure to satisfy these conditions can result, for example, in damage to the vessel and/or added discomfort to the patient, wasted time for the patient and the medical professional, and/or wasted expense due to the need to use an additional needle delivery system to form a different insertion site in the patient.

Moreover, known catheter delivery systems can suffer from difficulties in addressing insertion-length issues. For example, catheters typically are formed of relatively compliant materials, which can make it difficult to advance the catheters to significant distances within a vessel on their own. In particular, the catheters can lack sufficient rigidity or columnar strength to be independently advanced deep into a vessel, particularly if attempts are made to pass the catheters through one or more valves, e.g., within a deep vessel. Often, when pushed up against a valve, a compliant catheter will fold back on itself. Folding or other deformations of a catheter can close off the catheter and render it inefficient or ineffective for fluid delivery and/or collection, can otherwise damage the catheter, and/or can damage the vessel. Catheters may fold over on themselves or otherwise deform in other regions of vessels as well. Accordingly, in various instances, guidewires or stiffening stylets may be used to advance catheters to desired depths within vessels.

In some systems, a guidewire is introduced into the vessel through an introduction needle to assist in advancement of the catheter to a target depth within a vessel. Although the guidewire can, in some instances, prevent the catheter from bending back on itself and/or scraping the inner wall of the vessel, systems that employ guidewires may not be used reliably in many instances. Many guidewire systems can suffer from a variety of drawbacks.

For example, in some instances, a particular guidewire may suffer from minor imperfections or variations that may cause it to bend back on itself, which can render the guidewire inoperative for catheter advancement and/or can damage the vessel. In other or further instances, integrated systems that deploy both a guidewire and a catheter into a vessel can only employ guidewires of limited length. Often, the length of such guidewires is generally on the order of the length of the catheter deployed by the system—that is, the guidewires may be substantially the same lengths as or even shorter than the catheter they are meant to guide into a vessel. Attempts to advance a catheter beyond the distal end of such a limited-length guidewire, particularly where one or more valves are positioned beyond the guidewire end, can result in foldback or other undesirable deformations of the catheter. Thus, the deployment systems generally only work where the guidewire is advanced to a desired or target depth ahead of the catheter, and the catheter is then advanced over the guidewire to the target depth. However, increasing the length of the guidewires in existing systems in order to achieve greater insertion depths would, to the extent possible, render the systems far more complicated, expensive, and/or unwieldy. Deployment systems that employ guidewires thus likewise suffer from insertion length issues.

In other instances, a stiffening stylet is positioned within a lumen of a catheter to increase rigidity and assist in advancing the catheter to a target depth. Such systems, however, require insertion of a dilator and introducer into the target vessel to a significant depth (often involving cutting the patient's skin to permit the insertion), removal of the dilator, and insertion of the catheter/stylet combination through the introducer while the introducer remains inserted in the vessel. Such procedures can, relatively speaking, increase patient discomfort and/or can be lengthier, more complicated, more intrusive, and/or generally more onerous for both the practitioner and the patient.

In other simple over-the-needle catheter systems, the needle may be used to support the catheter during initial insertion into a vessel or, in some instances, delivery of the catheter to a target depth. Such systems also suffer from significant drawbacks. For example, certain of such systems are limited to relatively short catheter lengths for a variety of reasons, such as needle-based stability and control considerations. By way of illustration, in some catheter deployment systems, the catheter sheaths a length of a needle and the distal tip of the needle extends just beyond the distal end of the catheter, when the system is in an undeployed state. The needle extends proximally through the catheter and through a catheter hub that is affixed to the proximal end of the catheter, and the needle is secured at its proximal end to a needle hub. When the system is in the undeployed state, the needle and catheter hubs are in an approximated orientation, relative to each other. When using the system, a practitioner holds the needle hub and/or the catheter hub and advances the entirety of the system distally such that the needle and catheter move together in unison, with the needle tip cutting through the skin and piercing the vessel wall. The distal tip of the catheter follows the piercing tip of the needle through the vessel wall into a lumen of the vessel. Once the catheter tip is within the vessel lumen, the practitioner attempts to hold the needle hub steady while moving the catheter hub distally to advance the catheter distally over the needle and further into the vessel, or stated otherwise, into the vessel to a greater depth. Once the catheter is in position, the practitioner holds the catheter hub steady and pulls the needle hub proximally relative to the catheter hub to remove the needle from the system.

In such systems, the needle must always be longer than the catheter to ensure that the distal tip of the needle extends through the catheter hub, through the catheter, and beyond the distal tip of the catheter. Accordingly, the length of the catheter is limited by a maximum length of the needle. As needle length increases, it becomes increasingly difficult to control insertion of the needle and catheter into the vessel. For example, as one or more of the needle and catheter hubs is held during insertion, small angular movements of the hubs swing the needle tip by significant amounts, and this swinging effect increases with increasing needle length (i.e., the same magnitude of angular movements result in greater distances traveled by the needle tip) so as to make it difficult to accurately target an insertion site while holding the hubs. Moreover, the needles can be quite flexible (e.g., due to thin sidewalls and/or small diameters), and bending can become more pronounced with increasing needle length.

Various embodiments disclosed herein can resolve, remedy, ameliorate, and/or avoid one or more of the limitations of known catheter delivery devices, systems, and methods, such as those just described, and/or can be advantageous over one or more of these or catheter delivery devices, systems, and methods for other or further reasons, as will be apparent from the present disclosure. Some embodiments of a catheter delivery system include a catheter, a stiffener, and a needle. In some embodiments, a distal end of the catheter and a distal end of the stiffener are positioned proximally relative to a distal tip of the needle when the needle is first introduced into a vessel of a patient. In other or further embodiments, the distal end of the stiffener and the distal end of the catheter can be passed over an exterior surface of the needle to a position within the vessel that is distal to the distal tip of the needle. The stiffener can aid in breaking an adhesion between the distal end of the catheter and the distal end of the needle and/or can reinforce the catheter to enable the catheter to be fed or advanced to significant distances or target depths within the vessel. The stiffener can advance the catheter all the way to a target site within the vessel. Moreover, in certain embodiments, the relatively soft catheter tip can be positioned in advance of (e.g., distal to) the distal tip of the stiffener throughout deployment, thus providing a soft and substantially atraumatic leading tip for insertion. In some instances, the catheter delivery system is capable of positioning the catheter to significant distances within a vessel without the use of a leading guidewire. In other or further embodiments, a two-piece hub is employed which can, in some instances, permit the usage of relatively shorter needles and/or reduce an unsupported length of needles, increase the stability and control achievable during insertion, and/or provide other or further advantages. One or more of the foregoing advantages and/or other or further advantages of various embodiments will be apparent from the discussion that follows.

With reference to FIG. 1, in certain embodiments, a catheter delivery system 100 includes a catheter 102, a needle 104, and a stiffener 106. The catheter 102 includes a proximal end 110 having a proximal tip 112 at an extremity thereof, and further includes a distal end 114 having a distal tip 116 at an extremity thereof. Likewise, the needle 104 includes a proximal end 120 having a proximal tip 122 at an extremity thereof, and further includes a distal end 124 having a distal tip 126 at an extremity thereof. Similarly, the stiffener 106 includes a proximal end 130 having a proximal tip 132 at an extremity thereof, and further includes a distal end 134 having a distal tip 136 at an extremity thereof. In various embodiments, the stiffener 106 may also be referred to as, or may have an alternate form that comprises at least one component that may be referred to as, a support, column, reinforcement, frame, scaffold, prop, strut, brace, spine, rod, tube, and/or cannula. For example, in the illustrated embodiment, the stiffener 106 may be referred to as a sheathing cannula, a cannular stiffener, etc. In the illustrated embodiment, the stiffener 106 is formed of an elongated tube that is positioned between an outer surface of the needle 104 and an inner surface of the catheter 102 when the system 100 is in an undeployed configuration, such as depicted in FIG. 1. As further discussed below, the tubular stiffener 106 may be flexible in the transverse dimension (e.g., in directions orthogonal to a longitudinal axis of the tube), yet may be substantially rigid or stiff in the axial direction to counteract axial forces (i.e., longitudinally directed force) applied thereto by the distal portion of the catheter 102 during insertion of the system 100 through the vessel wall and during advancement of the system 100 through the lumen of the vessel.

The system 100 likewise includes a proximal end 140 and a distal end 142. When the system 100 is in the undeployed configuration, the distal ends 114, 124, 134 of the catheter 102, the needle 104, and the stiffener 106, respectively, are all positioned at the distal end 142 of the system 100. More particularly, at least a portion of the distal end 124 of the needle 104 extends distally beyond the distal tip 116 of the catheter 102. Further, the distal tip 136 of the stiffener 106 is positioned proximal to the distal tip 116 of the catheter 102.

In the illustrated embodiment, the proximal end 110 of the catheter 102 is coupled with a catheter hub 146. The catheter hub 146 can be of any suitable form, and may include one or more connectors configured to establish one or more fluid connections with any suitable medical fluid devices (e.g., syringes, IV lines, power injectors, etc.). For example, in some embodiments, the catheter hub 146 may include at least one Luer fitting via which aspiration and/or injection may be achieved via the catheter 102 after the catheter 102 has been positioned within a vessel of a patient. For example, the catheter hub 146 may include a female Luer fitting. The catheter 102 can be fixedly secured to the catheter hub 146 in any suitable manner. The catheter 102 and the catheter hub 146 may together be referred to as a catheter assembly. The catheter hub 146 may also be referred to as a catheter connection hub 146. For example, the catheter hub 146 may be connected directly to the catheter 102 and/or may include a connection feature for coupling the catheter to other devices (e.g., fluid delivery devices).

In the illustrated embodiment, the proximal end 120 of the needle 104 is coupled with a needle hub 150. For example, the proximal end 120 of the needle 104 can be fixedly secured to a proximal portion of the needle hub 150 in any suitable manner. In the illustrated embodiment, the needle hub 150 includes a housing 152 to which the needle 104 is secured. Other fixation arrangements are contemplated. The needle hub 150 may also be referred to as a handle.

The needle hub 150 can further include an actuator 154 that is configured to selectively move relative to the housing 152. In the illustrated embodiment, the housing 152 defines a guide or track 156 along which the actuator 154 can slide or translate from a proximal position (shown in FIG. 1, see also FIGS. 4A and 4C) to a distal position (see FIGS. 4D and 4F-4H). Actuation of the actuator 154, such as by manually pushing the actuator 154 from the proximal to the distal position in the illustrated embodiment, can transition the system 100 from the undeployed configuration to a deployed configuration, as discussed further below.

In the illustrated embodiment, the proximal end 130 of the stiffener 106 is coupled to the actuator 154 in fixed relation. The actuator 154 may also be referred to as a stiffener hub. In the illustrated embodiment, the actuator 154 (or stiffener hub), includes an engageable portion (e.g., button, slider, gripping surface) that resides at an exterior of the housing 152, a neck (not shown) that extends through the track 156, and a receptacle (not shown) at an interior of the housing to which the proximal end of the stiffener 106 is attached. Any suitable fixed attachment between the actuator 154 and the stiffener 106 is contemplated. For example, the stiffener 106 may be glued or otherwise adhered to the actuator 154. In some instances, the actuator 154 comprises a substantially cylindrical receptacle that is disposed within the housing 152 of the needle hub 150, and the proximal end of the stiffener 106 is received within the cylindrical portion of the actuator 154. Of course, geometries other than cylindrical are possible and are contemplated by the present disclosure. Distal movement of the actuator 154, such as by pressing forward or distally on a portion of the actuator 154 positioned at an exterior of the housing 152 of the needle hub 150 (e.g., a button, slider, or other engagement element), effects like distal movement of the stiffener 106 relative to the housing 152. In the illustrated embodiment, the needle hub 150, the needle 104, the actuator 154, and the stiffener 106 may be referred to as an insertion assembly, a needle assembly, a needle-and stiffener assembly, or as a deployment assembly.

In the illustrated embodiment, the stiffener 106 extends through the catheter hub 146 and into an interior of the catheter 102. As further discussed below, the stiffener 106 may be capable of moving distally in unison with the catheter 102, but may be configured to be removed proximally from the catheter 102. Further, in the illustrated embodiment, the needle 104 extends through an entirety of each of the stiffener 106 and the catheter 102 in the operational state or undeployed state depicted in FIG. 1. Moreover, the stiffener 106 may be configured to slide or otherwise translate (e.g., freely translate) relative to the needle 104. Stated otherwise, the stiffener 106 may be sized to receive the needle 104 within a lumen thereof, and may freely translate over the needle 104.

The catheter hub 146 may be coupled with the actuator 154 in such a manner that distal movement of the actuator 154 may effect distal movement of both the catheter hub 146 and the catheter 102 relative to the housing 152. Accordingly, in some embodiments, distal movement of the actuator 154 may effect simultaneous distal movement of the stiffener 106 and the catheter 102. Stated otherwise, in certain embodiments, the stiffener 106 and the catheter 102 may move distally in unison with each other. For example, in some embodiments, the catheter hub 146 is directly attached to the actuator 154, such that movement of the actuator 154 effects like movement of the catheter hub 146. The attachment may be selectively releasable such that the actuator 154 can be readily decoupled from the catheter hub 146 after the catheter 102 has been positioned as desired within a vessel. In other or further embodiments, the catheter hub 146 is either additionally or solely connected to the actuator 154 indirectly via the catheter 102 and the stiffener 106. In particular, as discussed further below, the distal end 114 of the catheter can include a catching region that interfaces with a distal tip 136 of the stiffener 106 to permit the stiffener 106 to advance the catheter 102 in a distal direction. Accordingly, in certain embodiments, the actuator 154 is directly attached to the stiffener 106, a distal tip of the stiffener 106 interfaces with the distal end 114 of the catheter 102, and the proximal end 110 of the catheter 102 is directly attached to the catheter hub 146. The catheter hub 146 is thus coupled with the actuator 154 such that distal movement of the actuator 154 effects distal movement of both the catheter hub 146 and the catheter 102 relative to the housing 152. In particular, distal advancement of the actuator 154 relative to the housing 152 causes the distal tip 136 of the stiffener 106 to press against the distal end 114 of the catheter 102, thereby forcing the catheter 102 to move distally relative to the housing 152. Due to the attachment of the proximal end 110 of the catheter 102 to the catheter hub 146, the catheter hub 146 is drawn by the catheter 102 in the distal direction relative to the housing 152. That is, pushing distally on the actuator 154 causes the catheter hub 146 to be pulled or drawn distally due to interactions of the distal ends of the stiffener 106 and the catheter 102. The distal movements of the actuator 154, the stiffener 106, the catheter 102, and the catheter hub 146 can be substantially simultaneous and/or can proceed substantially in unison.

With the needle 104 being situated in fixed relation relative to the housing 152 of the needle hub 150, the stiffener 106 and the catheter 102 may move distally not only relative to the housing 152, but also relative to the needle 104. Accordingly, actuation of the actuator 154 by advancing the actuator 154 distally can deploy the stiffener 106 and the catheter 102 distally past the distal tip 126 of the needle 104, as discussed further below.

In some embodiments, the coupling between the catheter hub 146 and the actuator 154 is selectively releasable. For example, in some embodiments, at some point after the actuator 154 has been actuated, it may be desirable to decouple the catheter hub 146 from the actuator 154. Such decoupling can permit the needle hub 150 to be retracted proximally from the catheter hub 146. Any suitable selectively releasable mechanical coupling between the catheter hub 146 and the actuator 154 is contemplated. For example, in some embodiments, the catheter hub 146 and the actuator 154 are directly attached to each other and are held together via one or more resilient arms or catches (not shown), and depression of a cantilevered portion of the arm, a button, or any other suitable mechanical linkage can cause the arms to move to a decoupling orientation. In other embodiments, the catheter hub 146 and the actuator 154 are not directly attached to each other, but are coupled to each other via an interaction between the distal ends of the stiffener 106 and the catheter 102, as previously discussed. In certain of such embodiments, the coupling can be released merely by moving the actuator 154 proximally relative to the catheter hub 146, which moves the stiffener 106 proximally relative to, and out of engagement with, the distal end 114 of the catheter 102. In some instances, the actuator 154 may be moved proximally within the track 156, after having first been advanced distally along the track 156 for catheter deployment, to achieve the decoupling. In other or further instances, the catheter hub 146 may be deployed to a position external to the housing 152 when the actuator 154 is advanced distally along the track 156, and the decoupling of the catheter hub 146 and the housing 152 may be achieved by holding the catheter hub 146 at a fixed position while retracting the housing 152 proximally away from the catheter hub 146. For example, in some instances, the actuator 154 may be positioned at the extreme distal end of the track 156 during deployment of the catheter 102 and may contact the housing 102 thereat. Moving the housing 152 proximally thus may likewise pull the actuator 152 and the stiffener 106 that is attached thereto proximally due to interference between the housing 152 and the actuator 154 at the distal end of the track 156.

Accordingly, in various embodiments, retraction of the needle hub 150 from the catheter hub 146 can retract the stiffener 106 and the needle 104 from the catheter 102 and the catheter hub 146. In addition to previously discussed examples, in some embodiments, the actuator 154 may be configured to be locked in the fully actuated orientation in any suitable manner (e.g., via any suitable lock, latch, detent, or other suitable locking system). When the actuator 154 is locked relative to the housing 152 after actuation in this manner, the stiffener 106 may likewise be locked relative to the housing 152, such as by being locked against translational movement relative thereto. Accordingly, the stiffener 106 and the needle 102 may be in locked relation relative to each other, and thus may be configured to be retracted from the catheter 102 in unison with each other, as discussed further below.

Figure 2:
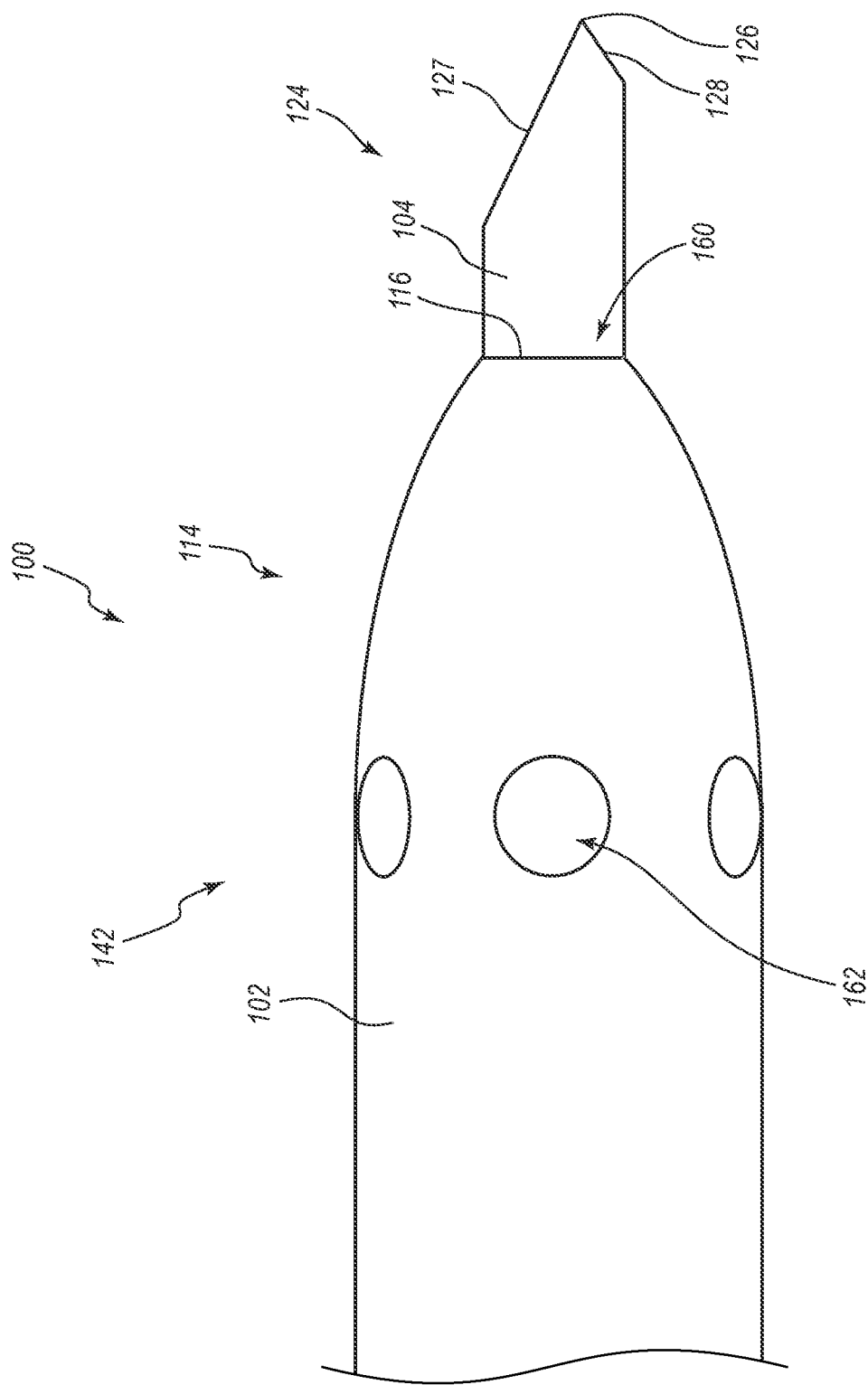
FIG. 2 is an enlarged side elevation view of a distal portion of the catheter delivery system of FIG. 1.

With reference to FIGS. 1 and 2 (see also FIG. 4K), the catheter 102 can define a distal port 160 through which the distal end 124 of the needle 104 passes when the system 100 is in the undeployed configuration. The distal port 160 is used for aspiration and/or infusion once the catheter 102 is positioned within the vessel of a patient. In some embodiments, the catheter 102 can include a plurality of side ports 162, which may likewise be used for aspiration and/or infusion. In the illustrated embodiment, the catheter 102 includes six side ports 162, which are equiangularly distributed about a circumference of the catheter 102 along a single plane that is oriented substantially orthogonally relative to a central longitudinal axis of the catheter 102. Any other suitable size, number, and/or arrangement of the side ports 162 is contemplated. For example, in some embodiments, more or fewer side ports 162 are present, and in other or further embodiments, the side ports 162 may be arranged at different distances from the distal tip 116 of the catheter 102.

With continued reference to FIG. 2, the distal end 124 of the needle 104 can have any suitable configuration. In the illustrated embodiment, the distal end 124 includes a primary bevel 127 and a back bevel 128. The distal tip 126 of the needle 104 is positioned at the distal intersection of the primary and back bevels 127, 128. In other embodiments, the needle 104 may have a single bevel, or a simple bias grind. The distal tip 126 can be particularly well suited to pierce through skin and through a vessel wall.

Figure 3:
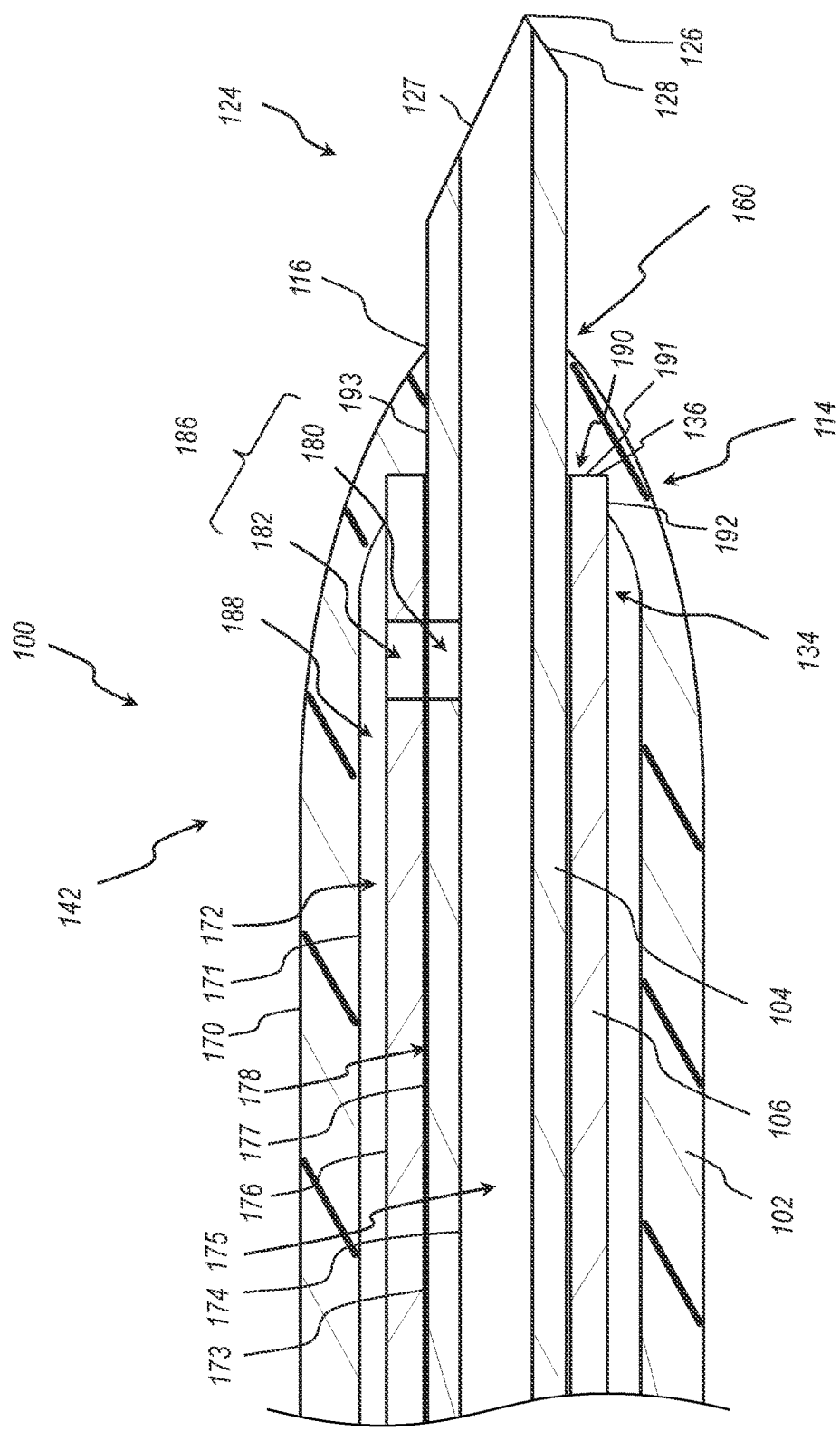
FIG. 3 is a cross-sectional view of the distal portion of the catheter delivery system taken along the view line 3-3 in FIG. 1.

FIG. 3 depicts a cross-sectional view of the distal portion 142 of the catheter delivery system 100 taken along the view line 3-3 in FIG. 1. Again, in this view, the system 100 is in the undeployed configuration. The dimensions shown are not necessarily to scale.

The catheter 102 can include an outer or exterior surface 170 and an inner or interior surface 171. The interior surface 171 of the catheter 102 can define a catheter lumen 172. The needle 104 can also include an outer or exterior surface 173 and an inner or interior surface 174. The interior surface 174 of the needle 104 can define a needle lumen 175. In the illustrated embodiment, the stiffener 106 includes an outer or exterior surface 176 and an inner or interior surface 177. The interior surface 177 of the stiffener 106 can define a stiffener lumen 178. In the illustrated embodiment, the needle 104 extends through both a proximal end of the catheter lumen 172 (see FIG. 1) and through a distal end of the catheter lumen 172. Stated otherwise, the needle 104 (e.g., a significant portion of the needle 104) is positioned within the catheter lumen 172 and extends through an entirety thereof. The stiffener 106 is similarly positioned within the catheter lumen 172, but does not extend through an entirety thereof. In particular, the distal end 134 of the stiffener 106 is positioned within the catheter lumen 172 and engages a portion of an interior of the catheter, and the stiffener 106 extends proximally through the catheter lumen 172 and extends out of a proximal end of the catheter lumen 172 (see FIG. 1). The stiffener 106 may be said to be at an exterior of the needle 104. The catheter 102 may be said to be at an exterior of the stiffener 106.

The needle 104 is similarly positioned within the stiffener lumen 178. In the illustrated embodiment, the needle 104 extends through both a proximal end of the stiffener lumen 178 (see FIG. 1) and through a distal end of the stiffener lumen 178. Stated otherwise, the needle 104 (e.g., a significant portion of the needle 104) is positioned within the stiffener lumen 178.

Stated otherwise, the needle 104 is nested within the stiffener 106, and the stiffener is nested within the catheter 102. In the illustrated embodiment, the needle 104, the stiffener 106, and the catheter 102 are coaxial. Stated otherwise, each of the needle 104, the stiffener 106, and the catheter 102 defines its own central longitudinal axis, and each such axis is collinear with a central longitudinal axis of the system 100.

In some embodiments, the outer surface 173 of the needle 104 is sized to fit loosely (e.g., close, but with little or no touching) or snugly (e.g., in contact, yet with the capability of sliding engagement) within the inner surface 177 of the stiffener 106. In some embodiments, the outer surface 176 of the stiffener 106 fits loosely within the inner surface 171 of the catheter 102.

In the illustrated embodiment, a sidewall of the needle 104 defines a port 180 through which blood may flow from the needle lumen 175. A sidewall of the stiffener 106 similarly defines a port 182 for permitting blood flow. Together, the ports 180, 182 define a passageway 186. The ports 180, 182 can be aligned with each other to form the passageway 186. In some embodiments, the stiffener 106 and the needle 104 are rotationally locked relative to each other in the illustrated arrangement, which can ensure that the ports 180, 182 remain aligned during at least an insertion stage in a method of using the system 100.

For example, with reference again to FIG. 1, as previously discussed with respect to the illustrated embodiment, the proximal end 120 of the needle 104 is fixedly secured to the needle hub 150, and thus is rotationally fixed relative to the housing 152. Moreover, the stiffener 106 is fixedly secured to the actuator 154, which is positioned within the track 156. Accordingly, when the actuator 154 is in the undeployed state, the actuator 154 is restrained by the track 156 from any side-to-side movement that would rotate the stiffener 106 about a longitudinal axis of the housing 152. Thus, both the needle 104 and the stiffener 106 are rotationally fixed relative to the housing 152 and relative to each other.

It is also noted that the actuator 154 is constrained to translate along the track 156. As the track 156 is substantially linear and is aligned with a longitudinal axis of the system 100, the actuator 154 does not undergo any rotation about the longitudinal axis of the system 100 as it moves along the track 152. Thus, the stiffener 106, although moveable relative to the housing 152, is nevertheless rotationally fixed relative to the housing 152 due to the rotational constraints imposed on the actuator 154 even during deployment of the catheter 102.

Although the needle 104 is depicted with a lumen in the illustrated embodiment, in other embodiments, the needle 104 may not define a lumen. For example, in some embodiments, the needle 104 can comprise a solid trocar, pointed rod, or the like.

With reference again to FIG. 3, the inner surface 171 of the catheter 102 can cooperate with the outer surface 176 of the stiffener 106 to define an elongated annular lumen 188 through which blood received from the passageway 186 may flow proximally through the catheter 102. The passageway 186 and the lumen 188 thus provide a channel through which a flash of blood can pass to indicate that the distal end 124 of the needle 104 has entered a vessel. In some embodiments, the spacing between the inner surface 171 of the catheter 102 and the outer surface 176 of the stiffener 106 is sufficiently small to give rise to capillary action, which can draw or assist in drawing the flash of blood proximally through the lumen 188.

The distal end 134 of the stiffener 106 can engage the distal end 114 of the catheter 102. The catheter 102 can define a catching region 190 that can interface with the distal tip 136 of the stiffener 106. For example, the catching region 190 can be formed generally as a recess that extends distally relative to the portion of the inner surface 171 of the catheter 102 that defines the lumen 188 (see also FIG. 4I). In the illustrated embodiment, the catching region 190 includes an engagement surface, abutment face, transverse extension, shelf, or ledge 191 having a reduced diameter, relative to more proximal regions of the catheter 102, against which the distal tip 136 of the stiffener 106 can exert a distally directed force. In some embodiments, the distal tip 136 of the stiffener 106 and the ledge 191 may generally only interact with each other when the stiffener 106 is urged distally or otherwise pressed against the ledge 191, such as during insertion of the catheter 102 into the vessel of a patient. In the illustrated embodiment, the distal tip 136 can also be referred to as an engagement surface, an abutment surface, etc. In the illustrated embodiment, the ledge 191 defines a planar annulus, and the plane of the annulus is orthogonal to a longitudinal axis of the catheter 102.

The illustrated catching region 190 also includes a lateral face 192, which in some instances, may provide a relatively weak connection between the distal end 134 of the stiffener 106 and the catheter 102. For example, the lateral face 192 of the catheter 102 may be in direct contact with the stiffener 106 and may grip and/or adhere thereto. In some instances, an adhesion may result from natural interaction between the materials of which the catheter 102 and the stiffener 106 are formed. In some instances, the catheter 102 is tipped on a mandrel that includes a surface similar to the outer surface 176 of the stiffener 106 at the distal end thereof, but having a slightly reduced diameter relative thereto. Accordingly, when the distal end 134 of the stiffener 106 is inserted into the preformed catheter 102, the lateral face 192 of the catheter 102 may press inwardly against the stiffener 106. In addition to the gripping or frictional forces imparted by such an arrangement, an adhesive bond also may form over time due to interactions of the catheter and stiffener materials. For example, in some embodiments, the stiffener 106 is formed of stainless steel, and the catheter 102 is formed of a polymeric material.

In other embodiments, it may be desirable for there to be little or no engagement between the stiffener 106 and the lateral face 192 of the catching region 190. For example, it can generally be desirable for the stiffener 106 to readily release from the catheter 102 when the stiffener 106 is withdrawn relative thereto in a proximal direction. That is, once the stiffener 106 has assisted in positioning the catheter 102 within a vessel of a patient, it can be desirable to remove the stiffener 106 from the catheter 102. Further, it can be desirable for the stiffener 106 to be removed without deforming, significantly deforming, and/or permanently deforming the distal end 114 of the catheter 102 and/or without substantially altering a positioning of the distal end 114 of the catheter 102 within the vessel of the patient. In some embodiments, the catheter 102 is tipped on a mandrel that includes a surface similar to the outer surface 176 of the stiffener 106 at the distal end thereof, and having a diameter that is substantially the same as or slightly larger than the diameter thereof. In some embodiments, the catheter 102 does not define a lateral surface 192 and/or only contacts the distal tip 136 of the stiffener 106 via the abutment face 191.

Whether or not any adhesion is present between the lateral face 192 of the catheter 102 and the stiffener 106, it can be desirable for the stiffener 106 to selectively engage the distal end 114 of the catheter 102. In particular, it can be desirable for the stiffener 106 to impart at least a distally directed force on the distal end 114 of the catheter 102 during insertion of the catheter 102 through a vessel wall and during advancement of the catheter 102 within the vessel of a patient. Further, it can be desirable for the stiffener 106 to readily disengage from the distal end 114 of the catheter 102 when the stiffener 106 is withdrawn in a proximal direction relative thereto.

In some embodiments, the distal end 114 of the catheter 102 can be adhered or otherwise bonded to the outer surface 173 of the needle 104. For example, the illustrated catching region 190 includes a lateral face 193, which in some instances, may provide a relatively strong connection between the catheter 102 and the distal end 124 of the needle 104. For example, the lateral face 193 of the catheter 102 may be in direct contact with the outer surface 173 of the needle 104 and may grip and/or adhere thereto. In some instances, an adhesion may result from natural interaction between the materials of which the catheter 102 and the needle 104 are formed. In some instances, the catheter 102 is tipped on a mandrel that includes a surface similar to the outer surface 173 of the needle 104 at the distal end thereof, but having a reduced diameter relative thereto. Accordingly, when the distal end 124 of the needle 104 is inserted through the preformed catheter 102, the lateral face 193 of the catheter 102 may press inwardly against the needle 104. In addition to the gripping or frictional forces imparted by such an arrangement, an adhesive bond also may form over time due to interactions of the catheter and stiffener materials. For example, in some embodiments, the needle 104 is formed of stainless steel, and the catheter 102 is formed of a polymeric material.

Adhesion between the distal ends of the catheter 102 and the needle 104 can assist in inserting the distal end of 114 of the catheter 102 through the sidewall of a vessel at the insertion site formed by the needle 104. For example, stronger adhesions between the distal end 114 of the catheter 102 and the outer surface 173 of the needle 104 reduce the chances of the catheter 102 being pushed back by the vessel wall during insertion, which could cause the needle 104 to undesirably pass through the backwall of the vessel before the catheter 102 enters the vessel. Tighter adhesion can also reduce the likelihood of other undesirable catheter tip deformations, such as fish-mouthing, during insertion through the vessel wall.

Moreover, due to the interactions between the stiffener 106 and the catheter 102 described above, relatively strong adhesive connections between the catheter 102 and the needle 104 can be achieved without fear of the catheter 102 bunching or deforming in an accordion-like manner when attempts are made to separate the catheter 102 from the needle 104. In particular, the stiffener 106 stiffens, reinforces, braces, supports, engages, or otherwise interacts with the catheter 102 as the stiffener 106 is advanced in a distal direction relative to the needle 104 to separate the adhesive connection. As previously mentioned, in some embodiments, the stiffener 106 and the catheter 102 can be advanced distally relative to the needle 104 simultaneously. The distal end 134 of the stiffener 106 can push distally against and provide axial support to the distal end 114 of the catheter 102 to assist in separating the catheter 102 from the needle 104. Such an arrangement can also inhibit similar deformation to the catheter 102 that might otherwise occur as the catheter 102 is passed through an insertion site through a vessel wall.

Accordingly, some embodiments can effectively eliminate adhesion issues for catheter/needle insertion assemblies. As previously discussed, some prior art systems struggle to address adhesion issues due to difficulties in ensuring that adhesion between the catheter and the needle is neither too loose nor too tight. However, permitting higher levels of adhesion between the catheter expands the window of acceptable adhesion strengths in a manner that avoids both the "too loose" and "too tight" scenarios. For example, stronger adhesion strengths can be used, thus avoiding the lower end of the acceptable-strength window altogether. Moreover, the upper end of the acceptable-strength window can be raised to the point where it, too, is of little to no concern. That is, the stiffener 106 may be capable of assisting in urging the catheter 102 from its connection to the needle 104 over such a large range of adhesion strengths that various manufactured systems 100 can perform as desired even in the presence of fluctuations that may arise from the manufacturing process, materials, length of time spent in storage (which can increase bond strength, in some instances), etc.

In certain embodiments, the stiffener 106 can have a flexural strength greater than that of the catheter 102. Accordingly, the stiffener 106 can assist in advancing the catheter 102 within a vessel for a significant length without the assistance of a guidewire. For example, in some embodiments, the catheter 102 can be advanced into a vessel to a depth that is equal to or greater than a depth that could otherwise be achieved for the same catheter configuration by using a guidewire. In various embodiments, a flexural strength of the stiffener 106 is greater than a flexural strength of the catheter 102.

In other or further embodiments, the stiffener 106 can have a flexural strength that is less than a flexural strength of the needle 104. That is, the stiffener 106 may be more compliant than the needle 104, and thus may be advanced through the vessel and conform to a natural shape thereof more readily than do known over-the-needle arrangements.

In various embodiments, the stiffener 106 can comprise superelastic nitinol. In other embodiments, the stiffener 106 comprises shape-memory nitinol, polycarbonate, or any other suitable material, such as may readily permit lateral bending while maintaining sufficient longitudinal rigidity to advance the catheter 106 in manners such as disclosed herein.

In various embodiments, the needle 104 can comprise stainless steel, such as, e.g., 304 stainless steel. In various embodiments, the catheter is formed of any suitable biocompatible material, such as, for example, medical grade polyurethane. In some embodiments, the catheter 102 comprises a polyurethane with a shore A durometer of or of no greater than about 91, 93, or 97. In some embodiments, the catheter 102 comprises a shore D durometer of or of no greater than about 55.

FIGS. 4A-4K depict various stages of an illustrative method of using the system 100 with a patient P. For clarity, some hidden components, or portions thereof, may not be depicted in some of these drawings. However, FIGS. 1-3 and the previous discussion associated therewith should inform the reader with respect to the relationships among the various components at each of the stages depicted in FIG. 4A-4K, to the extent such relationships are not specifically shown or mentioned. Moreover, it is noted that each drawing, or in some instances, different portions of a single drawing, are not necessarily to scale.

Figure 4A:
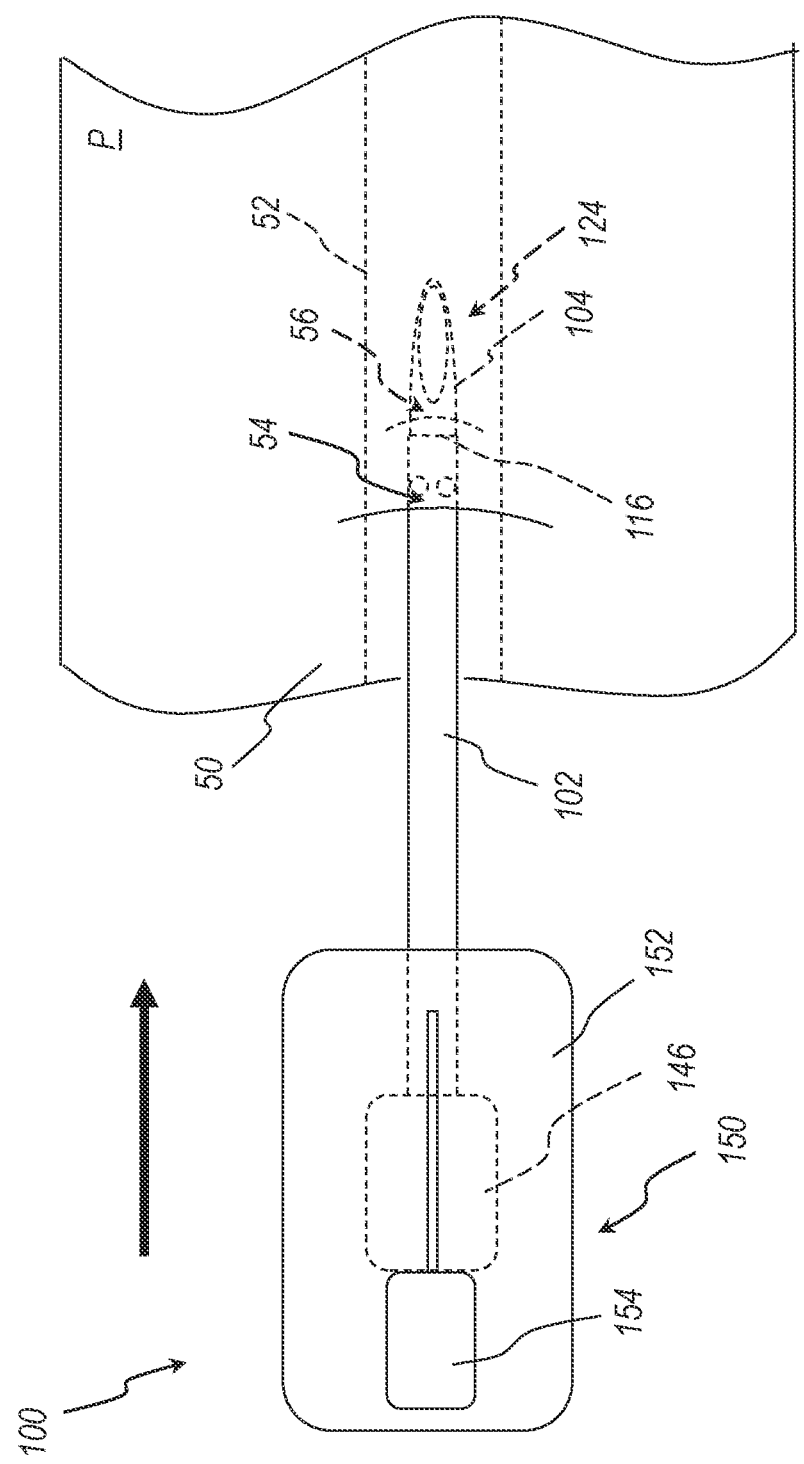
FIG. 4A is another top plan view of the catheter delivery system of FIG. 1 in an early stage of an illustrative method of using the system, wherein the system is moved in unison to advance a distal tip of a needle into a vessel of a patient.

With reference to FIG. 4A, a portion of the skin 50 of a patient may be prepped in any suitable fashion for catheter introduction into a vessel 52, such as according to a generally accepted standard of care. The system 100 may then be advanced in unison in a distal direction, as depicted by a rightward arrow. As the system 100 is thus advanced, the distal end 124 of the needle 104 can be inserted through the skin 50 at a skin insertion site 54. As the system 100 is further advanced, the distal end 124 of the needle 104 can be introduced into the vessel 52 at a vessel insertion site 56.

At the stage illustrated in FIG. 4A, only the distal end 124 of the needle 104 has been inserted into the vessel 52. The distal end 116 of the catheter 102, although having been inserted through the skin insertion site 54, remains at an exterior of the vessel 52.

The system 100 remains in the undeployed configuration in the illustrated stage. That is, the actuator 154 has not yet been actuated (advanced distally relative to the housing 152). Moreover, the catheter hub 146 in the illustrated configuration is in a coupled relation with the actuator 154, and is likewise in an undeployed configuration. In the illustrated embodiment, the catheter hub 146 is contained within the housing 152 of the needle hub 150 when in the undeployed configuration.

Figure 4B:
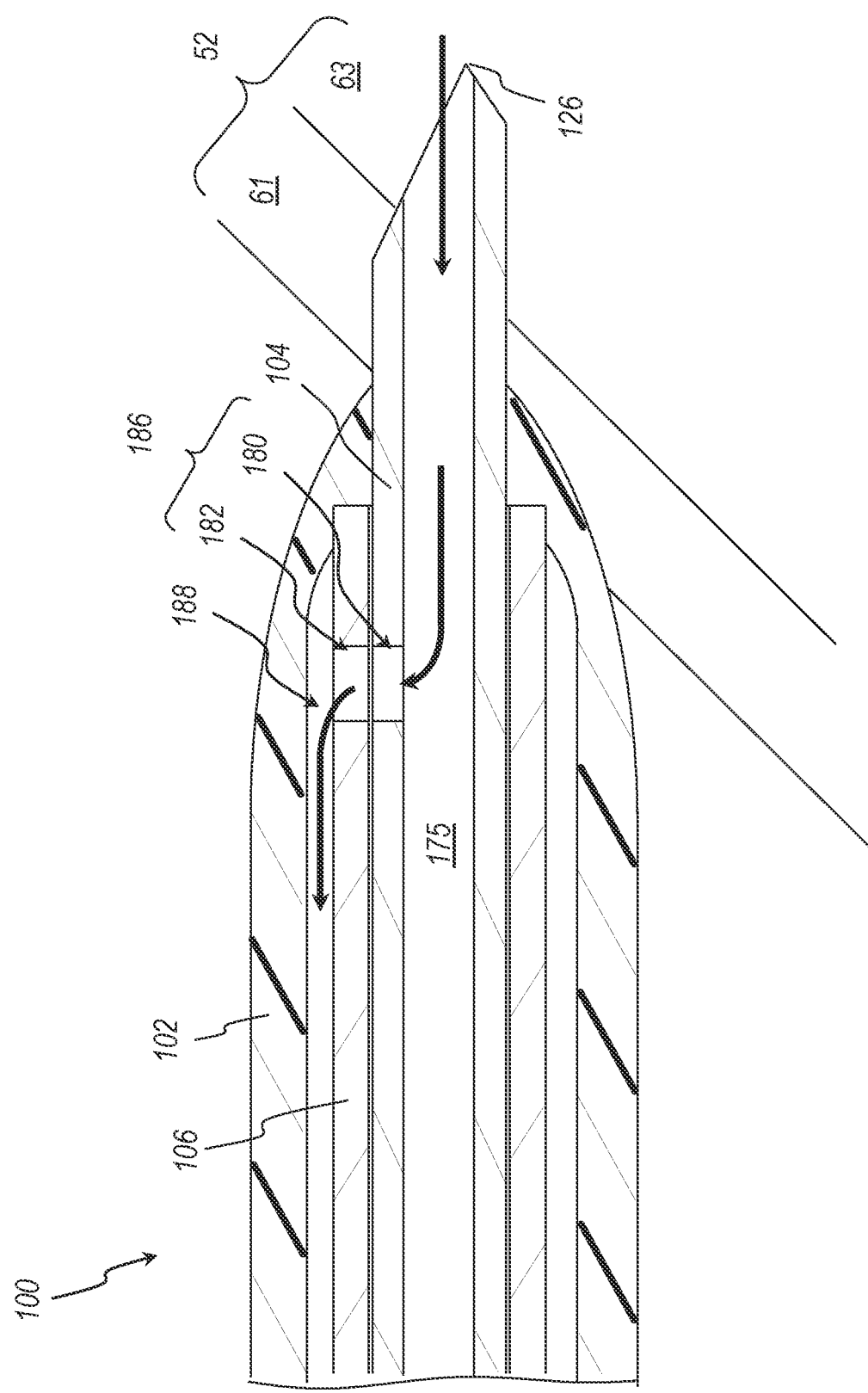
FIG. 4B is a cross-sectional view of a distal portion of the catheter delivery system, similar to that depicted in FIG. 3, at a point in time after the distal tip of the needle has been advanced through an insertion site of the patient and into the vessel of the patient.

FIG. 4B is a cross-sectional view of the distal portion of the system 100 at a point in time just after the distal tip 126 of the needle 104 has passed through a vessel wall 61 and entered a lumen 63 of the vessel 52. Blood, as represented by arrows, travels proximally through the lumen 175 of the needle 104. Blood is also permitted to flow through the passageway 186 defined by the ports 180, 182 through the sidewalls of the needle 104 and the stiffener 106, respectively. The blood thereafter flows proximally through the annular channel 188 defined by the catheter 102 and the stiffener 106.

Figure 4C:
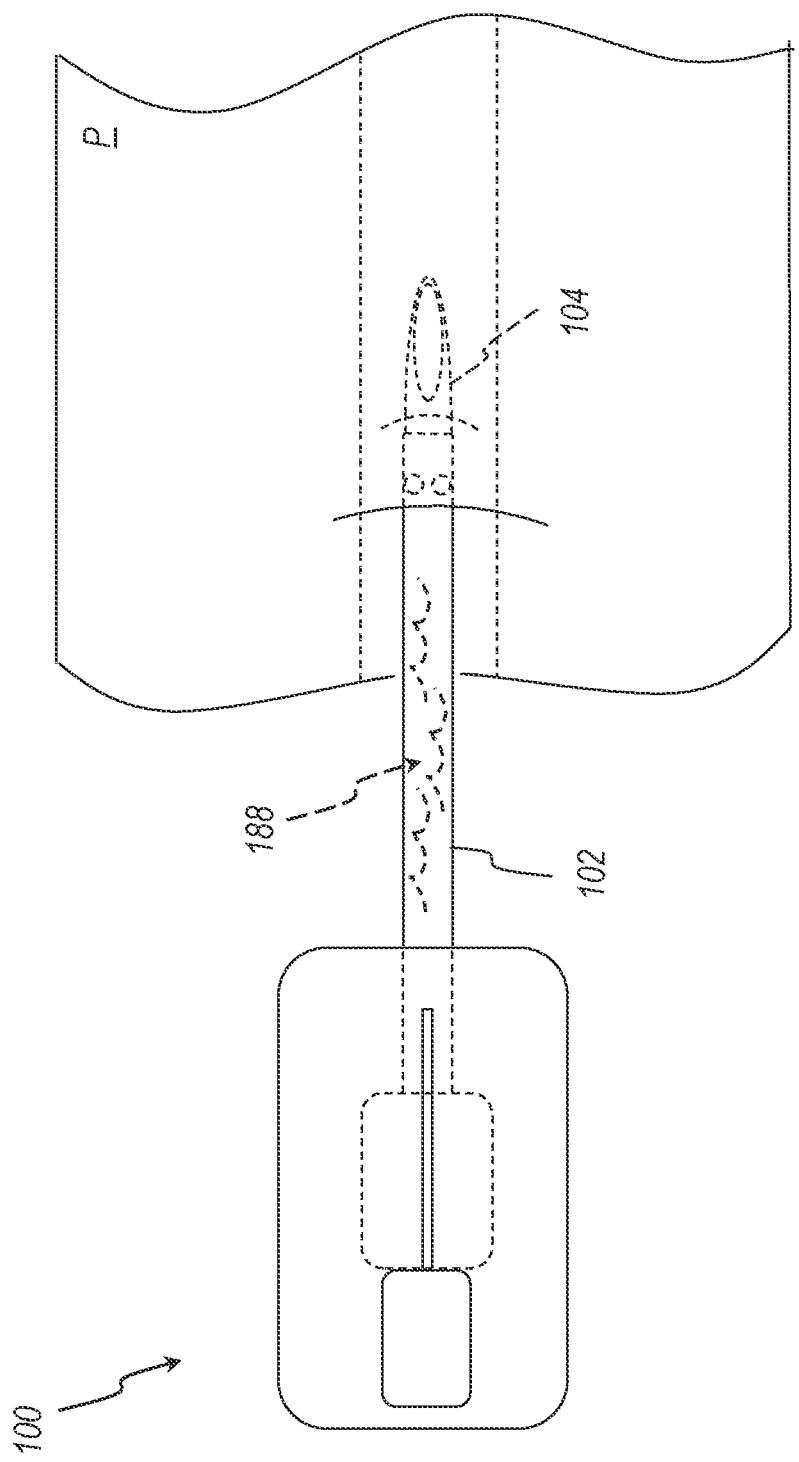
FIG. 4C is another top plan view of the catheter delivery system at a point in time after that depicted in FIG. 4B illustrating a flash of blood proceeding proximally through a catheter.

FIG. 4C depicts a stage shortly after that depicted in FIG. 4B. An initial flash of blood (indicated by wavy lines) continues to flow proximally through the channel 188. The catheter 102 may include at least a portion that is sufficiently transparent or translucent to permit visualization of the flash of blood. The flash of blood can indicate that the needle 104 has been properly placed and that the delivery system 100 can be used to deploy the catheter 102 over the needle 104.

Figure 4D:
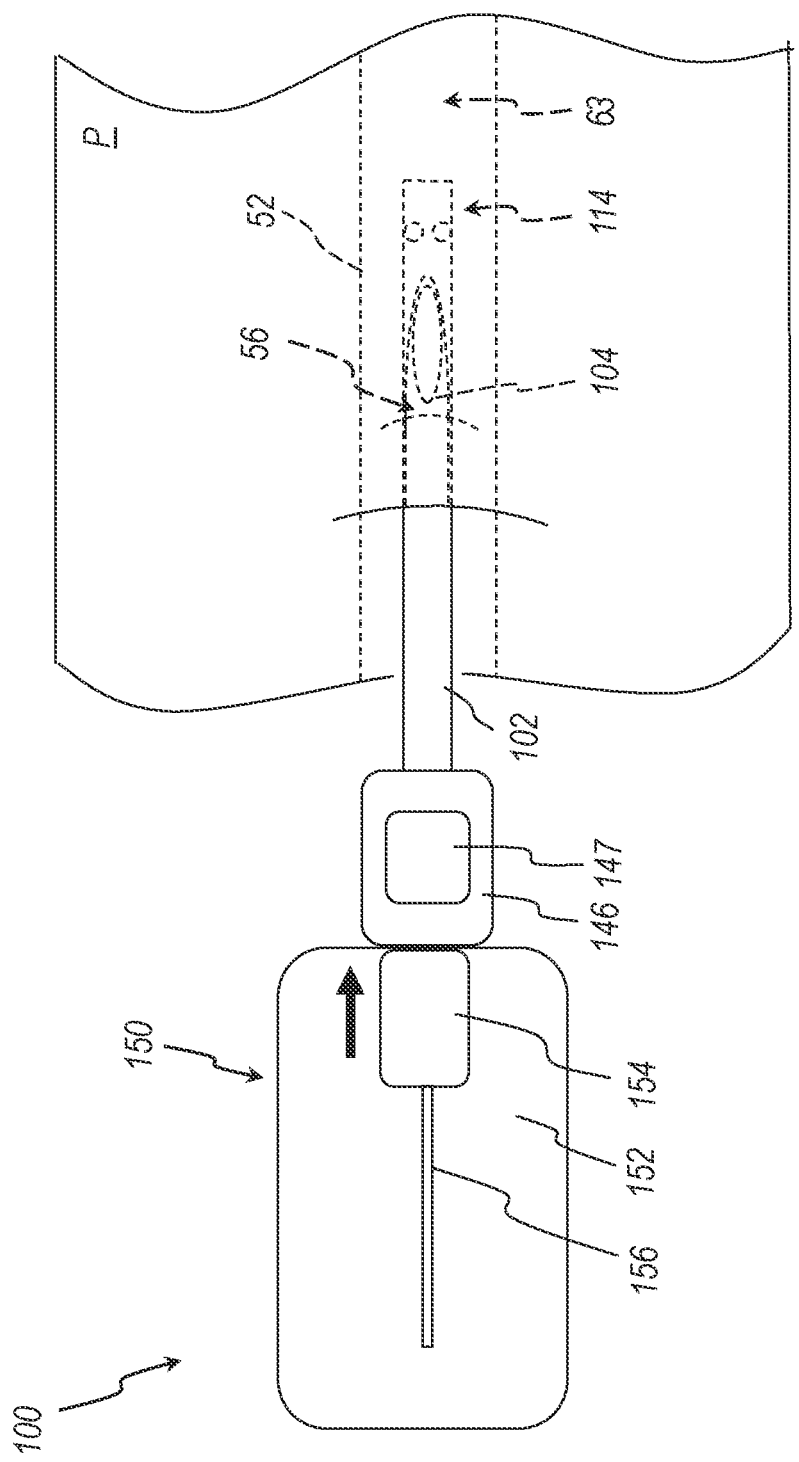
FIG. 4D is another top plan view of the catheter delivery system demonstrating deployment of the catheter into the vessel over the distal end of the needle.
Figure 4E:
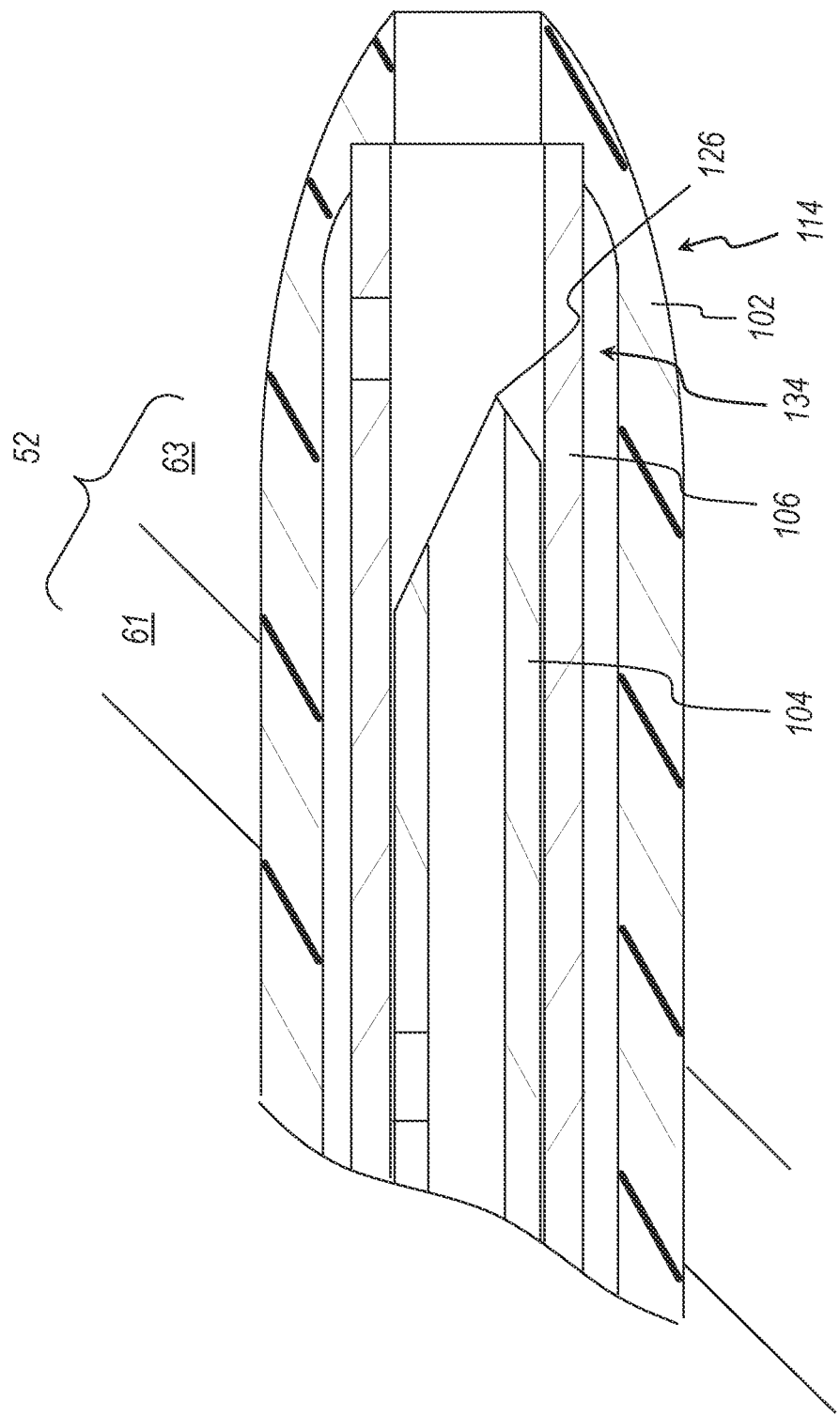
FIG. 4E is another cross-sectional view of the distal portion of the system after the catheter has been deployed over the distal tip of the needle.

FIGS. 4D and 4E depict different views of the same stage of the illustrative method of using the device 100. As seen in these drawings, actuation of the actuator 154 deploys the distal end 114 of the catheter 102 into the vessel 52 of the patient P. In particular, with reference to FIG. 4D, while the needle hub 150 (or handle) is held steady relative to the patient P, the actuator 154 is manually advanced distally to a distal end of the track 156. As previously discussed, this distal movement of the actuator 154 advances both the catheter 102 and the stiffener 106 (see FIG. 4E) in unison in the distal direction. The distal ends 114, 134 of the catheter 102 and of the stiffener 106, respectively, are thus advanced into the lumen 63 of the vessel 52 through the vessel insertion site 56. Holding the needle hub 150 steady relative to the patient P also maintains the needle 104 steady relative to the patient P. The catheter 102 and the stiffener 106 are thus advanced distally over the needle 104 while being advanced into and through the lumen 63 of the vessel 52.

As shown in FIG. 4D, in the illustrated embodiment, the catheter hub 146 is advanced to a position outside of the housing 152 of the needle hub 150 when the system 100 is in the deployed configuration. In some embodiments, moving the catheter hub 146 may expose an actuator 147 thereon, such as a button, a switch, a lever, or any other suitable release mechanism, that can be actuated to decouple the catheter hub 146 from the needle hub 150. For example, the actuator 147 may be directly mechanically coupled with the actuator 154 of the needle hub 150 via any suitable mechanical linkage, and actuation of the actuator 147 may decouple the actuator 147, and hence the catheter hub 146, from the actuator 154, and hence from the needle hub 150.

In other embodiments, as previously discussed, no such direct mechanical linkage may exist between the actuator 154 and the catheter hub 146. In certain of such embodiments, the actuator 154 (and needle hub 150) may be decoupled from the catheter hub 146 merely by withdrawing the needle hub 150 proximally relative to the catheter hub 146.

With reference to FIG. 4E, the catheter 102 and the stiffener 106 have been deployed over the distal tip 126 of the needle 104. The stiffener 106 thus shields or hoods the distal tip 126. This shielding prevents the needle 104 from damaging the catheter 102 and/or the vessel 52 as the system 100 is advanced further into the lumen 63 of the vessel 52.

Figure 4F:
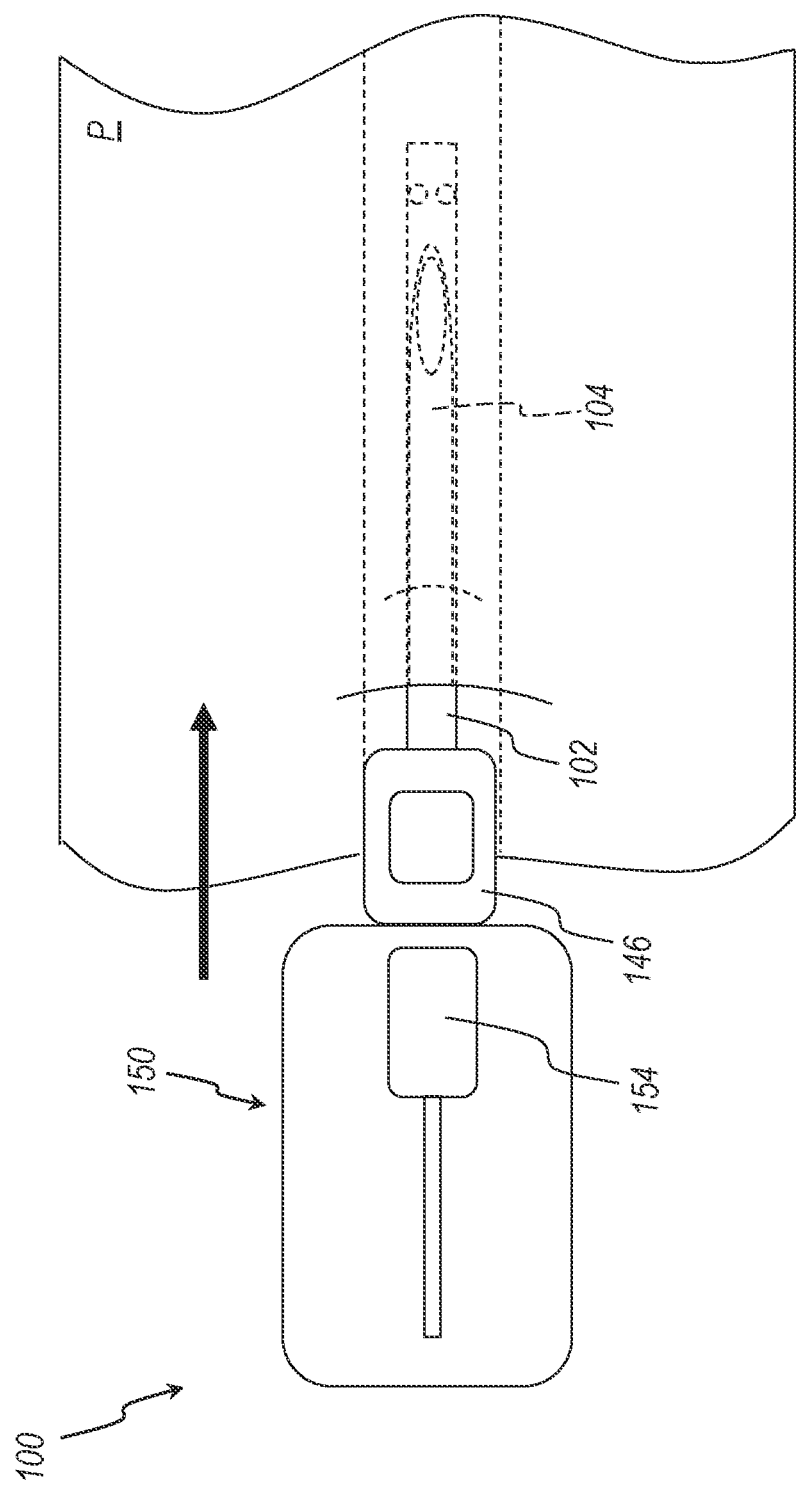
FIG. 4F is another top plan view of the catheter delivery system demonstrating movement of the full system in a distal direction to advance the catheter further into the vessel.

FIG. 4F demonstrates that after the system 100 has been deployed to advance the catheter 102 into the vessel 52, the full system 100 can be moved distally in unison to advance the catheter 102 further into the vessel 52. As previously discussed, the catheter 102, the needle 104, and the stiffener 106 may be moved substantially simultaneously or substantially in unison during this further insertion. The catheter hub 146 can remain coupled with needle hub 150 during this stage.

In other embodiments (see, e.g., FIG. 6 and associated description), the advancement stage of FIG. 4F is omitted. For example, in some embodiments, advancement of the actuator 154 along the track 156 advances the catheter 102 to a desired depth within the vessel, such that no further advancement of the entire system 100 is desired or required. In some instances, an arrangement in which actuation of the actuator 154 fully deploys the catheter can be desirable for a one or more of a variety of reasons. For example, in some instances, full advancement of the catheter 102 in this manner can reduce the risk of trauma to the vessel during advancement of the catheter 102 into the vessel. This can result, for example, from a decrease in rigidity, as the combination of the catheter 102 and the stiffener 106 can be less rigid than the combination of the catheter 102, the stiffener 106, and the needle 104. Such arrangements can also have a relatively shorter needle 104, which can facilitate initial insertion of the system 100 into the vessel. For example, a shorter needle 104—or more specifically, a shorter effective length of the needle, which can be the unsupported portion that extends distally from the housing 152—can be more readily controlled by manipulation of the housing 152.

In some embodiments, however, the combination of the catheter 102, the stiffener 106, and the needle 104 may nevertheless be sufficiently compliant, in lateral directions (i.e., in directions transverse to a longitudinal axis of the system), to permit a relatively longer needle to be advanced to significant distances within the vessel prior to being retracted from the needle hub 150. For example, in certain embodiments of the system depicted in and described below with respect to FIG. 5, the catheter, stiffener, and needle can be sufficiently compliant in lateral directions to permit the combination thereof to readily bend at the insertion site of the needle and be advanced to significant distances within the vessel while the distal tip of the needle is shielded by the tubular stiffener.

Figure 4G:
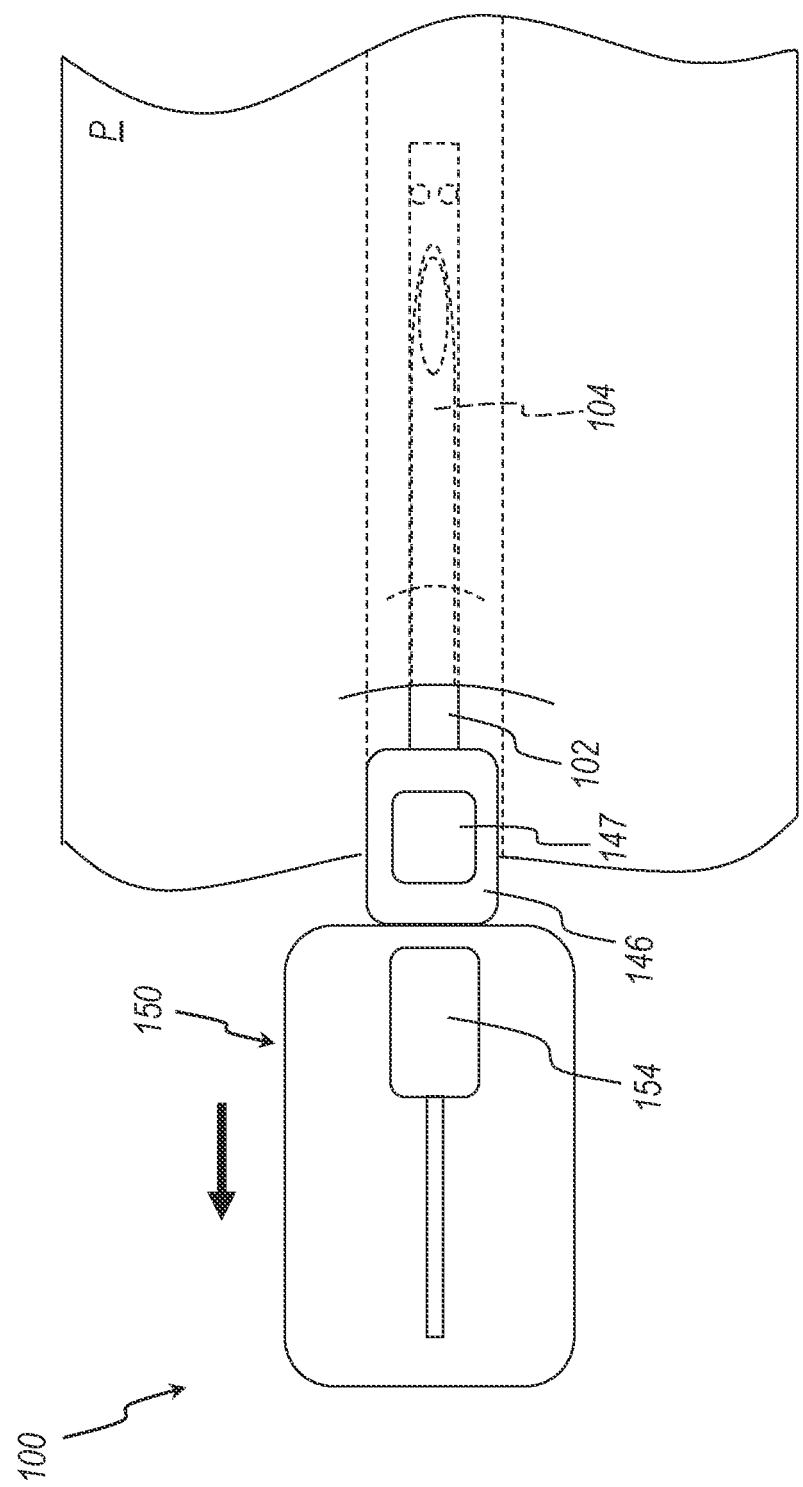
FIG. 4G is another top plan view of the catheter delivery system demonstrating removal of a needle hub, which is coupled with both the needle and a stiffener, from a catheter hub that is coupled with the catheter.

FIG. 4G demonstrates a stage in which the needle hub 150 is decoupled from the catheter hub 146. In the illustrated embodiment, the actuator 147 of the catheter hub 146 is actuated (e.g., depressed, rotated, or otherwise moved), which can release, for example, a mechanical coupling between the actuator 147 and the actuator 154 of the needle hub 150. Upon release of the mechanical coupling, the needle hub 150 can be withdrawn from the catheter hub 146. For example, as demonstrated in FIG. 4G, the catheter hub 146 may be held steadily in place (e.g., via one hand of a practitioner), and the needle hub 150 may be moved proximally relative thereto (e.g., via the other hand of the practitioner). In other embodiments, the actuator 147 may be omitted and catheter hub 146 may be directly coupled to the stiffener actuator 154 in any suitable releasable fashion, such as via threading. The catheter hub 146 thus may be rotated relative to the stiffener actuator 154 to disengage the threads and release the catheter hub 146, thus permitting removal of the needle hub 150, the needle 104, the stiffener actuator 154, and the stiffener 106 proximally from the catheter 106 and the catheter hub 146. In still other embodiments, as previously discussed, no direct mechanical linkage is provided between the needle hub 150 and the catheter hub 146, and thus the needle hub 150 may merely be withdrawn proximally from the catheter hub 146 after the catheter 102 has been positioned as desired within the vessel.

As previously discussed, in some embodiments, the actuator 154 of the needle hub 150 may be locked in place once it has been actuated. This may effectively lock the stiffener 106 relative to the needle hub 150. Further, in some embodiments, the needle 104 is fixedly secured to the needle hub 150. Accordingly, retraction of the needle hub 150 from the catheter hub 146 may cause both the needle 104 and the stiffener 106 (see FIG. 4H) to retract in unison from the catheter 102 and from the catheter hub 146. Stated otherwise, in some embodiments, the insertion assembly may be fully removed from the catheter assembly.

Figure 4H:
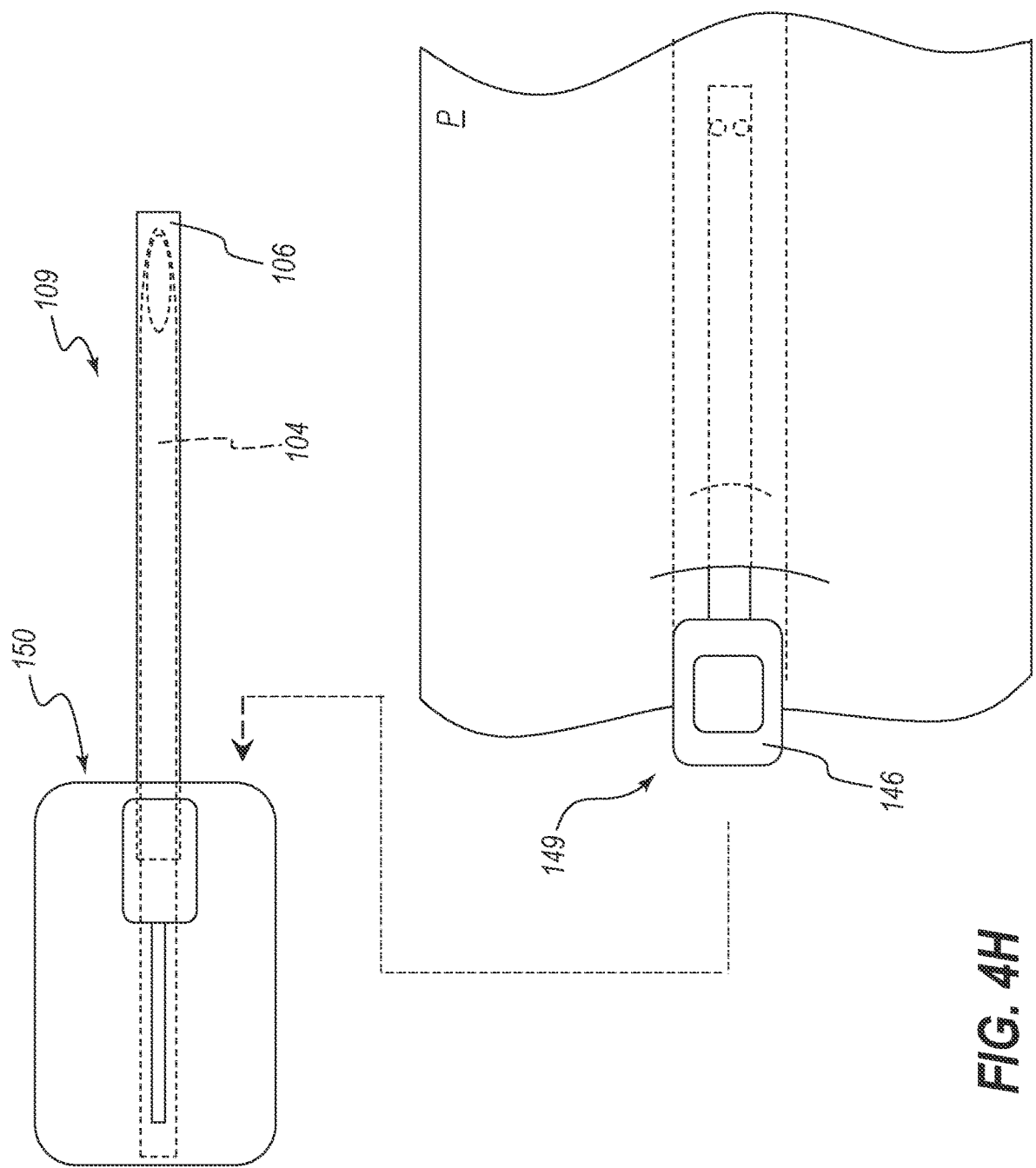
FIG. 4H is another top plan view of the catheter delivery system after the needle hub has been removed from the catheter hub while the catheter remains in place within the vessel of the patient.

FIG. 4H depicts the needle hub 150, or more generally, what may be termed the insertion assembly 109, after having been fully withdrawn from the catheter hub 146, or more generally, from what may be termed the catheter assembly 149. In some embodiments, the stiffener 106 is locked in place in a position where the distal end of the stiffener shields or hoods the distal end of the needle 104. Such an arrangement can advantageously provide protection against inadvertent needle sticks. Stated otherwise, the stiffener 106 can cover, encompass, enshroud, encircle, protect, extend a significant distance beyond, or otherwise shield the distal tip of the needle 104 so as to inhibit or prevent inadvertent contact with the needle 104. As such, the stiffener 106 can inhibit, prevent, or avoid sharps injuries and the concomitant transmission of blood-borne illnesses. The stiffener 106 thus may also be referred to as a sheath, shield, stick-prevention element, etc. Note that although the stiffener 106 can define an opening at a distal end thereof, such that the needle tip may theoretically be viewable through the opening or otherwise be exposed to air, daylight, etc. through the opening, and hence not entirely "covered" in some senses of the word, the shielding 106 provided by the stiffener 106 by extending past the distal tip and preventing contact with the needle tip may nevertheless be referred to herein as "covering" the needle tip.

Figure 4I:
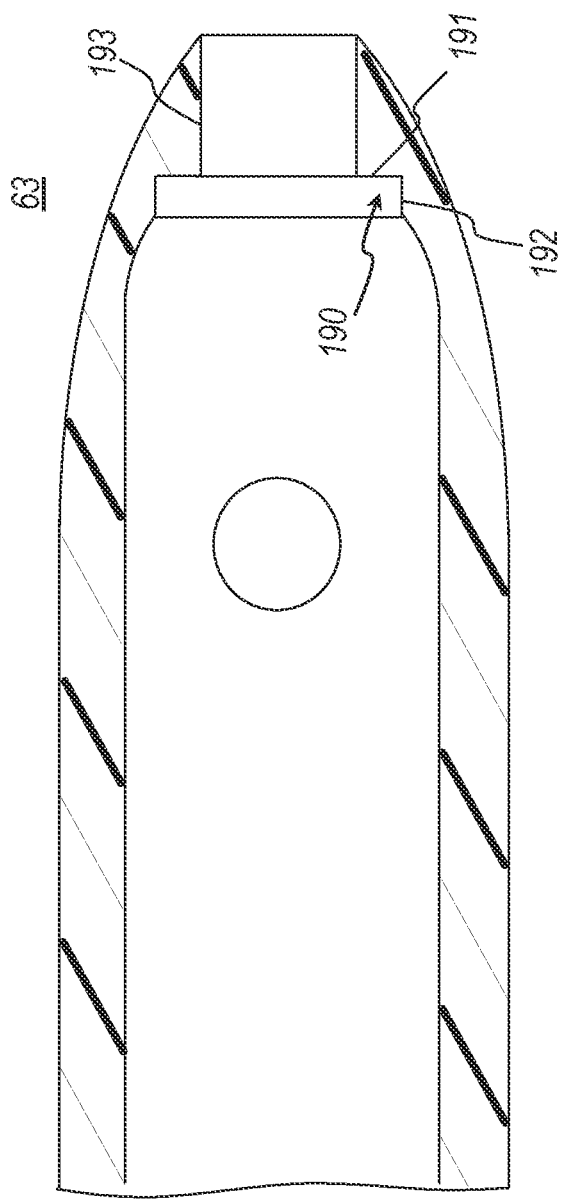
FIG. 4I is another cross-sectional view of a distal portion of the catheter that remains within the vessel of the patient for fluid delivery or aspiration.

FIG. 4I depicts the catheter 102 after it has been positioned in the lumen 63 of the vessel 52 and after the stiffener 106 and the needle 104 have been removed therefrom. The catching region 190, the ledge 191, the lateral face 192, and the lateral face 193, which were previously discussed, are seen in this view. In various embodiments, the catheter 102 may be used for any suitable aspiration and/or injection procedure.

Figure 4J:
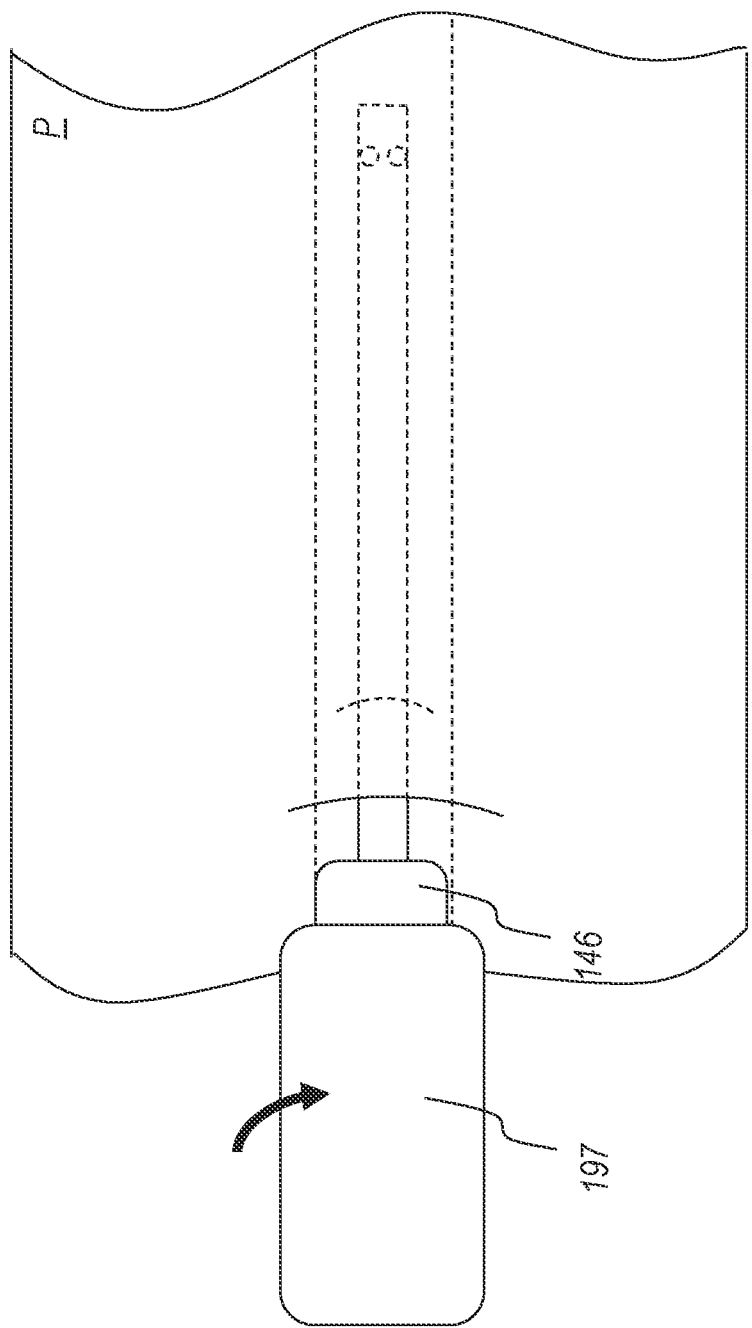
FIG. 4J is another top plan view of the catheter assembly that depicts a medical fluid component being coupled with the catheter hub.

FIG. 4J depicts a medical fluid component 197 being coupled with the catheter hub 146. In the illustrated embodiment, coupling is achieved via rotating the medical fluid component 197 relative to the catheter hub 146. For example, in some embodiments, the medical fluid component 197 may include a medial connection interface of any suitable variety, such as a Luer fitting (e.g., a male Luer fitting) that can couple with a complementary Luer fitting (e.g., a female Luer fitting) of the catheter hub 146. Any suitable medical fluid component 197 is contemplated, such as, for example, a syringe, an IV line, a power injector, etc.

Figure 4K:
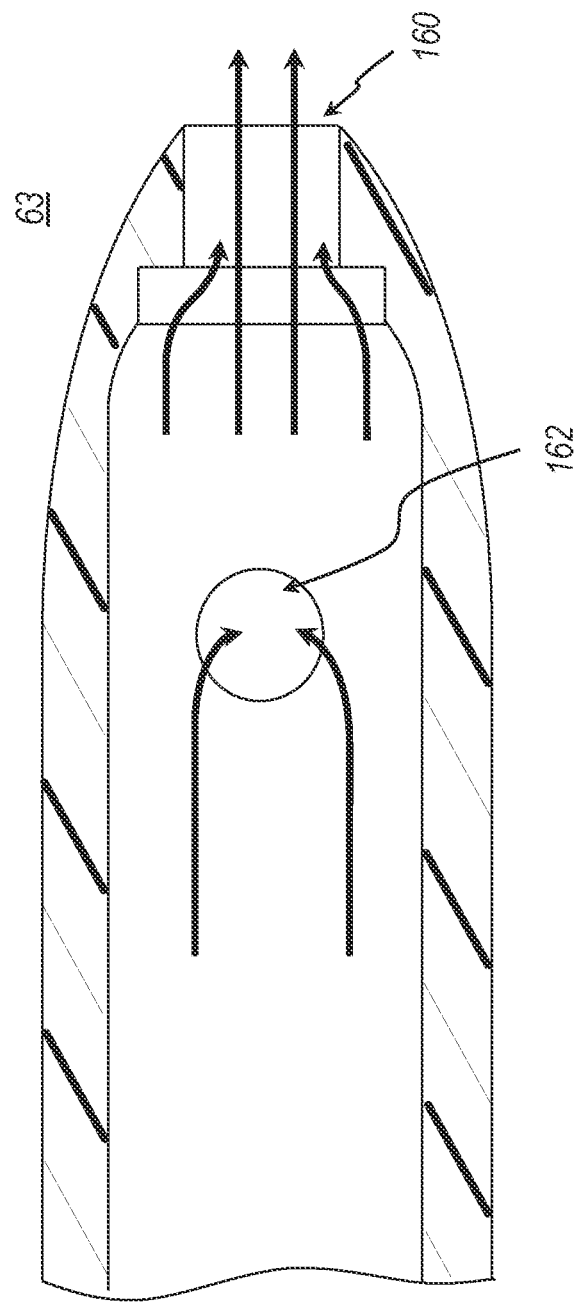
FIG. 4K is another cross-sectional view of the distal portion of the catheter that remains within the vessel of the patient that depicts fluid being delivered from the medical fluid component, through the catheter, and into the vessel of the patient.

FIG. 4K depicts fluid being delivered from the medical fluid component 197, through the catheter 102, and into the lumen 63 of the vessel of the patient. In some embodiments, a relatively smaller needle 104 may be used in the system 100. For example, in some instances, the stiffener 106 may define an outer diameter that is substantially the same as the outer diameter of needles that are generally used in known catheter delivery systems. As a result, the distal port 160 may be relatively smaller than distal ports of other catheter systems. Stated otherwise, the catching region 190 of the catheter 102 may reduce the size of the distal port 160, as compared with other over-the-needle catheter systems that do not use a stiffener 106 and in which the catheter has the same outer diameter. However, it may be desirable for the catheter 102 to yield substantially the same flow rates as may be achieved by other catheter systems. In some embodiments, a flow rate of the catheter 102 is enhanced with the presence of the side ports 162.

In various embodiments, a maximum diameter of the catheter 102 is no larger than 18, 20, or 22 gauge (approximately 1.2, 1.0, 0.8 millimeters, respectively) or no larger than 5 French or 6 French (1.67 or 2 millimeters, respectively). In further embodiments, the catheter 102 includes only the distal port 160 and is capable of delivering water or water-based fluids (e.g., 0.9 percent saline at 37° C.) at a flow rate of no less than 3, 4, 5, 6, or 7 milliliters per second without rupturing. In various embodiments, a diameter of the distal port 160 is no greater than 55, 60, 70, or 75 percent of a maximum diameter of the catheter 102. For example, in some embodiments, the catheter 102 has a maximum diameter of about 1.24 millimeters, whereas the distal port has a diameter of about 0.071 millimeters, while in other embodiments, the catheter 102 has a maximum diameter of about 1.0 millimeters, whereas the distal port has a diameter of about 0.056 millimeters.

In other embodiments in which the catheter 102 has a maximum diameter within the ranges set forth above, the catheter 102 includes the distal port 160 and a plurality of ports 162. In some embodiments, all of the ports 160, 162 are collectively capable of delivering water or water-based fluids (e.g., 0.9 percent saline at 37° C.) at a flow rate of no less than 3, 4, 5, 6, or 7 milliliters per second without rupturing.

Figure 5:
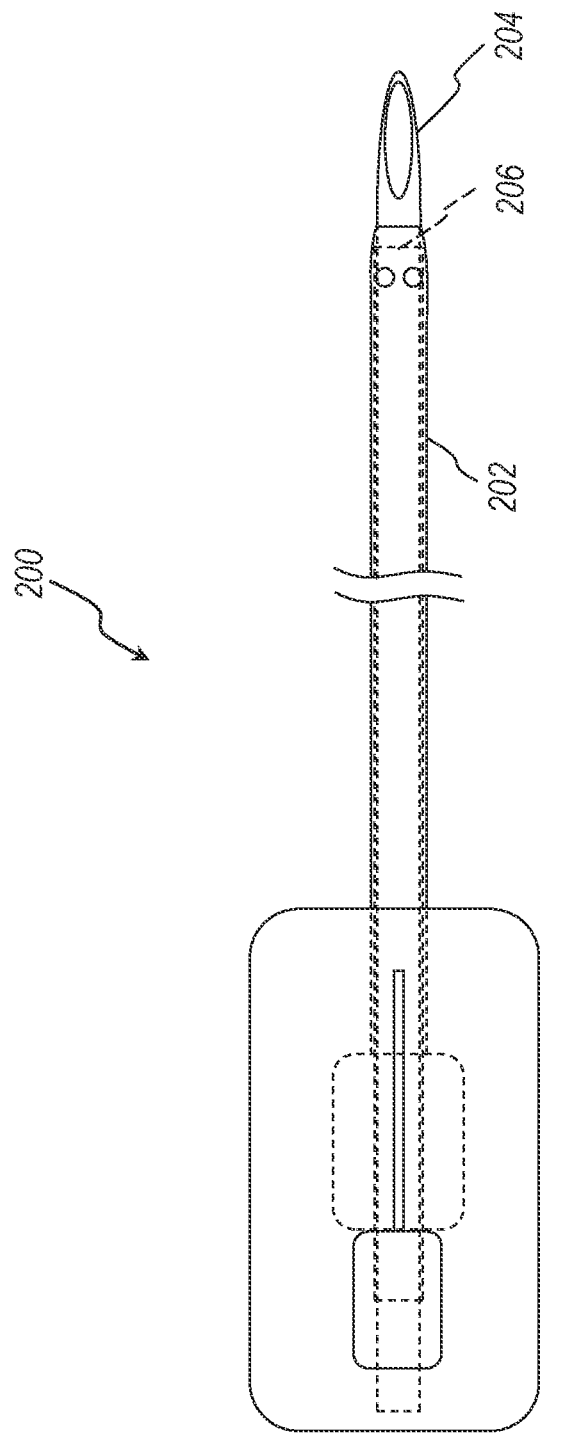
FIG. 5 is a top plan view of another embodiment of a catheter delivery system such as that depicted in FIG. 1 that defines a significantly greater length.

FIG. 5 is a top plan view of another embodiment of a catheter delivery system 200. The system 200 can resemble the system 100 described above in certain respects. Accordingly, like features are designated with like reference numerals, with the leading digits incremented to "2." Relevant disclosure set forth above regarding similarly identified features thus may not be repeated hereafter. Moreover, specific features of the system 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 200. Any suitable combination of the features and variations of the same described with respect to the system 100 can be employed with the system 200, and vice versa. This pattern of disclosure applies equally to further embodiments depicted in subsequent figures and described hereafter, wherein the leading digits may be further incremented.

The system 200 includes a catheter 202, a needle 204, and a stiffener 206 that define substantially greater lengths than the catheter 102, the needle 104, and the stiffener 106, respectively. In various embodiments, the system 200 can be used for peripheral intravenous, midline, PICC, or other applications.

Figure 6:
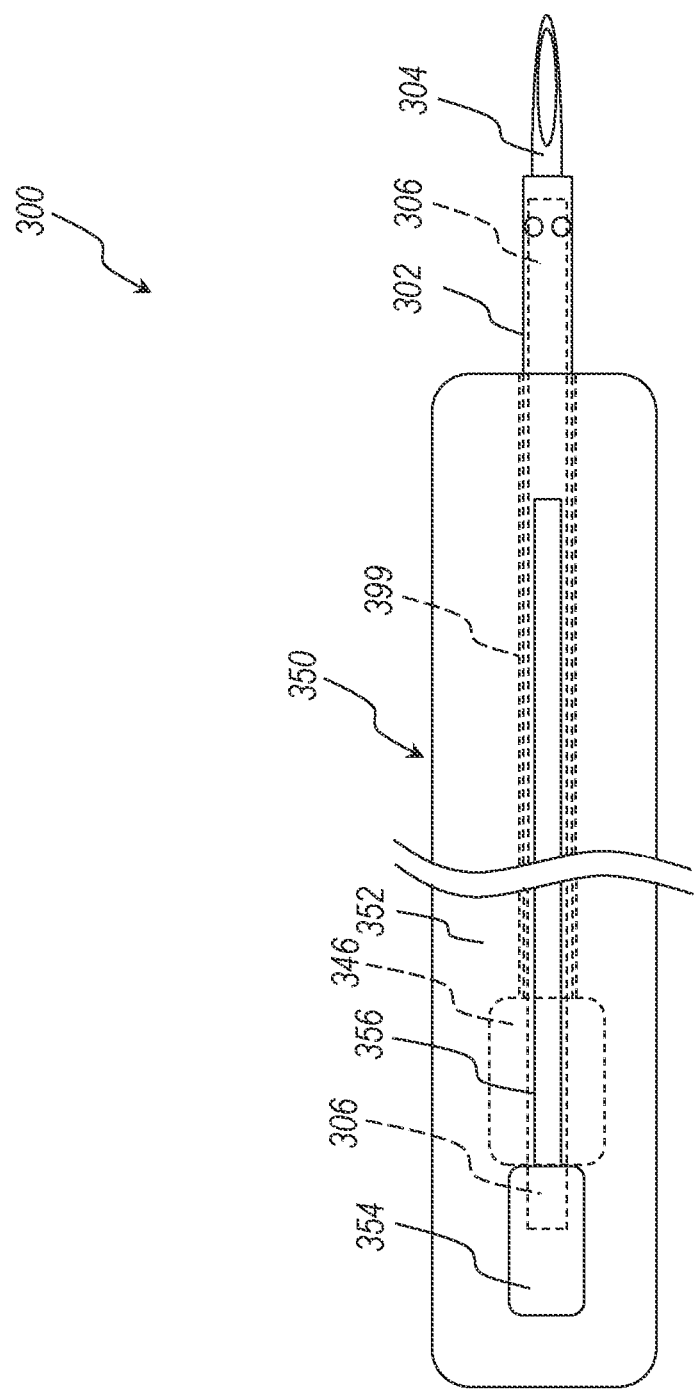
FIG. 6 is a top plan view of another embodiment of a catheter delivery system that includes an elongated guide that inhibits lateral deformations of a catheter during deployment of the catheter within a vessel of a patient.

FIG. 6 is a top plan view of another embodiment of a catheter delivery system 300 that includes an elongated guide 399 that inhibits lateral deformations of a catheter 302 during deployment of the catheter 302 within the vessel 52 of the patient P. In the illustrated embodiment, the guide 399 is positioned within an elongated housing 352 of a needle hub 350. The guide 399 can be of any suitable variety. For example, in some embodiments, the guide 399 includes sidewalls that are molded as parts of the housing 352. In other or further embodiments, the guide 399 includes a tube having a sufficiently large lumen to accommodate the catheter 302 and permit translation of the catheter 302 within the tube.

The system 300 includes a stiffener 306, such as those previously described, which can assist in placement of the catheter 302 within the vessel 52. The stiffener 306 is coupled to an actuator 354. Similarly, the catheter 302 is attached to a catheter hub 346, which is releasably coupled with the actuator 354.

The needle hub 350 can include an actuator 354 and an elongated track 356 that runs substantially the full length of the housing 352, and can be coupled with a needle 304. The needle 304 may be fixedly secured to the housing 352 in manners such as previously described.

In use, the distal end of the needle 304 is inserted into the vessel 52. Once a flash of blood is observed, the catheter 302 is deployed via the actuator 354. In particular, the actuator 354 is moved distally, which moves a large length of the catheter 302 and stiffener 306 over the needle 304. In the illustrated embodiment, the portions of the catheter 302 and the stiffener 306 that are inserted into the vessel are much longer than the portion of the needle 304 that is inserted into the vessel.

An effective, active, or unsupported length of the needle 304 is substantially smaller than the effective, active, or unsupported length of the needle 204 depicted in FIG. 5. That is, a length of the needle 304 that extends distally from the housing 352 is substantially smaller than the length of the needle 204 that extends from the housing in FIG. 5. As previously discussed, an arrangement such as depicted in FIG. 6 can facilitate initial insertion of the system 300 into the vessel. For example, the needle 304, and the distal tip thereof in particular, can be more readily controlled by manipulation of the housing 352 and/or can be less prone to unintended or undesirable bending.

Any suitable length of the catheter 302 is contemplated. In various embodiments, the length of the catheter 302 is suitable for peripheral intravenous, midline, PICC, or other applications.

Figure 7A:
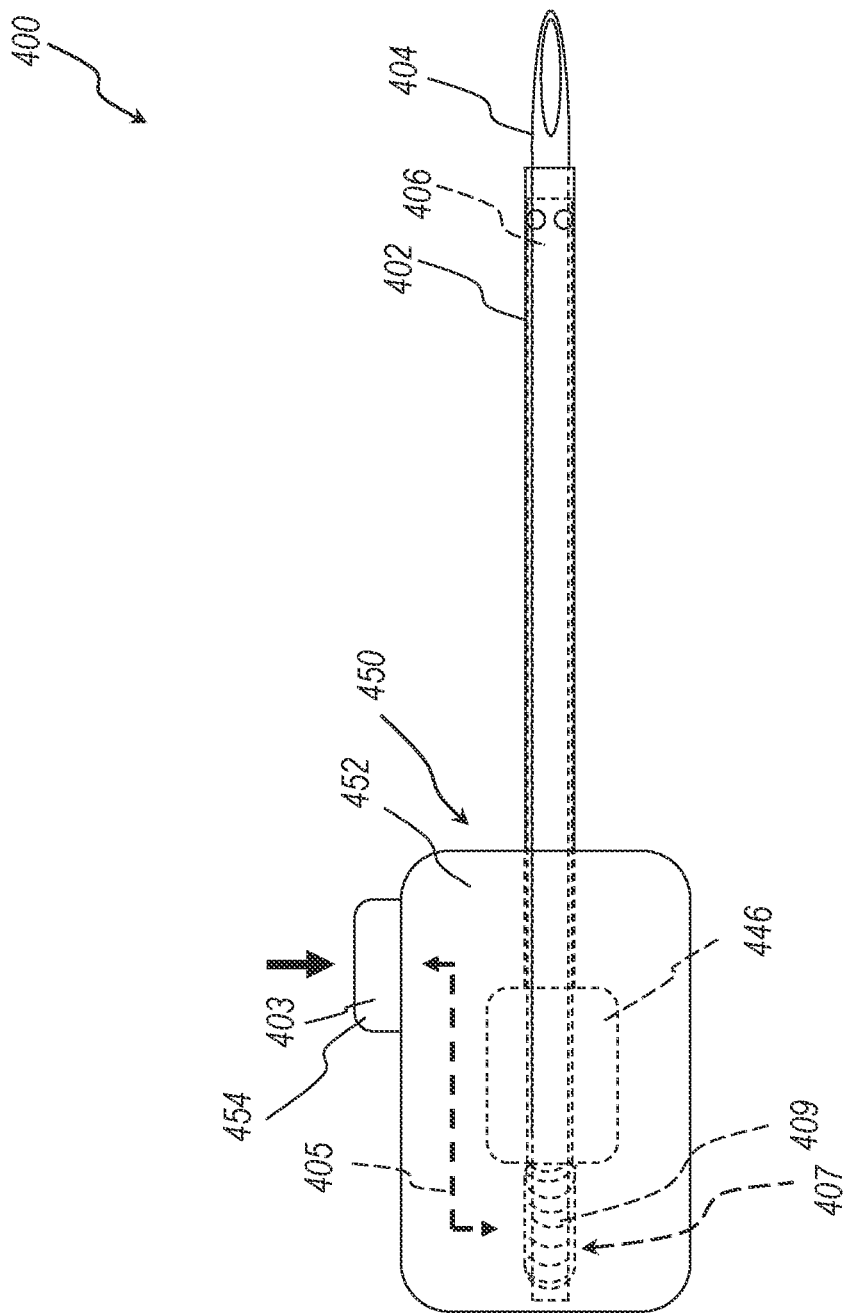
FIG. 7A is a top plan view of another embodiment of a catheter delivery system that is configured for automatic deployment of the catheter over the distal tip of the needle, wherein the system is depicted in an undeployed state.
Figure 7B:
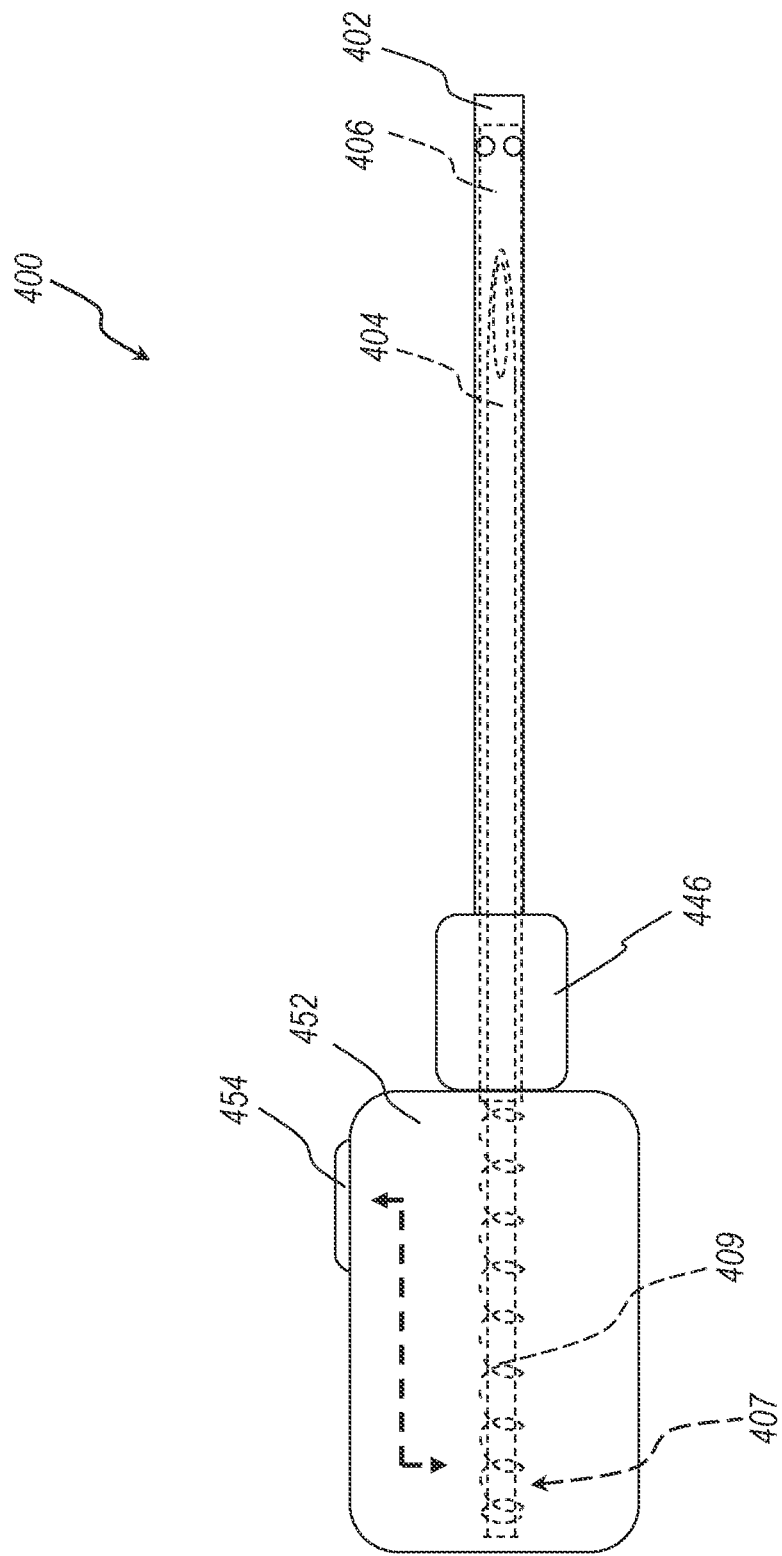
FIG. 7B is another top plan view of the catheter delivery system of FIG. 7A after an actuator has been actuated, wherein the system is depicted in a deployed state.

FIGS. 7A and 7B depict another embodiment of a catheter delivery system 400 that is configured to automatically deploy a catheter 402 and a stiffener 406 over a distal end of a needle 404. In FIG. 7A, the system 400 is in an undeployed state, and in FIG. 7B, the system 400 has been deployed.

The system 400 can include a needle hub 450 and a catheter hub 446 similar to like-named features described above. However, the needle hub 450 includes an automatic actuator 454. The actuator 454 includes a user interface 403, such as a depressible button, and a biasing member 407. The user interface 403 is coupled with the biasing member 407 in any suitable manner, such as via a mechanical linkage 405. Activation of the user interface 403 thus can cause the biasing member 407 to automatically deploy the catheter 402 and the stiffener 406. In the illustrated embodiment, the biasing member 407 includes a coiled spring 409. Any other suitable biasing device is contemplated.

In the illustrated embodiment, the needle 404 is fixedly secured to the housing 452, the catheter 402 is releasably secured to the biasing member 407 via the catheter hub 446, and the stiffener 406 is fixedly secured to the biasing member 407. Accordingly, as shown in FIG. 7B, when the actuator 454 is activated, the catheter 402 and the stiffener 406 are automatically deployed over the needle 404. The actuator 454 is this coupled to the stiffener 406 and is configured to control movement of the stiffener 406. In particular, the actuator 454 is coupled with the biasing member 407, which is directly attached to the stiffener 406, such that actuation of the actuator 454 effects distal advancement of the stiffener 406.

Figure 8A:
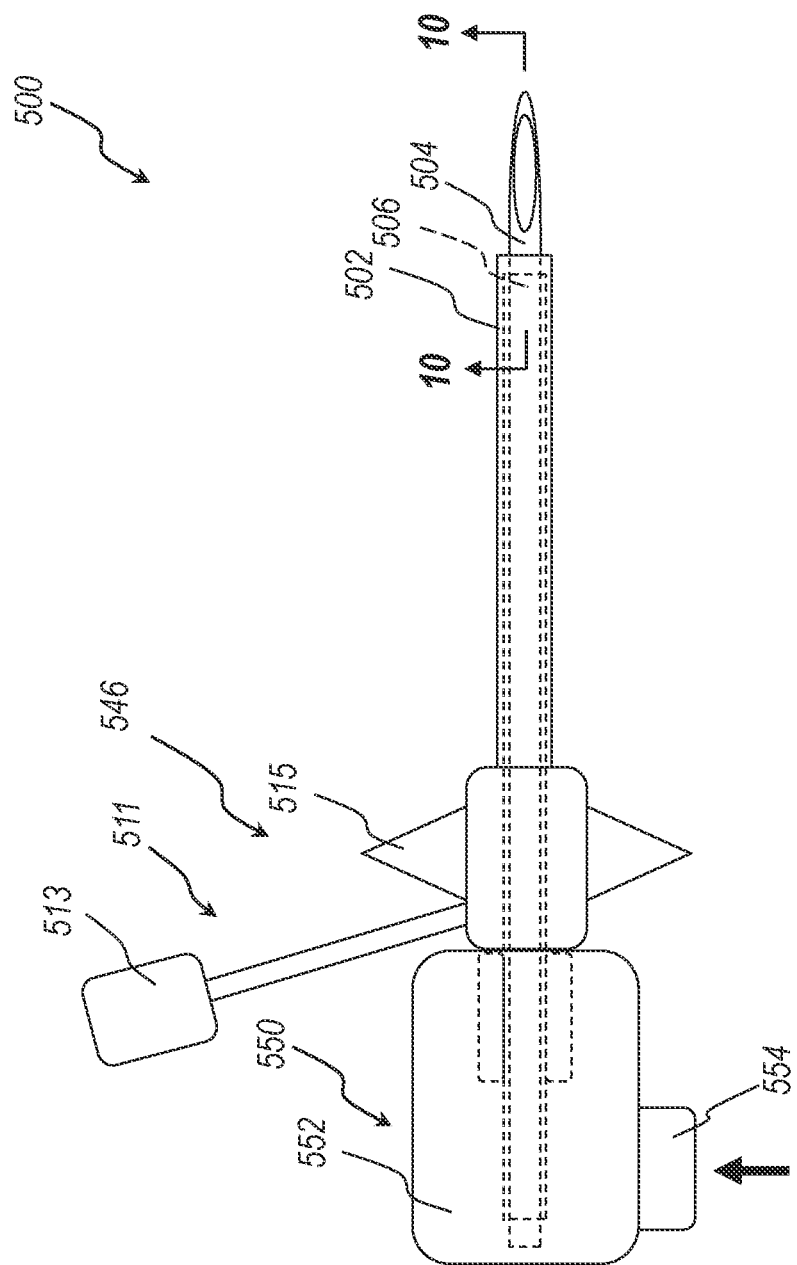
FIG. 8A is a top plan view of another embodiment of a catheter delivery system that is configured for automatic deployment of the catheter over the distal tip of the needle, wherein the system is depicted in an undeployed state, and wherein the system includes a catheter hub disposed outside of a housing portion of a needle hub.
Figure 8B:
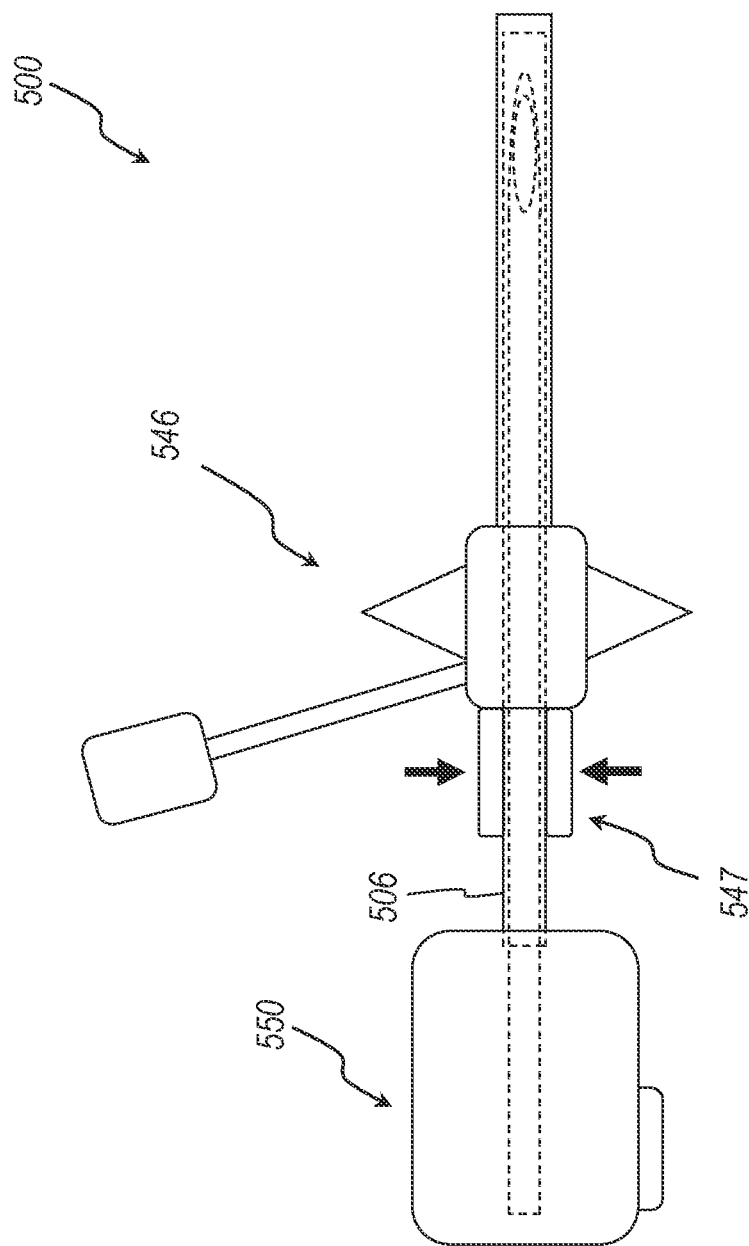
FIG. 8B is another top plan view of the catheter delivery system of FIG. 8A after an actuator has been actuated, wherein the system is depicted in a deployed state, and wherein the system includes a further actuator configured to decouple the catheter hub from the needle hub.

FIGS. 8A and 8B depict another embodiment of a catheter delivery system 500 that is configured for automatic deployment of a catheter 502 and a stiffener 506 over a distal end of a needle 504. FIG. 8A depicts the system 500 in an undeployed state, and FIG. 8B depicts the system 500 in a deployed state.

The system 500 includes a catheter hub 546 that is disposed outside of, or at an exterior of, a housing 552 portion of a needle hub 550 when the system 500 is undeployed. As shown in FIG. 8B, deployment of the system 500 moves the catheter hub 546 distally away from the needle hub 550.

In some embodiments, one of the catheter hub 546 or the stiffener 506 includes an actuator 547 that is configured to decouple the catheter hub 546 from the stiffener 506. More generally, the actuator 547 can be activated to decouple the catheter hub 546 from the needle hub 550. Any suitable actuator arrangement is contemplated, such as those previously described. In the illustrated embodiment, the actuator 547 includes pressure pads at opposing sides of the stiffener 506 that can be activated via a pinching action. Pinching the pressure pads can decouple a mechanical linkage via which the catheter hub 546 is connected to the stiffener 506.

With reference to FIG. 8A, the illustrated catheter hub 546 can include a side port 511 that extends at an angle from a longitudinal axis of the system 500. In some embodiments, a fluid connector 513 is disposed at an end of the side port 511. For example, in some embodiments, the fluid connector 513 includes a Luer fitting (e.g., a female Luer fitting).

Figure 9:
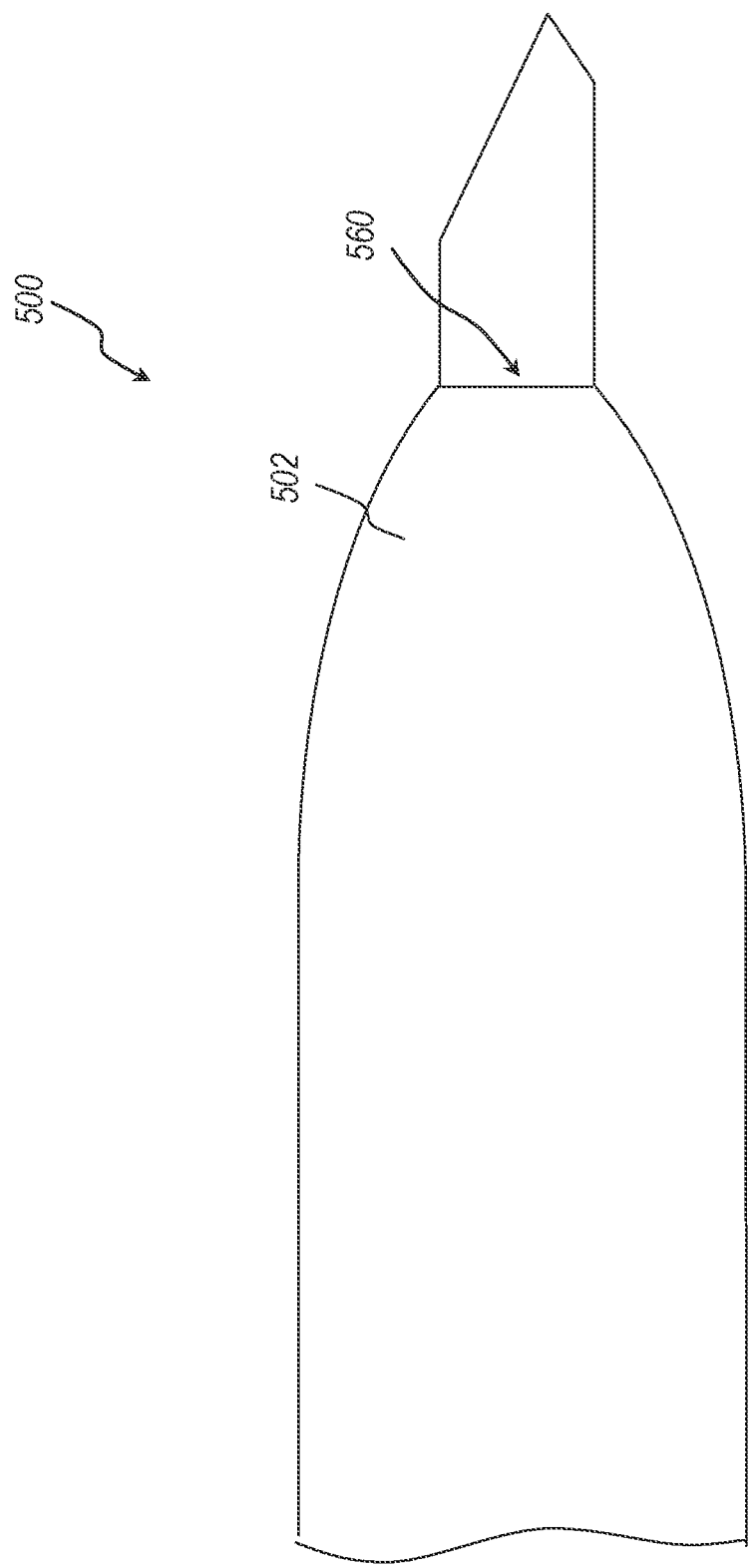
FIG. 9 is a side elevation view of a distal end of the catheter delivery system of FIG. 8A that depicts a catheter of the system that has a distal end with single fluid transfer port, which is positioned at a distal tip of the catheter, and that is devoid of fluid transfer ports through a sidewall thereof.

FIG. 9 is a side elevation view of a distal end of the system 500. In the illustrated embodiment, the catheter 502 defines only a single fluid transfer port 560, which is positioned at a distal tip of the catheter 502. The catheter 502 is devoid of any further fluid transfer ports, such as through a sidewall of the catheter 502.

Figure 10:
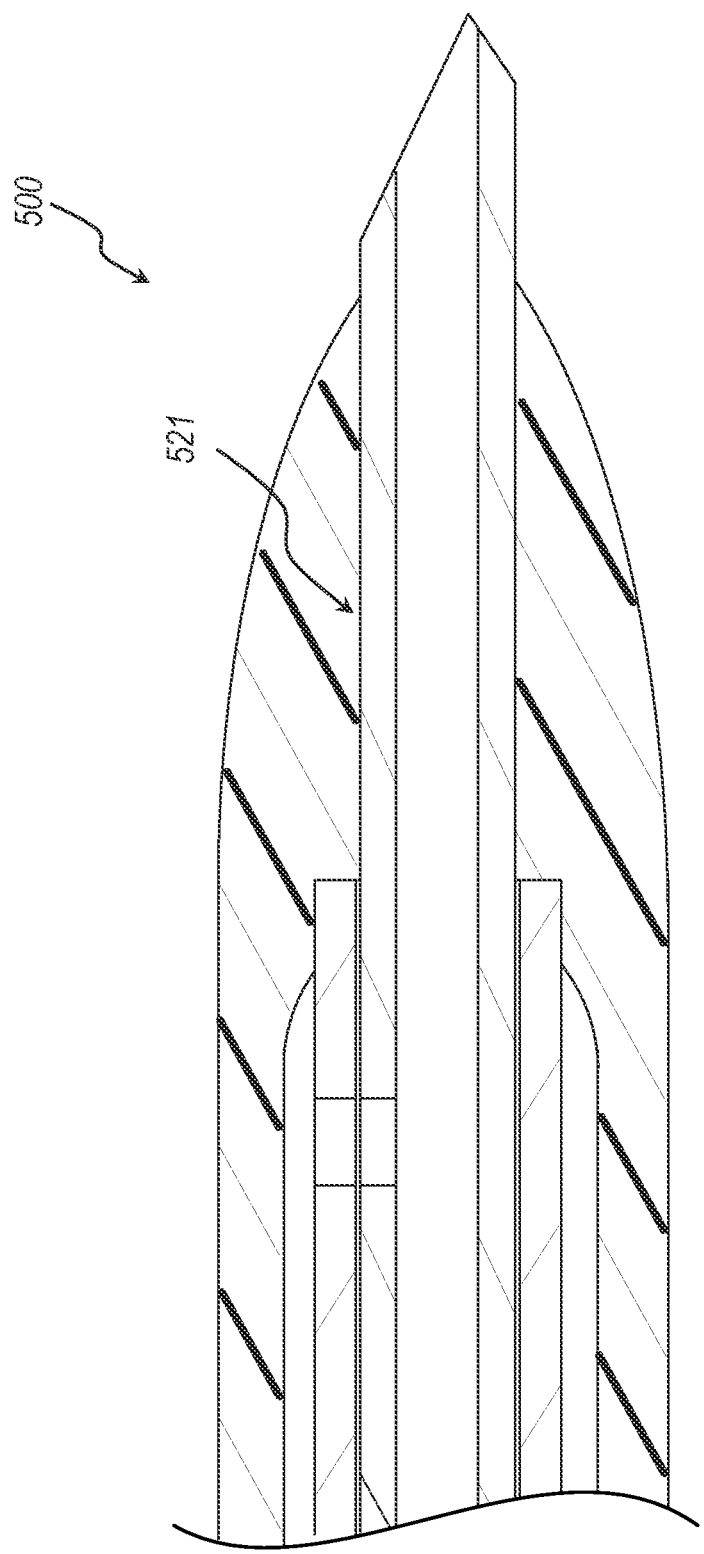
FIG. 10 is a cross-sectional view of the distal end of the catheter delivery system of FIG. 8A taken along the view line 10-10 in FIG. 8A that depicts a lengthened adhesion region.

FIG. 10 is a cross-sectional view of the distal end of the catheter delivery system 500 of FIG. 8A taken along the view line 10-10 in FIG. 8A. The system 500 includes an adhesion region 521 that is significantly longer than a similar region previously discussed with respect to the system 100. Inclusion of a stiffener 506 can permit higher adhesion strengths between the catheter and the needle at the distal end of the catheter, as previously discussed.

Figure 11:
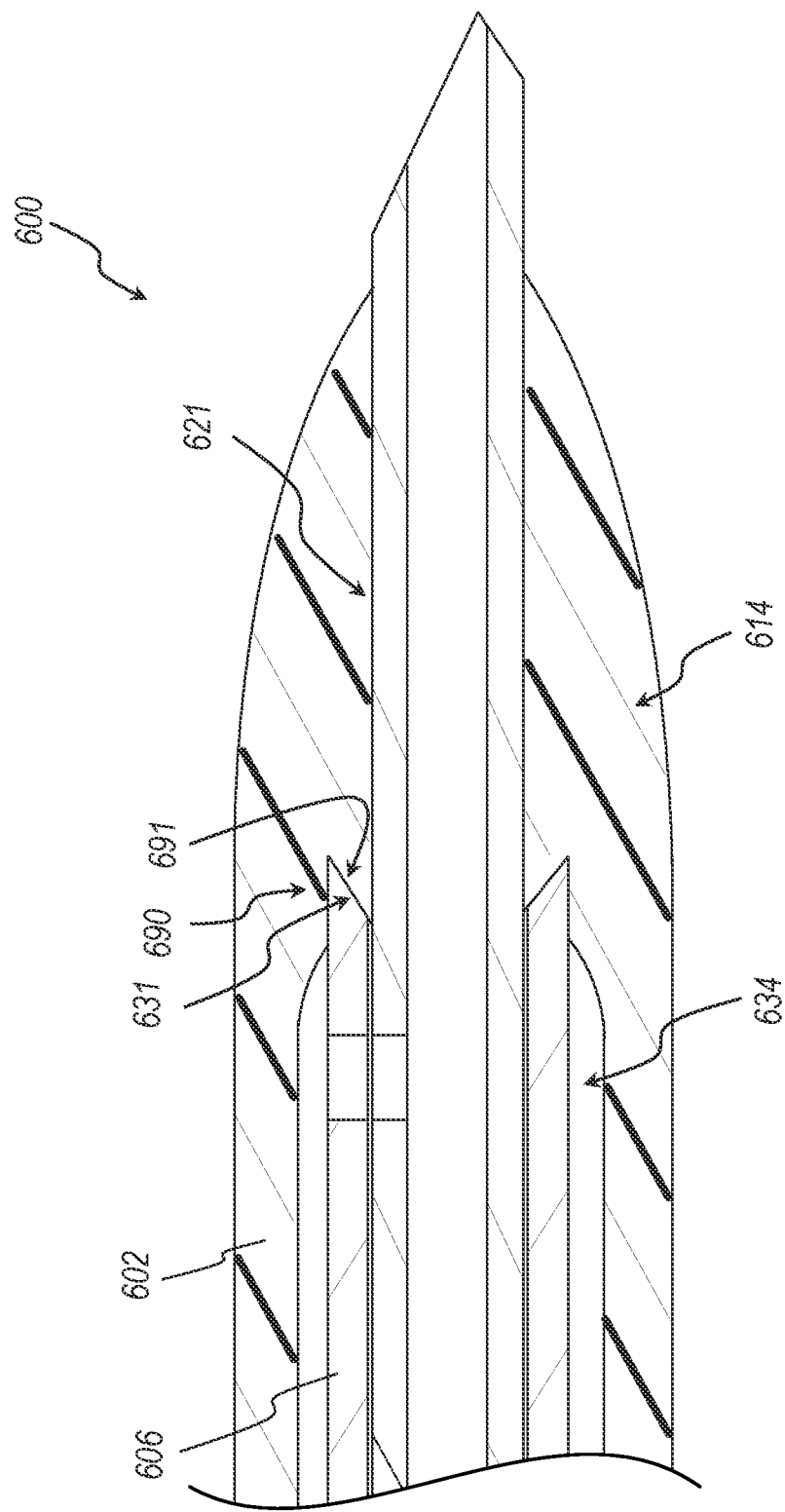
FIG. 11 is a cross-sectional view, similar to the views depicted in FIGS. 3 and 10, of another embodiment of a catheter delivery system that includes a lengthened adhesion region and a stiffener that includes a gripping interface at a distal tip thereof for engaging a distal end of the catheter.
Figure 12:
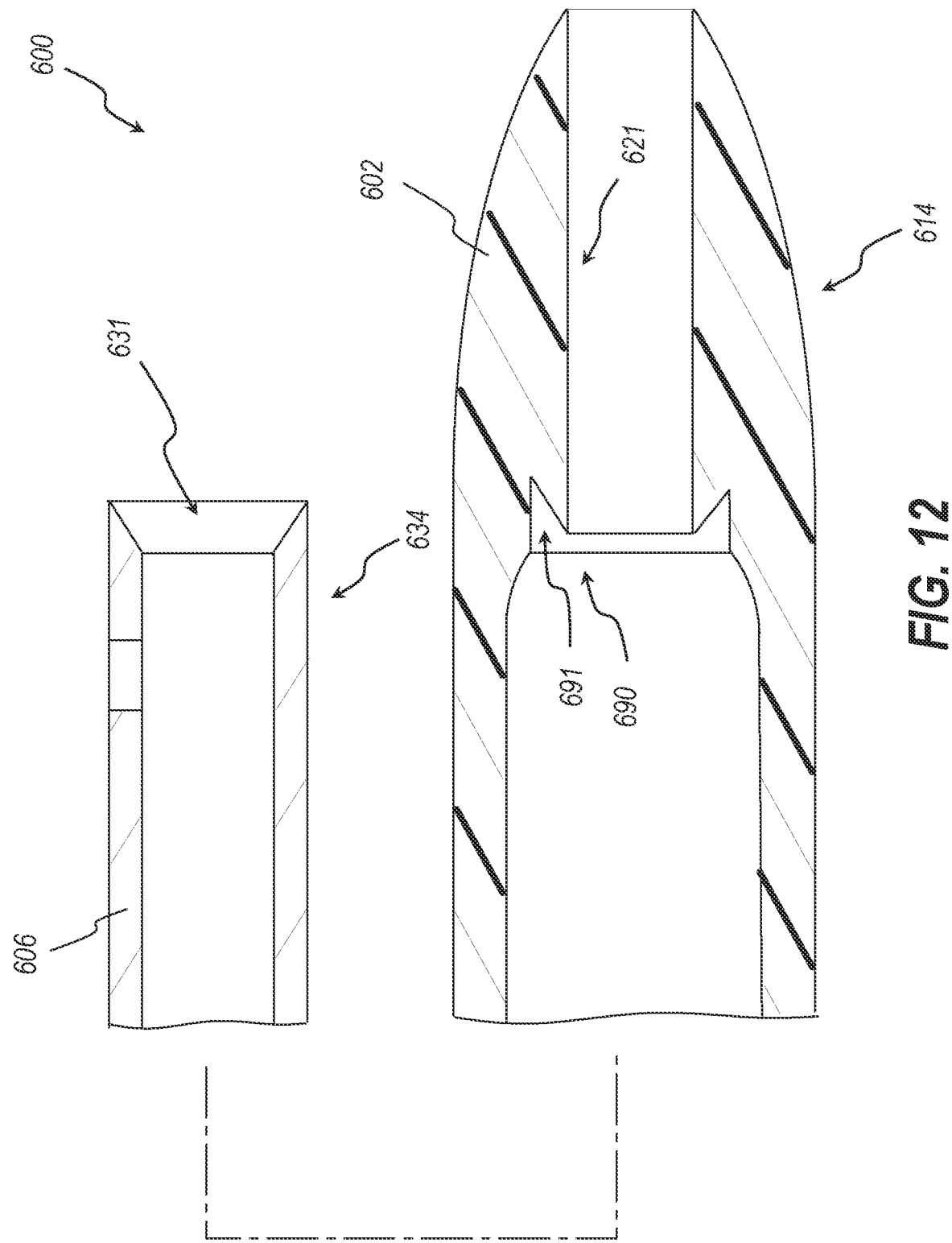
FIG. 12 is an exploded cross-sectional view of a portion of the catheter delivery system of FIG. 11 that further depicts the gripping interface at a distal tip of the stiffener and at a distal end of the catheter.

FIGS. 11 and 12 are cross-sectional views of another embodiment of a distal end of a catheter delivery system 600. As shown in FIG. 11, the system 600 includes a lengthened adhesion region 621, such as the adhesion region 521. As shown in both FIGS. 11 and 12, the system 600 also includes a stiffener 606 that has a gripping interface 631 at a distal tip thereof for engaging a distal end 614 of a catheter 602. The catheter 602 can define a catching region 690 that interfaces with the gripping interface 631. In the illustrated embodiment, the catching region 690 and the gripping interface 631 are shaped substantially complementarily.

The catching region 690 can include a distally extending recess 691. In the illustrated embodiment, the recess 691 includes a substantially cylindrical outer face and a substantially conical inner face that are joined at a distal end of the recess 691. Similarly, the gripping interface 631 of the stiffener 606 includes a substantially cylindrical face and a substantially conical face joined at the distal ends thereof. The recess 690 receives the gripping interface 631 of the stiffener 606. Accordingly, the distal end 614 of the catheter 602 is securely retained on the distal end 634 of the stiffener 606 when the stiffener urges the catheter 602 in a distal direction. In some instances, the catching region 690 is shaped or otherwise configured to readily permit the gripping interface 631 of the stiffener 606 to release therefrom when the stiffener 606 is withdrawn from the catheter 602 in the proximal direction.

In some embodiments, the recess 691 is formed via a mandrel in a tipping process that is completed prior to insertion of the stiffener 606 into the catheter 602. In other embodiments, the recess 691 is directly formed via the stiffener 606. For example, the stiffener 606 may serve as the mandrel during the tipping process, and the distal end of the catheter may be reshaped onto the stiffener 606 to achieve the complementary shape. In some instances, it may be easier for the stiffener 606 to release from the catheter 602 when the catheter 602 is tipped on a separate mandrel.

Figure 13:
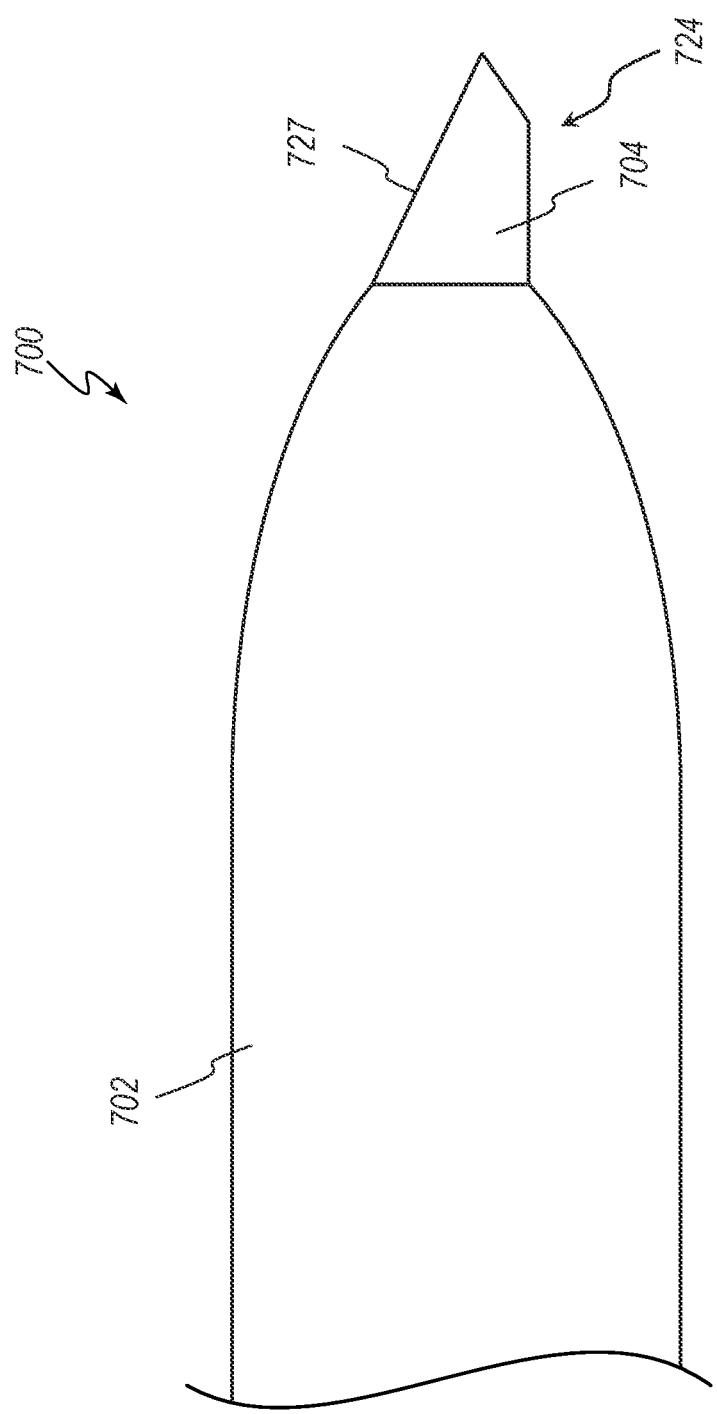
FIG. 13 is a side elevation view, similar to the views depicted in FIGS. 2 and 9, of another embodiment of a catheter delivery system that includes a catheter tip that extends substantially to a proximal end of an angled distal tip of a needle.
Figure 14:
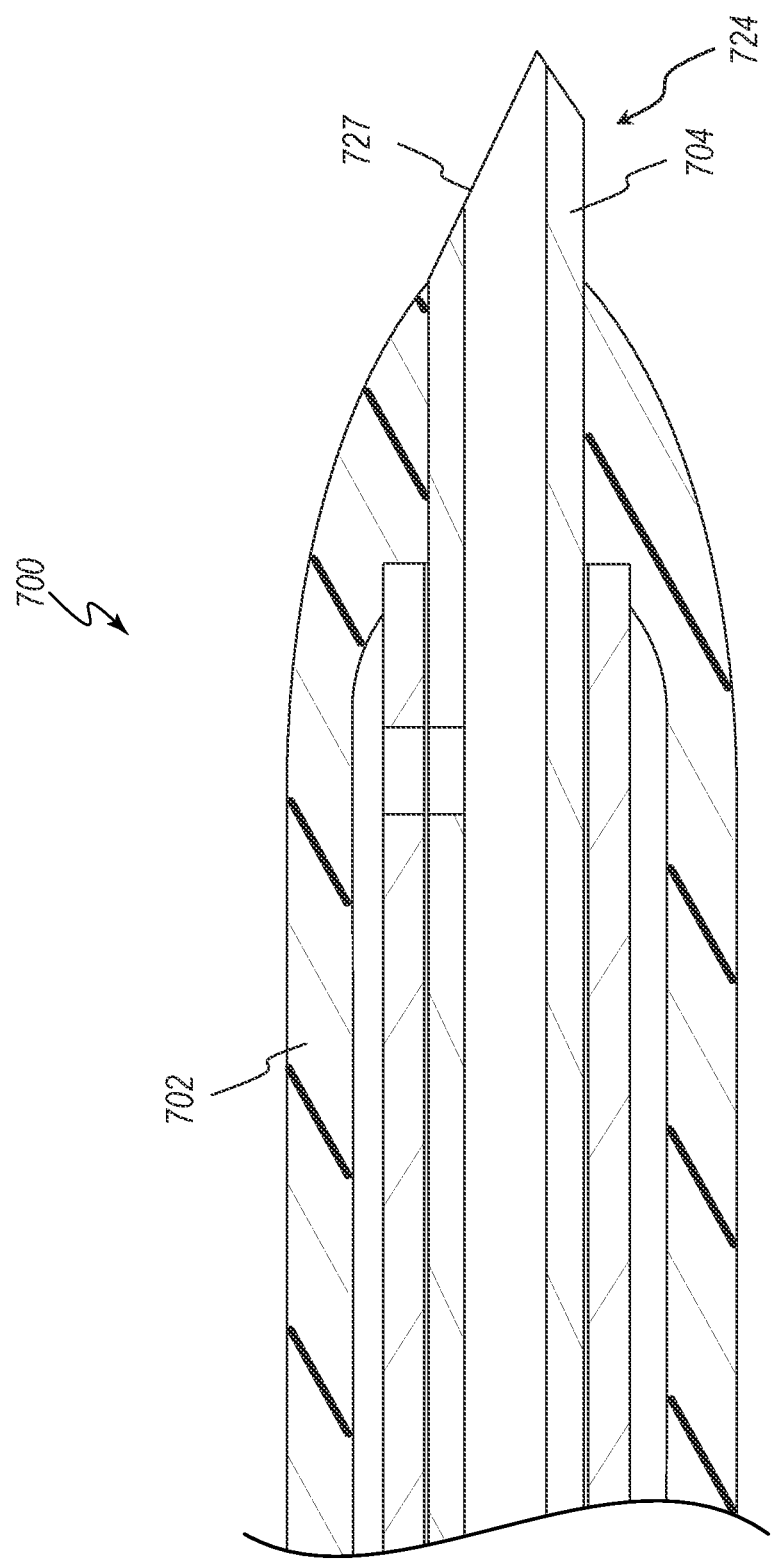
FIG. 14 is a cross-sectional view of the catheter delivery system of FIG. 13.

FIGS. 13 and 14 depict another embodiment of a catheter delivery system 700 that includes a catheter 702 having a tip 716 that extends substantially to a proximal end of a primary bevel 727 of a distal end 724 of a needle 704. In some instances, such an arrangement can facilitate insertion of the catheter 702 through the sidewall of the vessel.

Figure 15A:
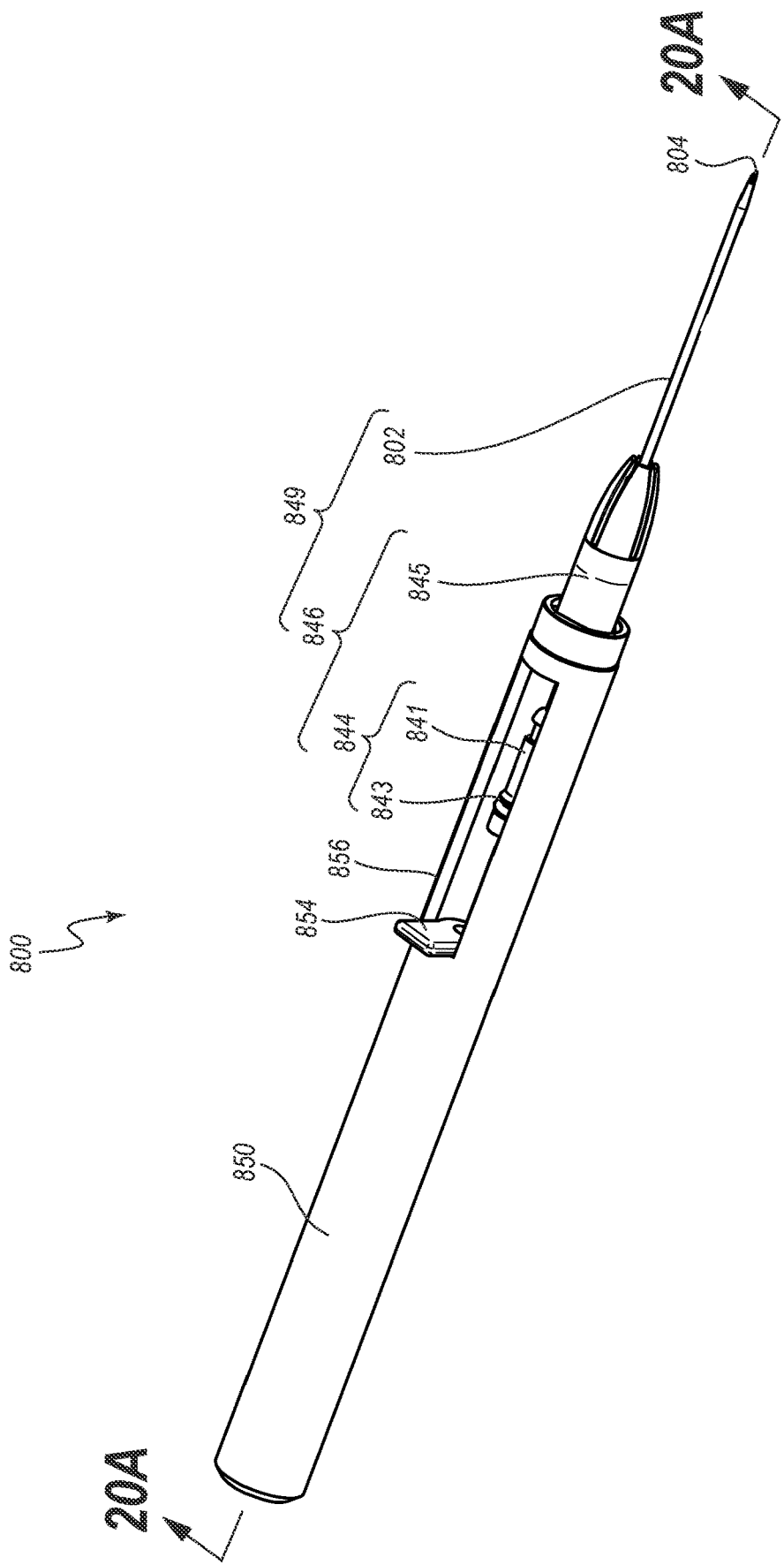
FIG. 15A is a perspective view of another embodiment of a catheter delivery system.
Figure 15B:
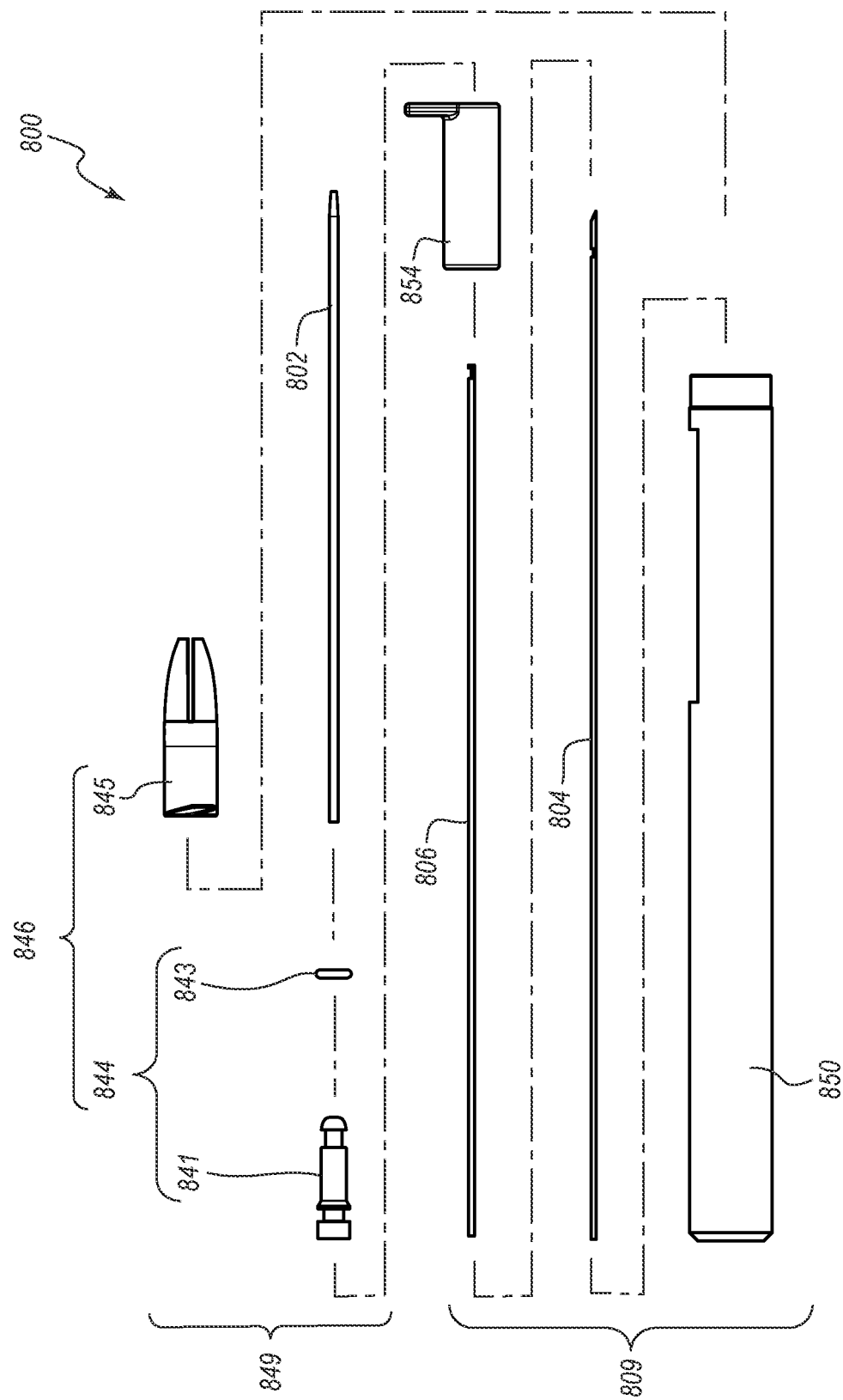
FIG. 15B is an exploded view of the catheter delivery system of FIG. 15A.

FIGS. 15A and 15B depict another embodiment of a catheter delivery system 800. The system 800 includes many of the features discussed above with respect to other embodiments of catheter delivery systems. Moreover, consistent with the disclosure conventions previously discussed, any suitable combination of the features of other systems disclosed herein, or components thereof, is contemplated for the system 800, and any of the features of the system 800, or components thereof, may be employed with other systems, or components thereof, disclosed herein, as applicable.

As discussed more fully hereafter, the system 800 can include a multi-part catheter hub, of which disparate portions can be in a separated orientation and/or distanced apart prior to deployment of the catheter, and can be assembled together during deployment of the catheter. In the illustrated embodiment, the catheter hub includes two distinct portions, one of which is secured to the handle (or needle hub) so as to be selectively removable therefrom, and the other of which is fixedly secured to the catheter. As the catheter is advanced distally, the portion that is attached to the catheter ultimately joins with the portion that is attached to the handle. The handle, and all components attached thereto, can be separated from and withdrawn from the assembled catheter hub and catheter. In various embodiments, such an arrangement can allow for the use of a relatively long catheter and/or can facilitate at least the initial insertion of the catheter into a vessel, such as by reducing an effective or unsupported length of the insertion needle that initially extends beyond a distal tip of the catheter. One or more of these and/or other advantages will be apparent from the present disclosure.

As shown in FIG. 15A and/or FIG. 15B, the system 800 can include a catheter 802, a needle 804, and a stiffener 806, which can be nested when assembled in manners such as previously described. The system 800 can further include a needle hub or handle 850, which can be fixedly secured to the needle 804 in any suitable manner, such as via friction fit, adhesion, overmolding, welding, and/or any other suitable technique. The system 800 can further include an actuator 854, which may also be referred to as a stiffener hub 854. In particular, the stiffener hub 854 comprises a unitary part that includes both a hub portion, or body, and an actuator portion, as described further below. The stiffener hub 854 can be fixedly secured to the stiffener 806 in any suitable manner, such as via friction fit, adhesion, overmolding, welding, and/or any other suitable technique. With reference to FIG. 15B, when assembled, the handle 850, the needle 804, the stiffener hub 854, and the stiffener 806 can be referred to as an insertion assembly 809, or may also be referred to as a deployment assembly, a needle-and-stiffener assembly, or a needle assembly.

The system 800 can further include a catheter assembly 849, which can comprise the catheter 802 and a multi-component or multi-part catheter hub 846. The catheter hub 846 can include a catheter hub core 841, which may alternatively be referred to as an internal or inner catheter hub component, a catheter hub shuttle, or as a first catheter hub member. The catheter hub core 841 can be fixedly secured to the catheter 802 in any suitable manner, such as via adhesion, overmolding, welding, and/or any other suitable technique.

In some embodiments, the core 841 is coupled with a seal member 843, such as an O-ring. Together, the core 841 and the seal member 843 form a core assembly 844. In the illustrated embodiment, the catheter hub 846 further includes a catheter connection hub 845, which may alternatively be referred to as an external or outer catheter hub component, a catheter hub housing, a catheter hub casing, a catheter hub shell, or as a second catheter hub member. As discussed in further detail below, the core assembly 844 can be separate from the connection hub 845 when the system 800 is in an undeployed state, and the core assembly 844 can be attached to the catheter connection hub 845 upon deployment of the catheter 802.

The catheter connection hub 845 can be releasably, removably, or selectively connected to the handle 850 of the insertion assembly 809 in any suitable manner. In the illustrated embodiment, the connection hub 845 is releasably connected to a distal end of the handle 850. As discussed further below, in some embodiments, once the catheter hub 846 has been assembled, or stated otherwise, upon or after deployment of the catheter 802, the connection hub 845 can be detached from the handle 850. The handle 850, and all components connected thereto—e.g., the needle 804, the stiffener 806, and the stiffener hub 854—can be withdrawn from the catheter assembly 849. Stated otherwise, after deployment of the catheter 802 to a desired depth within the vasculature of the patient, the insertion assembly 809 can be decoupled and removed from the catheter assembly 849. In the illustrated embodiment, the catheter assembly 849 and the insertion assembly 809 are joined by, and are detachable from each other at, a connection interface (e.g., complementary threading) between the connection hub 845, and the handle 850, respectively.

FIGS. 16A and 16B depict further details of the handle 850. The handle 850 includes a housing 852, which can be formed in any suitable manner. The housing 852 can define a track 856 through which a portion of the stiffener hub 854 can extend, as shown in FIG. 15A. In the illustrated embodiment, the track 856 substantially defines an elongated rectangular window or opening 901 through a sidewall of the housing 852.

The housing 852 can define a cavity 902 within which various components of the system 800, or portions thereof, can be received. The housing 852 may further define a wall 904 at a proximal end of the cavity 902, from which a connection protrusion 906 can extend distally into the cavity 902. The connection protrusion 906 can receive the proximal end of the needle 904. The needle 904 can be attached to the connection protrusion 906 in any suitable manner. In some embodiments, the connection protrusion 906 is sized to form a friction fit with the needle 904. In other or further embodiments, the needle 904 can be adhered to an inner sidewall of the protrusion 906. In the illustrated embodiment, the protrusion 906 defines a funnel or tapered region 908 that can assist in the insertion of the proximal end of the needle 904 into the protrusion 906 during assembly of the system 800.

The housing 852 can further define a connection interface 910, which can be configured to selectively couple with the connection hub 845. In the illustrated embodiment, the connection interface 910 is positioned at a distal end of the housing 852. The illustrated connection interface 910 comprises internal threading 912, which can couple with external threading on the connection hub 845. For example, in some embodiments, the threading 912 can be suitable for a quarter-turn connection between the housing 852 and the connection hub 845. Any other suitable connection interface 910 is contemplated.

Figure 17A:
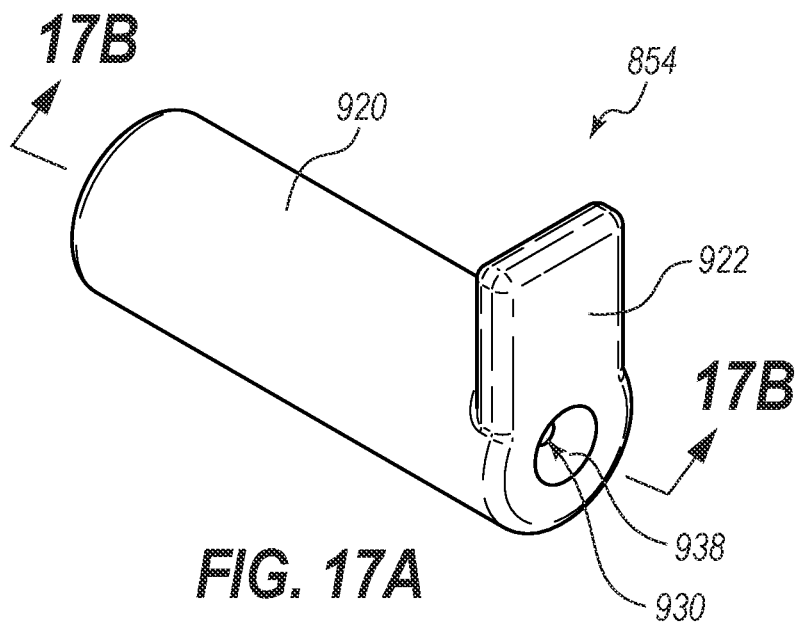
FIG. 17A is a perspective view of an embodiment of a stiffener hub that is compatible with the catheter delivery system of FIG. 15A.
Figure 17B:
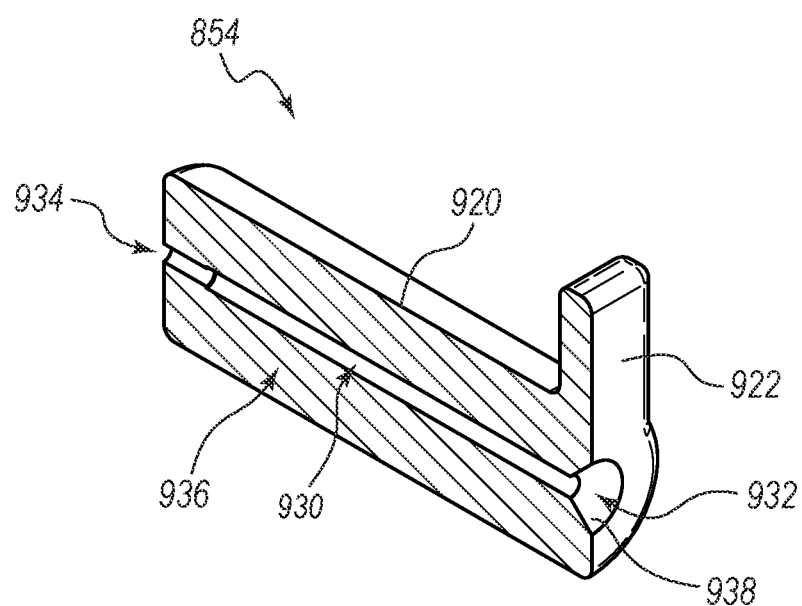
FIG. 17B is a cross-sectional view of the stiffener hub of FIG. 17A taken along the view line 17B-17B in FIG. 17A.

FIGS. 17A and 17B depict further details of the stiffener hub 854, which, again, may alternatively be referred to as an actuator in some instances—in the illustrated embodiment, the stiffener hub 854 is formed of a unitary part that includes a receptacle portion for coupling with a proximal end of the stiffener 806, and further includes an actuator portion engageable by a user to move the receptacle portion relative to the housing 852. In particular, the stiffener hub 854 can include a body 920, which can be positioned within the cavity 902 of the handle 852, and can further include a tab, button, grip, slide or slider, protuberance, projection, engagement element, or actuator 922 that extends laterally from the body 920. The actuator 922 can extend outwardly through the opening 901 defined by the track 856 of the handle 850 when the body 920 is positioned within the cavity 902 of the handle 850. Accordingly, in the illustrated embodiment, the actuator 922 of the stiffener hub 854 is manipulable at a position external to the handle 850. For example, in some instances, a practitioner can hold the handle 850 with a hand and can press distally on the actuator 922 (e.g., with a finger of the same or other hand) to advance (e.g., slide) the actuator 854 distally relative to the handle 850. In the illustrated embodiment, the body 920 is substantially cylindrical, and may readily slide within a cylindrical cavity 902 defined by the housing 852, and the actuator 922 is sized to slide within the opening 901 defined by the track 856. The body 920 can be sized to remain within the cavity 902, even when in the vicinity of the track 856. Stated otherwise, the body 920 can define a transverse width larger than a width of the track 856 so as to remain within the housing 852 and slide along the track 856. Other arrangements are also contemplated. For example, other complementary shapes are contemplated for an interior of the housing 852 and an outer surface of the actuator body 920 that can facilitate sliding or other relative movement, whether with or without contact.

With continued reference to FIGS. 17A and 17B, the body 920 can define a channel 930, which may extend through an entirety of the body 920. The channel 930 can have a distal end 932 and a proximal end 934. The distal end 932 can be sized to permit the stiffener 806 to extend therethrough, and the proximal end 934 can be sized to permit the needle 804 to extend therethrough. Accordingly, when the needle 804 is positioned within the stiffener 806, the needle 804 can extend through an entirety of the channel 930. In contrast, the stiffener 806 may only extend through the distal end 932 of the channel 930.

The channel 930 can include a recessed region 936, which can have a slightly enlarged inner diameter. The recessed region 936 can be connected with a proximal end of the stiffener 806 in any suitable manner (overmolding, adhesion, etc.).

In some embodiments, the body 920 includes a funnel 938 at the distal end 932 of the channel 930, which can assist with assembly of the system 800. For example, in some instances, the proximal end of the stiffener 806 is inserted proximally through the funnel 938 into the recessed region 936 so as to be connected therewith. The funnel 938 can facilitate such insertion of the stiffener 806 into the body 920 by directing the stiffener 806 into the narrow channel 930.

Figure 18A:
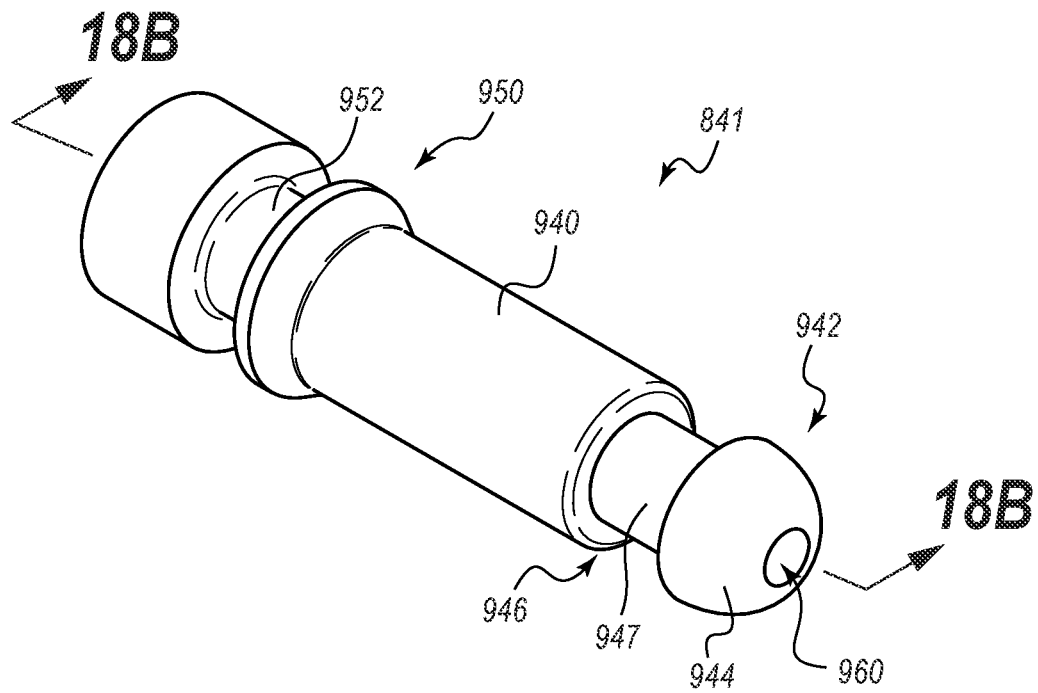
FIG. 18A is a perspective view of an embodiment of a catheter hub core that is compatible with the catheter delivery system of FIG. 15A.
Figure 18B:
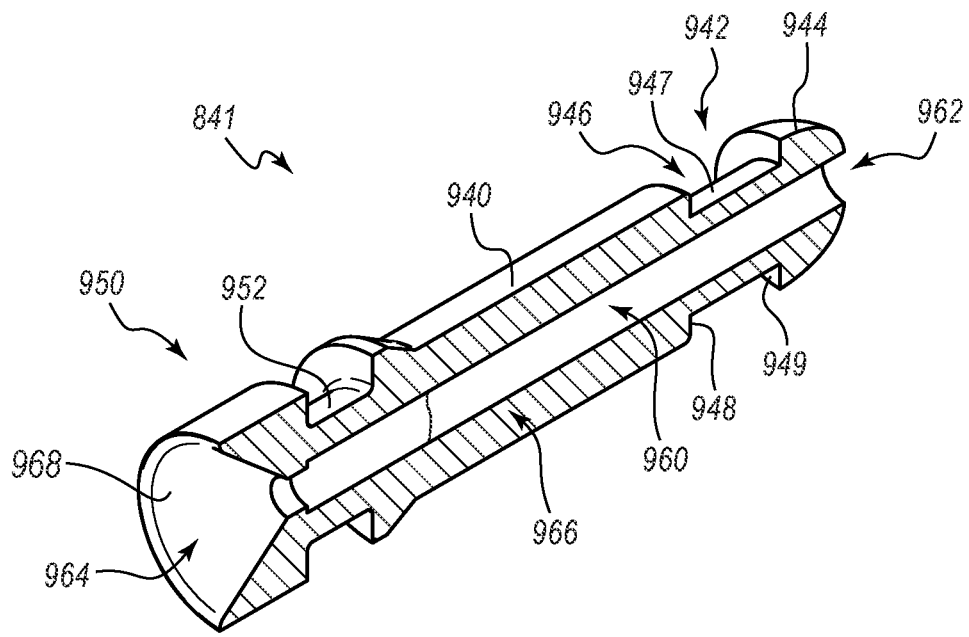
FIG. 18B is a cross-sectional view of the catheter hub core of FIG. 18A taken along the view line 18B-18B in FIG. 18A.

FIGS. 18A and 18B depict further details of the catheter hub core 841, which can include a body 940. The body 940 can include a connection region 942 and a sealing region 950. The connection region 942 can be configured to attach the body 940 to the catheter connection hub 845, as discussed further below. In the illustrated embodiment, the connection region 942 includes a separation nose 944 that expands from a smaller outer diameter to a larger outer diameter in the distal-to-proximal direction, and is configured to force or spread apart resiliently flexible arms as the hub core 841 is advanced distally between the arms. The illustrated separation nose 944 is shaped substantially as a paraboloid, although other shapes and configurations are contemplated (for example, conical, hemispherical, etc.).

The connection region 942 further includes a connection interface 946 that is configured to interact with portions of the catheter connection hub 845 to secure the catheter hub core 841 to the catheter connection hub 845. In the illustrated embodiment, the connection region 942 includes a groove 947 into which portions of the catheter connection hub 845 are received to lock the catheter hub core 841 and the catheter connection hub 845 to each other, as described further below. The groove 947 can include a proximal sidewall 948 and a distal sidewall 949. In some embodiments, the sidewalls 948, 949 are substantially transverse to a longitudinal axis of the catheter hub core 841. For example, the sidewalls 948, 949 may each define a separate plane that extends orthogonally to the longitudinal axis.

The sealing region 950 can be configured to form or assist in forming one or more of an airtight, liquid-tight, or fluid-tight seal between the catheter hub core 941 and the catheter connection hub 845. The term "fluid" is used herein in its ordinary sense and includes materials that have no fixed shape, yield easily to external pressure, or are flowable, such as gases (e.g., air, nitrogen, etc.) and liquids (e.g., saline, deionized water, etc.). Accordingly, a fluid-tight seal can be both an airtight seal and a liquid-tight seal. In the illustrated embodiment, the sealing region 950 includes a channel or groove 952 sized to receive the seal member 843 therein.

With continued reference to FIGS. 18A and 18B, the body 940 can define a channel 960, which may extend through an entirety of the body 940. The channel 960 can have a distal end 962 and a proximal end 964. The proximal end 964 can be sized to permit the stiffener 806 to extend therethrough, and the distal end 962 can be sized to permit the catheter 802 to extend therethrough. Accordingly, when the needle 804, the stiffener 806, and the catheter 802 are in a nested orientation, such that the needle is positioned within the stiffener 806 and the stiffener 806 is positioned within the catheter 802, the needle 804 and the stiffener 806 can extend through an entirety of the channel 960. In contrast, the catheter 802 may only extend through the distal end 962 of the catheter hub core 841.

The channel 960 defined by the catheter hub core 841 can include a recessed region 966, which can have a slightly enlarged inner diameter. The recessed region 966 can be connected with a proximal end of the catheter 802 in any suitable manner (overmolding, adhesion, etc.). In the illustrated embodiment, the catheter hub core 841 is overmolded onto the catheter 802.

In some embodiments, the body 940 includes a funnel 968 at the proximal end 964 of the channel 960, which can assist with assembly of the system 800. For example, in some instances, the distal ends of the needle 804 and of the stiffener 806 are inserted distally through catheter hub core 841 and through the catheter 802. The funnel 968 can facilitate such insertion of the needle 804 and the stiffener 806 into the body 940 by directing these components into the narrow channel 960.

Figure 19A:
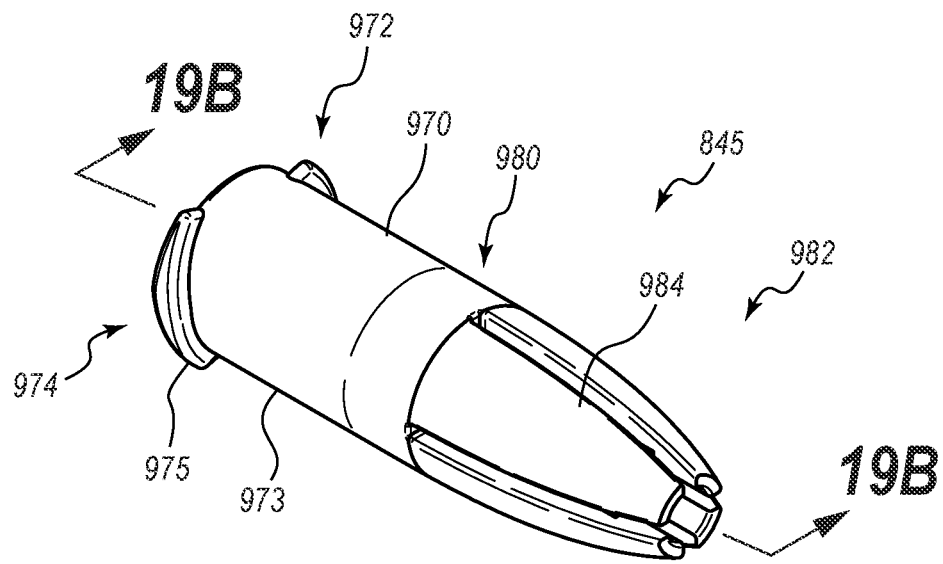
FIG. 19A is a perspective view of an embodiment of a catheter connection hub that is compatible with the catheter delivery system of FIG. 15A.
Figure 19B:
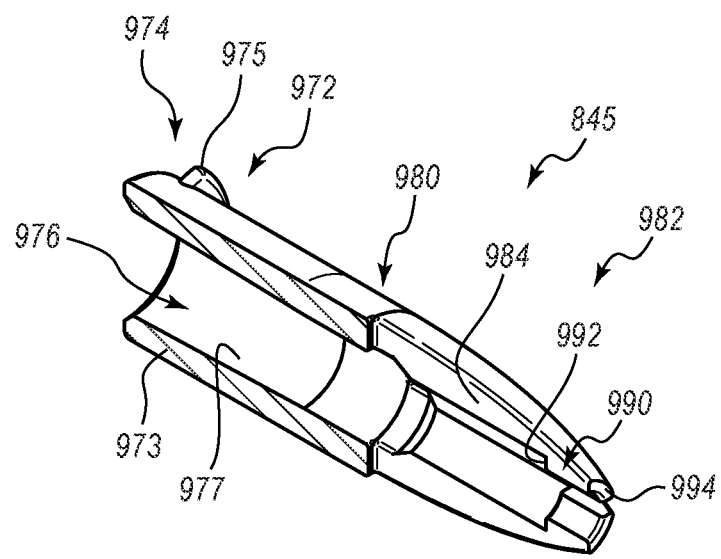
FIG. 19B is a cross-sectional view of the catheter connection hub of FIG. 19A taken along the view line 19B-19B in FIG. 19A.

FIGS. 19A and 19B depict further details of the catheter connection hub 845. The hub 845 includes a body 970 that defines a medical interface or medical connector 972 via which the catheter connection hub 845 can be coupled with any suitable medical device, such as, for example, any of the medical fluid components discussed above with respect to the medical fluid component 197. In the illustrated embodiment, the medical connector 972 is formed as a female luer fitting 973, which can couple, for example, with any medical fluid component that includes a complementary male luer fitting. In particular, the medical connector 972 can include any suitable connection interface 974, which comprises external threading 975 in the illustrated embodiment. Moreover, the body 970 can define a lumen 976 through which fluid may pass. In the illustrated embodiment, the portion of the lumen 976 associated with the connection interface 974 defines a luer taper 977.

The body 970 can further define a base 980 at a distal end of the medical connector 972. In some embodiments, the base 980 comprises the distalmost portion of the medical connector 972. In the illustrated embodiment, the base 980 is a region of the body 970 that extends distally from the medical connector 972. The body 970 can define a hub connection interface 982 that is configured to interact with the connection interface 946 of the catheter hub core 841 to secure the catheter connection hub 845 to the catheter hub core 841. In the illustrated embodiment, the connection interface 982 includes a plurality of resiliently flexible arms 984 that extend distally from the base 980. The illustrated embodiment includes four resiliently flexible arms 984. Other embodiments include more or fewer arms. Each resiliently flexible arm 984 includes an inward protrusion or catch 990 that is configured to directly interact with the connection interface 946 to secure the catheter connection hub 845 to the catheter hub core 841. In particular, the catches 990 can spring inwardly into the groove 947 defined by the catheter hub core 841 to secure the catheter connection hub 845 to the catheter hub core 841. The catches 990 can each include a proximal face 992 and a distal face 994 that can interact with the proximal and distal sidewalls 948, 949, respectively, of the groove 947 to prevent distal or proximal movement, respectively, of the hub core 841 relative to the connection hub 845 once the catches 990 have been received into the groove 947.

Other connection interfaces via which the catheter hub core 841 and the catheter connection hub 845 can be joined together are also contemplated. For example, in some embodiments, the catch-and-groove configuration can be reversed. For example, the connection interface 946 of the catheter hub core 941 can include one or more outwardly directed catches and the connection interface 982 of the catheter connection hub 845 can include one or more outwardly directed grooves. The catches can be sized to securely fit within the one or more grooves.

Figure 20A:
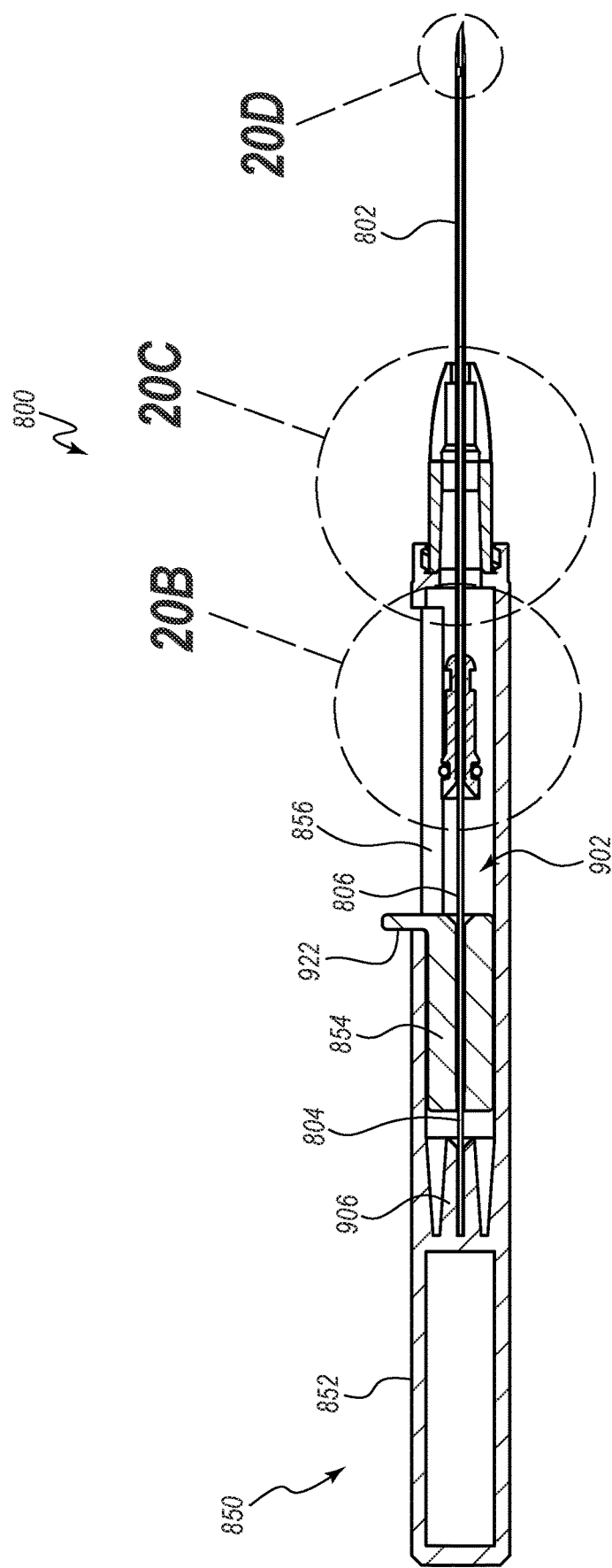
FIG. 20A is a cross-sectional view of the catheter delivery system of FIG. 15A in an undeployed state, the cross-sectional view being taken along the view line 20A-20A in FIG. 15A.

FIGS. 20A-20D are various cross-sectional views of the assembly 800 in an assembled and undeployed state. With reference to FIG. 20A, in this configuration, a proximal end of the needle 804 is fixedly attached to the handle 850. In particular, the needle 804 extends through the cavity 902 defined by the housing 852 and is adhered within the connection protrusion 906 defined by the housing 852.

The stiffener hub 854 is positioned over the needle 804 within the cavity 902 of the housing 852, with the actuator 922 of the stiffener hub 854 extending through the track 856 defined by the housing 852. The stiffener 806 is positioned within and attached to the stiffener hub 854, and the stiffener 806 is positioned over the needle 804. Stated otherwise, the needle 804 is nested within the stiffener 806. The stiffener 806 can slide or otherwise translate proximally over the needle 804 from the position shown in FIG. 20A.

Figure 20B:
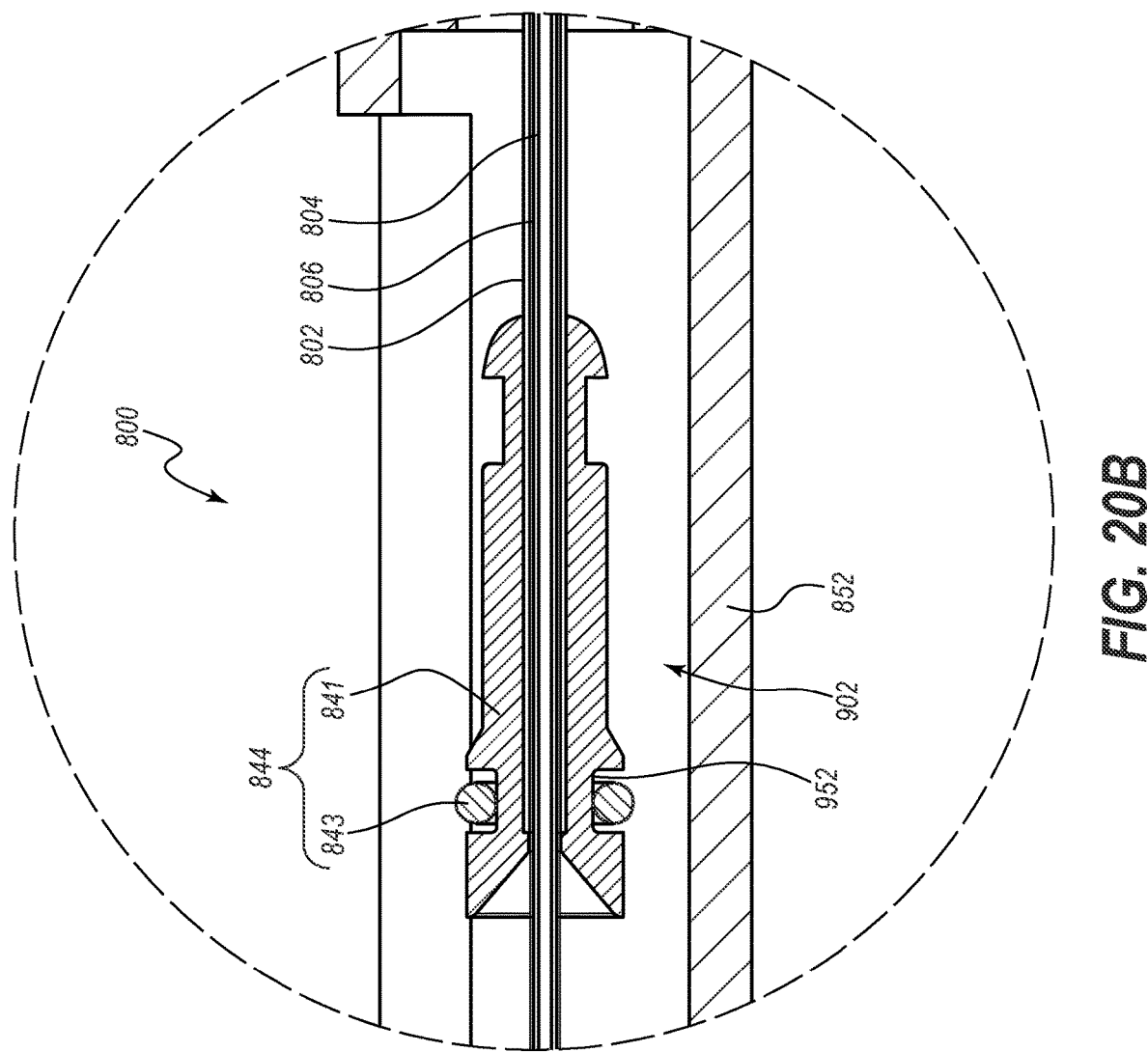
FIG. 20B is an enlarged cross-sectional view of the catheter delivery system taken along the view region 20B identified in FIG. 20A.

With reference to FIG. 20B, the core assembly 844 is secured to the catheter 802 so as to move in unison therewith. In particular, the catheter hub core 841 is positioned over the stiffener 806 within the cavity 902 of the housing 852. The catheter 802 is positioned within and attached to the catheter hub core 841, and is positioned over the needle stiffener 806. Stated otherwise, the stiffener 806 and the needle 804 are nested within the catheter 802. The stiffener 806 and the catheter 802 can translate (e.g., together, or in unison) over the needle 804 from the position shown in FIG. 20B. The seal member 843 is positioned within the groove 952 defined by the catheter hub core 841.

With reference to FIG. 20C, the catheter connection hub 845 is secured to the housing 852 and is positioned over the needle 804, the stiffener 806, and the catheter 802. In particular, the connection interfaces 910, 974 of the housing 852 and the catheter connection hub 845, respectively, are joined together. In the illustrated embodiment, this securement is achieved via complementary threading. The catheter 802, the stiffener 806, and the needle 804 extend through the lumen 976 and between the resilient arms 984 of the catheter connection hub 845.

With reference to FIG. 20D, when the system 800 is in the undeployed state, at least a portion of a distal end 824 of the needle 804 extends distally beyond a distal tip 816 of the catheter 802. As with other embodiments discussed herein, the illustrated needle 804 can include a distal tip 826, which can be formed by a primary bevel 827 and a back bevel 828.

As with other embodiments described herein, a distal end 814 of the catheter 802 can be attached to the needle 804. The attachment may be, for example, a friction fit between and/or a physical bond between the materials of the catheter 802 and the needle 804. In particular, an inner face 893 of the catheter 802 can frictionally engage and/or bond to the needle 804. The distal end 814 of the catheter 802 can further include an engagement face or abutment surface 891 that can be engaged by a distal tip 836 of the stiffener 806 in manners such as previously described.

The needle 804 can define a lumen 875 and a port 880. The stiffener 806 can also define a port 882 that can be aligned with the port 880 to form a passageway 886. The catheter 802 and the stiffener 806 can cooperate to define a channel 888. The lumen 875, the passageway 886, and the channel 888 can demonstrate a flash of blood to a practitioner when the system 800, in the illustrated undeployed state, is introduced into a blood vessel, in manners such as previously described. Similarly, the system 800 can maintain alignment of the ports 880, 882 in manners such as previously described. In particular, with reference again to FIG. 20A, the stiffener hub 854 can be rotationally locked relative to the housing 852, which in turn maintains a rotationally locked orientation between the port 882 of the stiffener 806 and the port 880 of the needle 804. In the illustrated embodiment, the actuator 922 is restrained from any rotation, or is restrained to only small rotations, within the track 856 defined by the housing 852, which achieves the rotational lock between the stiffener hub 854 and the housing 852.

FIGS. 21A-21D are various cross-sectional views of the system 800 in a partially deployed state. As previously discussed, the distal end of the system 800 may be advanced into the vessel of a patient when in the undeployed configuration depicted in FIGS. 20A-20D, and once a flash of blood is viewed, the system 800 may be deployed to advance the catheter over the needle to a further distance within the vessel.

Figure 21A:
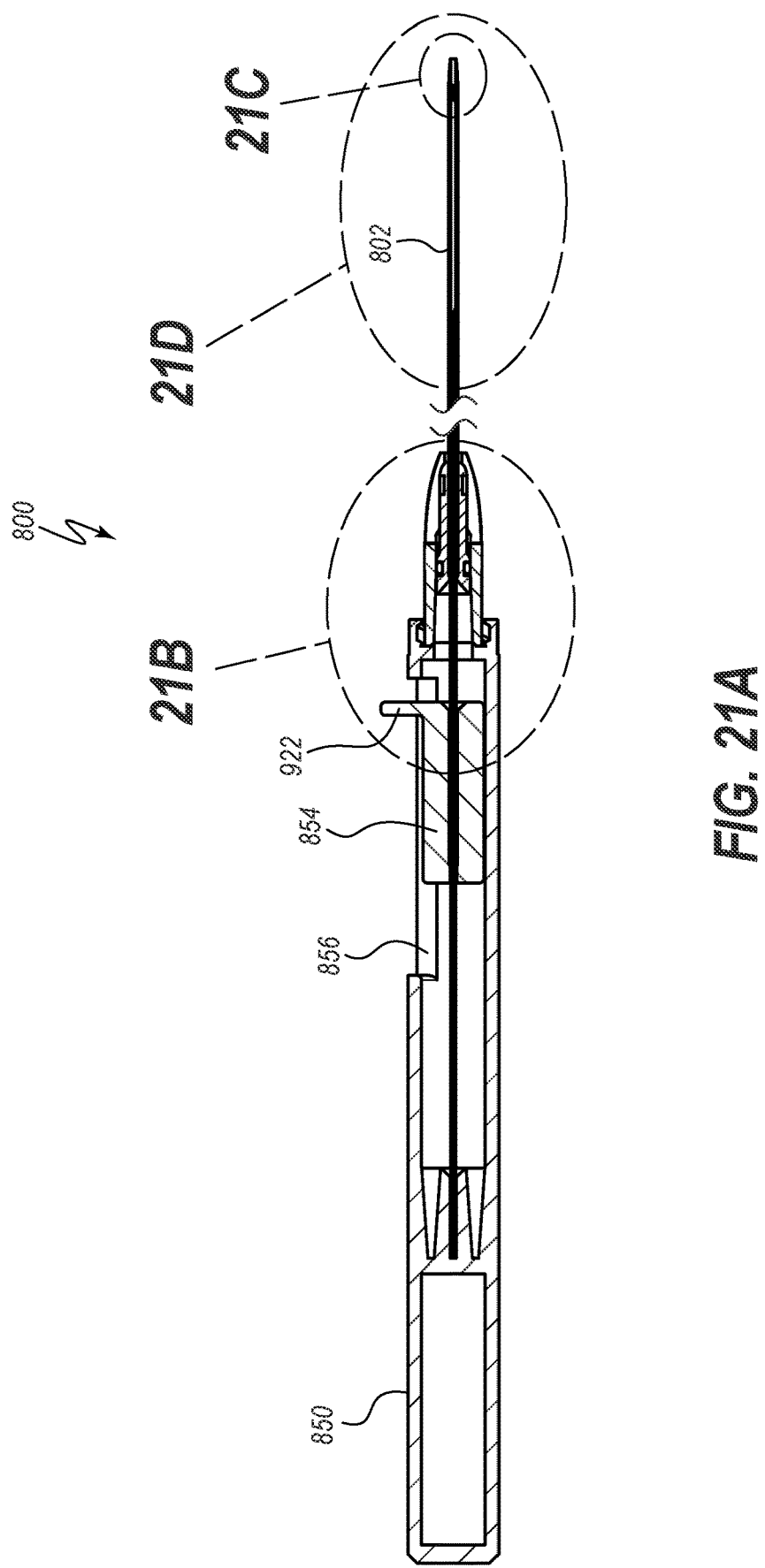
FIG. 21A is another cross-sectional view of the catheter delivery system of FIG. 15A in a partially deployed state.

With reference to FIG. 21A, in the illustrated partially deployed configuration, the stiffener hub 854 has been advanced in a forward or distal direction along the track 856, almost to a distal end of the track 856. In some instances, a practitioner may hold the handle 850 with one hand and push forward on the actuator 922 with a finger of the same hand (e.g., with the index finger or thumb) to advance the stiffener hub 854 distally to the position shown. For example, in some embodiments, a practitioner can hold the handle 850 between the thumb and one or more fingers (potentially including the index finger) of one hand to insert the distal tips of at least the needle 804 and the catheter 802 into a vessel of a patient. Thereafter, the practitioner can continue holding the handle 850 with the hand, and may use the index finger of the hand to engage the actuator 922 and advance the stiffener hub 854 distally. For example, in some instances, the practitioner may curl the index finger and urge a proximal face of the actuator 922 distally with at least a portion of the fingernail of the index finger (e.g., a surface of the fingernail) while uncurling the index finger.

Other methods of actuation are also contemplated. For example, in other instances of one-handed deployment, a tip of the index finger may be used, rather than the back surface of the fingernail. In still other instances, the thumb may be used. In other embodiments, a practitioner may use two-handed deployment.

Figure 21B:
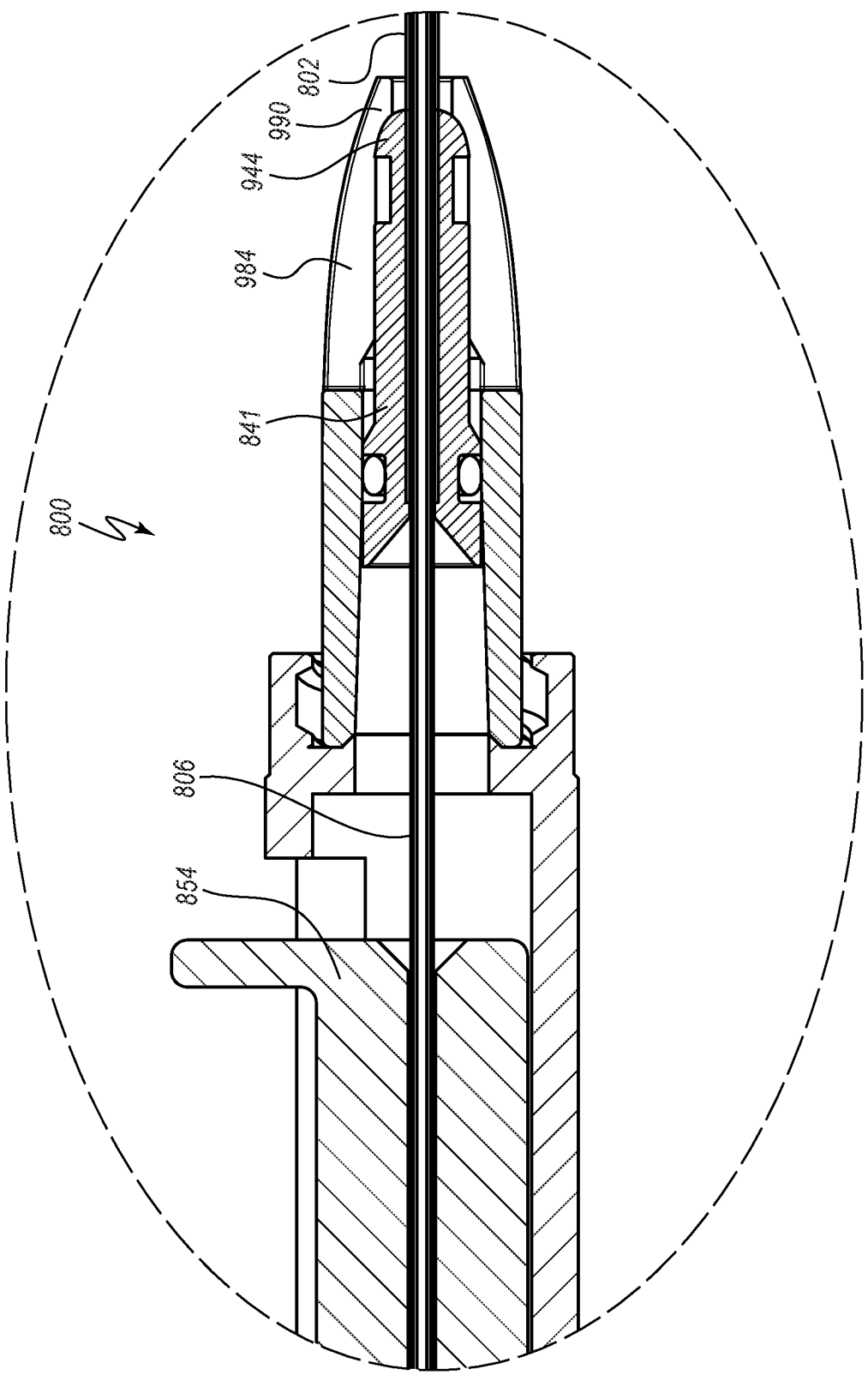
FIG. 21B is an enlarged cross-sectional view of the catheter delivery system taken along the view region 21B identified in FIG. 21A.
Figure 21C:
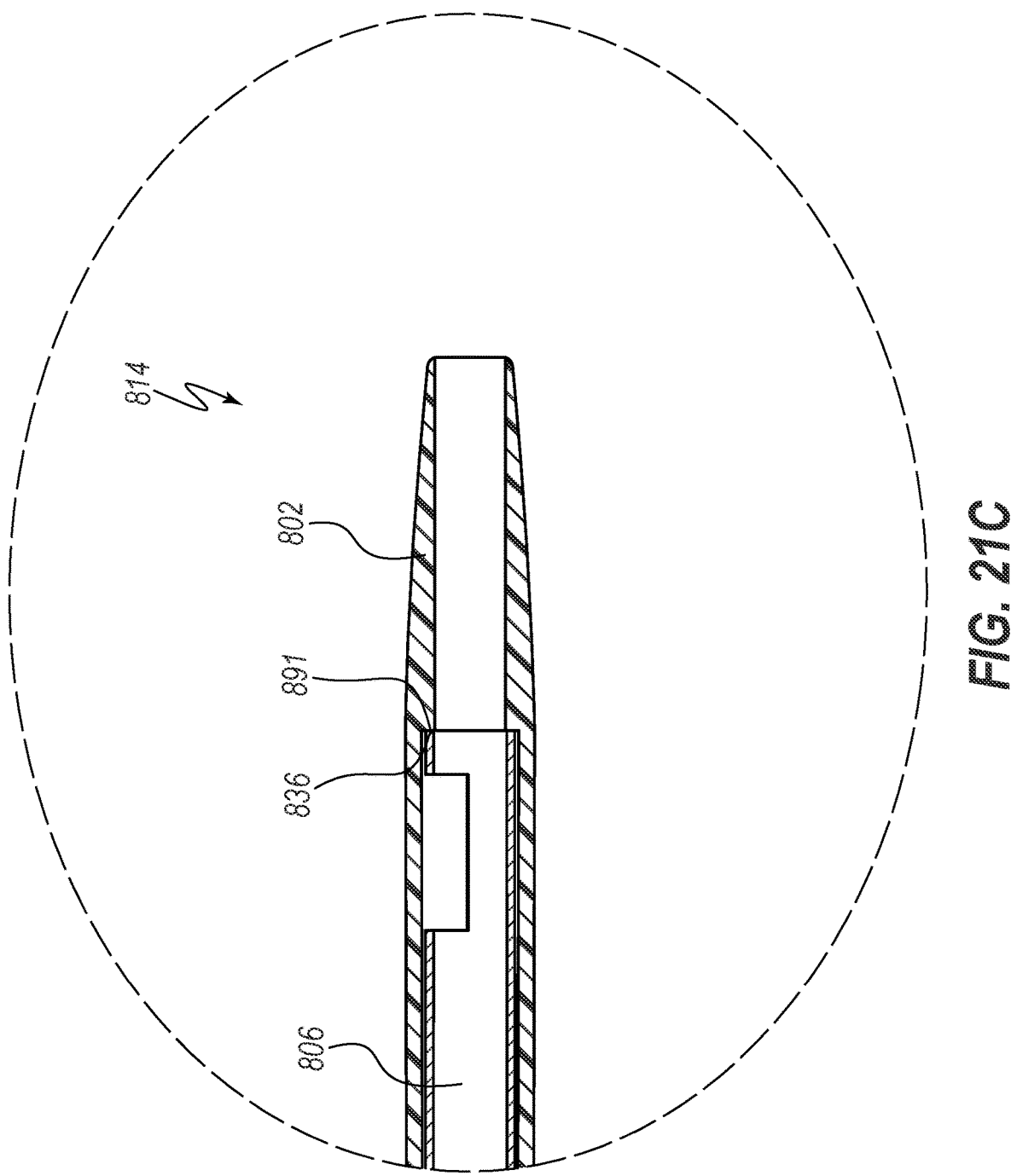
FIG. 21C is another enlarged cross-sectional view of the catheter delivery system taken along the view region 21C identified in FIG. 21A.

With reference to FIGS. 21B and 21C, distal advancement of the stiffener hub 854 can effect distal advancement of the catheter hub core 841. In the illustrated embodiment, distal advancement of the stiffener hub 854 urges the stiffener 806 distally, given that the stiffener 806 is fixedly secured to the stiffener hub 854. As shown in FIG. 21C, the distal tip 836 of the stiffener 806 can engage, or stated otherwise, can press distally on the abutment surface 891 of the catheter 802. The force thus applied to the distal end 814 of the catheter 802 can urge the catheter 802 distally. The force can be sufficient to overcome any friction and/or break any bonds between the catheter 802 and the needle 804, as discussed above with respect to FIG. 20D.

With reference to FIG. 21B, distal movement of the catheter 802 can effect simultaneous distal movement of the catheter hub core 841, given that the catheter hub core 841 is fixedly secured to the catheter 802. That is, the stiffener 806 can apply distally directed force to the distal end 814 of the catheter 802 (see FIG. 21C), which can in turn draw the catheter hub core 841 distally.

The stiffener 806 can desirably be substantially rigid or non-compressible in a longitudinal dimension or direction. The stiffener 806 thus may impart axial support to or otherwise impart columnar rigidity to the catheter 802 so as to be able to longitudinally strengthen the catheter 802. Stated otherwise, the stiffener 806 can be strong in the longitudinal dimension and can longitudinally reinforce the catheter 802. The stiffener 806 thus can enable distal advancement of the catheter 802 within the vessel. In some instances, a feel of advancing the catheter 802 within the vessel via an internally disposed stiffener 806 can resemble the feel of advancing a catheter of like diameter and composition, but that is devoid of a stiffener, over a guidewire within the vessel.

The stiffener 806 can also desirably be relatively soft or flexible in lateral dimensions or directions (e.g., in dimensions orthogonal to a longitudinal axis of the stiffener 806). Stated otherwise, the stiffener 806 may desirably have a low bending stiffness in transverse dimensions. Such flexibility can permit the stiffener 806 to readily bend within the vessel to facilitate insertion of the stiffener 806 and catheter 802 into the vessel and/or advancement of the stiffener 806 and catheter 802 within the vessel. For example, such bendability can be desirable to permit the stiffener 806 (and the catheter 802) to be advanced through a vessel puncture site into the vessel, which can generally occur at an angle relative to a lumen of the vessel, and to thereafter readily make an initial bend to follow the lumen of the vessel. The stiffener 806 (and the catheter 802) can also more readily follow a contour of the vessel as the stiffener 806 is advanced to greater depths within the vessel.

In various embodiments, the longitudinally rigid and laterally flexible properties just described can be achieved by adjusting an area moment of inertia of the stiffener 806. For example, in some embodiments, the stiffener 806 is formed as a thin-walled tube. A thickness of the tube can be adjusted to achieve the desired lateral flexibility. In some instances, the flexibility is substantially the same in all lateral directions, or stated otherwise, the stiffener 806 is substantially symmetrically flexible in all dimensions transverse to the longitudinal axis thereof. In some embodiments, it can be desirable for the stiffener 806 generally and/or the material of which the stiffener 806 is formed to be as soft as possible while maintaining sufficient columnar strength to advance the catheter 802 to a final target depth within a vessel of a patient.

Figure 21D:
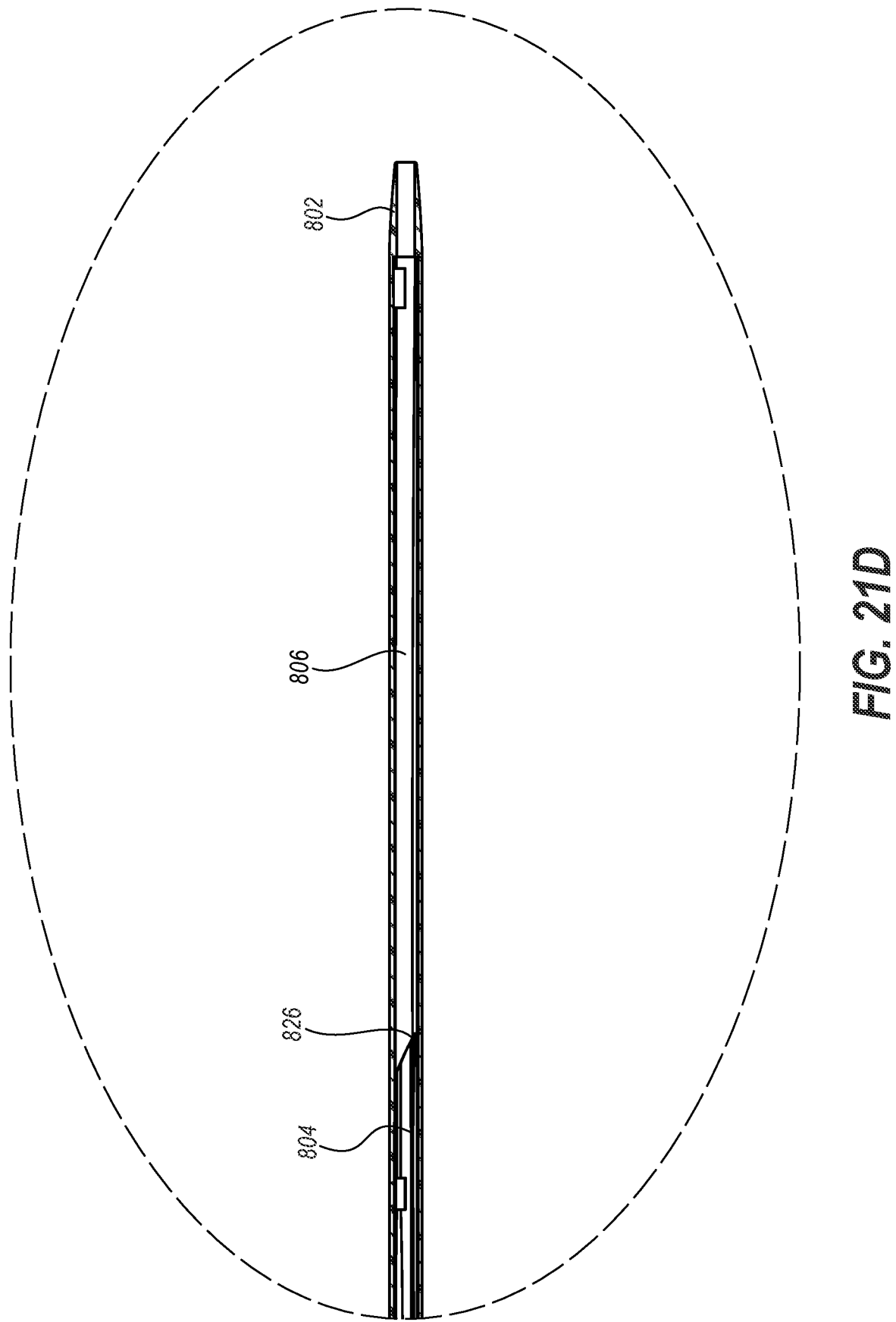
FIG. 21D is another enlarged cross-sectional view of the catheter delivery system taken along the view region 21D identified in FIG. 21A.

With reference to FIG. 21D, in some embodiments, the stiffener 806 may desirably be puncture-resistant, such that the distal tip 826 of the needle 804 may not pass through the stiffener 806, such as through a sidewall of a tubular stiffener 806. For example, as previously discussed, in some embodiments, the stiffener 806 can shield the needle 804 after the catheter 802 has been deployed via the system 800. That is, the stiffener 806 can shield the stiffener 806 during and after removal of the needle 804 and the stiffener 806 from the catheter 802.

Any suitable material is contemplated for the stiffener 806. In various embodiments, the stiffener 806 can be formed entirely of or include a superelastic material. For example, in some embodiments, the stiffener 806 comprises superelastic nitinol, such as superelastic nitinol tubing. In other or further embodiments, the stiffener 806 is formed entirely of or includes a suitable plastic, such as a polycarbonate, an engineering thermoplastic, such as DELRIN® (available from DuPont), shape-memory nitinol, etc.

With reference again to FIG. 21B, in the illustrated state of deployment, the catheter hub core 841 has been advanced distally until the separation nose 944 has come into contact with proximal surfaces of the catches 990 of the resiliently flexible arms 984 of the catheter connection hub 845. Upon further distal advancement of the catheter hub core 841, the rounded separation nose 944 will force the catches 990 outwardly, thus flexing the arms 984 radially outwardly to permit passage thereby of the separation nose 944. Stated otherwise, the separation nose 944 is configured to spread outwardly, displace (e.g., radially displace), or expand the arms 984 to permit passage thereby of the separation nose 944.

With reference again to FIG. 21D, as the system 800 is deployed, the stiffener 806 and the catheter 802 are advanced in unison into the vessel over the needle 804. As previously discussed, the stiffener 806 can provide desirable reinforcement of the catheter 802 so as to achieve insertion depths that may not be achievable in the absence of the stiffener 806. The stiffener 806 can permit insertion depths that may otherwise only be achieved by advancing a similarly configured catheter over a guidewire. Moreover, the stiffener 806 can shield the catheter 802 from contact with the needle 804, and particularly from contact with the distal point 826 of the needle 804, during deployment of the catheter 802 into the vessel and/or during retraction of the stiffener 806 and the needle 804 from the catheter 802 after placement of the catheter 802.

Figure 22B:
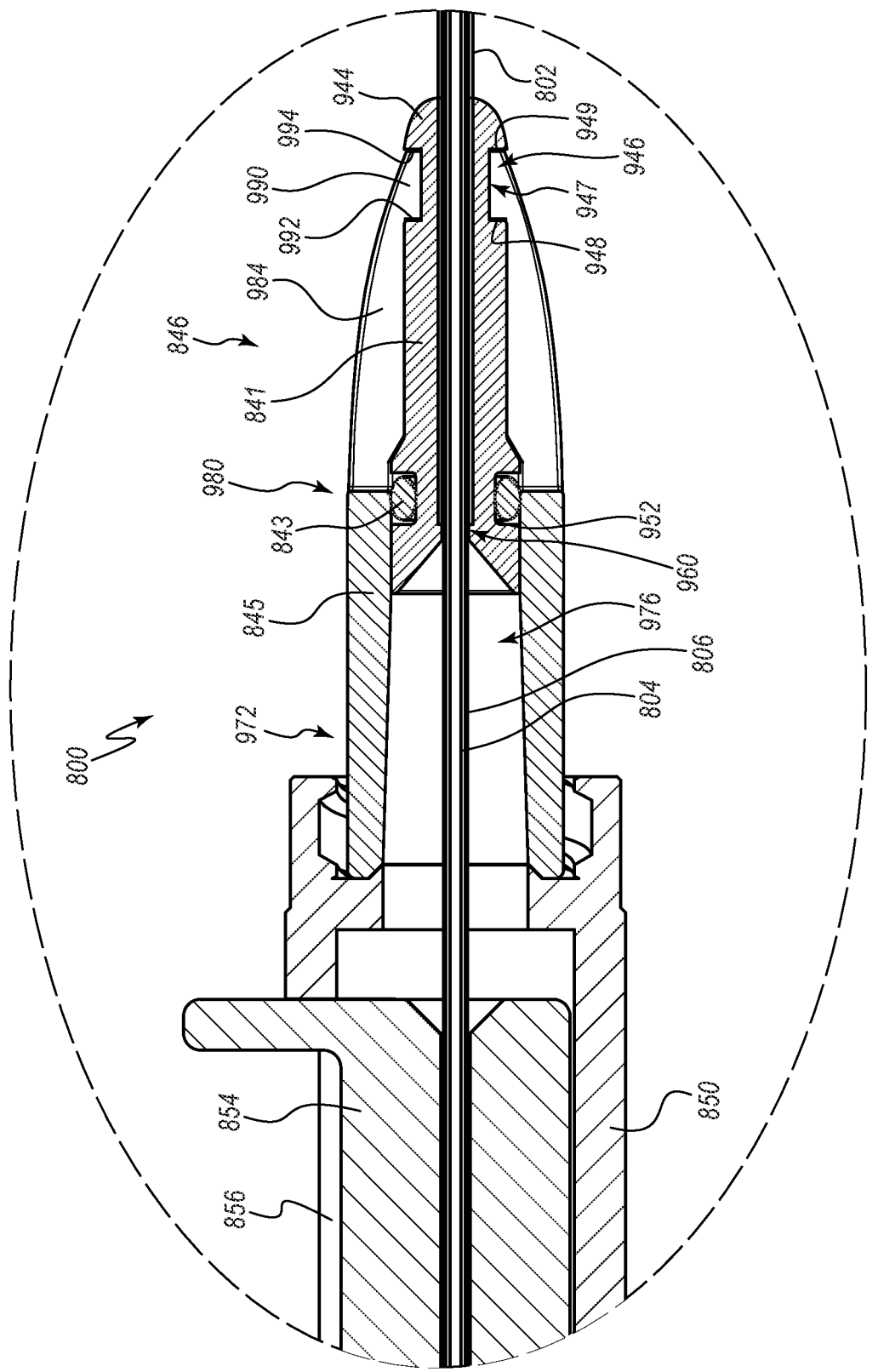
FIG. 22B is an enlarged cross-sectional view of the catheter delivery system taken along the view region 22B identified in FIG. 22A.

FIGS. 22A and 22B are cross-sectional views of the system 800 in a fully deployed state. In the illustrated embodiment, the stiffener hub 854 is advanced into close proximity to a distal end of the track 856 to fully deploy the catheter 802.

With reference to FIG. 22B, to achieve full deployment of the catheter 802, the separation nose 944 of the catheter hub core 841 is advanced distally by a sufficient amount to no longer force apart the flexible arms 984 of the catheter connection hub 845. Accordingly, upon full advancement of the catheter hub core 841, the flexible arms 984 snap back or resiliently return toward their natural state, such that the catches 990 of the arms 984 enter into the groove 947 of the catheter hub core 841. Thereafter, the proximal and distal faces 992, 994 of the catches 990 interact (e.g., abut or interfere with) the proximal and distal sidewalls 948, 949 of the groove 947, respectively, to inhibit or prevent relative translational movement between the catheter connection hub 845 and the catheter hub core 841. In some embodiments, the catches 990 can grip a base wall of the groove 947 sufficiently, or otherwise interact with the catheter hub core 841, to inhibit or prevent relative rotational movement between the catheter connection hub 845 and the catheter hub core 841.

Stated more generally, upon full deployment of the catheter 802, the hub connection interface 984 of the catheter connection hub 845 and the connection interface 946 of the catheter hub core 841 interact with each other to join the catheter connection hub 845 and the catheter hub core 841. Stated otherwise, deployment of the catheter 802 assembles the multi-part catheter hub 846. Stated in yet another way, the catheter hub core 841 can be separated from and positioned at a distance from the catheter connection hub 845 when the system 800 is in the undeployed state, and upon transition of the system 800 to the deployed state—or upon deployment of the catheter 802—the catheter hub core 841 is coupled with or directly attached to the catheter connection hub 845. In some embodiments, assembly of the catheter hub core 841 and the catheter connection hub 845 into a unitary hub is irreversible, or stated otherwise, the catheter hub core 841 is nonreturnable from its engagement with the catheter connection hub 845 (e.g., separation cannot be achieved without use of tools, or inadvertent separation is inhibited or prevented).

When the multi-part catheter hub 846 has been assembled, the seal member 843 can form a seal (e.g., a fluid-tight seal) with an interior surface of the catheter connection hub 845 and with an external surface of the catheter hub core 841. In particular, in the illustrated embodiment, the seal member 843 comprises a resiliently deformable O-ring that is positioned within the groove 952 of the catheter hub core 841. When the catheter hub 846 is assembled, the seal member 843 is compressed such that an outer portion thereof seals against an internal surface of the base 980 of the catheter connection hub 845, and such that an inner portion thereof seals against the groove 952, which is defined by an external surface of the catheter hub core 841.

After full deployment of the system 800, the handle 850, the stiffener hub 854, the stiffener 806, and the needle 804 can be removed. As previously noted, these components, which are removable from the catheter hub 846 and the catheter 802, can be referred to as the insertion assembly 809. In particular, the handle 850 can be disconnected from the catheter connection hub 845, which in the illustrated embodiment, comprises rotating one or more of the housing 850 and the catheter connection hub 845 relative to the other (e.g., a quarter turn) to disengage the complementary threads. The handle 850 and all components coupled therewith can then be withdrawn from the catheter hub 846. For example, a practitioner can hold the catheter connection hub 845 with one hand, and can withdraw the handle 850 proximally with the other hand, thereby drawing the needle 804 and the stiffener 806 from the catheter 802. Stated more generally, after deployment of the catheter 802 and concomitantly assembling the catheter hub 846, the insertion assembly 809 can be removed from the catheter assembly 849.

In some embodiments, the stiffener hub 854 is nonreturnable, relative to the housing 852, once it has been advanced distally to deploy the catheter 802. Stated otherwise, the stiffener hub 854 can be locked relative to the handle 850 when fully deployed, which can maintain the stiffener 806 in a shielding configuration relative to the needle 804. In such an arrangement, a practitioner can merely pull proximally on the handle 850 to remove the entirety of the insertion assembly 809. That is, the needle 804 is drawn proximally due to its fixed securement to the housing 850, and both the stiffener hub 854 and the stiffener 806 are simultaneously drawn proximally due to the stiffener hub 854 being locked in place (e.g., secured in a fixed longitudinal orientation) relative to the handle 850.

After removal of the insertion assembly 809 from the catheter hub 846, any suitable medical fluid component 197 (see FIG. 4J) can be coupled with the catheter hub 846 in manners such as described above. With continued reference to FIG. 22B, the seal formed by the seal member 843 can prevent fluid from leaking from the multi-part catheter hub 846, such as by passing between the catheter connection hub 845 and the catheter hub core 841. For example, fluid introduced into the catheter hub 846 from a medical fluid component 197 for delivery to the vessel through the catheter 802 can pass through the lumen 976 defined by the medical connector 972 end of the catheter connection hub 845, and can then pass through the proximal end of the channel 960 of the catheter connection hub 845 and into the catheter 802. Any fluid that may pass between the catheter connection hub 845 and the catheter hub core 841 is stopped by the seal member 843.

In some embodiments, the seal member 843 may assist in maintaining the catheter connection hub 845 and the catheter hub core 841 in a fixed relationship relative to each other. For example, the seal member 843 can frictionally engage surfaces of both components to inhibit relative translational and/or rotational movement between them. In some instances, the inhibition of movement provided by the seal member 843 is supplemental to like inhibition of relative translational and/or rotational movement provided by the interaction of the catches 990 and the groove 947.

Figure 23A:
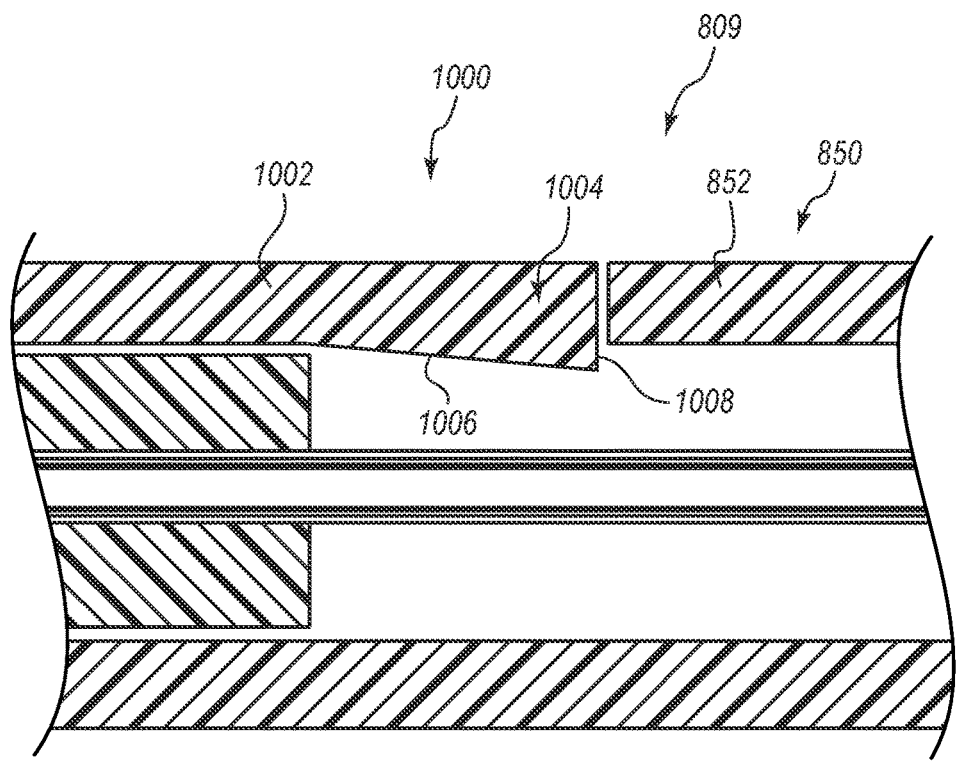
FIGS. 23A, 23B, and 23C are cross-sectional views of different stages of use of an embodiment of a catheter delivery system that includes a lock to prevent proximal return of a stiffener hub after deployment of the catheter.
Figure 23B:
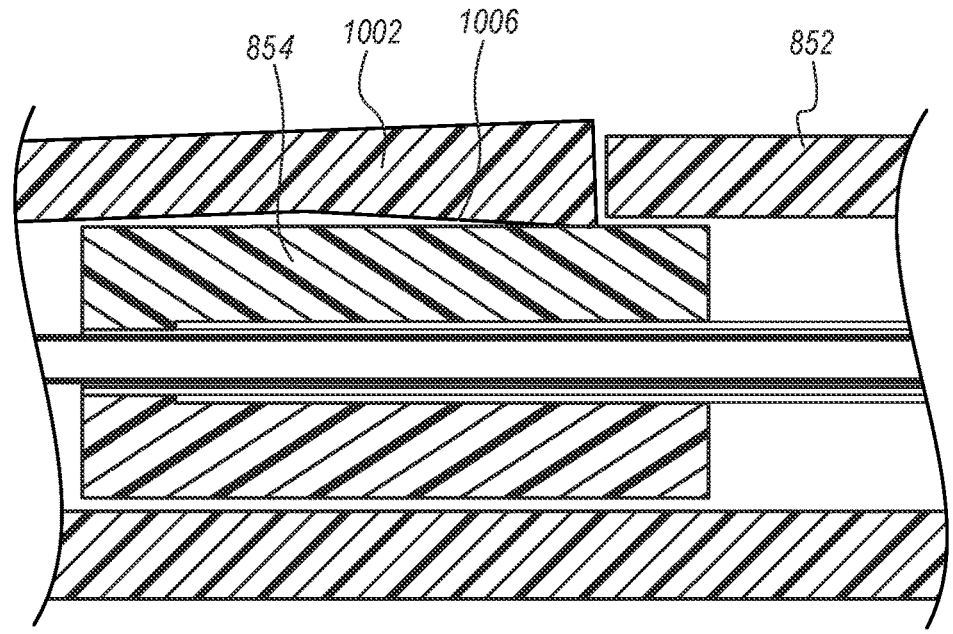
Figure 23C:
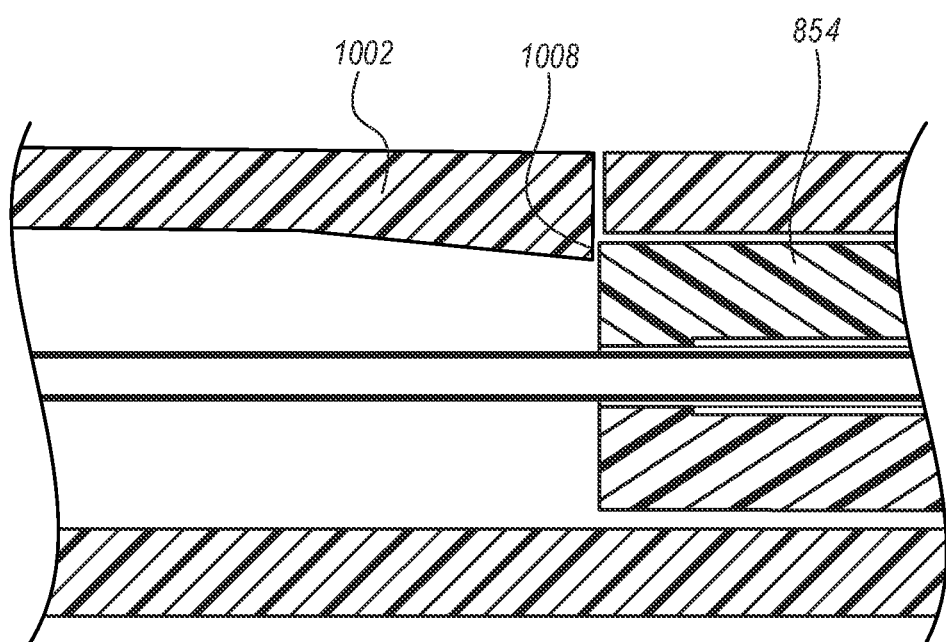

FIGS. 23A-23C depict an illustrative embodiment of a non-return mechanism or lock 1000 that can be employed with needle assemblies described herein, such as the insertion assembly 809. The cross-sectional views depicted in these drawings are taken along a plane that is rotated 90 degrees about the longitudinal axis, as compared with the views depicted in FIGS. 20A-22B. The lock 1000 includes a resiliently flexible arm 1002 that is formed in the housing 852 of the handle 850. For example, in some embodiments, the housing 852 is formed of a unitary piece of material, and the arm 1002 is formed as an integral component of the housing 852. The arm 1002 can include a catch 1004 at a distal end thereof. The catch 1004 can include a ramp surface 1006 and a stop 1008.

As shown in FIG. 23B, as the stiffener hub 854 is advanced distally within the housing 852, the stiffener hub 854 can engage the ramp surface 1006 and displace the flexible arm 1002 outwardly. As shown in FIG. 23C, after the stiffener hub 854 has passed beyond the arm 1002, the resiliently flexible arm can automatically return to its non-deflected state, in which the stop 1008 prevents proximal movement of the stiffener hub 854. Any other suitable non-return mechanism or lock is contemplated.

Figure 24A:
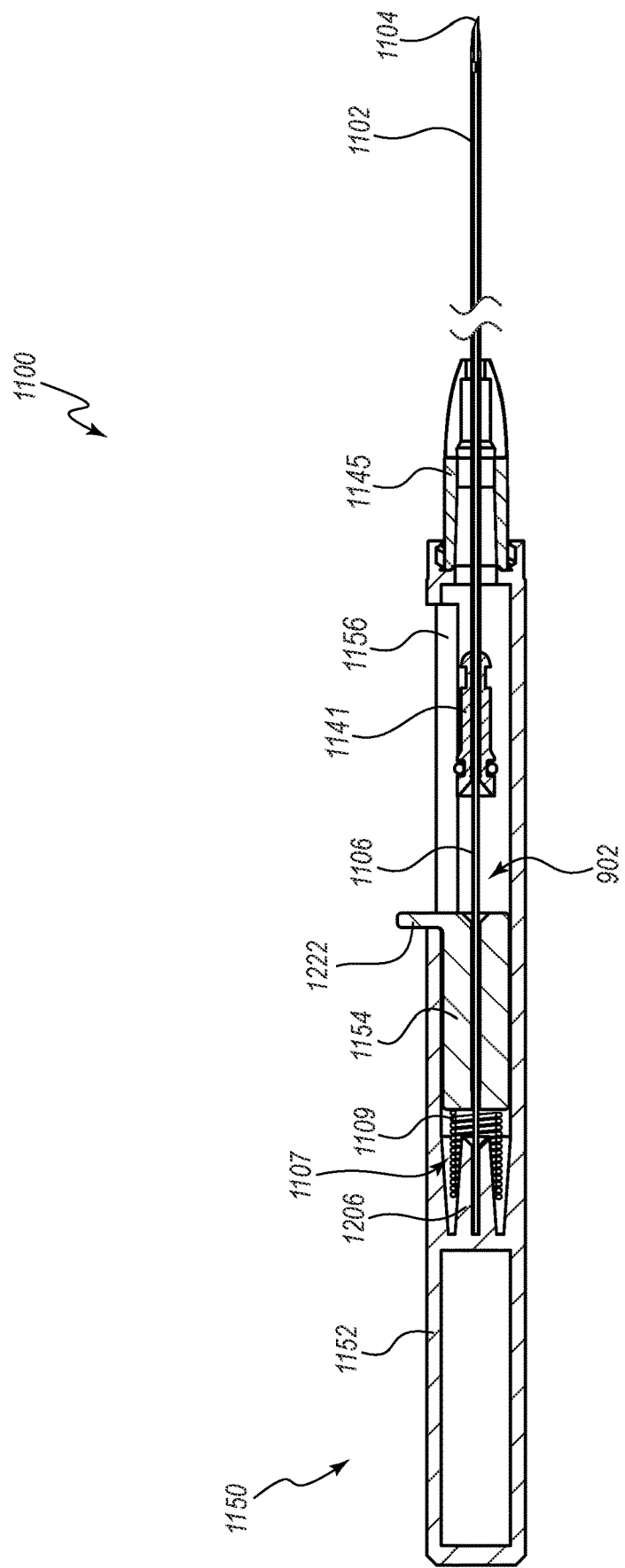
FIG. 24A is a cross-sectional view of another embodiment of a catheter delivery system configured for automatic deployment of a catheter, the system being depicted in an undeployed state.

FIG. 24A depicts another embodiment of a catheter deployment system 1100, which can resemble other systems disclosed herein. The system 1100 is configured to automatically deploy a catheter 1102. The system 1100 includes a handle 1150 that is at least partially formed by a housing 1152, similar to other embodiments described herein. The housing 1152 can define a track 1156 along which a stiffener hub 1154 can be deployed.

The stiffener hub 1154 can be releasably coupled with the housing 1152 in the illustrated retracted or proximal position in any suitable manner. In particular, an actuator 1222 can be mechanically coupled with the housing 1152 in any suitable manner. Upon actuation of an actuator 1222 to decouple or disengage the actuator 1222 from the housing 1152, the stiffener hub 1154 can be permitted to translate distally relative to the housing 1152.

In the illustrated embodiment, the system 1100 includes a biasing member 1107 that applies a distally directed force to the stiffener hub 1154. In particular, in the illustrated embodiment, the biasing member 1107 comprises a coiled spring 1109 that is coupled at a proximal end thereof to a connection protrusion 1206 defined by the housing 1152, and is coupled at a distal end thereof to the stiffener hub 1154. When the system 1100 is in the undeployed state, the spring 1109 is in a compressed state and stores sufficient potential energy to deploy the catheter 1102.

Figure 24B:
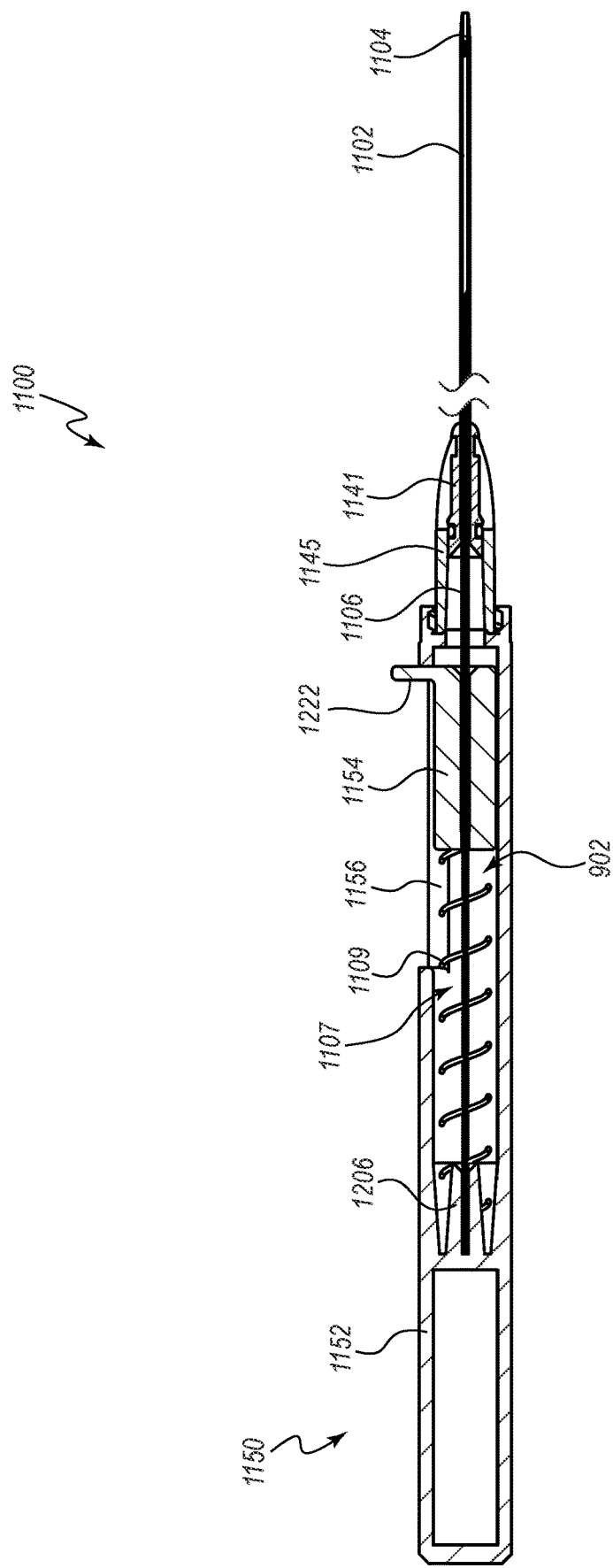
FIG. 24B is another cross-sectional view of the catheter delivery system of FIG. 24A in a deployed state.

With reference to FIG. 24B, in the illustrated embodiment, the catheter 1102 can be deployed upon actuation of the actuator 1222. In particular, actuation of the actuator 1222 can release the mechanical coupling that maintains the stiffener hub 1154 in a fixed longitudinal position relative to the housing 1152, thereby permitting the compressed spring 1109 to decompress and automatically urge the stiffener 1106 distally. Distal movement of the stiffener 1106 can likewise move the catheter 1102 distally to deploy the catheter 1102 in manners such as previously described.

In the illustrated embodiment, the actuator 1222 includes a protrusion that extends laterally from the stiffener hub 1154 outwardly through the track 1156. In some embodiments, the actuator 1222 may further act as a stop to terminate deployment of the catheter 1102. In particular, the actuator 1222 may abut a distal end of the track 1156 to arrest distal movement of the stiffener hub 1154. More generally, the stiffener hub 1154 interacts with the housing 1152 to arrest forward movement of the stiffener hub 1154. Other arrangements for stopping forward motion of the stiffener hub 1154 are also contemplated.

When the system 1100 is in the fully deployed state depicted in FIG. 24B, the spring 1109 may be in a relaxed state, or the spring 1109 may remain in a compressed state, although in a state less compressed than it is when the system 1100 is undeployed.

In other embodiments, the spring 1109 is instead placed in tension when in the undeployed state. For example, a distal end of the spring 1109 may be coupled with a distal end of the housing 1152, and a proximal end of the spring 1109 may be coupled with the stiffener hub 1154. In either arrangement, the spring 1109 may transition from a displaced state when the system 1100 is undeployed to a less displaced or more relaxed (or even fully relaxed) state, when the system 1100 is fully deployed.

In some embodiments, the system 1100 can be configured to deploy the catheter 1102 in a smooth and/or controlled manner. Stated otherwise, a rate of deployment of the catheter, such as may be determined by a rate of translation of the stiffener hub 1154 relative to the housing 1152, can be substantially constant. For example, in various embodiments, a maximum deployment rate of the catheter 1102 may vary from a final rate of deployment of the catheter 1102 (e.g., at a point in time just prior to termination of the deployment, at which the catheter 1102 no longer advances relative to the handle 1150) by no greater than 5, 10, 15, 20, 25, 30, 40, 50, or 75 percent.

In some embodiments, a controlled deployment can desirably reduce the risk of trauma to the vessel of a patient. For example, in certain embodiments that do not control a deployment rate of the catheter 1102, the catheter 1102 may initially accelerate or jut rapidly in the distal direction upon initial actuation of the automated delivery system, and may slow down as the deployment proceeds. This may result, for example, from the spring 1109 being at its greatest compression when the system is in the undeployed state, thus providing the greatest force upon initial deployment. The deployment force provided by the spring 1109 can decrease as the spring 1109 relaxes throughout the course of deployment, as the amount of deployment force supplied thereby diminishes correspondingly. An initial lurching or jutting such as just described can potentially damage one or more inner layers of the vessel wall (e.g., the endothelium), particularly at the initial deployment stage where the catheter 1102 has just entered the vessel. Typically, the catheter 1102 and the stiffener 1106 enter into the vessel at an angle relative to a longitudinal axis of the vessel, and thus the catheter 1102 and the stiffener 1106 may be rapidly driven into the vessel wall at this insertion angle. The wall can deflect the catheter 1102 and the stiffener 1106 from the angled insertion trajectory so they thereafter follow a contour of the vessel. In some instances, the larger the force at which the catheter 1102 meets the sidewall to be deflected, the greater the possibility that damage to the sidewall may result from the initial deflection and/or subsequent contact with the catheter 1102. For the foregoing and/or other reasons, in some instances, controlled deployment of the catheter 1102 may be desirable.

In various embodiments, a dampening agent is used to achieve a controlled, automated deployment of the catheter 1102. For example, in various embodiments a damping oil, grease, compound, paste, and/or coating is applied to an external surface of the stiffener hub 1106 and/or to an internal surface of the housing 1152. For example, a quantity of a silicone-based damping oil may be included in the housing 1152 to achieve the controlled deployment. In some embodiments, the damping agent can include a viscoelastic material. In various embodiments, the dampening agent can provide greater resistance to relative movement between the stiffener hub 1154 and the housing 1152 at the initial stages of deployment, when greater force is applied thereto via the spring 1109, and can provide less resistance to the relative movement at later stage of deployment as the force provided by the spring 1109 is reduced as the spring 1109 relaxes. Accordingly, the stiffener hub 1154 can achieve a relatively steady rate of movement relative to the housing 1152.

In some instances, automating deployment of the catheter 1102 can yield a more predictable and/or reliable delivery of the catheter 1102. For example, in some embodiments, the catheter delivery system 1100 can reliably deliver the catheter 1102 at a rate that never reaches or exceeds an upper limit. The upper limit may correspond to a rate at which damage to the vessel may occur. Stated otherwise, in some instances, multiple automated catheter delivery systems 1100 may be produced (e.g., mass produced), and each of the systems 1100 may be within a specified tolerance that is sufficiently lower than the upper limit to ensure that the deployments occur at rates that do not meet or exceed the upper limit. In contrast, certain manually deployable embodiments may not limit a rate at which a practitioner may deploy the catheter.

In some embodiments, the automated system 1100 is configured to deploy only when the distal tip of the catheter 1102 is positioned at an interior of a vessel. Stated otherwise, the automated system 1100 may not deploy the catheter 1102 the distal tip thereof is not within the vessel, such as may occur when the needle has not yet been advanced sufficiently to enter the vessel, or as may occur with inadvertent excessive advancement of the needle through the vessel wall (e.g., back puncture). In such instances, an attempt to deploy the catheter 1102 would urge the distal tip of the catheter 1102 against tissue of the patient (e.g., fat, muscle), rather than into the lumen of the vessel. In order to advance the catheter 1102 in such circumstances, the system 1100 would need to urge the distal tip of the catheter 1102 through the tissue, which requires greater force than it does to urge the distal tip of the catheter 1102 to greater depths within the vessel after the catheter tip has already been positioned within the vessel. Accordingly, the spring 1109 may provide sufficient force to advance the catheter 1102 through the vessel, to greater distances or depths within the vessel, after the distal tip of the catheter 1102 is already within the vessel, but insufficient force to advance the distal tip of the catheter 1102 through tissue of the patient. Stated otherwise, the spring 1109 may provide insufficient force to advance the distal tip of the catheter 1102 through tissue that is positioned external to the vessel and that has not previously been pierced via the distal tip of the needle 1104.

In the illustrated embodiment, an unsuccessful attempt to deploy the catheter 1102 may proceed as follows. If the tip of the catheter 1102 is not within the vessel, a practitioner may activate the actuator 1222 to release the stiffener hub 1154 from locked engagement with the housing 1152. The spring 1109 applies a distally directed force on the stiffener hub 1154, which force is communicated to the distal tip of the stiffener 1106 and, thereby, to the distal tip of the catheter 1102. Because the catheter tip 1102 is not within the vessel, however, and because the force provided by the spring 1109 is insufficient to cause the distal tip of the catheter 1102 to penetrate through the tissue within which it is in contact, the stiffener hub 1154 can remain substantially at the proximal end of the track 1156, and the catheter 1102 can remain in an undeployed state—e.g., a distal tip of the catheter 1102 can remain positioned proximally relative to a distal end of the needle 1104. Upon realization that the automatic deployment has not occurred, a practitioner may then manipulate the system 1100 backward, forward, or otherwise until the catheter tip is within the vessel and is capable of being deployed.

For example, in some instances where the tip of the needle 1104 has penetrated, potentially along with the tip of the catheter 1102, the back wall of the vessel (e.g., a back-puncture event), the system 1100 can be retracted proximally, such as by pulling rearward on the handle 1150, until the tips of the needle 1104 and the catheter 1102 are within the lumen of the vessel. Once the distal tip of the catheter 1102 is within the vessel and is able to advance distally over the tip of the needle 1104, the distally directed force of the spring 1109 can be sufficient to deploy the catheter 1102 into the vessel, which can occur automatically or spontaneously once the system 1104 has been withdrawn to an appropriate position.

In other instances, where the tip of the needle 1104 has not yet penetrated the vessel wall, the system 1100 can be advanced distally into the vessel. Upon sufficient advancement of the system 1100 into the vessel, the force of the spring 1109 can be sufficient to deploy the catheter 1102 into the vessel.

In various embodiments, the amount of energy stored in the biasing member and the deployment force provided by the biasing member 1107 throughout a deployment event can be sufficient to (1) break any bond that may exist between the distal tips of the catheter 1102 and the needle 1104; (2) advance the catheter 1102 through an insertion tract through the skin of the patient and over the needle 1104 body into the lumen of a vessel, when the catheter tip is appropriately positioned within the vessel; (3) urge a catheter hub core 1141 into connection with a catheter connection hub 1145 in manners such as described above (e.g., by separating and deflecting resiliently flexible arms of the catheter connection hub 1145 until they snap back into engagement with a groove in the catheter hub core 1141); and/or (4) deploy or otherwise activate a non-return mechanism to prevent retraction of the stiffener hub 1154 (such as described above with respect to FIGS. 23A-23C). In other or further embodiments, the deployment force provided by the biasing member 1107 at any stage of a deployment event can be insufficient to urge the distal tips of the catheter 1102 and the stiffener 1106 through tissue of the patient, so as to puncture the tissue thereby. Stated otherwise, the deployment force can be insufficient to force the distal tip of the catheter 1102 through tissue (e.g., fat, muscle) that has not previously been punctured by the distal tip of the needle 1104.

The foregoing discussion regarding the designed-in inability of certain embodiments of automatic systems 1100 to deploy the catheter 1102 over the needle 1104 when the needle is not properly situated within the vessel have similar applicability to certain embodiments of manual systems, such as, for example, embodiments of the system 800. In particular, the presence of the stiffener 1106 can advantageously provide tactile feedback to the practitioner indicating that the distal tip of the catheter 1102 is either incapable of being advanced distally, or may only be advanced distally with the application of force significantly greater than would be required to deploy the catheter 1102 within the vessel. This tactile feedback can indicate to the practitioner that the system is not properly positioned for catheter deployment. Such tactile feedback can be advantageous over prior art systems that merely include an over-the-needle catheter, as the pliability of the catheter can permit the catheter to readily bunch up or accordion within the patient as the practitioner advances the catheter distally relative to the needle when the needle is not properly positioned. Such over-the-needle catheters may not provide any tactile feedback, or may provide tactile feedback that is difficult to detect, when the catheter is thus prematurely or improperly deployed, due to the relatively lower longitudinal rigidity of the catheters. That is, in certain prior art arrangements, the catheters readily bunch up as they are advanced distally relative to the needle, thus providing little or no tactile indication to the user of improper placement, whereas in certain embodiments that employ a stiffener 1106, the stiffener 1106 communicates to the practitioner that that the distal end of the catheter 1102 is encountering unfavorable advancement conditions and is not properly situated for catheter deployment.

Figure 25:
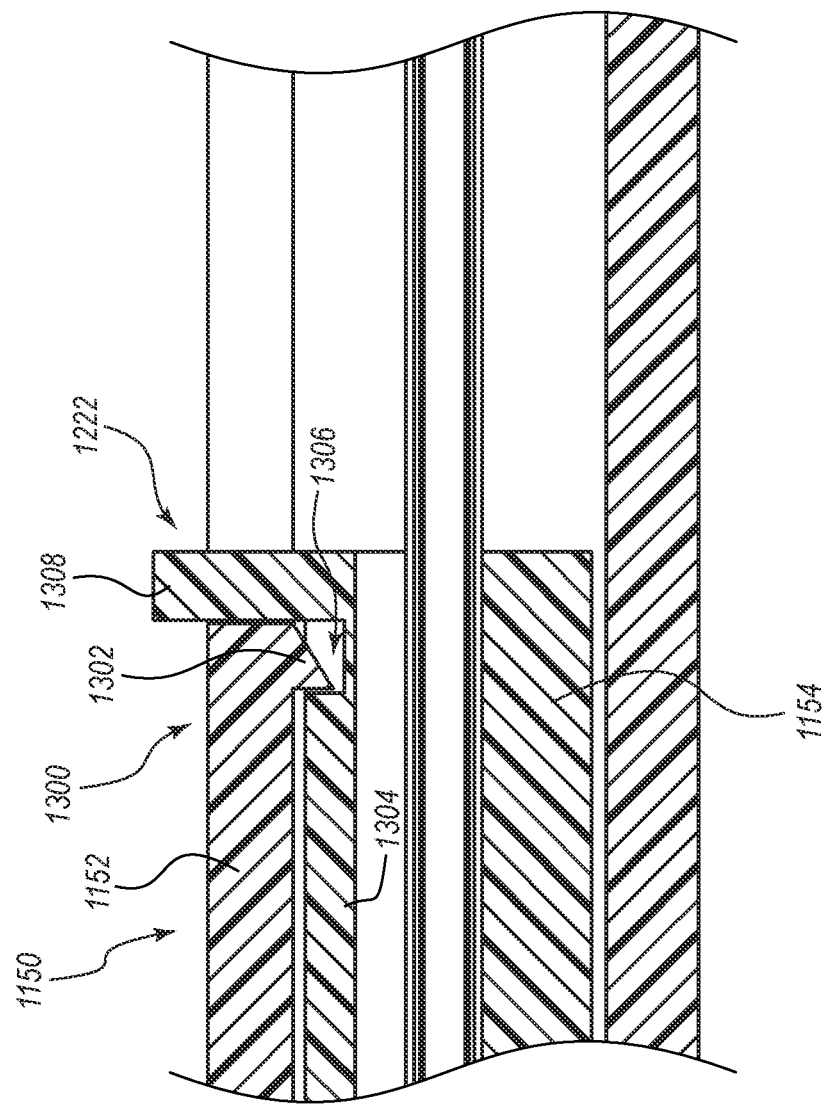
FIG. 25 is a cross-sectional view of a portion of an embodiment of a catheter delivery system such as that of FIG. 24A in an undeployed state, the system including an actuator that releases a catch to permit automatic deployment of a catheter.

FIG. 25 depicts an illustrative example of an embodiment of a mechanical coupling 1300 that can selectively secure the stiffener hub 1154 to the housing 1152 of the handle 1150 in an automated system 1100. In the illustrated embodiment, the mechanical coupling 1300 includes a catch 1302 that extends inwardly from the housing 1152. In the illustrated embodiment, the catch 1302 is integrally formed with the housing 1152.

The mechanical coupling 1300 further includes the actuator 1222. In the illustrated embodiment, the actuator 1222 includes a resiliently flexible arm 1304 that defines a recess 1306 into which the catch 1302 is received when the system 1100 is in the undeployed state. The flexible arm 1304 includes an engagement surface 1308 that a practitioner can depress to initiate deployment of the catheter 1102. In the illustrated embodiment, the arm 1304 is integrally formed with a body 1320 of the stiffener hub 1154 and is capable of radially inward deformation.

To actuate the automatic system 1100, a practitioner can press inwardly on the engagement surface 1308, which deflects the arm 1304 inwardly and out of its engagement with the catch 1302. The stiffener hub 1154 is then free to move distally under the influence of the biasing member 1107 in manners such as previously discussed.

Figure 26A:
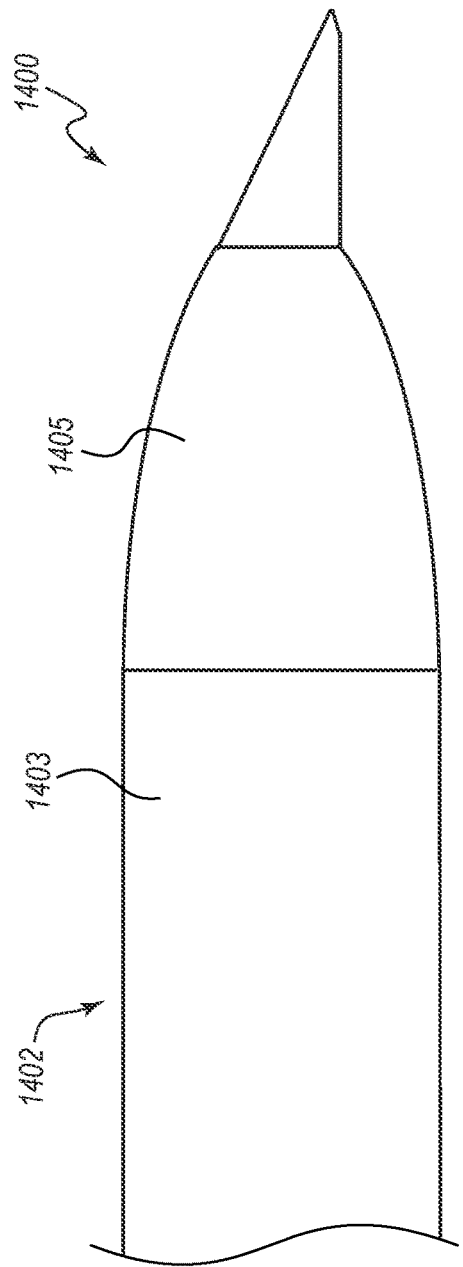
FIG. 26A is an elevation view of a distal portion of another embodiment of a catheter deployment system that includes a two-part catheter that includes a catheter body and a separately formed tip joined thereto.
Figure 26B:
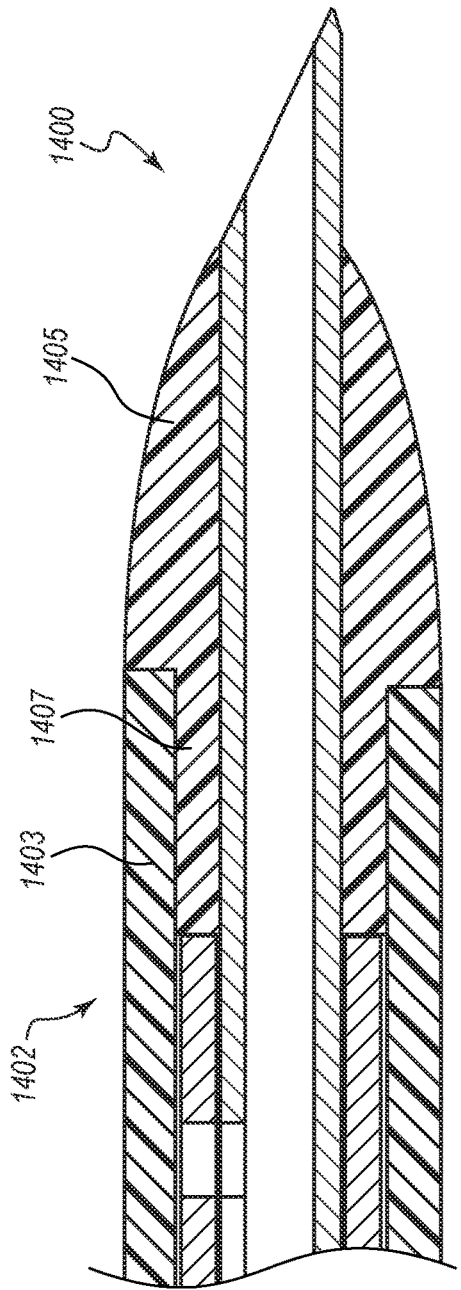
FIG. 26B is a cross-sectional view of the distal portion of the catheter deployment system of FIG. 26A.

FIGS. 26A and 26B depict another embodiment of a catheter deployment system 1400 that includes a multi-part catheter 1402. In particular, the catheter 1402 includes a body 1403 and a tip 1405. In some embodiments, the body 1403 is relatively stiffer or harder than is the tip 1405. The tip 1405 may be much softer than the body 1405, or may be atraumatic, so as to avoid damaging an inner surface of the vessel. A relatively stiffer body 1403 may be more resistant to bunching or accordioning. The body 1403 and the tip 1405 may, in some embodiments, be formed of different materials.

The body 1403 and the tip 1405 can be joined together in any suitable manner, such as via one or more adhesives, injection molding, welding (e.g., ultrasonic or RF welding). In the illustrated embodiment, the tip 1405 includes a flange 1407 or protrusion that extends proximally into a lumen defined by the body 1403 and is secured to the body 1403.

In other embodiments, such as in certain embodiments of the catheter 102 depicted in FIGS. 2 and 3, a relatively soft tip, as compared with the shaft of the catheter, may instead be achieved by employing a blending gradient during extrusion.

Figure 27:
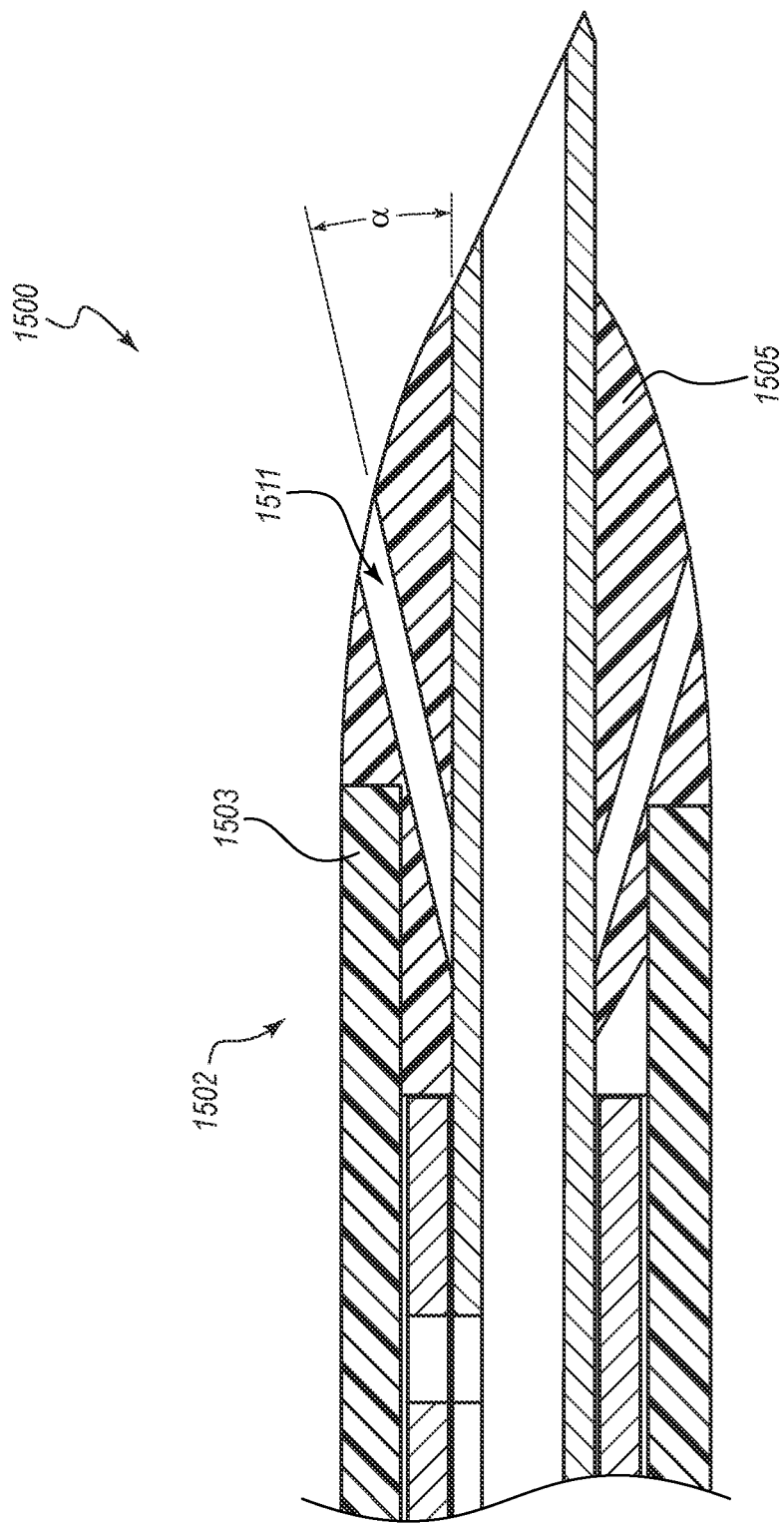
FIG. 27 is a cross-sectional view of another embodiment of a catheter deployment system that includes another embodiment of two-part catheter.

FIG. 27 is another embodiment of a catheter deployment system 1500 that includes a multi-part catheter 1502 having a body 1503 and a tip 1505, and further includes a plurality of side ports 1511 that extend through the tip 1505. In particular, in the illustrated embodiment, each of the side ports 1511 extends at an angle α relative to a longitudinal axis of the catheter 1502. In various embodiments, the angle α is within a range of from about 10 to about 120 degrees, from about 15 to about 105 degrees, from about 45 to about 90 degrees, or is no greater than about 15, 30, 45, 60, 90, or 120 degrees. Any suitable number and arrangement of the side ports 1511 is contemplated.

In some embodiments, the side ports 1511 are drilled through the tip 1505. In other embodiments, the side ports 1511 are formed via core pins during a molding process. Any other suitable technique for forming the side ports 1511 is contemplated.

In some embodiments, the side ports 1511 are arranged symmetrically around the tip 1505. The side ports 1511 can, in some configurations, enhance stability of the distal end of the catheter 1502 during injections, which can inhibit trauma to the vessel.

Figure 28:
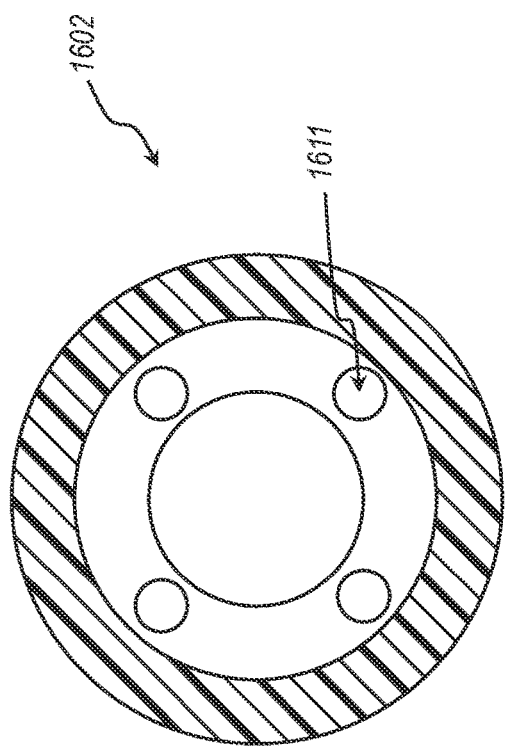
FIG. 28 is a cross-sectional view of a distal portion of another embodiment of a two-part catheter, the cross-sectional view being taken along a transverse plane through a longitudinal axis of the catheter and directed distally.

FIG. 28 depicts another embodiment of a catheter 1602 similar to the catheter 1502. However, proximal openings of side ports 1611 that can extend through one or more of a tip 1605 and a body 1603 are positioned on an abutment face 1691 defined by a proximal end of the tip 1605. The proximal openings can be directly in the path of fluid that flows distally through the body 1603.

Figure 29:
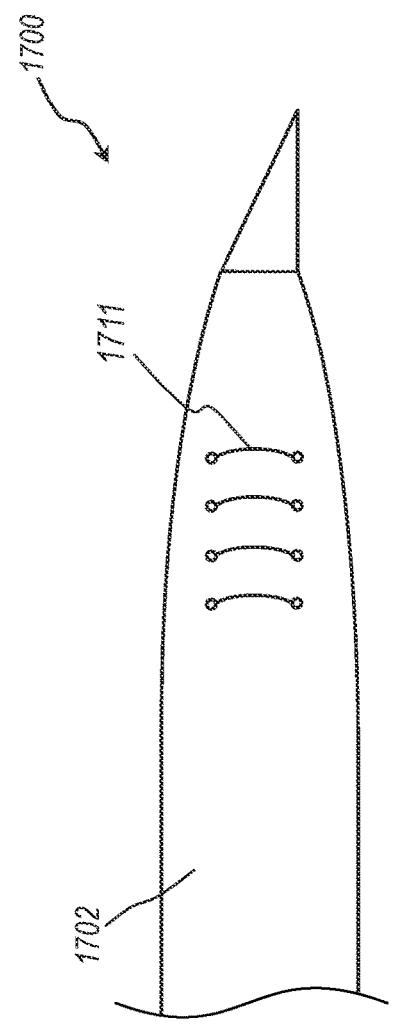
FIG. 29 is an elevation view of a distal end of another embodiment of a catheter delivery system.

FIG. 29 depicts another embodiment of a catheter delivery system 1700 with a catheter 1702 having a plurality of side ports 1711. In the illustrated embodiment, the side ports 1711 are formed as slits that can open to permit fluid flow therethrough and can close when a pressure differential between the interior and exterior of the catheter 1702 is sufficiently small. The illustrated side ports 1711 are formed substantially as slits that resemble fish gills. Any other suitable arrangement of the side ports 1711 is contemplated.

Figure 30:
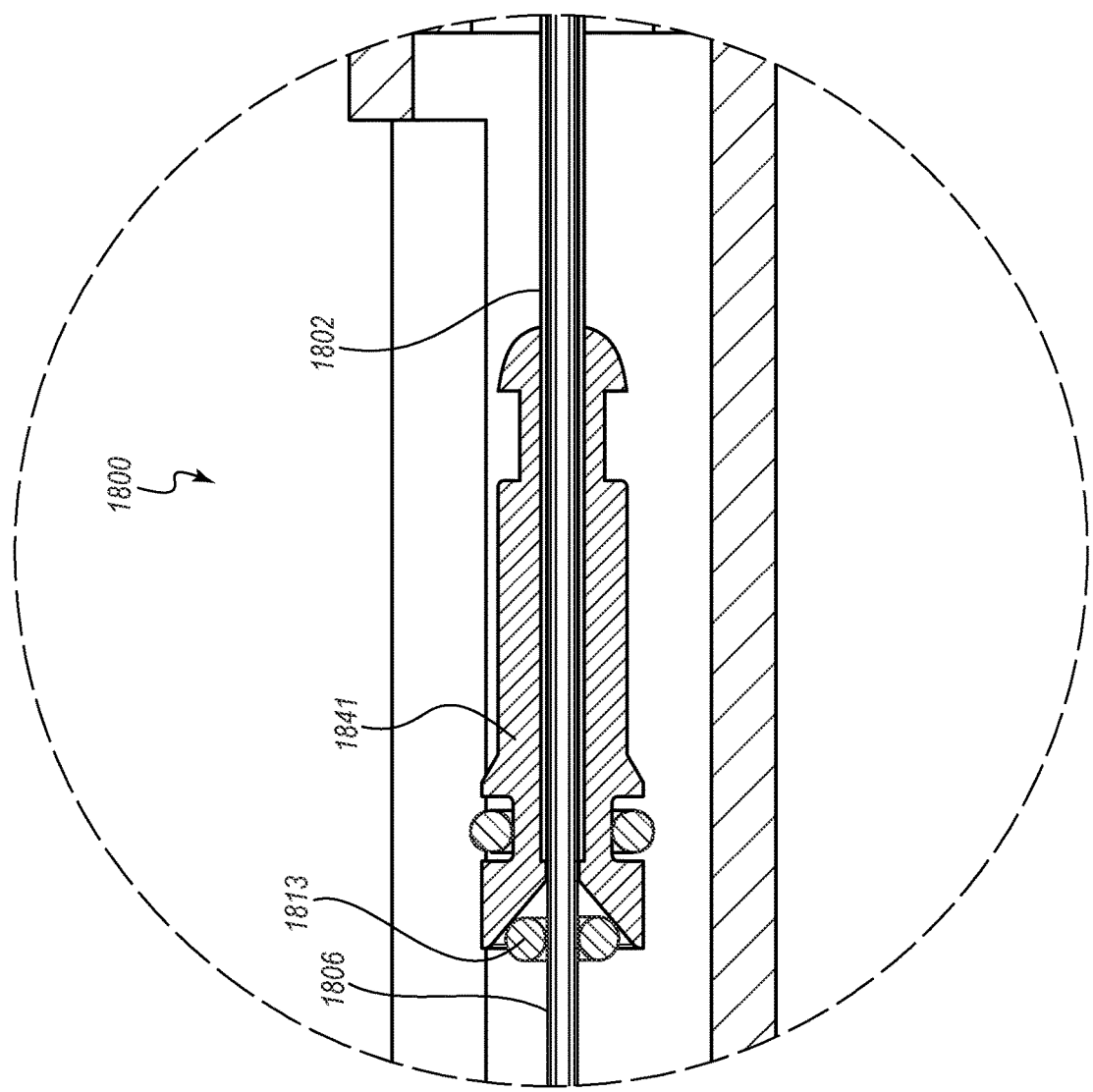
FIG. 30 is a cross-sectional view of a portion of another embodiment of a catheter delivery system in which an engagement member positioned proximal of a catheter hub core is configured to urge the catheter hub core in a distal direction during deployment of a catheter.

FIG. 30 depicts a portion of another embodiment of a catheter delivery system 1800 in which a catch or engagement member 1813 of any suitable variety is fixedly secured to a stiffener 1806, which can achieve or which can assist in achieving distal movement of a catheter hub core 1841. In the illustrated embodiment, the engagement member 1813 comprises a ring that is fixedly secured to the stiffener 1806, although any other suitable protrusion or other arrangement is contemplated. The engagement member 1813 can contact a proximal end of the catheter hub core 1841 and urge the same forward during forward advancement of the stiffener 1806. Such an arrangement can, in some instances, reduce an amount of force applied to a distal tip of a catheter 1802 by a distal tip of the stiffener 1806. For example, in some arrangements, the distal end of the stiffener 1806 interacts with the distal end of the catheter 1802 primarily to resist proximal accordioning of the catheter tip during insertion into a vessel, to push the catheter off of the needle, and to advance the catheter deeper into the vessel. Such interaction of the distal end of the stiffener 1806 with the distal end of the catheter 1802 can also pull the catheter hub core 1841 forward into coupling engagement with a catheter connection hub, such as depicted in and described with respect to FIGS. 21B and 22B. The engagement member 1813, however, can also transfer force directly from the stiffener 1806 to the catheter hub core 1841 during such assembly of the catheter hub, which can reduce strain and the distal end of the catheter 1802 during catheter hub assembly.

Figure 31:
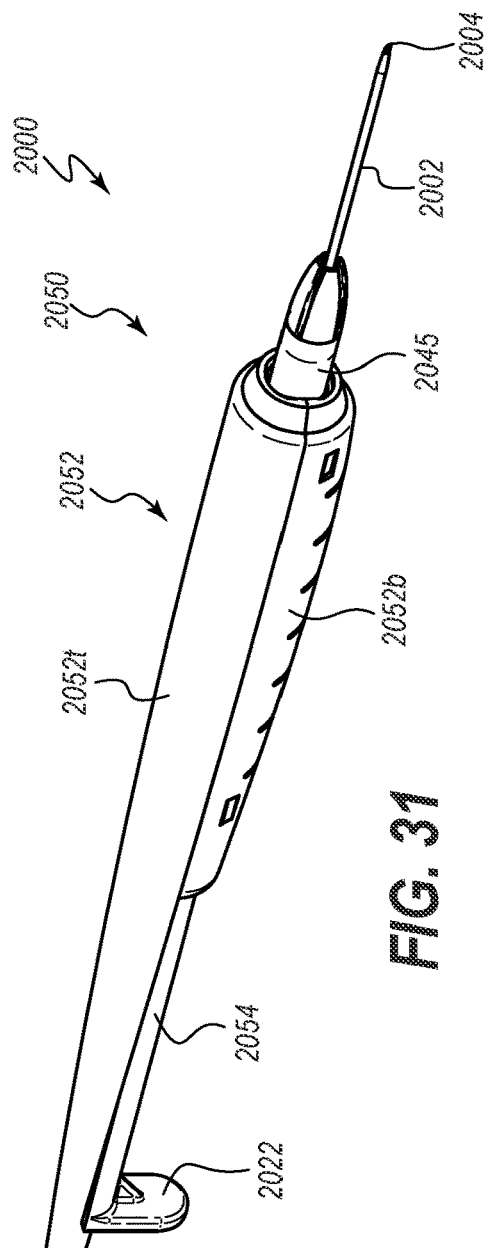
FIG. 31 is a perspective view of another embodiment of a catheter delivery system.
Figure 32:
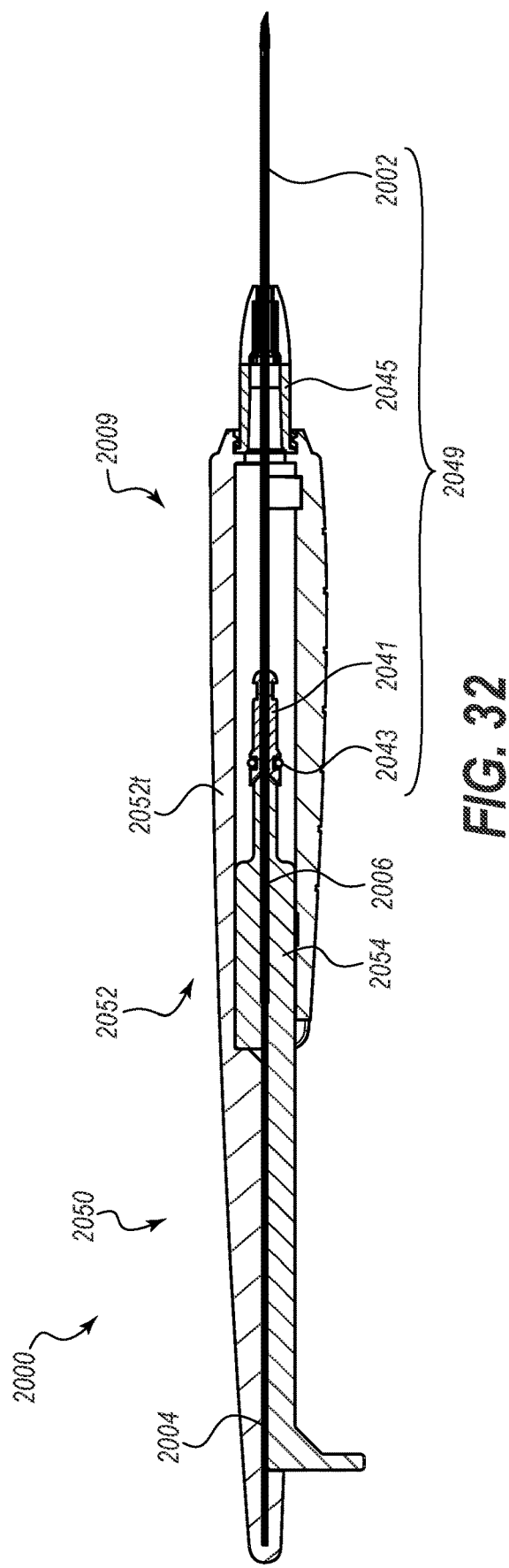
FIG. 32 is a cross-sectional view of the catheter delivery system of FIG. 31 taken along the view line 32-32 in FIG. 31.

FIGS. 31 and 32 depict another embodiment of a catheter delivery system 2000 similar to other systems disclosed herein. For example, the catheter delivery system 2000 can resemble the system 800 discussed above in many respects and, as previously stated, any suitable combination of the features and variations of the same described with respect to the system 800, as well as other systems disclosed herein, can be employed with the system 2000, and vice versa. This pattern of disclosure applies equally to further embodiments depicted in subsequent figures and described hereafter, wherein the leading digits may be further incremented.

The catheter delivery system 2000 includes a handle 2050, or needle hub, having an ergonomic contour. In the illustrated embodiment, the handle 2050 is formed of a housing 2052 that includes a top or upper housing element 2052*t* and a bottom or lower housing element 2052*b*. Rather than defining a longitudinally extending track along which an actuator passes to advance the stiffener distally, the housing 2052 instead defines a channel or opening 2051 at a mid or intermediate region thereof through which a portion of a stiffener hub 2054 extends. An actuator 2022 can be engaged (e.g., by one hand of a user) to advance the stiffener hub 2054 distally relative to the housing 2052 (e.g., which may be held by the other hand of the user) to deploy a catheter 2002. As with other embodiments herein, the actuator 2022 may be coupled with the stiffener hub 2054 in any suitable manner. In the illustrated embodiment, the actuator 2022 is integrally formed with the stiffener hub 2054. In some instances, the stiffener hub 2054 may itself more generally be referred to as an actuator. Stated otherwise, the actuator 2022, which can include an elongated extension that protrudes longitudinally rearward from a body portion of the stiffener hub 2054, can be advanced into the housing 2052 to advance a stiffener 2006, to which the stiffener hub 2054 is coupled, in the distal direction and thereby advance the catheter 2002 in the distal direction. As shown in FIG. 32, the body portion of the stiffener hub 2054 is positioned within a cavity defined by the housing 2052.

Rather than being positioned at the top of the system 2000, the actuator 2022 extends downwardly relative to the top housing element 2052t. Such an arrangement may advantageously permit a practitioner to hold the handle 2050 with one hand positioned over the top of the handle 2050 and in close proximity to a needle 2004, while reaching under the handle 2050 with the other hand to advance the actuator 2022 forward. By being initially positioned at a rearward end of the system 2000 and/or by extending downwardly, the actuator 2022 may be less prone to inadvertent actuation during initial introduction of a needle 2004 and the catheter 2002 into the vessel of a patient. In the illustrated embodiment, the actuator 2022 is at a position that is slightly forward of, or distal to, a proximal end of the housing 2052 when the actuator 2022 is in a starting position, or stated otherwise, when the system 2000 is in an undeployed state.

The system 2000 can further include a catheter hub core 2041, a seal member 2043, and a catheter connection hub 2045 that substantially resemble like-numbered and like-named components discussed above (e.g., the like-numbered components 841, 843, 845; 1141, 1145). The catheter 2002, the catheter hub core 2041, the seal member 2043, and the catheter connection hub 2045 may collectively be referred to as a catheter assembly 2049. The remaining components of the system 2000 may collectively be referred to as an insertion assembly 2009. As with other embodiments described herein, the catheter assembly 2049 can be assembled during deployment of the catheter 2002, and the insertion assembly 2009 can be selectively removed from the catheter assembly 2049 after deployment of the catheter 2002 to a desired depth within a vessel of a patient.

Figures 33, 34:
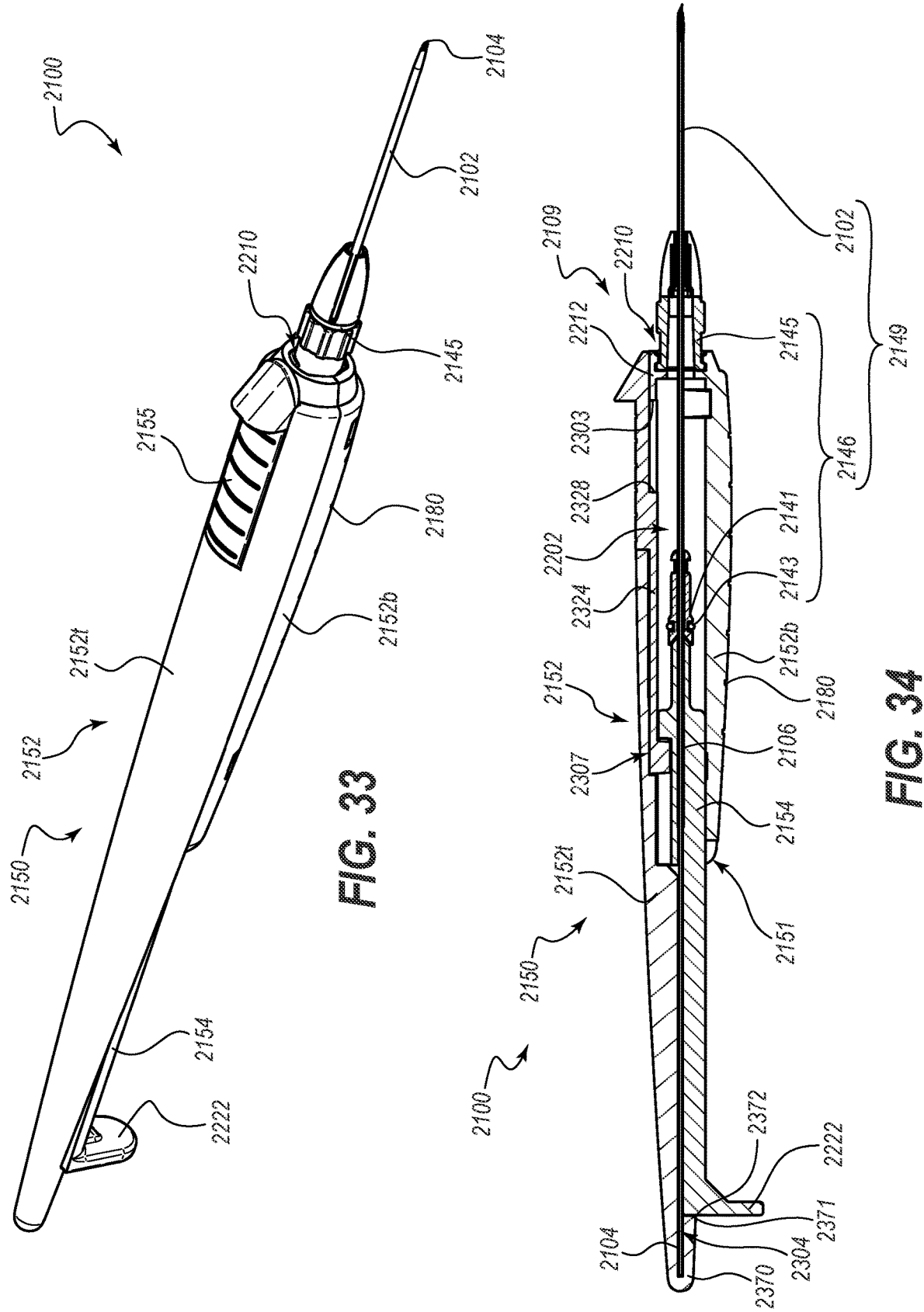
FIG. 33 is a perspective view of another embodiment of a catheter delivery system.
FIG. 34 is a cross-sectional view of the catheter delivery system of FIG. 33 taken along the view line 34-34 in FIG. 33.

FIGS. 33 and 34 depict another embodiment of a catheter delivery system 2100 similar to other systems disclosed herein. In particular, the system 2100 can operate in manners such as those described with respect to previously disclosed embodiments (e.g., the systems 800 and 2000), and may include other or further features as described hereafter. The system 2100 includes an insertion assembly 2109 that is selectively attached to a catheter assembly 2149. As with other embodiments discussed above, the insertion assembly 2109 is configured to deploy a catheter 2102 to a desired depth within a vessel of a patient. In so doing, the insertion assembly 2109 transitions the catheter assembly 2149 from a disassembled state to an assembled state. After deployment of the catheter 2102 and after transition of the catheter assembly 2149 to the assembled state, the insertion assembly 2109 can be detached from the catheter assembly 2149 and withdrawn therefrom, thus leaving the catheter assembly 2149 in place within the vasculature of the patient. Deployment of the catheter 2012 and transition of the catheter assembly 2149 to the assembled state are events of which at least a portion may occur simultaneously. For example, assembly of a hub portion of the catheter assembly 2149 may occur during a final phase of deployment of the catheter 2102 in manners such as described above with respect to the system 800.

The illustrated catheter assembly 2149 resembles other catheter assemblies discussed above. In particular, the catheter assembly 2149 includes the catheter 2102, a catheter hub core 2141, a seal member 2143, and a catheter connection hub 2145, each of which resembles like-named and like-numbered components previously described. The catheter hub core 2141 is secured to the catheter 2102 (e.g., overmolded over a proximal end of the catheter 2102). The seal member 2143 can be coupled with the catheter hub core 2141 in any suitable manner, such as by being positioned within a groove defined by the catheter hub core 2141 as previously described. In the illustrated disassembled state of the catheter assembly 2149, which corresponds to the undeployed state of the system 2100, the catheter hub core 2141 is spaced from and positioned rearward of (proximal to) the catheter connection hub 2145, and the catheter 2102 extends through an entirety the catheter connection hub 2145. The catheter hub core 2141, the seal member 2143, and the catheter connection hub 2145 can be assembled together to form a catheter hub 2146.

In the illustrated embodiment, the insertion assembly 2109 includes a handle 2150, which can comprise a housing 2152. The housing 2152 can be shaped to have an ergonomic contour that can be readily gripped by a hand of a user. The illustrated housing 2152 includes a top or upper housing element 2152t and a bottom or lower housing element 2152b. The housing elements 2152t, 2152b can cooperate to define an opening, port, or channel 2151 through which a stiffener hub 2154 extends. The channel 2151 is positioned at a mid or intermediate region of the housing 2152.

In the pre-use, pre-deployment, initial, or as-packaged state depicted in FIGS. 33 and 34, the housing 2152 is connected at a distal end thereof with the catheter connection hub 2145. As with other embodiments, the catheter connection hub 2145 can be selectively releasable from the housing 2152.

A stiffener 2106, which may be referred to in a variety of other manners such as those previously discussed (e.g., a sheathing cannula), is positioned within the catheter 2102 in manners such as previously described. The stiffener 2106 is fixedly secured to the stiffener hub 2154.

An insertion needle 2104 is positioned within the stiffener 2106 and extends through an entirety of the catheter 2102 (e.g., extends distally past a forward end of the catheter 2102 and extends proximally past a rearward end of the catheter 2102), through an entirety of the stiffener 2106, and through most of the housing 2152. In particular, the needle 2104 extends through a distal end of the housing 2152 and a proximal end of the needle 2104 is attached, internally, to a proximal end of the upper housing element 2152t.

As with other embodiments described herein, the stiffener 2106 is secured at a proximal end thereof to the stiffener hub 2154, which is movable within and relative to the housing 2152. The stiffener hub 2154 can include an actuation element 2222, such as a protrusion (e.g., a push element) that extends laterally (e.g., downwardly) at a proximal end of the stiffener hub 2154, as discussed further below. The actuation element 2222 may protrude away from the housing 2152 to be engageable by the hand (e.g., one or more fingers) of a user. The stiffener hub 2154 may generally be referred to as an actuator, such as in the illustrated embodiment in which the stiffener hub 2154 is rigidly fixed to (e.g., integrally formed with) the actuation element 2222 such that the stiffener hub 2154 and the actuation element 2222 move in unison as a single body. Alternatively, the stiffener hub 2154 may be said to be coupled to (e.g., integrally formed with or otherwise) an actuator. Thus, in the illustrated embodiment, a body portion of the stiffener hub 2154 may be said to be attached to the actuation element 2222. The actuation element 2222 may also be referred to as an actuator, a deployment actuator, an advancement actuator, a primary actuator, a first actuator, a direct stiffener hub actuator, a lower actuator, a rear actuator, etc. Moreover, in many instances, reference to the actuator 2222 may more generally be understood as a reference to the stiffener hub 2154 in its entirety.

The insertion assembly 2109 can further include an initiation actuator 2155, which is described further below. The initiation actuator 2155 may also be referred to as an insertion actuator, a stabilization actuator, a supplemental actuator, an optional actuator, a second actuator, an indirect stiffener hub actuator, an upper actuator, a forward actuator, etc. With respect to the designation of the actuators 2222, 2155 as lower or upper actuators, respectively, it should be understood that these terms refer to the positions depicted in the views shown in FIGS. 33 and 34, and are not limiting with respect to other arrangements. That is, the terms "upper" and "lower" are used illustratively herein for convenience, it being understood that these terms are readily substituted with other suitable appellations for the actuators 2222, 2155, such as those set forth above. For example, in other embodiments, the actuators 2222, 2155 are reversed, such that the actuator 2222 is accessible at an upper end of the housing 2152 and the actuator 2155 is accessible at the lower end of the housing 2152. In still other embodiments, the positions of the actuators 2222, 2155 may be fully altered, such as by being at lateral positions. For example, rather than being at opposing or opposite upper and lower sides of the housing 2152, the actuators 2222, 2155 can be positioned at other opposing sides (e.g., left and right sides) of the housing 2152.

The initiation actuator 2155 can selectively couple with the stiffener hub 2154 to move the stiffener hub 2154 forward by an initial amount, as further discussed below. In the illustrated embodiment, when the system 2100 is in the pre-use or pre-deployment configuration, the initiation actuator 2155 can be adjacent to or in coupling contact with the stiffener hub 2154 (see FIG. 34) such that forward or distal movement of the actuator 2155 effects immediate (or nearly immediate, such as where the initiation actuator 2155 moves a short distance prior to engaging the stiffener hub 2154), simultaneous or concurrent forward movement of the stiffener hub 2154 (and, thereby, forward movement of the stiffener 2106 and catheter 2012).

As further discussed hereafter, the system 2100 can operate in manners similar to those described above with respect to the system 800. For example, in some instances, the system 2100 can be fully deployed using only the lower actuator 2222. Thus, the same deployment phases depicted in FIGS. 20A through 22B can be achieved with the system 2100, with a significant exception being that the lower actuator 2222 as actuated at a position below the housing 2152, as opposed to the actuator 922 of the system 800 being actuatable along an upper portion of the housing 852. In other instances, however, the system 2100 can be deployed in two separate phases: first, by advancing the upper actuator 2155 to insert the catheter 2102 to a first depth within the vessel of a patient; and second, by advancing the lower actuator 2222 to further advance the catheter 2102 to a second depth within the vessel that is greater than the first depth. In either case, deployment of the catheter 2102 via the stiffener 2106 and assembly of the multi-part catheter hub 2146 proceed substantially as described above with respect to the system 800. Indeed, the configurations and relative orientations of the needle 2104, the stiffener 2016, and the various components of the catheter assembly 2149 during various phases of use of the system 2100 are substantially the same as those depicted with respect to the system 800 in FIGS. 20B, 20C, 20D, 21B, 21C, 21D, and 22B. Reference may thus be made to these drawings with respect to operation of the system 2100.

Further details of the upper housing element 2152t are depicted in FIGS. 35A and 35B. In some embodiments, the upper housing element 2152t includes a sliding surface 2201 and a track or guide channel 2302. The guide channel 2302 begins at a rearward end of the sliding surface 2201 and terminates toward a distal end of the sliding surface 2201. That is, a distal end 2303 of the guide channel 2302 is positioned rearward of a distal end of the sliding surface 2201. In the illustrated embodiment, the sliding surface 2201 is generally at a forward end of the upper housing element 2152t and extends to and terminates at a front face of the upper housing element 2152t. The initiation actuator 2155 can slide over or against the sliding surface 2201, and a path of such sliding can be controlled by the guide channel 2302.

As shown in FIG. 35B, the upper housing element 2152t can also define an internal track 2307, which can be configured to receive therein a portion of the initiation actuator 2155, as discussed further below. The internal track 2307 can be aligned with (e.g., can be collinear with) the guide channel 2303. The internal track 2307 extends rearwardly from a proximal end of the guide channel 2302. The internal track 2307 may be formed as a recess in a sidewall of the upper housing element 2152t.

The upper housing element 2152t can further define a needle channel 2304 within which a proximal portion of the needle 2104 is received. The needle channel 2304 is formed as a groove in the illustrated embodiment. A distal end of the needle channel 2304 can define a flared entry port or tapered region 2308 to assist in assembly of the system 2100, such as previously described with respect to the tapered region 908. The forward portion of the needle channel 2304 can, in some instances, define a semi-circular profile sized to receive therein only an upper side (e.g., an upper half or other fraction) of the needle 2104. As shown in FIG. 34, a rearward end of the needle channel 2304 can extend into and terminate within a rear portion 2370 of the upper housing element 2152t. A cross-sectional profile of the needle channel 2304 within the rear portion 2370 can be substantially circular. The rear portion 2370 can be said to fully encompass or encircle the proximal end of the needle 2104. The needle 2104 can be secured within the rear portion 2370 in any suitable manner.

The rear portion 2370 of the upper housing element 2152t can define a stopping surface or stop 2371. In the illustrated embodiment, the stop 2371 is formed as a substantially planar face that extends substantially orthogonally relative to a longitudinal axis of the upper housing element 2152t, or more generally, relative to a longitudinal axis of the system 2100 when in an assembled state. As shown, e.g., in FIG. 34, the stop 2371 can interact with a rearward end of the lower actuator 2222 to delimit rearward movement of the stiffener hub 2154. In some instances, the lower actuator 2222 likewise includes a stop 2372 of any suitable variety (see also FIG. 38B). In the illustrated embodiment, the stop 2372 likewise is defined as a substantially planar rearward face of the actuator 2222, which extends substantially orthogonally relative to the longitudinal axis of the assembled system 2100. The stops 2371, 2372 may be in close proximity to (e.g., in contact with or very near) each other when the system 2100 is in an initial, packaged, or undeployed state, as depicted in FIG. 34.

The upper housing element 2102t can define an orientation surface 2373, which can assist in achieving a rotational lock between the housing 2152 and the stiffener hub 2154, and thus in achieving a rotational lock between the needle 2104 (which is securely fastened to the housing 2152) and the stiffener 2106 (which is securely fastened to the stiffener hub 2154). Stated otherwise, the orientation surface 2373 can assist in maintaining a fixed angular orientation among specific components of the system 2100, which components include the handle 2150, the needle 2104 that is attached to the handle 2150, the stiffener hub 2154, and the stiffener 2106 that is attached to the stiffener hub 2154. Maintenance of such a fixed angular orientation can ensure that openings or ports at the distal ends of the needle 2104 and the stiffener 2106 are aligned when the system 2100 is in a pre-deployed state to define a continuous passageway through which a flash of blood can pass, as previously discussed with respect to the system 800 (see FIG. 20D, ports 880, 882, and passageway 886).

In the illustrated embodiment, the orientation surface 2373 comprises a substantially planar surface. In various embodiments, the plane of the orientation surface 2373 passes through, or is close to and passes parallel to, the longitudinal axis of the assembled system 2100. As discussed further below, the orientation surface 2373 can interact with an orientation surface of the stiffener hub 2154 to achieve the rotational or angular lock described above.

Figure 36A:
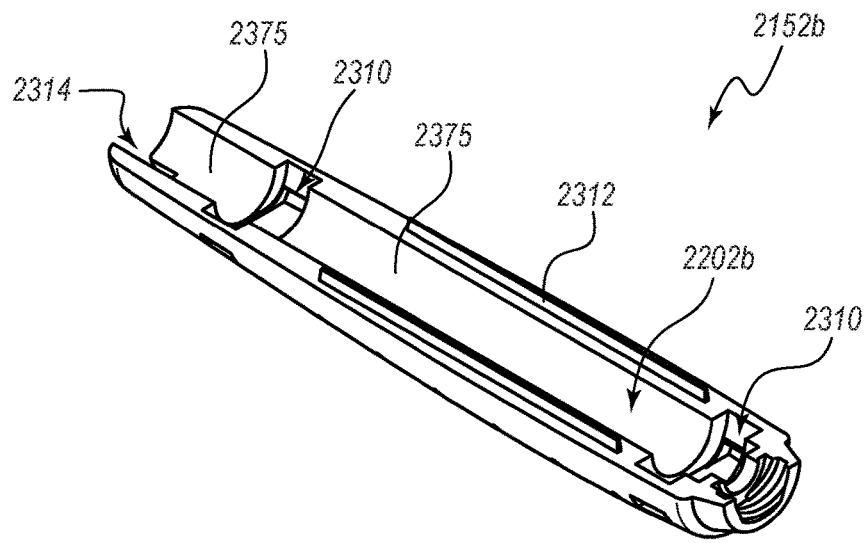
FIG. 36A is a perspective view of an embodiment of a lower housing element compatible with the catheter delivery system.
Figure 36B:
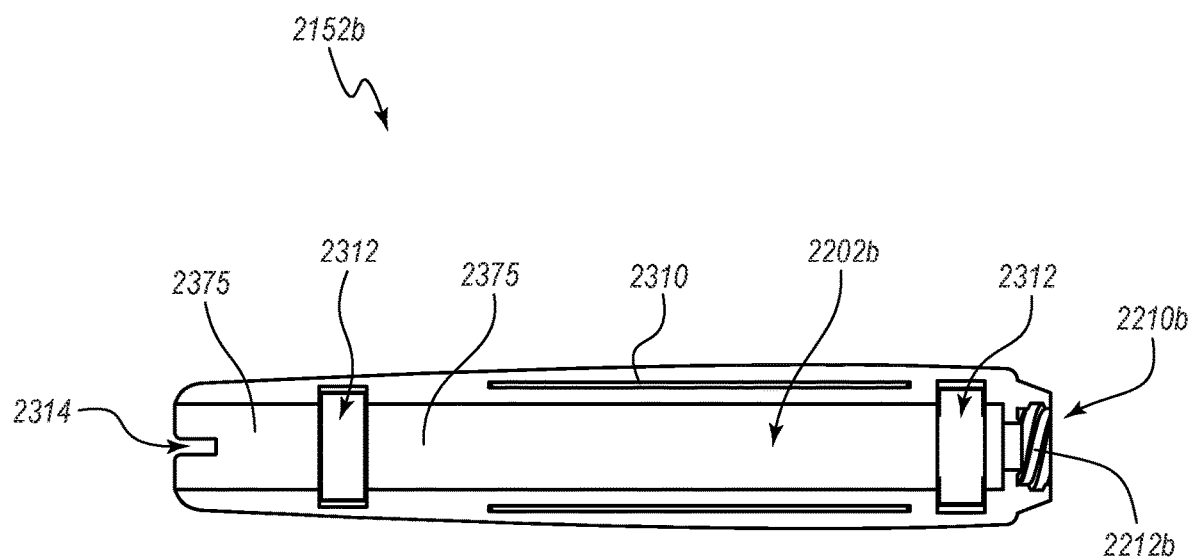
FIG. 36B is a top plan view thereof.

With reference to FIGS. 36A and 36B, the lower housing element 2152b can define a curved inner surface 2375, which can extend to a proximal end of the lower housing element 2152b. The proximal end of the curved inner surface 2375 can cooperate with the orientation surface 2372 of the upper housing element 2152t to define the channel 2151 through which the stiffener hub 2154 passes. The channel 2151 thus may define a keyed shape. The portion of the stiffener hub 2154 that extends through the channel 2151 may be complementary to the channel 2151 or may otherwise be shaped so as to pass through the channel 2151 in only a single angular orientation. In the illustrated embodiment, the channel 2151 is substantially semicircular. Other configurations are contemplated.

With reference to FIGS. 35A-36B, the upper housing element 2152t can include a recess 2102t that cooperates with a recess 2102b defined by the lower housing element 2152b to define a cavity 2202 (see FIG. 34), such as the cavity 902 discussed above. In the illustrated embodiment, the cavity 902 comprises a generally cylindrical profile along substantially a full length thereof.

The upper housing element 2152t can further define coupling elements to couple with the lower housing element 2152b. In the illustrated embodiment, the upper housing element 2152t includes four snaps, catches, or tabs 2305 that are inserted into two receptacles or slots 2312 defined by the lower housing element 2152b to secure the upper and lower elements together. Further coupling features include two longitudinally extending recesses 2306 defined by the upper housing element 2152t (FIG. 35B) and two complementary longitudinally extending protrusions 2312 defined by the lower housing element 2152b (FIGS. 36A and 36B) that are configured to fit within the recesses 2306. The tabs and slots and/or the protrusions and recesses can be reversed and/or other or further coupling features may be used. In some embodiments, the housing 2102 is assembled without any adhesive.

As shown in FIGS. 33, 34, 35B, and 36B, the upper and lower housing elements 2152t, 2152b can define a connection interface 2210 configured to selectively couple with the catheter connection hub 2145. In particular, the upper and lower housing elements 2152t, 2152b each defines a connection interface portion 2210t, 2210b, respectively, that cooperate to define the connection interface 2210. In the illustrated embodiment, the connection interface 2210 comprises internal threading 2212—specifically, threading portions 2212t, 2212b—that is configured to interface with complementary external threading on the catheter connection hub 2145. In the illustrated embodiment, the connection interface 2210 is positioned at the distal end of the housing 2152. Any suitable selective coupling our connection interface is contemplated. For example, in other embodiments, the housing 2152 may define a latch system that is configured to selectively disengage from the catheter connection hub 2145.

As shown in FIGS. 33-35B, the upper housing element 2152t can define an elongated, generally semi-conical shape that tapers from the front end to the rearward end thereof. An outer surface of the upper housing element 2152t can be rounded. Similarly, as shown in FIGS. 33, 34, 36A, and 36B, the lower housing element 2152b can define an elongated, generally frustoconical shape. Along at least the side edges of the lower housing element 2152b, the contour of the lower housing element 2152b substantially or smoothly matches the taper of the upper housing element 2152t. The lower housing element 2152b can be significantly shorter than the upper housing element 2152t. The upper and lower housing elements 2152t, 2152b can cooperate to define a handle 2150 that can be readily gripped and manipulated by a user in a single hand.

In the illustrated embodiment, the lower housing element 2152b defines a plurality of gripping features 2180 (see FIGS. 33, 34, 42). In the illustrated embodiment, the gripping features 2180 are laterally extending grooves. Any suitable friction-enhancing surface features, layers, or coatings are contemplated.

In some embodiments, the upper and lower housing elements 2152t, 2152b are formed of a polycarbonate (PC) and acrylonitrile butadiene styrene (ABS) blend (i.e., PC/ABS). In other embodiments, the upper and lower housing elements 2152t, 2152b are formed of polycarbonate, acetal, etc. Any suitable material is contemplated.

Figure 37A:
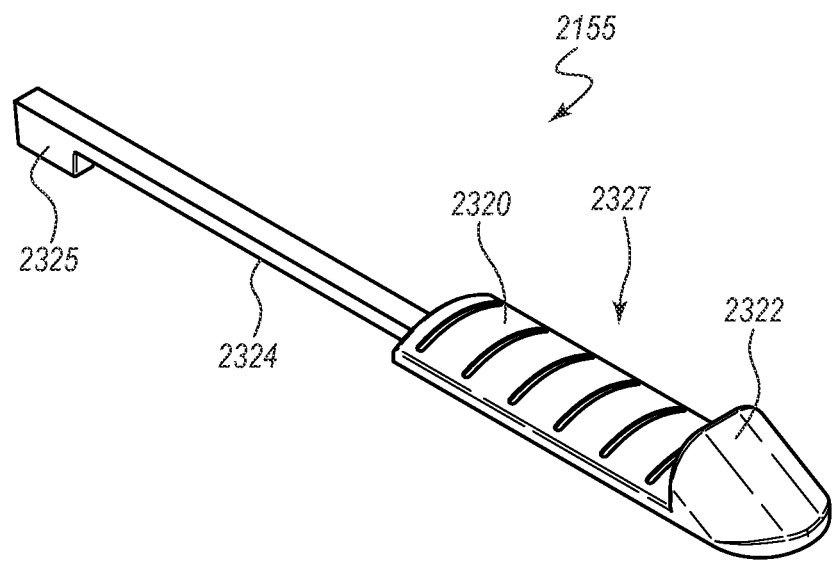
FIG. 37A is a perspective view of an embodiment of an upper actuator compatible with the catheter delivery system.
Figure 37B:
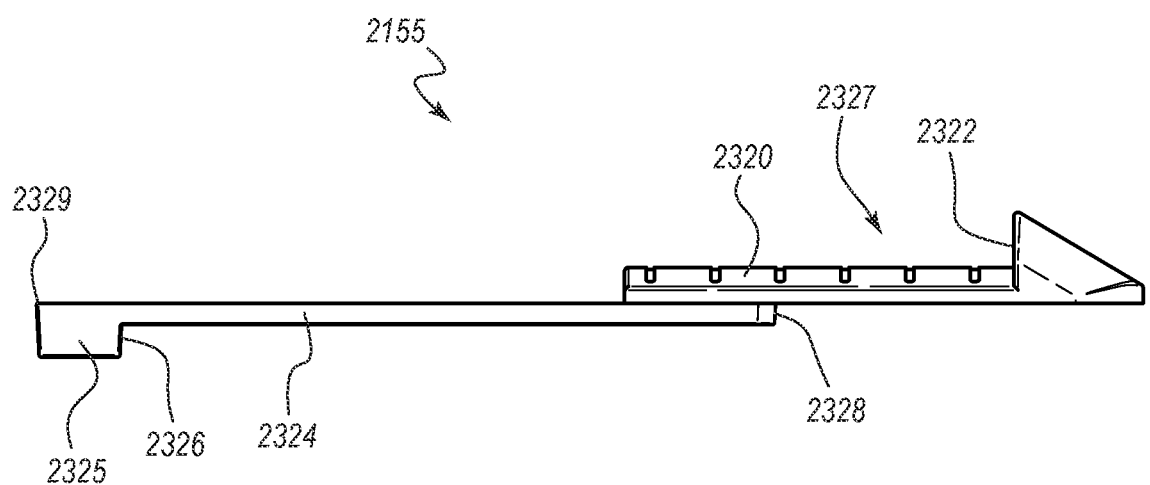
FIG. 37B is a side elevation view thereof.

With reference to FIGS. 37A and 37B, the upper actuator 2155 can include an actuation region 2327 that includes a grip 2320 and a catch 2322. The grip 2320 can include gripping features, such as lateral grooves, to enhance friction. The grip 2320 can be sized to be actuated by a fingertip, such as the tip of an index finger or a thumb. The grip 2320 can extend longitudinally to permit the fingertip to roll forward and backward over the grip 2320 while maintaining contact therewith. In other instances, a fingertip may be pressed firmly against the grip 2320 and maintain a substantially fixed orientation relative thereto to slide the upper actuator 2155 forward (and/or, in some instances, backward). Any suitable friction-enhancing surface features, layers, or coatings are contemplated for the grip 2320.

The catch 2322 can extend upwardly at a distal end of the grip 2320. In some instances, a proximal face of the catch 2322 can be engaged by a fingernail (e.g., a top surface of the fingernail) and the finger can be moved forward to advance the upper actuator 2155 forward. In some instances, the arrangement is particularly well suited for actuation via a flick of the index finger or via a more controlled forward unrolling of a curled or semi-curled index finger against the catch 2322, and in either case, the top surface of the fingernail can press forward on the rear surface of the catch 2322 to move the actuator 2155 forward. In other instances, the user may engage the angle atop the catch 3233 with a fingertip to move the upper actuator 2155 forward. Accordingly, the upper actuator 2155 may be engaged in a variety of manners to effect movement thereof.

The upper actuator 2155 can further include a longitudinal stem 2324 that connects the actuation region 2327 with an engagement protrusion 2325. The stem 2324 may also be referred to as a guide or slider. The engagement protrusion 2325 that extends from the stem 2324 can be configured to engage the stiffener hub 2154 within the housing 2152, as discussed further below. For example, in the illustrated embodiment, the engagement protrusion 2325 includes an engagement face 2326 that interferes with a surface of the stiffener hub 2154 when the upper actuator 2155 is advanced distally. The illustrated engagement face 2326 is a substantially planar face at a distal end of the engagement protrusion 2325 which, when positioned within the assembled system 2100, extends substantially transverse or orthogonal to the longitudinal axis of the system 2100.

The longitudinal stem 2324 can be sized (e.g., can define a width) to fit within the track 2307 of the upper housing element 2152*t* (FIG. 35B). As the upper actuator 2155 is advanced or retracted along the guide channel 2302 of the upper housing element 2152*t*, the longitudinal stem 2324 can slide or otherwise translate within the track 2307. The track 2307 and/or the guide channel 2302 can constrain movement of the upper actuator 2155, and in particular, can constrain movement of the longitudinal stem 2324. For example, the track 2307 and/or the guide channel 2302 can inhibit or prevent lateral movement of the longitudinal stem 2324.

As shown in FIG. 37B, the longitudinal stem 2324 can define a distal end 2328 and a proximal end 2329. The track 2307 of the upper housing element 2152*t* can be sufficiently long to accommodate the longitudinal stem 2324 in every position between and including a fully retracted state (e.g., a proximal-most state) and a fully advanced state (e.g., a distal-most state) of the upper actuator 2155. In some embodiments, when the upper actuator 2155 is in the fully retracted state, the proximal end 2329 of the longitudinal stem 2324 may be in close proximity to (e.g., may contact or be adjacent to) a proximal end of the track 2307 (see FIG. 34). When the upper actuator 2155 is in the fully advanced state, the distal end 2328 of the longitudinal stem 2324 may contact the distal end 2303 of the guide channel 2302 (see FIGS. 34, 35A, 37B). Thus, the distal end 2328 of the longitudinal stem 2324 may act as a stop to delimit forward movement of the upper actuator 2155.

In some embodiments, the upper actuator 2155 is formed of PC/ABS. In other embodiments, the upper actuator 2155 is formed of polycarbonate, acetal, etc. Any suitable material is contemplated.

Figure 38A:
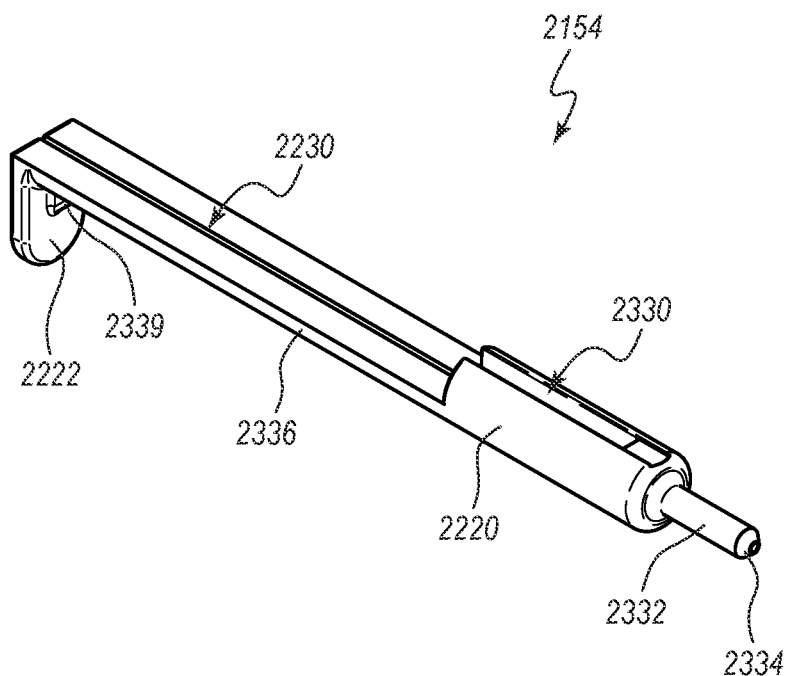
FIG. 38A is a perspective view of an embodiment of a lower actuator or stiffener hub compatible with the catheter delivery system.
Figure 38B:
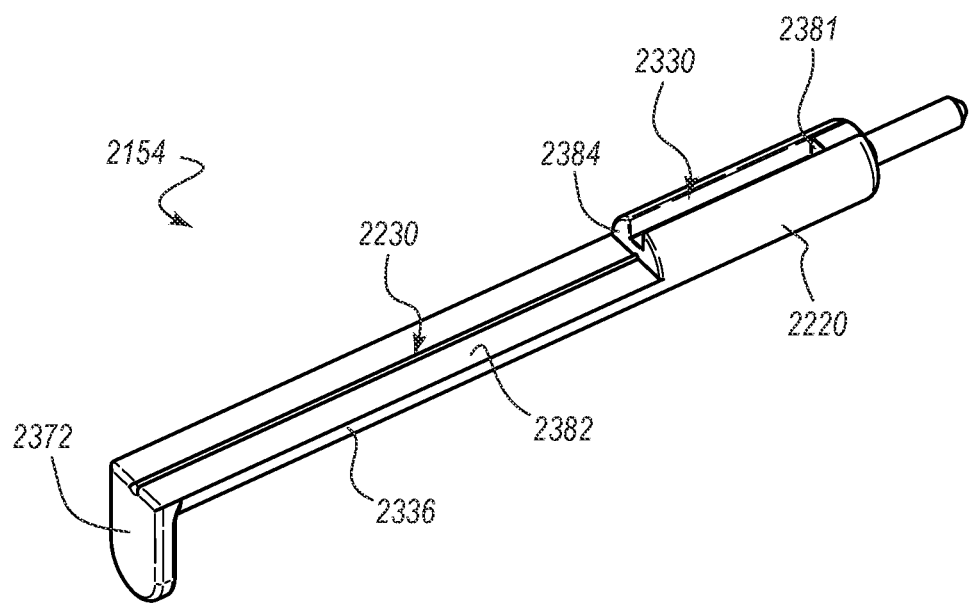
FIG. 38B is another perspective view thereof.
Figure 38C:
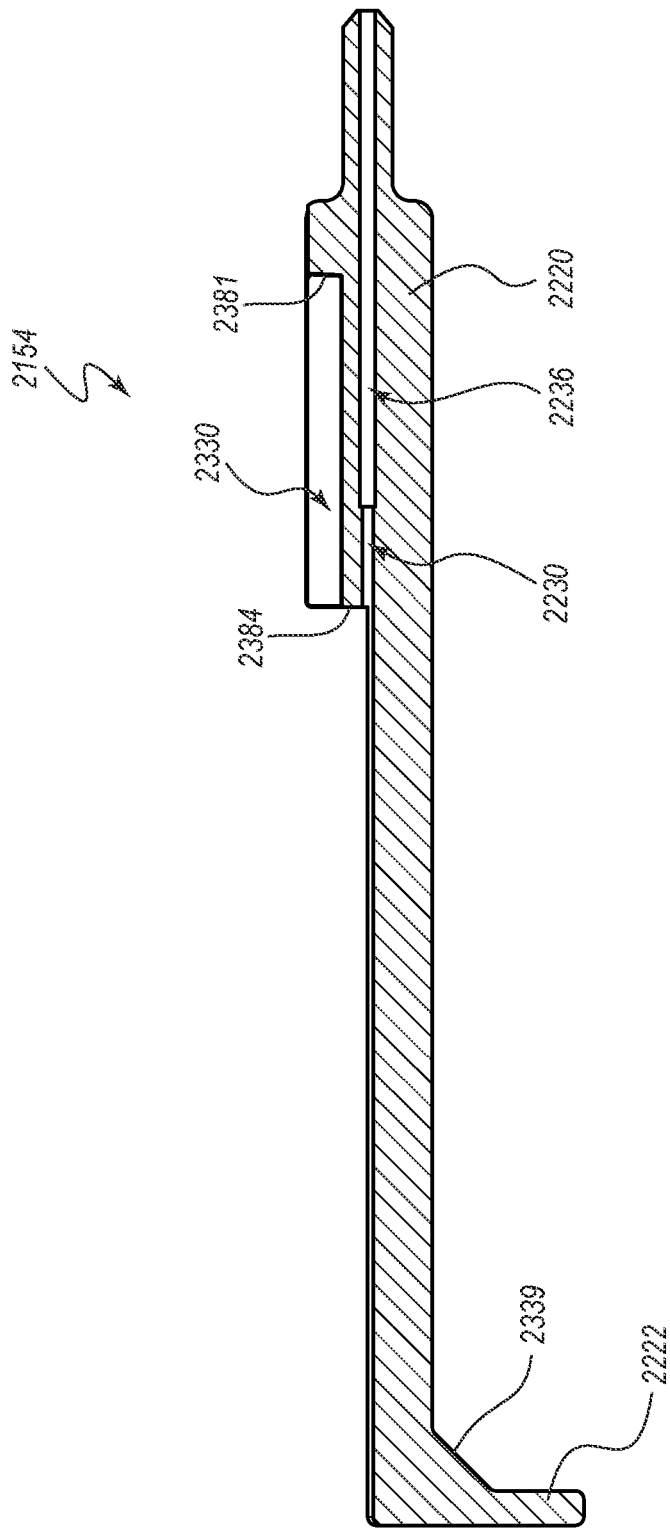
FIG. 38C is a cross-sectional view thereof.

With reference to FIGS. 38A, 38B, and 38C, the stiffener hub 2154 includes a body 2220 that resembles the body 920 discussed above in many respects. For example, as shown in FIG. 38C, the body 2220 can define an internal channel 2230 that includes a recessed region 2236 for coupling with the stiffener 2106, similar to the channel 930 and recessed region 936 discussed above.

The body 2220, however, can further define a track, guide path, or channel 2230 at an upper end thereof through which the engagement protrusion 2325 of the upper actuator 2155 (FIGS. 37A, 37B) can pass. The engagement protrusion 2325 can be sized to translate within the channel 2230 in an uninhibited manner. The engagement face 2326 of the engagement protrusion 2325 (FIG. 37B) can interface with (e.g., interfere with) an engagement face 2381 at a distal end of the channel 2230 to effect forward movement of the stiffener hub 2154. For example, in the illustrated embodiment, the engagement face 2381 defines a substantially planar surface that extends substantially orthogonally relative to a longitudinal axis of the assembled system 2100. The opposing engagement faces 2326, 2381 of the channel 2230 of the stiffener hub 2154 and of the engagement protrusion 2325 of the upper actuator 2155, respectively, thus can interfere with each other, or selectively engage with each other, when the upper actuator 2155 is advanced distally. The engagement faces 2326, 2381 can disengage from each other when the upper actuator 2155 is retracted proximally.

The stiffener hub 2154 can further include a protrusion 2332 that extends distally from the body 2220. The protrusion 2332 can include a tapered tip 2334 at a distal end thereof that fits within a tapered mouth 2264 of the catheter hub core 2141 (see FIGS. 34 and 39). The tapered tip 2334 of the stiffener hub 2154 can directly engage the catheter hub core 2141, and may function as (and be referred to as) an engagement member, e.g., such as the engagement member 1813 discussed above.

The stiffener hub 2154 can further include a stem, column, bridge, or extension 2336 that extends rearwardly from the body 2220 to couple the body 2220 to the actuator 2222. The extension 2336 may also be viewed as a forward extension of the actuator 2222, which transfers forces applied on the actuator 2222 to the body 2220. The extension 2336 can define a portion of the needle channel 2230. In the illustrated embodiment, the portion of the needle channel 2230 defined by the extension 2336 is a groove that is sized to permit ready passage therethrough of the needle 2104. In some embodiments, interaction of the channel 2230 and the needle 2104 can maintain or assist in maintaining a longitudinal axis of the stiffener hub 2154 in alignment with a longitudinal axis of the assembled system 2100.

The extension 2336 can define an orientation surface 2382 that is configured to interface with the orientation surface 2373 of the upper housing element 2102*t* to achieve a rotational lock. In the illustrated embodiment, the orientation surface 2382 substantially defines a plane that passes through, or is close to and passes parallel to, the longitudinal axis of the assembled system 2100. The orientation surfaces 2382, 2373 can slide along or past one another to maintain a fixed angular relationship between the stiffener hub 2154 and the upper housing element 2012*t*.

A cross-section or outer contour of the extension 2336 can be keyed to the shape of the rear channel 2151 defined by the housing 2152 (see FIG. 34), as previously discussed. In the illustrated embodiment, the outer contour of the extension 2336 substantially defines a semicircle.

In some embodiments, the stiffener hub 2154 defines an angled rib 2339 that can interface with a groove 2314 of the lower housing element 2152*b* (see FIGS. 36A, 36B, 42C). For example, the rib 2339 can be received within the groove 2314 when the stiffener hub 2154 is advanced forward to a fully deployed state. In some instances, the rib 2339 can arrest forward movement of the stiffener hub 2154 relative to the housing 2152, as discussed further below. The rib 2339 can strengthen the actuator 2222 or can stabilize the actuator 2222 relative to the extension 2336.

The body 2220 of the stiffener hub 2154 can be configured to readily pass through the chamber 2202 of the housing 2152. In the illustrated embodiment, the body 2220 defines a generally cylindrical outer surface, relative to which the channel 2330 is recessed. The cylindrical outer surface can be sized to translate within (e.g., slide within) the generally cylindrical inner surface of the housing 2152. Any other suitable arrangement is contemplated for the body 2220 and the chamber 2202. For example, the body 2220 and the chamber 2202 may not be complementarily shaped in other embodiments. The chamber 2202 may be said to constrain movement of the body 2220 therein, such as to ensure a substantially linear path of movement that is substantially aligned with the longitudinal axis of the system 2100.

In the illustrated embodiment, the body 2220 of the stiffener hub 2154 defines a stop 2384, which may also be referred to as an abutment surface. The illustrated stop 2384 comprises a substantially planar face at a proximal end of the body 2220. The plane of the face is substantially transverse or orthogonal to the longitudinal axis of the assembled system 2100. As discussed further below, the stop 2384 can prevent or inhibit removal of the stiffener hub 2154 from the housing 2152.

In various embodiments, the stiffener hub 2154 is formed of one or more of acetal, polycarbonate, PC/ABS, etc. Any suitable material is contemplated.

Figure 39:
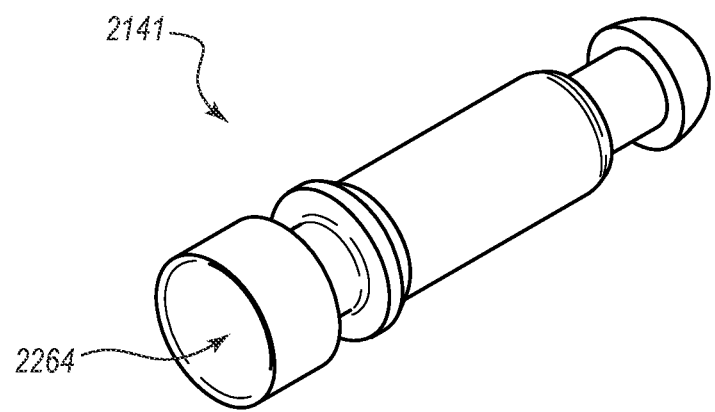
FIG. 39 is a perspective view of an embodiment of a catheter hub core compatible with the catheter delivery system.

With reference to FIG. 39, the catheter hub core 2141 can substantially resemble other like-named and like-numbered components previously discussed. For example, the catheter hub core 2141 can be substantially identical to the catheter hub core 841 depicted in FIGS. 18A and 18B. As previously mentioned, the tapered mouth 2264 at the proximal end of the catheter hub core 2141 can receive and interfere with the tapered tip 2334 of the stiffener hub 2154. The stiffener hub 2154 can thereby directly transfer forces to the catheter hub core 2141, such as during coupling of the catheter hub core 2141 to the catheter connection hub 2145. As with other like-named and like-numbered components within the present disclosure, previous discussions of the catheter hub cores 841, 1141, 1841, 2041 are equally applicable to the catheter hub core 2141.

In some embodiments, the catheter hub core 2141 is formed of polyurethane, such as, for example, Isoplast®, available from Lubrizol, of Wickliffe, Ohio. Another illustrative example of a suitable material includes polycarbonate. Any suitable material is contemplated.

Figure 40:
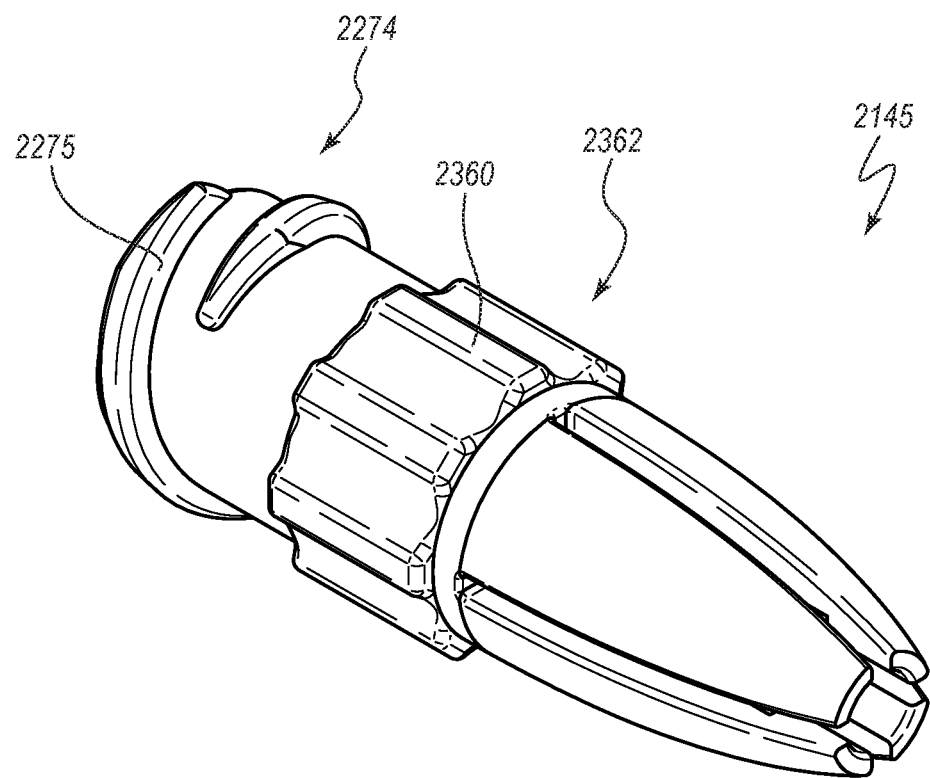
FIG. 40 is a perspective view of an embodiment of a catheter connection hub compatible with the catheter delivery system.

With reference to FIG. 40, the catheter connection hub 2145 can substantially resemble other like-named and like-numbered components previously discussed, and thus prior disclosures with respect to such components are equally applicable to the catheter connection hub 2145. For example, the catheter connection hub 2145 includes a connection interface 2274 configured to selectively couple the catheter connection hub 2145 to the housing 2152 and selectively decouple the catheter connection hub 2145 from the housing 2152 in manners such as previously disclosed. In the illustrated embodiment, the connection interface 2274 comprises external threading 2275. In other embodiments, one or more external lugs or protrusions that can suitably couple with the threading 2212 of the housing 2142 may be used in place of the threading 2275. Any suitable connection interface 2274 is contemplated.

In the illustrated embodiment, the catheter connection hub 2145 can include a friction-enhancing feature 6 of any suitable variety to facilitate decoupling of the catheter assembly 2149—specifically, for decoupling the catheter connection hub 2145—from the handle 2150. In the illustrated embodiment, the friction-enhancing feature 2362 comprises a knurled annulus 2360, which can facilitate rotation of the catheter connection hub 2145. Other arrangements are also contemplated.

In some embodiments, the catheter connection hub 2145 is formed of polyurethane, such as, for example, Isoplast®, available from Lubrizol. Another illustrative example of a suitable material includes polycarbonate. Any suitable material is contemplated.

Figure 41A:
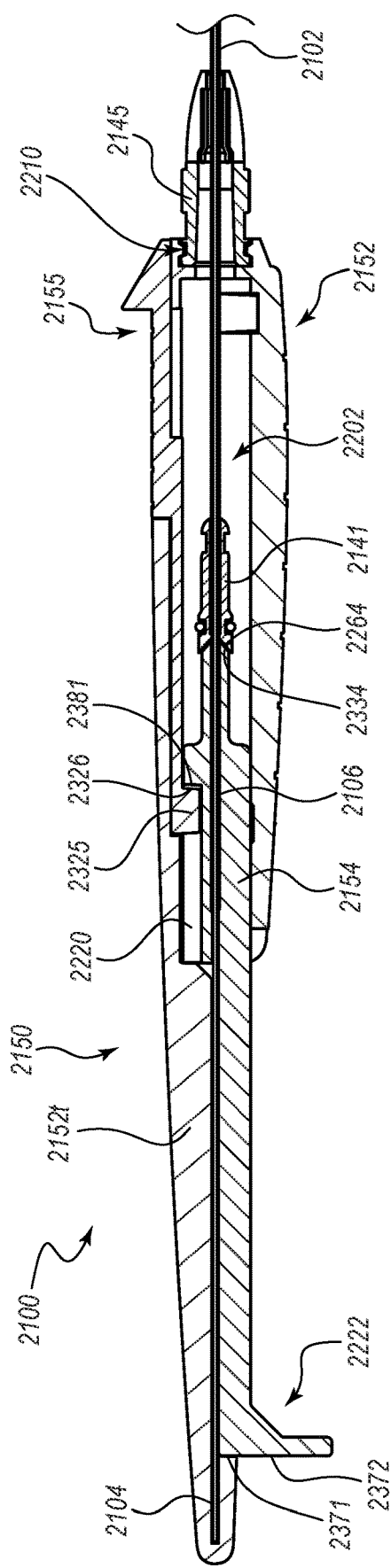
FIG. 41A is a cross-sectional view of the catheter delivery system in a pre-use or pre-actuation state.
Figure 41B:
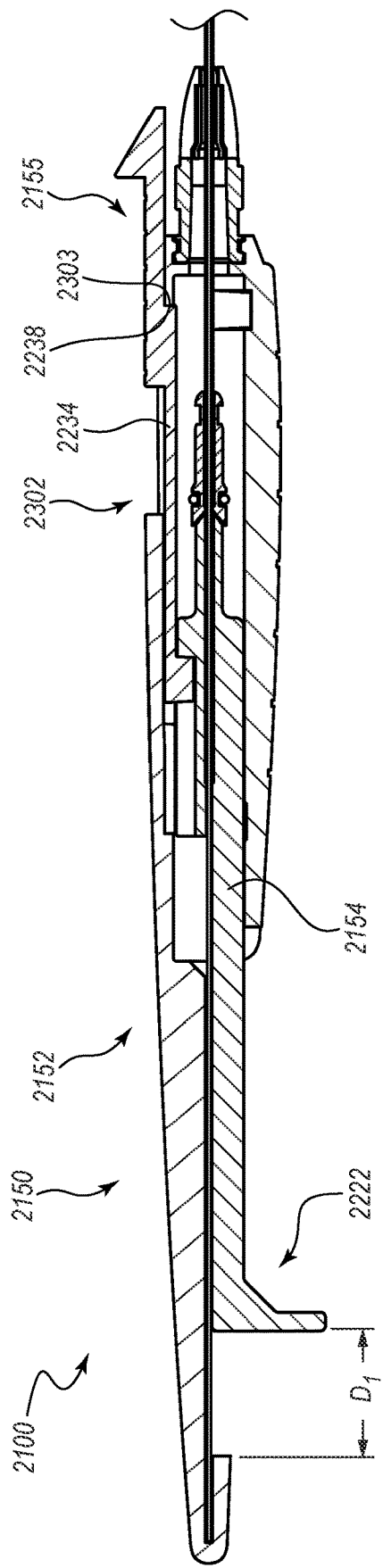
FIG. 41B is another cross-sectional view of the catheter delivery system in a partially deployed or preliminarily actuated state.

FIGS. 41A-41C depict various stages of operation of the system 2100. Stated otherwise, FIGS. 41A-41C depict various stages or steps of illustrative methods, such as methods of using the system 2100. Accordingly, the following discussion of these drawings disclose both operational details of embodiments of the system 2100, as well as illustrative methods, including methods that specifically employ embodiments of the system 2100.

FIG. 41A depicts the system 2100 in an undeployed, pre-use, as-packaged, or initial state. For example, the system 2100 is shown in a state in which the system 2100 may be sterilized, packaged, delivered to a user, and/or removed from packaging by the user. Stated otherwise, the user may, in some instances remove the system 2100 from packaging in substantially the illustrated configuration.

In some embodiments, the system 2100 includes a cap (not shown), which can cover the distal tip of the needle 2104 to prevent inadvertent sticks prior to intended use. Any suitable mechanisms may also be employed to maintain the upper actuator 2155 and the lower actuator 2222 in their respective retracted states. For example, in some embodiments, the cap and/or a separate spacer or stop element (not shown) can be configured to maintain the upper actuator 2155 in the fully retracted or undeployed orientation. Further, in some embodiments, a separate cap, spacer, or stop element and/or packaging for the system 2100 can prevent actuation of the lower actuator, such as during transport.

As previously mentioned, the general arrangement of and relationships between the catheter 2102, the needle 2104, and the stiffener 2106 in the illustrated pre-use configuration are substantially the same as those depicted and described with respect to the catheter 802, the needle 804, and the stiffener 806 in FIGS. 20A-20D. Moreover, any suitable materials may be used for the catheter 2102, the needle 2104, and the stiffener 2106, such as those previously described (e.g., with respect to the catheter 102, the needle 104, and the stiffener 106).

In the pre-use configuration, each of the upper and lower actuators 2155, 2222 is in a fully retracted position. Stated otherwise, each of the upper and lower actuators 2155, 2222 is at a proximal-most or fully rearward position. Accordingly, the stiffener hub 2154 is also in a fully retracted position. In the illustrated embodiment, the stop 2384 defined by the body 2220 of the stiffener hub 2154 abuts an inner surface of the upper housing element 2152t, which can prevent or inhibit removal of the stiffener hub 2154 from the housing 2152. Similarly, the stop 2372 of the lower actuator 2222 contacts the stop 2371 defined by the proximal portion of the upper housing element 2152t, which likewise can prevent or inhibit removal of the stiffener hub 2154 from the housing 2152. In other embodiments, only one of the stops 2372, 2384 of the stiffener hub 2154 may contact the upper housing element 2152t when the stiffener hub 2154 is retracted, such as may result from variances within acceptable tolerance ranges. The multiple stops 2372, 2384 may provide redundancy to ensure the stiffener hub 2154 remains within the housing 2152 when retracted.

In the illustrated embodiment, the upper actuator 2155 does not initially engage the stiffener hub 2154 when both components are in their retracted orientations. In particular, as can be seen in FIG. 41A, a small space or gap is present between the engagement face 2326 of the engagement protrusion 2325 of the upper actuator 2155 and the engagement face 2381 of the stiffener hub 2154. Accordingly, the upper actuator 2155 is advanced forwardly a short distance to initially engage the stiffener hub 2154.

In other embodiments, the engagement faces 2326, 2381 of the upper actuator 2155 and the stiffener hub 2154 are in abutting contact in the pre-use state of the system 2100, such that forward movement of the upper actuator 2155 immediately achieves concurrent forward movement of the stiffener hub 2154. In some instances, the presence and/or size of any initial gap between the engagement faces 2326, 2381 can vary from system 2100 to system 2100 within an acceptable tolerance range, such that no forward movement or only slight movement of the upper actuator 2155 is required prior to the upper actuator 2155 engaging the stiffener hub 2154 for any of the systems 2100 manufactured within specification.

As previously noted, the distal tip 2334 of the stiffener hub 2154 is complementary to the tapered proximal mouth 2264 of the catheter hub core 2141 and can fit snugly therein to efficiently apply deployment forces to the stiffener hub 2154 in the distal direction. In the illustrated embodiment, the distal tip 2334 of the stiffener hub 2154 engages the proximal mouth 2264 of the catheter hub core 2141 while the system 2100 is in the pre-use or pre-deployment state. In some instances, it can be desirable to ensure that the stiffener hub 2154 engages the catheter hub core 2141 in this initial state of the system 2100 to ensure that the stiffener 2106 and catheter 2102 move substantially in unison immediately upon actuation of the stiffener hub 2154. That is, the stiffener hub 2154 immediately transfers force to the catheter hub core 2141 such that both components move forward in unison. Such an arrangement can alleviate strain forces along the length of the catheter 2106 that might otherwise arise in the absence of the stiffener hub 2154 pushing the catheter hub core 2141 forward.

For example, as previously discussed (with respect to other embodiments), advancement of the stiffener 2106 causes the distal tip of the stiffener 2106 to push forwardly on the distal tip of the catheter 2102. This not only causes the distal tip of the catheter 2102 to move forward, but also draws the remainder of the catheter 2102 forward as well, due to stresses exerted along the length of the catheter 2102. Should forward movement of the catheter hub core 2141 be impeded, strain along the length of the catheter 2102 can increase.

By urging the catheter hub core 2141, to which the proximal end of the catheter 2102 is attached, forward, the stiffener hub 2154 alleviates stresses along at least a portion of the length of the catheter 2102. This stress alleviation can be particularly pronounced, and particularly useful, at latter stages of the catheter deployment for certain embodiments, where increased force may need to be provided to the catheter hub core 2141 to spread open the resilient arms at the distal end of the catheter connection hub 2145 during coupling of the catheter hub core 2141 to the catheter connection hub 2145 (in manners such as previously discussed). In such instances, all or substantially all force required to couple the catheter hub core 2141 to the catheter connection hub 2145 can be provided directly to the catheter hub core 2141 by the stiffener hub 2154.

The strain relief provided to the catheter 2102 by the interfacing of the stiffener hub 2154 with the catheter hub core 2141 can be explained in other terms. For example, by ensuring a direct coupling between the stiffener hub 2154 and the catheter hub core 2141 exists in the initial, pre-use state of the system 2100, both the proximal ends and distal ends of the catheter 2102 and the stiffener 2106 move forward at the same rate. Stated otherwise, a length of the catheter 2102 and a length of the stiffener 2106 are each substantially constant throughout deployment, and further, the catheter 2102 and the stiffener 2106 move forward in unison.

In other embodiments, a space or gap may be present between the distal tip 2334 of the stiffener hub 2154 and the tapered proximal mouth 2264 of the catheter hub core 2141 when the system is in the initial or pre-use orientation, and potentially through at least some of the subsequent phases of deployment. For example, a small gap may be present due to manufacturing tolerances or the like. In certain of such instances, the stiffener hub 2154 does not assist in translating the catheter hub core 2141 forward unless and until sufficient strain on the catheter 2102 elongates the catheter 2102 into contact with the stiffener hub 2154. For example, in certain of such embodiments, the catheter hub core 2141 may be pulled distally by the catheter body 2102 up until the catheter hub core 2141 comes into contact with the resilient arms of the catheter connection hub 2145. Due to the increased resistance to distal movement provided by the catheter connection hub 2145, the catheter body 2102 may elongate as the stiffener 2106 is urged distally to the point where the stiffener hub 2154 engages the proximal end 2334 of the catheter hub core 2141. At this point, the stiffener hub 2154 can directly push on the catheter hub core 2141, thereby supplementing the distal forces on the catheter hub core 2141 that are also provided to the catheter hub core 2141 through an indirect path—specifically, the stiffener hub 2154 urges the stiffener 2106 forward, which urges the distal tip of the catheter 2106 forward, which pulls the proximal end of the catheter 2016 and the catheter hub core 2141 to which it is attached forward.

With continued reference to FIG. 41A, in the illustrated embodiment, when the system 2100 is in the pre-use or undeployed state, the catheter hub core 2141 is spaced from the catheter connection hub 2145. In particular, the catheter hub core 2141 is entirely separate from the catheter connection hub 2145, is not in contact therewith, and is distanced from the catheter connection hub 2145 by a significant length. The catheter hub core 2141 is positioned rearward of or proximal to the catheter connection hub 2145. The catheter hub core 2141 is positioned at an interior of the housing 2142, or stated otherwise, is fully received within the cavity 2202 of the housing 2142. The housing may 2142 may be said to encompass, encircle, or enclose the catheter hub core 2141. Moreover, in the illustrated embodiment, no portion of the catheter hub core 2141 is encompassed, encircled by, or enclosed by the catheter connection hub 2145 when the system 2100 is in the pre-deployed state.

In contrast, in the illustrated embodiment, the catheter connection hub 2145 is coupled to a distal end of the housing 2152 in manners such as previously disclosed. Accordingly, the catheter connection hub 2145 is connected to the housing 2152 via a connection interface 2210. With the exception of the coupling interface 2210, substantially an entire exterior surface of the catheter connection hub 2145 is at an exterior of the housing 2142. An interior of the catheter connection hub 2145 is, however, in fluid communication with the cavity 2202 of the housing 2142. Further, in the illustrated embodiment, with the exception of the proximal portion of the catheter connection hub 2145 that defines the connection interface 2210, a substantial portion or most of the catheter connection hub 2145 extends distally away from the housing 2142 and is external to the housing 2142.

In the initial state of the system 2100, the catheter hub core 2141 is free to translate within the housing 2141 in manners such as previously disclosed (e.g., slide longitudinally while remaining rotationally locked). In contrast, the catheter connection hub 2145 is in a selectively fixed relationship relative to the housing 2142.

As further discussed below, when the system 2100 is in the undeployed state, the distal end of the system 2100 (e.g., the distal tips of the needle 2104, the catheter 2102, and stiffener 2106) can be advanced through the skin of a patient, thereby establishing an insertion site of the skin (e.g., the insertion site 54 identified in FIG. 4A), and at least a distal tip of the needle 2104 can further be advanced into a vessel of the patient, thereby establishing a vessel insertion site (e.g., the vessel insertion site 56 identified in FIG. 4A). In some instances, deployment of the system 2100 begins after only the tip of the needle 2104 has been advanced into the vessel. In other instances, the distal tip of the catheter 2102—and, in further instances, the distal tip of the stiffener 2106 as well—likewise enters into the lumen of the vessel through the vessel insertion site by a relatively small amount while the system 2100 is in the undeployed state.

Once a suitable portion of the distal end of the system 2100 is within the lumen of the vessel, as indicated by a flash of blood in manners such as previously disclosed, the system 2100 can then be actuated or deployed to insert the catheter 2102 into the vessel and thereafter advance the catheter 2102 to a final or maximum depth within the vessel (e.g., where only the distal tip of the needle 2104 was initially inserted into the vessel lumen), or to advance the catheter 2102 to the final depth within the vessel (e.g., where at least the tip of the catheter 2102 was also initially inserted into the vessel lumen).

FIG. 41B depicts the system 2100 in a subsequent operational state. In particular, the system 2100 has been partially deployed or deployed an intermediate amount via the upper actuator 2155. A range of partial or intermediate deployments of the system 2100 are possible via the actuator 2155. In the illustrated stage, the upper actuator 2155 has been advanced to its maximum forward position, which has resulted in forward movement of the stiffener hub 2154, and hence concurrent forward movement of the stiffener 2106 and the catheter 2102 through a distance D1. In some embodiments, as discussed further below, the distance D1 can be selected to ensure that the stiffener 2106 and the catheter 2102 are advanced through the lumen of the vessel to a depth sufficient to maintain the catheter 2102 and the stiffener 2106 within the vessel for a temporary period prior to final advancement of the catheter 2102 and the stiffener 2106 to the maximum deployed depth via the lower actuator 2222.

Stated otherwise, as previously discussed, the upper actuator 2155 can be moved forward until a surface thereof (specifically, the stop surface at the distal end 2328 of the stem 2324) abuts the distal end 2303 of the track 2302 defined by the housing 2152. In so doing, the upper actuator 2155 can achieve movement of the stiffener hub 2154 through a distance D1. That is, due to engagement between the upper and lower actuators 2155, 2154, the lower actuator 2154 may be moved in unison with the upper actuator 2155 through the same or substantially the same distance as the upper actuator 2155. In some instances, the upper and lower actuators 2155, 2222 are already engaged with each other in the undeployed state of the system 2100, and the distance traveled by the upper actuator 2155 is equal to D1. In instances where the actuators 2155, 2222 are not engaged in this manner from the outset, the distance traveled by the upper actuator 2155 can be less than D1.

Stated yet another way, in the operational phase depicted in FIG. 41B, the upper actuator 2155 has been advanced along an entirety of the track 2302, and thus along a predetermined distance. This forward movement of the upper actuator 2155 pulls the stiffener hub 2154 forward by a corresponding or roughly corresponding amount. In particular, when the upper actuator 2155 is moved from its fully retracted position to its fully advanced position, as shown, the stiffener hub 2154 also moves a predetermined distance, which may be the same as or substantially the same as the predetermined distance travelled by the upper actuator 2155.

For reasons discussed further hereafter, the first deployment distance D1 traveled by the stiffener hub 2154 may also be referred to as a stabilization, anchoring, and/or retention distance, as advancing the catheter 2102 into the vessel to this distance can help to ensure that the catheter 2102 remains positioned within the vessel for at least an intermediate period. The intermediate period can begin after the initial deployment phase achieved via the upper actuator 2155 has ceased and can end once actuation of the lower actuator 2222 to achieve a final deployment of the system 2100 begins.

As previously discussed, in some instances, the upper actuator 2155 can conveniently be advanced forwardly in a variety of ways using a single finger (e.g., the index finger) of a hand while that same hand is holding the handle 2150. In the illustrated embodiment, the upper actuator 2155 is at the forward end of the handle 2150, which can facilitate this form of actuation.

As previously mentioned, the general arrangement of and relationships between the catheter 2102, the needle 2104, and the stiffener 2106 at various phases of deployment can resemble those illustrated elsewhere herein. For example, the relative positions of the distal ends of the catheter 2102, the stiffener 2106, and the needle tip 2104 in the operational phase depicted in FIG. 41B can be substantially as shown in, and as described with respect to, FIGS. 21C and 21D, with the exception that the distance between the needle tip 2104 and the catheter tip 2102 may be greater or smaller, depending on the overall length of the catheter 2102.

FIG. 41C depicts the system 2100 in a subsequent operational state. In particular, the system 2100 has been fully deployed or deployed a complete or maximum amount. The final amount of actuation has been achieved via the lower actuator 2222. A range of partial or intermediate deployments of the system 2100 are also possible via the lower actuator 2222. However, in the illustrated stage, the lower actuator 2222 has been advanced to its maximum forward position, which has resulted in forward movement of the stiffener hub 2154, and hence concurrent forward movement of the stiffener 2106 and the catheter 2102 through an additional distance D2. Accordingly, the system 2100—and, specifically, the stiffener hub 2154 of the system 2100—has been actuated through a total distance D3, which is the sum of D1 (resulting from the indirect actuation of the stiffener hub 2154 via the upper actuator 2155) and D2 (resulting from the direct actuation of the stiffener hub 2154 via the lower actuator 2222).

Stated otherwise, after initial actuation of the system 2100 via the upper actuator 2155, the lower actuator 2222 can be advanced the remainder of an available forward path to finish deploying the catheter 2102/stiffener 2106 combination over the needle 2104. Thus, the lower actuator 2222 may be advanced any additional distance up to a maximum additional distance of D2.

In the illustrated embodiment, no further forward movement of the upper actuator 2155 occurs during direct actuation of the lower actuator 2222. Stated otherwise, the upper actuator 2155 may disengage from the stiffener hub 2154 and remain stationary relative to the housing 2152 during the further forward advancement of the stiffener hub 2154.

The forward path traveled by the stiffener hub 2154 can be delimited by the catheter connection hub 2145. Stated otherwise, coupling of the catheter hub core 2141 with the catheter connection hub 2145 can terminate forward advancement of the stiffener hub 2154. In particular, in the illustrated embodiment, the lower actuator 2222 is urged (e.g., pressed) forward to directly advance the stiffener hub 2154 forward. As previously discussed, throughout either a portion of or an entirety of this forward advancement of the stiffener hub 2154, the stiffener hub 2154 can engage and press on a proximal end of the catheter hub core 2141, thus urging the catheter hub core 2141 forwardly. The user can be provided with a tactile feedback that the catheter hub core 2141 has begun engaging the resilient arms of the catheter connection hub 2145 as resistance to forward movement of stiffener hub 2154 can increase. Ultimately, the catheter hub core 2141 is advanced distally by a sufficient amount to permit the deflected engagement arms of the catheter connection hub 2145 to snap into a groove of the catheter hub core 2141 and firmly hold the catheter hub core 2141, as described more fully above with respect to FIGS. 21B and 22B. Because the catheter connection hub 2145 is securely connected to the housing 2152 and the catheter hub core 2141 is securely connected to the catheter connection hub 2145 at this point, the user can be prevented from advancing the stiffener hub 2154 any further relative to the housing 2152. This significant resistance or complete opposition to further advancement of the stiffener hub 2154 relative to the housing 2152 can provide further tactile feedback to the user, this time indicating that deployment is complete and the catheter assembly 2149 is fully assembled.

In some embodiments, the user may also receive auditory feedback that deployment is complete. For example, the catheter connection hub 2145 and/or the catheter hub core 2141 may individually or in cooperation generate an auditory signal upon coupling. In the illustrated embodiment, connection of the catheter connection hub 2145 to the catheter hub core 2141 generates an audible "click," indicating that coupling is complete.

In other or further instances, the forward path can be delimited by direct contact between the stiffener hub 2154 and the lower housing element 2152b. In any event, the stiffener hub 2154 may cooperate directly or indirectly with the housing 2152 to delimit forward movement of the stiffener hub 2154, with the total distance traveled throughout full actuation of the stiffener hub 2154 being D3 (i.e., D1+D2).

As previously discussed, in some instances, the lower actuator 2222 can conveniently be advanced forwardly by one hand of a user while the user holds the housing 2152 with the other hand. In some instances, it may be convenient or otherwise advantageous for the lower actuator 2222 to be positioned rearward of the lower housing element 2152b, generally rearward of the upper actuator 2155, and/or extend downward relative to the housing 2152 generally. In some instances, such an arrangement can yield a compact system 2100, as the lower actuator 2222 does not extend significantly beyond lower profile of the lower housing element 2152b. Nevertheless, the illustrated actuator 2222 is sufficiently large to be readily gripped and/or readily pushed to deploy, or further deploy, the system 2100. In some instances, such a significant rearward location of the lower actuator 2222 can permit the handle 2150 to be positioned close to the skin of the patient, which can permit shallow insertion angles.

As previously mentioned, the general arrangement of and relationships between the catheter 2102, the needle 2104, and the stiffener 2106 at various phases of deployment can resemble those illustrated elsewhere herein. For example, the relative positions of the distal ends of the catheter 2102, the stiffener 2106, and the needle tip 2104 in the operational phase depicted in FIG. 41C can be substantially as shown in, and as described with respect to, FIGS. 21C and 21D, with the exception that the distance between the needle tip 2104 and the catheter tip 2102 may be greater or smaller, depending on the overall length of the catheter 2102, and in any event, the distance between the needle tip 2104 and the catheter tip 2102 will have increased, as compared with the operational phase of FIG. 41B.

With further reference to FIGS. 41A-41C, a two-actuator system 2100 and two-phase deployment process, as just described can be advantageous in some instances. The first stage of actuation (e.g., an index finger flick or other advancement of the upper actuator 2155) can assist in an initial capture the vessel, and the second stage of actuation can then advance the catheter 2102 to its final or fully inserted position.

This may be particularly useful in deep vein placements of the catheter 2102. In such placements, a practitioner may use, e.g., the nondominant hand to press against the skin above the vessel to provide tension to the region and assist in positioning the vessel and/or aligning the system 2100 with the same. The other (e.g., dominant) hand can grip the system 2100 (or any desired portion thereof, such as the handle 2150), and advance the full system 2100 forward to introduce the needle tip (and potentially the catheter tip as well, at this stage) into the vessel until a flash of blood is seen.

Removal of the non-dominant hand from the skin of the patient at this point, prior to deployment of the catheter 2102 into the vessel over the needle 2104, could allow sufficient shifting of the vessel and surrounding tissues, or otherwise destabilize the region and/or allow inadvertent movement of the dominant hand and the system 2100 it is holding relative to the region, in a manner that the needle 2104 and catheter 2102 inadvertently emerge from the vessel. To prevent this, after placement of the needle tip in the vessel, it can be desirable to advance the catheter 2102 (e.g., via the sheathing cannula 2106) into the vessel to, e.g., at least ½ inch or so to prevent inadvertent removal of the catheter 2102 from the vessel when the nondominant hand is removed in order to actuate the lower actuator 2222 thereby. This is accomplished by advancing the upper actuator 2155 forward while both hands maintain steady positioning, such as pressure on the patient with the nondominant hand and gripping of the system 2100 with the dominant hand. After initial capture of the vessel in this manner and removal of the nondominant hand from the patient's skin, the nondominant hand can then be used to advance the lower actuator 2222 to finish advancing the catheter 2012 into the patient to the target depth, or stated otherwise, to the fully deployed position.

Capture of the vessel in the foregoing manner may be referred to in a variety of ways. For example such vessel capture may also be referred to as stabilizing or anchoring the system 2100 relative to the vessel. That is, the catheter 2102 is desirably advanced to a position within the vessel that will permit retention of the catheter 2102 within the vessel, despite small or inadvertent relative movements between the vessel and the system 2100. Accordingly, the initial distance to which the catheter 2102 is advanced over the needle within the vessel (e.g., the distance D1) may be referred to as a capture, stabilization, anchoring, or retention distance. Such advancement of the catheter 2102 is preparatory to the final deployment of the catheter 2102 to its final position within the vessel, which may also be referred to as the indwelling, fully advanced, or resident position, etc.

In some instances, placement of the lower actuator 2222 below the handle 2150 allows the dominant hand to maintain continuous contact with the handle 2150 throughout both the initial introduction of the catheter 2102 into the vessel and subsequent actuation of the system 2100 for further deployment the catheter 2102 to a final depth within the vessel. For example, by gripping the handle 2150 with the dominant hand, the fingers may wrap around the housing 2152, but not extend over the pathway along which the lower actuator 2222, or more generally, the stiffener hub 2154, is slid. As the dominant hand grips the housing 2152, with the index finger on one side and the other fingers on the other, the nondominant hand can engage the lower actuator 2222 and move it forward between the thumb and fingers of the dominant hand, without disrupting placement of the thumb and fingers of the dominant hand. In other instances, the roles of the dominant and nondominant hands can be reversed.

In the illustrated embodiment, the upper actuator 2155 captures or engages the stiffener hub 2154 when advanced in the distal direction, but not when pulled in the proximal direction. The stiffener hub 2154 does not capture or engage the upper actuator 2155 when moved in the forward direction, but the stiffener hub 2154 may capture or engage the upper actuator 2155 if the stiffener hub 2154 is pulled in the rearward direction (if the upper actuator 2155 has previously been advanced distally).

With reference again to FIG. 41A, in some instances, a user may forego using the upper actuator 2155 and may opt instead to use only the lower actuator 2222 to deploy the catheter 2102. That is, with reference to FIG. 41C, the lower actuator 2222 may be moved the full deployment distance D3 directly, or without use of the upper actuator 2155. In the illustrated arrangement, due to a lack of interaction between the stiffener hub 2154 and the upper actuator 2155 during forward movement of only the stiffener hub 2154 from the position depicted in FIG. 41A, the upper actuator 2155 may remain in its initial position during such a deployment. Thus, when the system 2100 is in the fully deployed state, the upper actuator 2155 may be positioned in a fully retracted state rather than the fully advanced state. With reference to FIG. 41C, then, upon full deployment of the system 2100 in this manner, the actuator 2155 would be positioned in its leftmost, rather than rightmost, orientation.

In some instances, a practitioner may opt to use such a one-stage actuation in contexts such as peripheral placements. For example, a practitioner may, in some instances, prefer to use only the lower actuator 2222 to deploy the catheter 2102 if vessel access is relatively straightforward. The practitioner may insert the tip of the needle 2104 (and potentially the tip of the catheter) into the vessel a desired initial amount (e.g., while the system 2100 is in the undeployed stated) without using the other hand for tensioning/positioning purposes, due to the relative accessibility (e.g., due to shallow position) of peripheral vessels. Once the system 2100 has been inserted into the vessel to an initial depth (which may also be referred to as an introduction depth), the practitioner may then slide only the lower actuator 2222 to advance the catheter 2102 into the vessel to the final or indwelling depth.

Accordingly, the system 2100 can be usable in two different deployment modes—i.e., in a two-phase deployment mode or a one-phase deployment mode. A user thus can select which mode to use based on preference, type of vessel being accessed, etc.

Illustrative methods of using the system 2100 have previously been described. Further details of certain of these or other methods will now be described.

A user of the system 2100 may remove the system 2100 from packaging, at which point the system 2100 can be in the pre-deployment state depicted in FIG. 41A. The user may prepare the skin of a patient at which an insertion site will be formed according to standard operating procedures. The user may then advance the distal end of the system 2100 (such as depicted in FIG. 20D) through the skin of a patient and into a vessel in manners such as previously described. Moreover, as previously described, the stiffener 2106 can facilitate and/or reduce or avoid deformation of the distal tip of the catheter 2102 during such insertion through the skin, as well as though the vessel wall. Once the distal end of the system 2100 has been inserted into the vessel by a sufficient amount, a flash of blood will become visible indicating proper introduction into the vessel has been achieved. At this point, the tip of the needle 2104 has entered the vessel, and possibly the distal tip of the catheter 2102 and the distal tip of the stiffener 2106 may have entered the vessel as well. To the extent the catheter 2102 has entered the vessel at this point, the depth to which the catheter 2102 has been inserted into the lumen of the vessel may be referred to as the introduction depth, initiation depth, preliminary depth, etc.

After viewing the flash of blood, the user may then deploy the catheter 2102 over the needle 2104 in either of the manners described above. For example, in some methods, the user may first advance the upper actuator 2155 forward, relative to the housing 2150 (which may be held substantially stationary, steady, stable, fixed, or immobile relative to the patient and/or relative to the vessel), to deploy the catheter 2102 to a capture depth within the vessel, and may thereafter advance the lower actuator 2222 forward, relative to the housing 2150 (which, again, may be held substantially stationary, steady, stable, fixed, or immobile relative to the patient and/or relative to the vessel), to further deploy the catheter to the final indwelling depth within the vessel, and also to assemble the catheter assembly 2149. In other methods, the user only utilizes the lower actuator 2222 to fully deploy the catheter to the final indwelling depth, and also to assemble the catheter assembly 2149. In either case, the user may be alerted that the indwelling depth has been reached via tactile feedback (e.g., difficulty advancing or inability to advance the lower actuator 2222) and/or auditory feedback (e.g., clicking of the catheter assembly 2149 into place).

FIG. 42 depicts the stiffener hub 2154 in the fully advanced position. In many embodiments, forward movement of the stiffener hub 2154 is not delimited by the housing 2152 directly, but rather, is delimited by the housing 2152 indirectly due to interactions and connections housing 2152 and the catheter assembly 2149. However, in some instances, the stiffener hub 2154 may directly contact the lower housing member 2152*b* in the illustrated operational state in an abutting fashion the delimits forward movement of the stiffener hub 2154. In some instances, such contact may only occur in situations at the extreme limits of manufacturing tolerances. In other or further instances, it may be desirable to ensure that at least some space exists between any stopping surfaces of the housing 2152 and the stiffener hub 2154 when the stiffener hub 2154 is fully advanced to ensure sufficient runway exists to permit full assemble the catheter hub.

As previously noted, the rib 2339 of the stiffener hub 2154 may be received within the groove 2314 of the lower housing element 2152*b* when the stiffener hub 2154 has been advanced to the fully advanced state. In many embodiments, this interaction between the rib 2339 and the stiffener hub 2154 does not prevent rearward movement of the stiffener hub 2154, or stated otherwise, permits retraction of the stiffener hub 2154 relative to the housing 2152. In other embodiments, the stiffener hub 2154 can cooperate with the housing 2152 to remain in the fully advanced position, or more generally, to remain in an advanced position (e.g., whether fully advanced or partially advanced relative to the final, distalmost position). By being restricted to such a forward position, the stiffener hub 2154 can effectively lock the stiffener 2106 over or past the distal tip of the needle 2104 to thereby shield the needle from inadvertent contact in manners such as previously described. Stated otherwise, in some embodiments (such as certain embodiments discussed hereafter), the stiffener hub 2154 can cooperate with the housing 2152 to prevent the stiffener 2106 from exposing the needle tip after a deployment event. Stated otherwise, the stiffener hub 2154 and the attached stiffener 2106 can be restrained to a position relative to the housing 2154 that maintains the stiffener 2106 in a shielding orientation relative to the tip of the needle 2104—e.g., in a position in which the stiffener 2106 extends distally past the distal tip of the needle 2104 by an amount sufficient to inhibit or prevent inadvertent contact with the needle tip.

Figure 43:
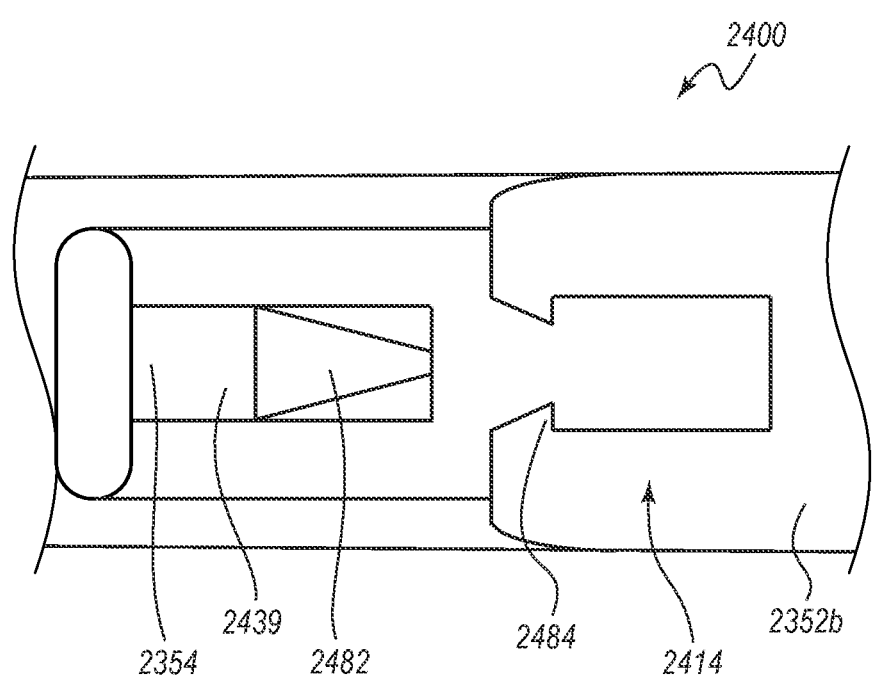
FIG. 43 is an enlarged bottom plan view of another embodiment of a catheter delivery system just prior to full deployment, wherein the catheter delivery system includes a non-return feature that prevents retraction of a stiffener relative to a housing after full deployment is achieved.

FIG. 43 is an enlarged bottom plan view of another embodiment of a catheter delivery system 2300 that includes a non-return, locking, shielding, or safety feature such as just described. That is, the non-return feature prevents retraction of a stiffener of the system 2300 relative to a housing after full deployment of the system 2300. The system 2300 is depicted just prior to full deployment thereof. In particular, the system 2300 includes a lower housing element 2352*b* that defines a groove 2414 that includes a pair of inwardly protruding catches 2484. The catches 2484 interface with a proximal surface of a locking protrusion 2482 defined by a rib 2439 of a stiffener hub 2354. Once these features are locked together, the stiffener hub 2354 cannot be retracted relative to the housing. Thus, the stiffener to which the lower actuator is attached is maintained in a fixed, shielding position over the needle tip (e.g., in a shielding position similar to that depicted in FIG. 51G).

In the illustrated embodiment, the stiffener is maintained in the fully deployed position, and thus extends a maximum length past the needle tip. In other embodiments, the non-return feature may permit some amount of proximal movement of the stiffener hub and stiffener relative to the housing after deployment, but prevent full retraction of the stiffener from over the needle. That is, the system can maintain at least some length of the stiffener past the distal end of the needle in an amount sufficient to shield the needle tip from inadvertent contact. Stated otherwise, the system can retain the stiffener in at least a partially deployed state. Illustrative examples of such systems are discussed further below.

Figure 44:
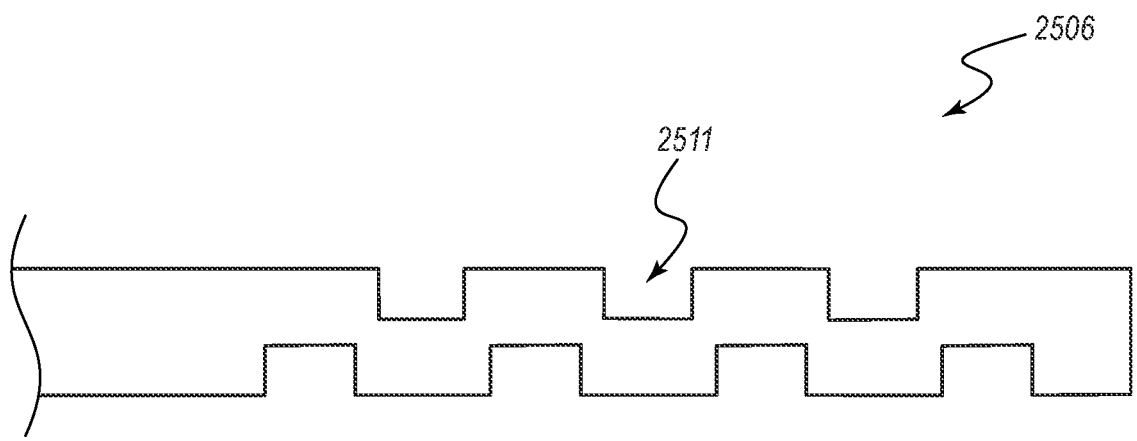
FIG. 44 is a side elevation view of an embodiment of a stiffener that includes a flexibility-enhanced distal end.

FIG. 44 is a side elevation view of an embodiment of a stiffener 2506, compatible with catheter delivery systems described herein, that includes a flexibility-enhanced distal end. In many embodiments, the stiffener 2506, or sheathing cannula, can be very flexible, as previously disclosed. For example, the sheathing cannula may be formed of a superelastic material (e.g., superelastic nitinol). To increase the flexibility (e.g., transverse flexibility) of the sheathing cannula, without negatively impacting the longitudinal support it provides (e.g., to the step feature at the distal end of the catheter), a series of notches, cuts, or other bending features 2511 may be placed in specific regions/orientations at or toward the distal end of the cannula. In some instances, the transverse flexibility-enhancing features can be positioned in a region near the distal end where a large amount of lateral bending is expected, such as during initial introduction into the vessel at an angle to a lumen defined by the vessel, and the immediate change-of-direction that results thereafter from being advanced within the lumen of the vessel.

Stated otherwise, the vessel can define a lumen that extends in a longitudinal direction, or that define a longitudinal axis. The longitudinal axis can extend longitudinally along and through a center of the vessel, and thus can follow a contour of the vessel. The contour may be substantially linear in some regions and/or may be substantially curvilinear in others. In general, a longitudinal axis of a system, such as the system 2100 discussed above, is inserted into the vessel generally in alignment with the longitudinal axis of the vessel, but at an angle (e.g., an approach angle) relative thereto. Often, this approach angle is as shallow as possible to facilitate insertion of the needle (which can generally be in alignment with the longitudinal axis of the system) and catheter into the vessel. Nevertheless, due to this angle, the catheter/stiffener pair of the system can enter the vessel at the approach angle. The catheter/stiffener pair, when initially advanced over the tip of the needle for intra-vessel or intraluminal deployment, may approach or come into contact with an inner surface of the vessel wall substantially at the approach angle. The catheter/stiffener pair may then bend to substantially follow the lumen of the vessel, thread along the lumen at the interior of the vessel, and/or generally advance in the direction of the longitudinal axis of the vessel. This initial bend may also be referred to as an entry bend or primary bend. After making the initial bend, the catheter/stiffener assembly can be advanced longitudinally through the vessel to the target site or target depth within the vessel, which target site can be relatively far removed from the vessel insertion site and primary bend.

With reference again to FIG. 44, the bending features 2511 can facilitate the initial creation of the entry bend of the catheter/stiffener pair, or stated more generally, can facilitate introduction into and/or initial advancement with in the vessel of the catheter/stiffener pair. In the illustrated embodiment, the bending features 2511 (e.g., the notches) may be placed in an alternating pattern, as depicted, or in any other suitable pattern or arrangement. The notches 2511 may be formed in any suitable manner, such as, for example, via laser cutting. In some embodiments, the notches 2511 are positioned no further than about 0.75, 1.0, or 1.5 inches from a distal tip of the stiffener 2506. In various embodiments, a depth of each notch 2511 is no greater than about 0.7, 0.8, or 0.9 times a radius of the stiffener 2506.

As previously discussed, embodiments of systems can include a rotational locking feature by which the stiffener 2506 maintains a fixed angular relationship relative to the handle or housing of the system. Such rotational locking can be used to ensure that the stiffener 2506 is oriented properly relative to the bending feature 2511. For example, in the illustrated embodiment, it can be desirable for the bending features 2511 to be oriented substantially vertically, relative to the longitudinal axis of the system during insertion (e.g., within a vertical plane that passes through both the upper and lower actuators of the system, such as the system 2100). Stated otherwise, within the vicinity of an insertion site of a patient, the vessel may extend substantially linearly. In some instances, it can be desirable to substantially align a longitudinal axis of the system (e.g., a longitudinal axis of the needle of the system) with the longitudinal axis of the insertion region portion of the vessel. The two longitudinal axes may be substantially coplanar. In the embodiment depicted in FIG. 44, the upper and lower bending features 2511 may each be intersected by this plane, which may facilitate bending of the stiffener 2506 to align with the longitudinal axis of the vessel.

Figure 45:
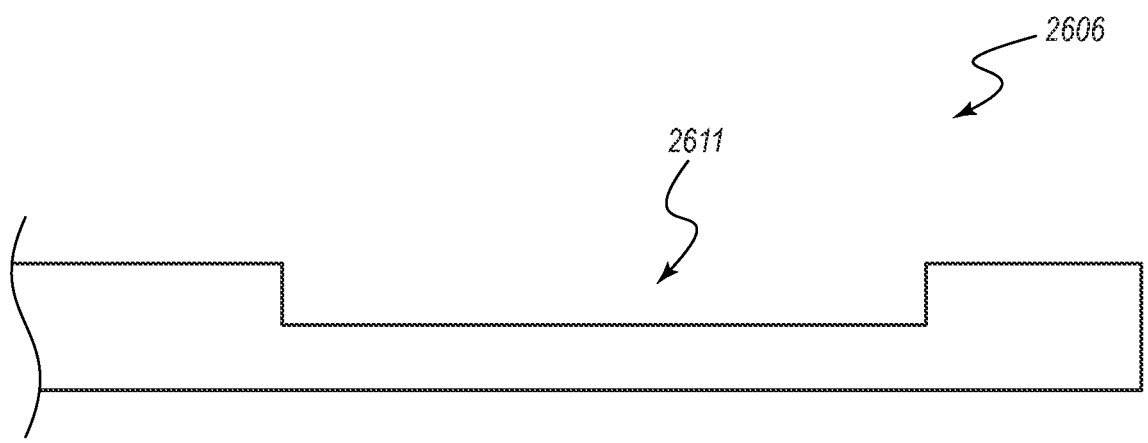
FIG. 45 is a side elevation view of another embodiment of a stiffener that includes a flexibility-enhanced distal end.

FIG. 45 depicts a side elevation view of another embodiment of a stiffener 2606, compatible with catheter delivery systems described herein, that includes a flexibility-enhanced distal end. In this embodiment, a single bending feature 2611 is provided. In particular, the bending feature 2611 comprises an elongated notch in one side of the cannular stiffener 2606. In some embodiments, the bending feature 2611 can be oriented upwardly with a catheter deliver system, such that the forward and rearward ends of the notch slightly angle toward each other when the stiffener 2606 bends upon entry into the vessel (e.g., initially forms a primary bend within the vessel).

Figure 46:
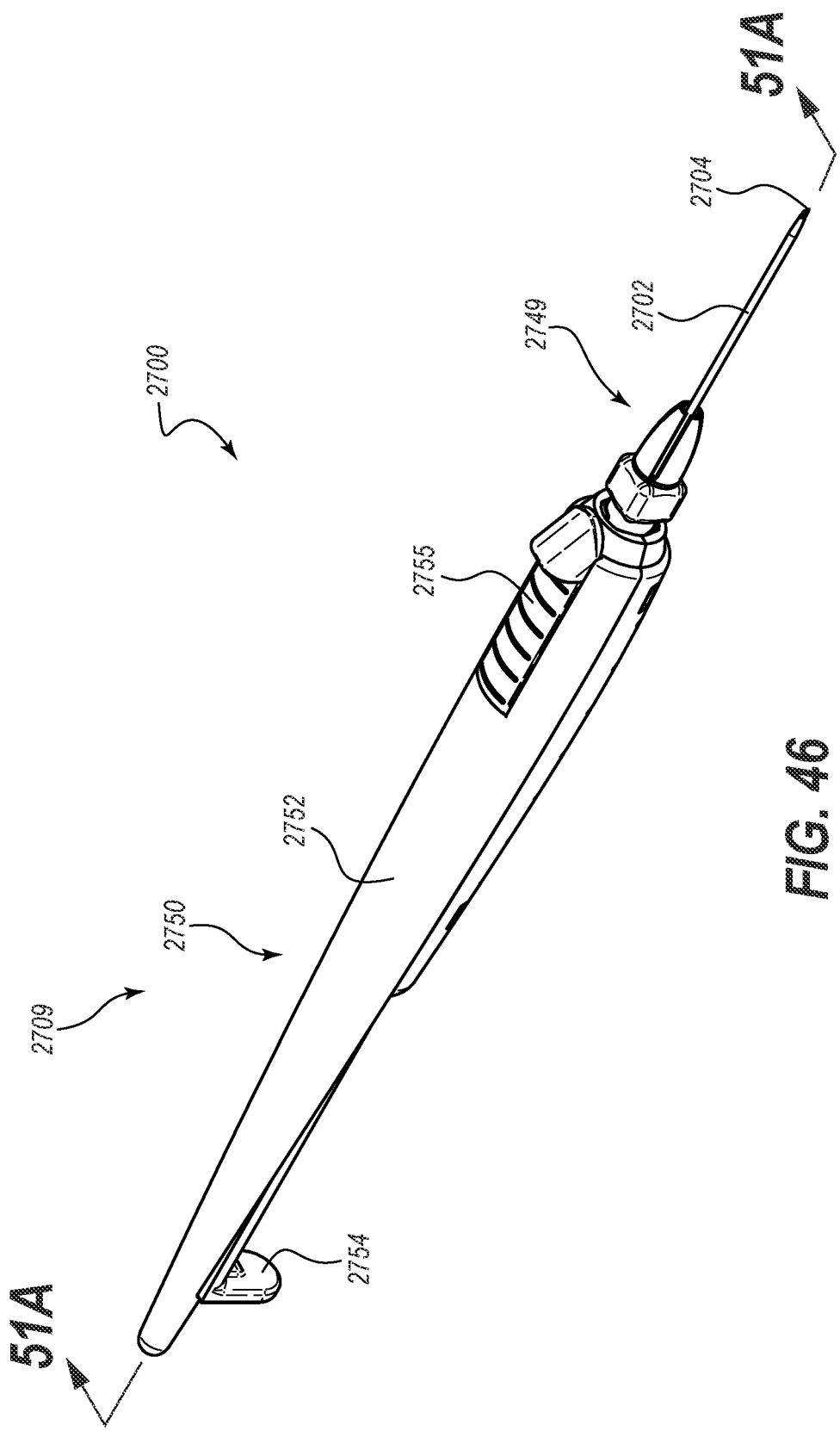
FIG. 46 is a perspective view of another embodiment of a catheter delivery system.

FIG. 46 depicts another embodiment of a catheter delivery system 2700 similar to other systems disclosed herein. In particular, the system 2700 can operate in manners such as those described with respect to previously disclosed embodiments (e.g., the systems 800, 2000, 2100), and may include other or further features as described hereafter. All relevant disclosures of the prior embodiments are incorporated hereby with respect to the system 2700, mutatis mutandis, consistent with the disclosure conventions previously outlined. The system 2700 includes an insertion assembly 2709 that is selectively attached to a catheter assembly 2749. As with other embodiments discussed above, the insertion assembly 2709 is configured to deploy a catheter 2702 to a desired depth within a vessel of a patient.

The catheter delivery system 2700 includes a catheter 2702, a needle 2704, and a stiffener 2706 (FIG. 51G) such as like-named and like-numbered components previously described. The system 2700 includes a non-return feature that can maintain a stiffener hub 2754 in an intermediate position to maintain the stiffener 2706 in a shielding orientation relative to the needle 2704. The system 2700 can further include a catch to prevent an upper actuator 2755 from inadvertent decoupling from a handle 2750, which may be formed by a housing 2752.

Figure 47:
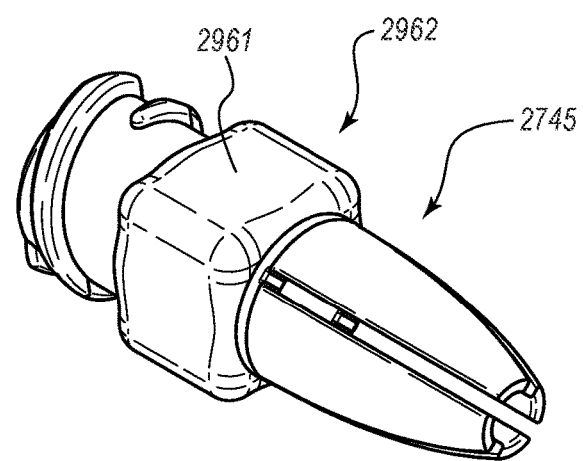
FIG. 47 is a perspective view of an embodiment of a catheter connection hub that is compatible with the catheter delivery system of FIG. 46.

With reference to FIG. 47, in some embodiments, the system 2700 includes a catheter connection hub 2745 that includes a differently shaped friction-enhancing feature 2962. In particular, the friction-enhancing feature 2962 includes a substantially cubical or parallelepiped-shaped region 2961 that can be readily manipulated by a user. Moreover, the region 2961 can include a plurality of substantially planar surface which may be readily printed with indicia.

Figure 48:
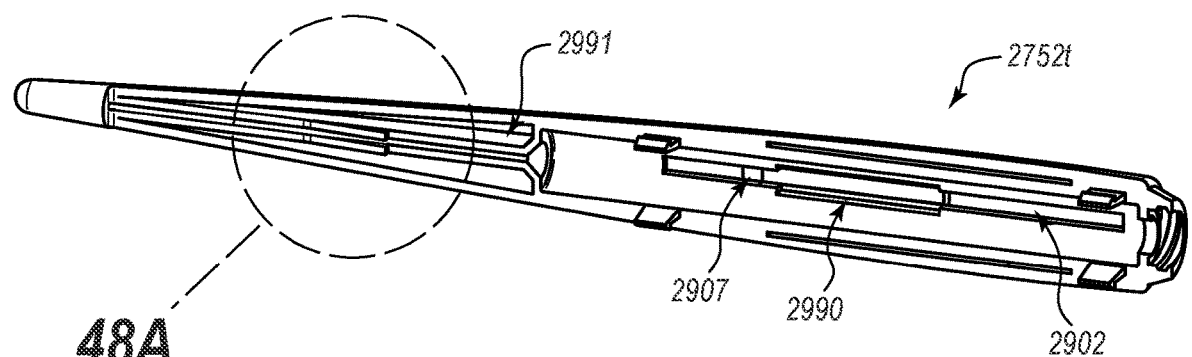
FIG. 48 is a perspective view of an embodiment of an upper housing element that is compatible with the catheter delivery system of FIG. 46.

With reference to FIG. 48, an upper housing element 2752t can define a track 2902 such as the track 2302. The track 2902 can define a first width. The housing element 2752t can further define an internal track 2907, which can have a proximal portion and a distal portion. The proximal portion may, in some instances, have substantially the same width as the track 2902. The distal portion of the track 2907 can include an enlarged region 2990 that defines a larger width. The enlarged width of the region 2990 permits accommodation of catches of the upper actuator 2755, which are discussed further below.

The upper housing element 2752t can include a pair of recesses 2991, which can, for example, reduce the amount of material used in the upper housing element 2752t and reduce manufacturing costs.

Figure 48A:
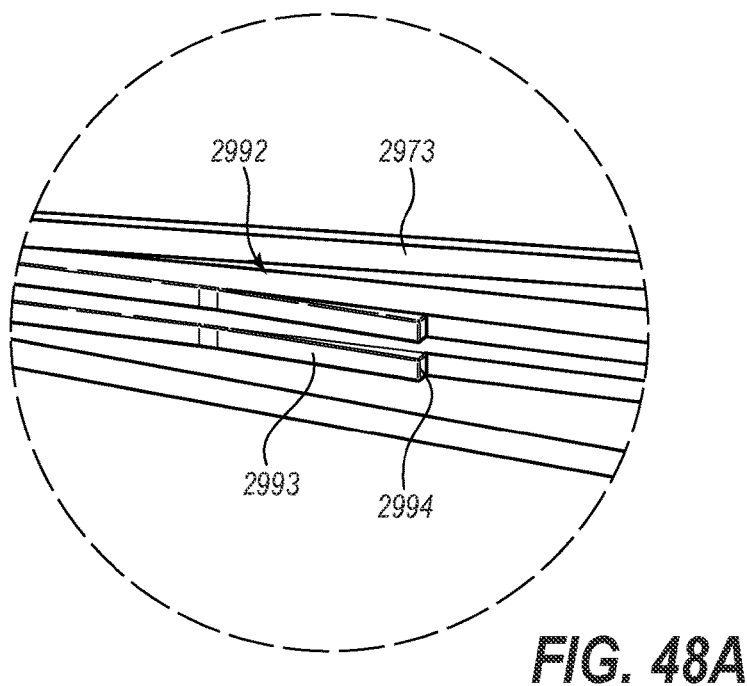
FIG. 48A is an enlarged perspective view of a portion of the upper housing element taken along the view region 48A identified in FIG. 48.

With reference to FIG. 48A, the upper housing element 2752t can define a stop 2992 which can prevent return of the stiffener 2706, as discussed further below. The illustrate stop 2992 includes a pair of ramps 2992, each of which includes a ramp surface 2993 and an abutment or engagement surface 2994. The stop 2992 can project away from a substantially planar orientation surface 2373.

Figure 49:
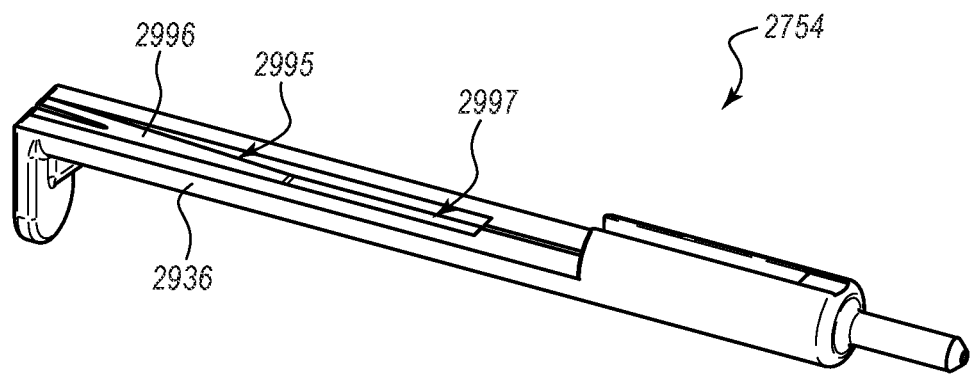
FIG. 49 is a perspective view of an embodiment of a stiffener hub that is compatible with the catheter delivery system of FIG. 46.

With reference to FIG. 49, in some embodiments, the stiffener hub 2754 can include a stop interface 2995, which in the illustrated embodiment includes a cavity 2997 and a ramp 2996. The stop interface 2995 is defined by an extension 2936 (such as the extension 2336 described above).

Figure 50:
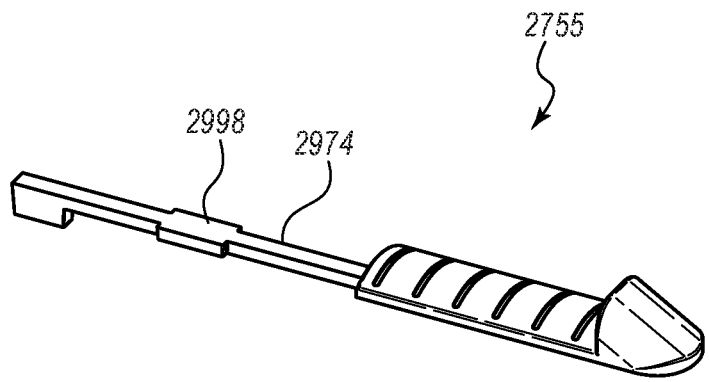
FIG. 50 is a perspective view of an embodiment of an upper actuator that is compatible with the catheter delivery system of FIG. 46.

With reference to FIG. 50, and as previously mentioned, the upper actuator 2775 can include a pair of catches 2998 that extend outwardly or laterally from a stem 2974. The catches 2998 are sized to be received within the enlarged region 2990 of the internal track 2907 defined by the upper housing element 2752t, but extend outwardly by a sufficient amount to be incapable of fitting through the track 2902, unless the actuator 2775 is twisted to an orientation that is otherwise inhibited by the presence of the stiffener hub 2757 within the housing 2752.

Figure 51A:
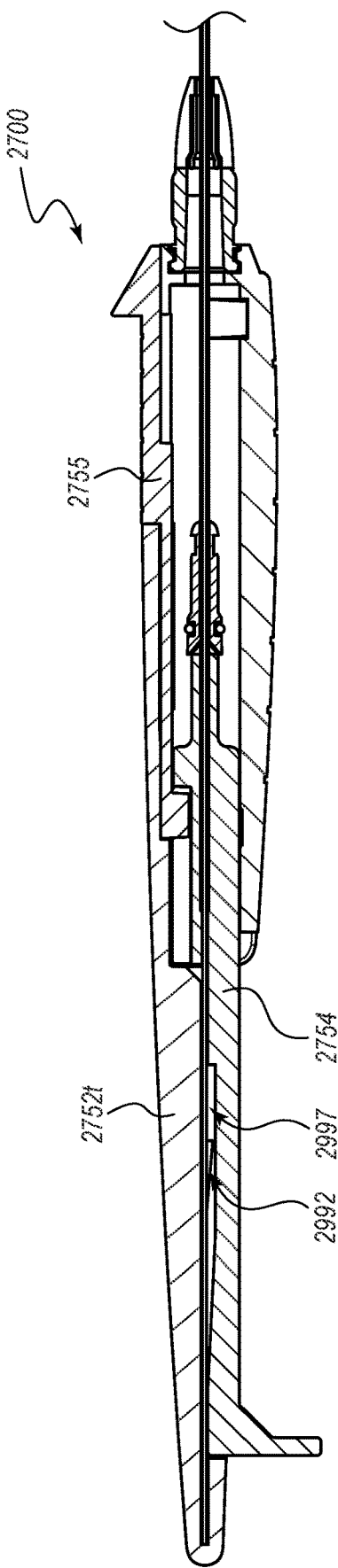
FIG. 51A is a cross-sectional view of the catheter delivery system of FIG. 46 taken along the view line 51A-51A in FIG. 46, which depicts the catheter delivery system in an undeployed state.

FIGS. 51A-51H depict various phases of operation of the system 2700. FIG. 51A depicts the system 2700 in an undeployed state. In this state, the upper actuator 2755 and the stiffener hub 2754 are each in a fully retracted position. The stop 2992 defined by the upper housing element 2752t is positioned within the cavity 2997 defined by the stiffener hub 2754.

Figure 51B:
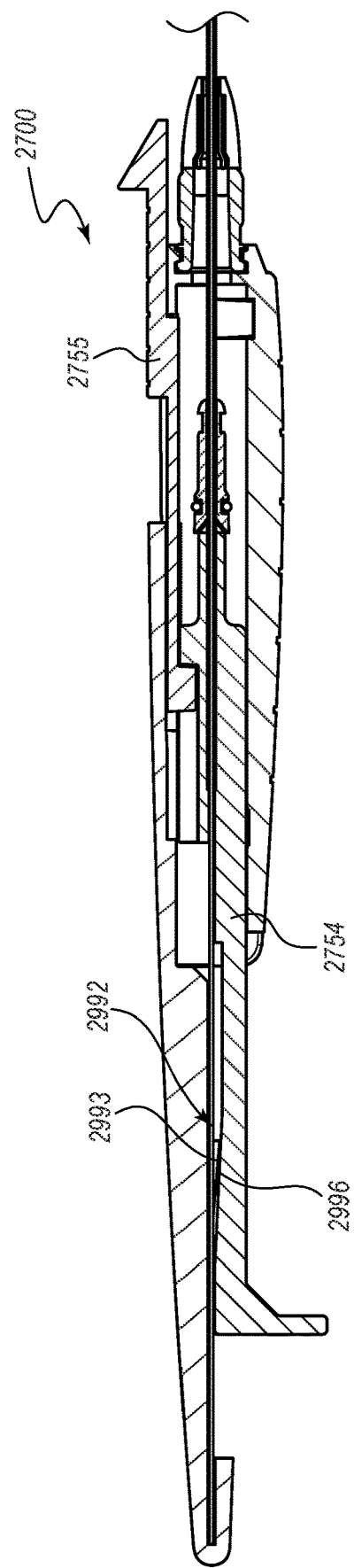

In FIG. 51B, the upper actuator 2755 has been advanced fully to its distalmost, advanced position. The upper actuator 2755 has pulled the stiffener hub 2754 forward by the same amount, but eh stiffener hub 2754 remains in only a partially actuated or partially deployed state. At this operational state, the ramp surface 2993 of the stop 2992 has not yet come into contact with the ramp surface 2996 of the stiffener hub 2754. Accordingly, the additional forces that come into play when the ramp surfaces 2993, 2996 interact with each other may not have any bearing on deployment of the upper actuator 2755.

As shown in FIG. 58A, In some embodiments, the ramp surfaces 2993, 2996 can be as shallow angles, such that little resistance to forward movement of the stiffener hub 2754 may result from interaction of the ramp surfaces 2993, 2996. In the illustrated embodiment, the upper housing element 2752t and the stiffener hub 2754 are formed of flexible (e.g., resiliently flexible) material and also define long moment arms in the longitudinal direction, and thus can readily bend by a small amount—away from each other—as the ramp surfaces 2993, 2996 advance past one another. Such interactions may occur soon after the stiffener hub 2754 is engaged by a user to continue deployment of the system 2700. The stage at which the ramp surfaces 2993, 2996 interact and outwardly bend (to a slight degree), in opposite directions, the upper housing element 2172t and the stiffener hub 2754 is not shown.

FIG. 51C shows a subsequent stage in which the stiffener hub 2754 has been advanced just past the stop 2992 and both the housing 2752 and the stiffener hub 2754 have snapped back into a substantially parallel orientation relative to each other. In some instances, only a small sound or no discernable sound may be made and/or only a slight difference in pushing force may be detectable by the user when this snap back occurs so as to avoid any confusion as to when the system 2700 has been fully deployed to the point that catheter hub core 2741 audibly snaps into the catheter connection hub 2745. Indeed, in the illustrated embodiment, all interactions between the ramp surfaces 2993, 2996 is completed before the catheter hub core 2741 comes into contact with the resiliently flexible gripping arms of the catheter connection hub 2745.

FIG. 51D illustrates that the stiffener hub 2754 has been further advance forward into contact with the inner surfaces of the gripping arms of the catheter connection hub 2745. In some instances, the increase in force required to push past the inner protrusions of the arms can be perceptible, relative to the forces used during all prior phases of deployment, so as to provide tactile feedback to the user regarding the status of the construction of the hub assembly 2149.

FIG. 51E depicts an operation state at which the resilient arms of the catheter connection hub 2745 have snapped into engagement with the catheter hub core 2741. In this embodiment, the fully deployed orientation of the system 2700 is depicted.

FIG. 51F depicts another stage of operation in which the upper actuator 2755 has been retracted away from the catheter connection hub 2745. In some instances, moving the upper actuator 2755 in this manner can facilitate removal of the catheter connection hub 2745 from the housing 2752. This view also demonstrates that the upper actuator 2755 does not engage the stiffener hub 2754 when moved rearwardly, and thus the stiffener hub 2754 remains in its forward, fully deployed position.

Figure 51G:
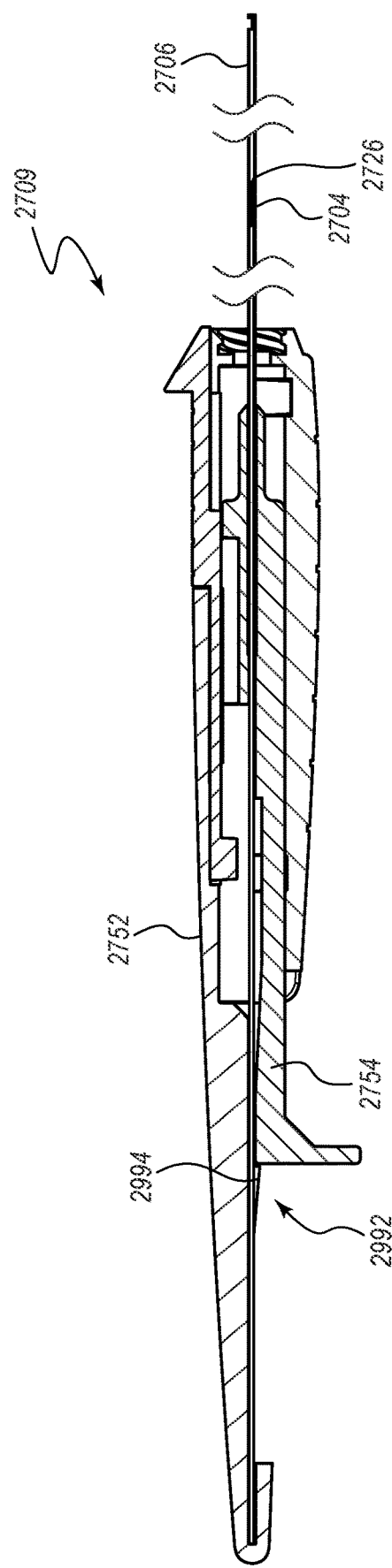
FIG. 51G is a cross-sectional view of an embodiment of an insertion assembly that has been removed from an embodiment of a catheter assembly in a further phase of use of the catheter delivery system.
Figure 51H:
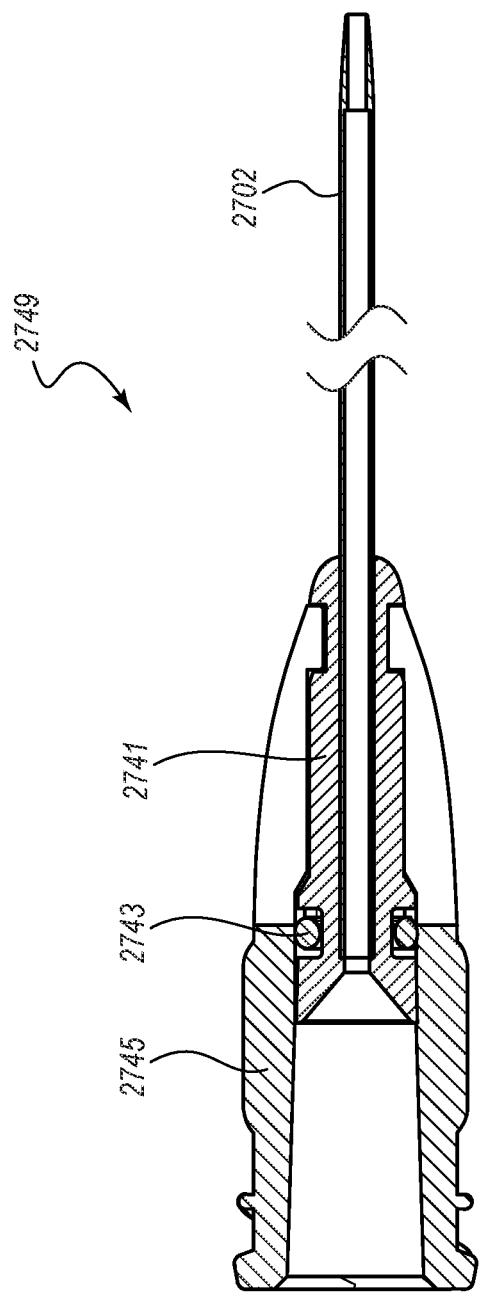
FIG. 51H is a cross-sectional view of the catheter delivery system after the insertion assembly has been removed therefrom.

FIGS. 51G and 51H depict a later stage of operation in which the insertion assembly 2709 has been removed from the catheter assembly 2749 while the latter assembly is held in place with the catheter positioned at its indwelling position with the vessel. For example, in some instances, the user can hold the catheter assembly 2749 steady or stationary relative to the patient with one hand while withdrawing the insertion assembly 2709 from the catheter assembly 2749 with the other.

As shown in FIG. 51G, in this embodiment, the stiffener hub 2754 can be permitted to move somewhat proximally relative to the housing 2752, but is prevented from fully retracting to the starting position by the stop 2992—specifically, by the engagement surface 2994 of the stop 2992. In this manner, a significant length of the stiffener 2706 extends distally beyond a distal tip 2726 of the needle 2704 to shield the needle tip from inadvertent contact (e.g., preventing inadvertent needle sticking of the user).

As shown in FIG. 51H, the catheter assembly 2749, which may remain in the patient, can include the deployed catheter 2702, the catheter hub core 2741, a seal member 2743, and the catheter connection hub 2745.

With reference again to FIG. 51C, in some embodiments, the system 2700 can be resettable. Stated otherwise, the non-return feature or stop 2992 may be selectively overridable to permit resetting of the device. In the illustrated embodiment, resetting of the device may be achieved by bending the upper housing element 2752t and the stiffener hub 2754 away from each other to move the stiffener hub 2754 proximally past the stop 2992 and back to the initial position of FIG. 51A. In some instances, the system 2700 may be used in a reset state to advance a catheter into a vessel, even after the bond between the catheter tip and the needle has been broken. For example, in some instances, the support provided by the stiffener 2706 can be sufficient to assist in urging the catheter tip through the vessel wall.

Figure 52:
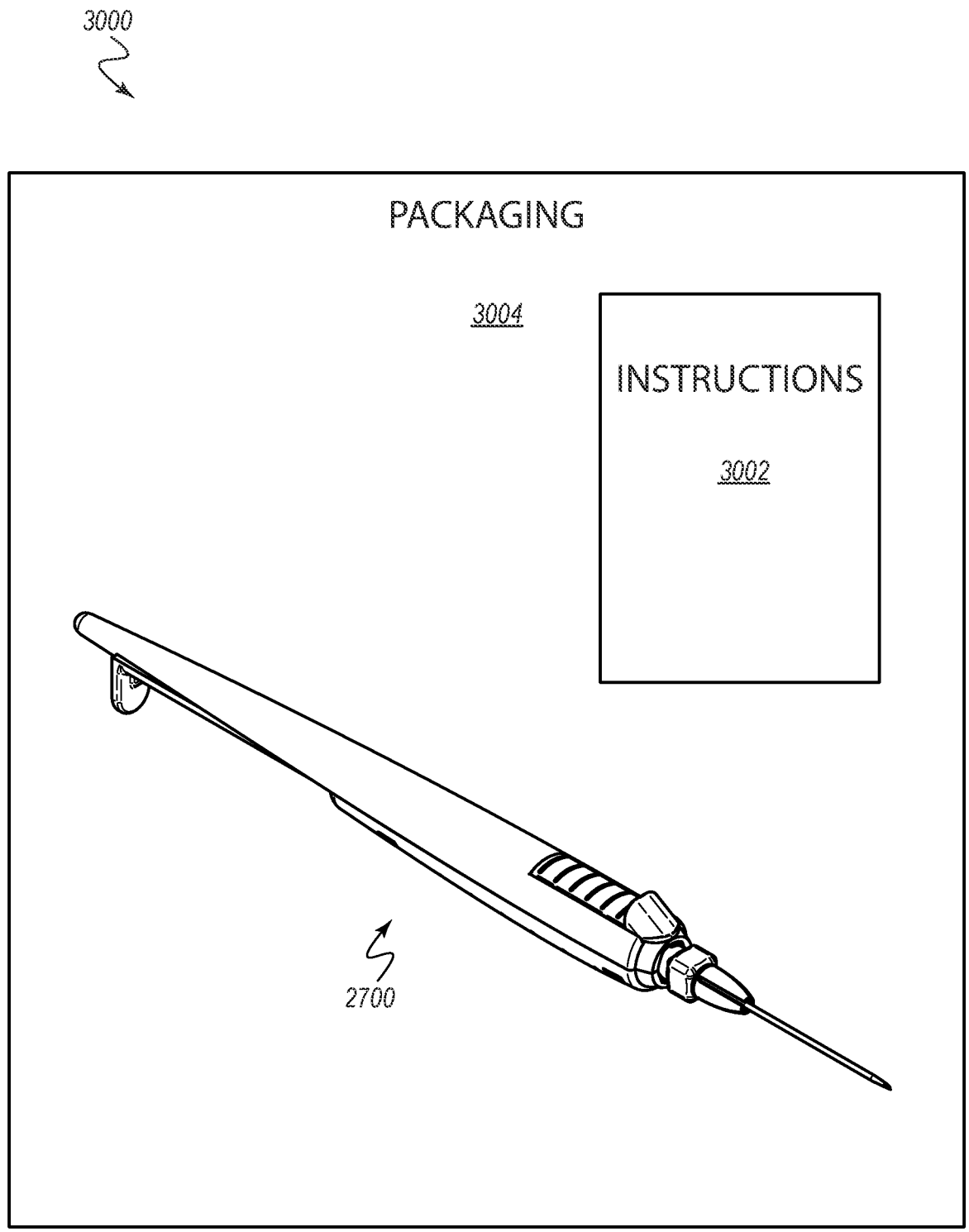
FIG. 52 is an elevation view of an embodiment of a kit that includes an embodiment of a catheter delivery system (shown in perspective) and instructions for using the same.

FIG. 52 depicts an embodiment of a kit 3000 for deploying a catheter into a vessel of a patient, or stated otherwise, depicts an embodiment of a catheter delivery kit 3000. The kit 3000 can include any of the catheter delivery systems disclosed herein and/or components thereof, or alternative components therefor. For example, in the illustrated embodiment, the kit 3000 includes the catheter delivery system 2700.

The kit 3000 can include instructions for use 3002, which may provide directions with respect to any of the methods or processes disclosed herein. For example, the instructions for use 3002 may recite any method and/or other portion of the present disclosure.

In various embodiments, the kit 3000—and, in particular, the instructions for use 3002 thereof—can be approved of or authorized by a regulating body of a particular jurisdiction. For example, the kit 3000, and the instructions for use 3002 thereof, may be approved of or authorized by the Food and Drug Administration of the United States of America and/or may comply with the regulations of other jurisdictions, such as by qualifying for CE marking in the European Union. The instructions for use 3002 and the system 2700 can be incorporated into any suitable packaging 3004.

Other features and advantages of various embodiments will now be discussed. In some embodiments, due to the presence of the sheathing cannula, the distal tip of the catheter (e.g., in the region distal of the distal end of the sheathing cannula) includes more material. Stated otherwise, for a given outer diameter of the catheter, as compared with standard over-the-needle catheter devices, certain embodiments disclosed herein have a smaller opening and, further, have more material in the tipped region. Although flow may potentially be restricted in certain of such arrangements, as previously discussed, such embodiments can benefit from other advantages.

For example, in standard over-the-needle catheter systems, the catheter wall thickness is substantially constant from proximal regions all the way to the distal tip. In certain embodiments disclosed herein, however, the catheter includes an internal stepped region at the distal end, which results in more material at the distal end—that is, the catheter wall at the distal end is thicker (e.g., in a transverse direction) along a longitudinal length of the distal end—extending (in the proximal direction) from the substantially pointed (in cross-section) tip rearward to the transverse sheathing cannula engagement ledge, at which point the wall thickness can become substantially constant, as with other catheter devices.

To avoid fishmouthing, some standard catheter devices have a strong catheter-to-needle adhesion at this distal tip. This makes it difficult to push the catheter off of the needle. A practitioner must apply force until the bond breaks, thus the practitioner does not a have a good tactile feel for what is transpiring at the distal end of the catheter during an insertion event. For example, the sudden changes in force due to the bond breakage to initiate separation of the catheter from the needle obscure other forces at play during the initial stage of insertion as the catheter is advanced into the vessel.

Certain embodiments disclosed herein do not require a strong adhesion to avoid fishmouthing. That is, the additional material and the geometric arrangement of the distal end of at least some of the catheters disclosed herein yield a stronger distal tip (having a greater hoop strength, etc.) that is less susceptible to deformation, such as by fishmouthing. Accordingly, a much smaller bond strength may be used/present, which can yield a smoother deployment, or one that has fewer force fluctuations. This can provide an improved tactile feedback for the practitioner, which is less obscured by the initial breaking of the bond.

Moreover, the stronger distal tip can be less susceptible to collapsing during aspiration. Even when the catheter is formed of a relatively softer material, the additional material and the strength provided by the structure thereof can resist closure of the distal tip during aspiration. To the extent there is any tendency toward collapse, the effect can be far less pronounced than in standard catheter systems.

Generally, the inclusion of a notched needle, e.g., for purposes of flash detection, in standard over-the-needle catheter systems is disadvantageous, as it weakens the needle tip. Standard catheter systems use such small needles that the weakness introduced by such notches permits undesired movement (e.g., lateral deflection) of the needle tips during placement. The weaknesses may even lead to breakage. The effect can be significant, given the toughness of vessel walls.

Embodiments disclosed herein, however, reinforce needles that have been notched for flash detection. For example, in certain embodiments, the sheathing cannula encompasses the needle—e.g., at regions both proximal of and, importantly, distal to the notch in the needle. Thus, forces that might otherwise deflect the notched needle are counteracted by the sheathing cannula. This can yield a stronger, more accurate, easier-to-use system.

Certain embodiments can permit usage of extremely soft catheters. Rather than being pushed into a vessel over a guidewire, and thus requiring inherent stiffness sufficient for such proximal advancement, certain embodiments are instead drawn into the vessel from the distal end thereof via the sheathing cannula, and thus any stiffness requirements for advancing into the vessel are achieved by the sheathing cannula, rather than the catheter.

Certain embodiments can be very well suited for delivering a catheter through a vessel that includes one or more valves therein. Indeed, the valves can be penetrated without first advancing a guidewire or other guide element in advance of the catheter. The catheter, reinforced by the stiffener, can be sufficiently rigid to pass through the valve otherwise unaided. As previously discussed, in some embodiments, the distal tip of the catheter can be at the distalmost end of the system (e.g., can be positioned distal to the distal end of the stiffener) throughout the full period of deployment of the catheter over the needle to the final target site within the vessel. In some instances, the catheter tip can be relatively soft and substantially atraumatic.

It will be understood by those having skill in the art that changes may be made to the details of the above-described embodiments without departing from the underlying principles presented herein. For example, any suitable combination of various embodiments, or the features thereof, is contemplated.

Although the foregoing detailed description contains many specifics for the purpose of illustration, a person of ordinary skill in the art will appreciate that many variations and alterations to the following details can be made and are considered to be included herein. Accordingly, the foregoing embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

As used in this specification and the appended claims, the singular forms "a," "an" and "the" include plural referents unless the context clearly dictates otherwise. Thus, for example, reference to "a layer" can include a plurality of such layers.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the component structures, steps, or the like specifically listed in conjunction with such terms, as well as that which is in accordance with U.S. patent law.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in any suitable manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly-complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Moreover, for references to approximations (which are made throughout this specification), such as by use of the terms "about" or "approximately," or other terms, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially perpendicular" is recited with respect to a feature, it is understood that in further embodiments, the feature can have a precisely perpendicular orientation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

References throughout this specification to "an example," if any, mean that a particular feature, structure, or characteristic described in connection with the example is included in at least one embodiment. Thus, appearances of the phrases "in an example" in various places throughout this specification are not necessarily all referring to the same embodiment.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of claims [x] through the claim that immediately precedes this one" where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. A system comprising:
   a housing;
   a needle fixedly secured to the housing, the needle comprising a distal tip configured to be inserted into a vessel of a patient, the needle defining an outer surface;
   a catheter that comprises a distal end and an inner surface that defines a lumen, wherein the catheter is configured to be in an undeployed state in which a portion of the needle is positioned within the lumen of the catheter and the distal tip of the needle is at a position that is distal to the distal end of the catheter, the catheter further comprising a catching region of reduced diameter that extends inwardly at the distal end of the catheter;
   a catheter connection hub releasably coupled to the housing, the catheter extending through and being movable relative to the catheter connection hub when the catheter is in the undeployed state;
   a catheter hub core fixedly secured to the catheter, the catheter hub core being configured to attach to the catheter connection hub as the catheter is advanced distally relative to the catheter connection hub from the undeployed state to a deployed state; and
   a longitudinally extending stiffener positioned between the outer surface of the needle and the inner surface of the catheter, the stiffener comprising a distal end that engages the catching region of the catheter as the catheter is advanced from the undeployed state to the deployed state.

2. The system of claim 1, wherein a distal tip of the stiffener engages the catching region of the catheter.

3. The system of claim 1, wherein the stiffener comprises an elongated tube.

4. The system of claim 3, wherein the catching region of the catheter comprises an inwardly directed surface in contact with a distal tip of the elongated tube.

5. The system of claim 4, wherein the catching region defines a distally directed recess sized to receive at least a portion of the distal tip of the elongated tube.

6. The system of claim 1, wherein the catching region of the catheter comprises an inwardly directed surface in contact with a distal tip of the stiffener.

7. The system of claim 1, wherein the catching region defines a distally directed recess sized to receive at least a portion of a distal tip of the stiffener.

8. The system of claim 1, wherein the catheter includes a recess in the distal end into which a distal tip of the stiffener is received.

9. The system of claim 8, wherein the recess is formed via a mandrel in a tipping process that is completed prior to insertion of the stiffener into the lumen of the catheter.

10. The system of claim 8, wherein the recess is directly formed via the stiffener when a tip of the catheter is reshaped onto the stiffener during a tipping process.

11. The system of claim 1, wherein the catheter hub core is fixedly secured to a proximal end of the catheter.

12. The system of claim 1, wherein the catheter defines an end port through which the needle extends when the catheter is in the undeployed state, and wherein the catheter defines a plurality of side ports that extend through a sidewall of the catheter at the distal end of the catheter.

13. The system of claim 1, wherein a maximum outer diameter of the catheter is no greater than about 1.2 millimeters, a diameter of an end port of the catheter is no greater than 70 percent of the maximum outer diameter of the catheter, and wherein the distal end of the catheter is capable of delivering a water flow rate of no less than 3 milliliters per second without rupturing.

14. The system of claim 1, wherein the catheter and the stiffener cooperate to define an elongated annular lumen through which a flash of blood can flow proximally when the distal tip of the needle is inserted into the vessel of the patient, and wherein a passageway extends through a sidewall of the needle and a sidewall of the stiffener to permit blood to flow from a position within the needle into the elongated annular lumen.

15. The system of claim 14, wherein the needle defines an opening and the stiffener defines an opening that are aligned to form the passageway.

16. The system of claim 1, wherein each of the needle, the catheter, and the stiffener comprises a separate elongated tube, and wherein all of the separate elongated tubes are coaxial.

17. The system of claim 16, wherein the needle and the stiffener are rotationally locked relative to each other when the needle and the stiffener are positioned within the catheter.

18. The system of claim 1, further comprising:
a catheter assembly that comprises the catheter and the catheter hub core; and
an insertion assembly that comprises the housing, the needle, the stiffener, and an actuator coupled with each of the housing and the stiffener.

19. The system of claim 18, wherein when the catheter is in the deployed state:
the catheter hub core is attached to the catheter connection hub; and
the catheter connection hub is configured to decouple from the housing to permit the insertion assembly to be removed from the catheter assembly.

20. The system of claim 1, further comprising an actuator coupled to the stiffener, the actuator being actuatable to transition the catheter from the undeployed state to the deployed state.

21. The system of claim 20, wherein the actuator is movable relative to the housing.

22. The system of claim 21, wherein the housing comprises a track and the actuator is configured to translate along the track.

23. The system of claim 1, wherein the catheter is configured to be advanced into the vessel of the patient over the needle, and wherein the stiffener is configured to be withdrawn proximally from the catheter while the catheter remains within the vessel of the patient.

24. The system of claim 1, wherein the distal end of the catheter defines an opening, and wherein a distal end of the needle extends through the opening of the catheter when the catheter is in the undeployed state.

25. The system of claim 1, wherein the catheter hub core and the catheter connection hub are unattached relative to one another when the catheter is in the undeployed state.

26. The system of claim 25, wherein the catheter hub core is spaced from and positioned proximal to the catheter connection hub when the catheter is in the undeployed state.

27. The system of claim 26, wherein the catheter hub core is fixedly secured to a proximal end of the catheter.

28. The system of claim 1, wherein the catheter hub core is spaced from and positioned proximal to the catheter connection hub when the catheter is in the undeployed state.

29. The system of claim 1, wherein the catheter extends through an entirety of the catheter connection hub when the catheter is in the undeployed state.

30. The system of claim 1, wherein the catheter comprises a proximal end that is spaced from and positioned proximal to the catheter connection hub when the catheter is in the undeployed state.

31. The system of claim 1, wherein the catheter connection hub is configured to be decoupled from the housing after the catheter hub core has been attached to the catheter connection hub.

32. The system of claim 1, wherein a proximal end of the catheter is movable relative to the catheter connection hub prior to attachment of the catheter hub core to the catheter connection hub and is in a fixed relationship relative to the catheter connection hub after attachment of the catheter hub core to the catheter connection hub.

33. The system of claim 1, wherein a proximal end of the catheter is longitudinally movable relative to the catheter connection hub when the catheter is in the undeployed state.

* * * * *